(12) United States Patent
Kauppinen et al.

(10) Patent No.: US 6,566,114 B1
(45) Date of Patent: May 20, 2003

(54) MANNANASES

(75) Inventors: Markus Sakari Kauppinen, Copenhagen N. (DK); Martin Schülein, Copenhagen Ø (DK); Kirk Schnorr, Copenhagen N. (DK); Lene Nonboe Andersen, Allerød (DK); Mads Eskelund Bjørnvad, Frederiksberg (DK)

(73) Assignee: Novozymes, A/S, Bagsvaerd (DK)

( * ) Notice: Subject to any disclaimer, the term of this patent is extended or adjusted under 35 U.S.C. 154(b) by 0 days.

(21) Appl. No.: 09/339,159

(22) Filed: Jun. 24, 1999

Related U.S. Application Data

(63) Continuation of application No. 09/111,256, filed on Jun. 10, 1998, now abandoned, and a continuation of application No. PCT/DK99/00314, filed on Jun. 10, 1998.
(60) Provisional application No. 60/123,641, filed on Mar. 10, 1999, provisional application No. 60/123,642, filed on Mar. 10, 1999, provisional application No. 60/123,623, filed on Mar. 10, 1999, provisional application No. 60/123,543, filed on Mar. 9, 1999, provisional application No. 60/105,970, filed on Oct. 28, 1998, and provisional application No. 60/106,054, filed on Oct. 28, 1998.

(30) Foreign Application Priority Data

| Oct. 20, 1998 | (DK) | 1998 01341 |
| Oct. 20, 1998 | (DK) | 1998 01340 |
| Dec. 23, 1998 | (DK) | 1998 01725 |
| Mar. 5, 1999 | (DK) | 1999 00307 |
| Mar. 5, 1999 | (DK) | 1999 00308 |
| Mar. 5, 1999 | (DK) | 1999 00309 |
| Mar. 5, 1999 | (DK) | 1999 00306 |

(51) Int. Cl.$^7$ ............ C12N 9/00; C12N 9/24; C12N 9/46
(52) U.S. Cl. ............ 435/211; 435/183; 435/200; 435/201; 435/202; 435/203; 435/204; 435/205; 435/206; 435/207; 435/208; 435/209; 435/210; 510/114
(58) Field of Search ............ 435/183, 200–211; 510/114, 392, 515

(56) References Cited

FOREIGN PATENT DOCUMENTS

| WO | WO 91/18974 | 12/1991 |
| WO | WO 94/25576 | 11/1994 |
| WO | WO 95/35362 | 12/1995 |
| WO | WO 97/11164 | 3/1997 |

OTHER PUBLICATIONS

Yoshida et al. PIR Database Accession No. JE0134, Jun. 3, 1998.*
Akino et al. PIR Database Accession No. A37219, Dec. 30, 1991.*
Talbot et al., Applied and Environmental Microbiology, vol. 56, pp. 3505–3510 (1990).
Mendoza et al., World Journal of Microbiology & Biotechnology, vol. 10, pp. 551–555.
Gibbs et al., Applied and Environmental Microbiology, vol. 58, No. 12, pp. 3864–3867 (1992).
Yosida et al., Biosci. Biotech. Biochem., vol. 61, No. 2, pp. 251–255 (1997).

* cited by examiner

*Primary Examiner*—Rebecca E. Prouty
*Assistant Examiner*—Manjunath N. Rao
(74) *Attorney, Agent, or Firm*—Elias J. Lambiris

(57) ABSTRACT

Novel mannanases comprising e.g. an amino acid sequence as shown in positions 31–330 of SEQ ID NO:2 or their homologues may be derived from e.g. Bacillus sp. I633, or may be encoded by polynucleotide molecules comprising a nucleotide sequence as shown in SEQ ID NO: 1 from nucleotide 91 to nucleotide 990, polynucleotide molecules that encode a polypeptide that is at least 65% identical to the amino acid sequence of SEQ ID NO: 2 from amino acid residue 31 to amino acid residue 330, or degenerate nucleotide sequences thereof. The mannanases are alkaline and are useful e.g. in cleaning compositions, in a fracturing fluid useful to fracture a subterranean formation, for modifying plant material, and for treatment of cellulosic fibers.

33 Claims, 3 Drawing Sheets

SEQUENCE LISTING

<160> NUMBER OF SEQ ID NOS: 55

<210> SEQ ID NO 1
<211> LENGTH: 1470
<212> TYPE: DNA
<213> ORGANISM: Bacillus sp. I633

<400> SEQUENCE: 1

| ttgaataatg gttttaaaaa aattttttct ataacattat cattactatt agctagctct | 60 |
|---|---|
| attctgttcg tttcaggaac ttctacagct aatgcaaatt ccggatttta tgtaagcggt | 120 |
| accactctat acgatgccaa tggaaaccca tttgtaatga gagggattaa ccatgggcac | 180 |
| gcatggtata aagaccaggc aactactgca attgaaggga ttgcaaatac cggtgctaat | 240 |
| acggtccgga ttgtgttatc tgatggggga caatggacaa aagatgacat ccatacagta | 300 |
| agaaaccttta tctctttagc ggaagataat catttggttg ctgttcttga agttcatgat | 360 |
| gctaccggtt atgattccat tgcttcgctc aatcgtgctg ttgattattg gattgaaatg | 420 |
| agaagtgctt taattggaaa ggaagatacc gtcattatta atattgcgaa tgaatggttt | 480 |
| ggttcgtggg aaggggatgc ttgggctgac gggtataaac aagcaatccc gcgattgcgt | 540 |
| aacgccggtc taaaccatac cttgatggta gatgctgcgg ggtggggaca atttccacaa | 600 |
| tcgattcatg attatggaag agaagttttt aatgctgacc ctcaacgaaa tacaatgttt | 660 |
| tcgattcata tgtatgaata tgcaggtggt aatgcatcgc aagttcgtac taatattgac | 720 |
| cgagttctta atcaagacct cgcattagtc attggtgaat tggacaccg tcatacaaat | 780 |
| ggtgacgtcg atgaagcaac gattatgagc tattctgaac aaagaggagt tgggtggttg | 840 |
| gcgtggtcat ggaaagggaa cggcccagaa tgggagtatt tagacctttc gaatgattgg | 900 |
| gctggaaata accttacagc ttggggaaat acaatagtga atggtccata tggtttaaga | 960 |
| gaaacttcga gattaagcac cgttttttaca ggtggaggat ctgatggagg aacttctccg | 1020 |
| acaactcttt atgattttga aggtagtatg caaggatgga ctggaagtag cttgagcgga | 1080 |
| ggtccttggg ctgtgacaga gtggtcttct aaaggaagtc attctttaaa agcggatatt | 1140 |
| caattgtcgt caaattcaca acattactta catgttattc aaaatacgtc tttacagcag | 1200 |
| aatagtagga tacaagctac tgttaaacat gcaaattggg gaagtgttgg taatggaatg | 1260 |
| actgcgcgtc tttatgtgaa aacaggacat ggttatacat ggtactctgg aagctttgtg | 1320 |
| ccgattaacg gttcatctgg aacaacgcta tctctagatt tatcaaatgt ccaaaatctt | 1380 |
| tctcaagtaa gggaaattgg agttcagttc caatcagcga gtgatagtag tggacaaaca | 1440 |
| tcgatttata ttgataatgt gattgtagaa | 1470 |

<210> SEQ ID NO 2
<211> LENGTH: 490
<212> TYPE: PRT
<213> ORGANISM: Bacillus

<400> SEQUENCE: 2

```
Leu Asn Asn Gly Phe Lys Lys Ile Phe Ser Ile Thr Leu Ser Leu Leu
1               5                   10                  15

Leu Ala Ser Ser Ile Leu Phe Val Ser Gly Thr Ser Thr Ala Asn Ala
            20                  25                  30

Asn Ser Gly Phe Tyr Val Ser Gly Thr Thr Leu Tyr Asp Ala Asn Gly
        35                  40                  45
```

```
Asn Pro Phe Val Met Arg Gly Ile Asn His Gly His Ala Trp Tyr Lys
 50                  55                  60

Asp Gln Ala Thr Thr Ala Ile Glu Gly Ile Ala Asn Thr Gly Ala Asn
 65                  70                  75                  80

Thr Val Arg Ile Val Leu Ser Asp Gly Gln Trp Thr Lys Asp Asp
                 85                  90                  95

Ile His Thr Val Arg Asn Leu Ile Ser Leu Ala Glu Asp Asn His Leu
                100                 105                 110

Val Ala Val Pro Glu Val His Asp Ala Thr Gly Tyr Asp Ser Ile Ala
                115                 120                 125

Ser Leu Asn Arg Ala Val Asp Tyr Trp Ile Glu Met Arg Ser Ala Leu
130                 135                 140

Ile Gly Lys Glu Asp Thr Val Ile Ile Asn Ile Ala Asn Glu Trp Phe
145                 150                 155                 160

Gly Ser Trp Glu Gly Asp Ala Trp Ala Asp Gly Tyr Lys Gln Ala Ile
                165                 170                 175

Pro Arg Leu Arg Asn Ala Gly Leu Asn His Thr Leu Met Val Asp Ala
                180                 185                 190

Ala Gly Trp Gly Gln Phe Pro Gln Ser Ile His Asp Tyr Gly Arg Glu
                195                 200                 205

Val Phe Asn Ala Asp Pro Gln Arg Asn Thr Met Phe Ser Ile His Met
                210                 215                 220

Tyr Glu Tyr Ala Gly Gly Asn Ala Ser Gln Val Arg Thr Asn Ile Asp
225                 230                 235                 240

Arg Val Leu Asn Gln Asp Leu Ala Leu Val Ile Gly Glu Phe Gly His
                245                 250                 255

Arg His Thr Asn Gly Asp Val Asp Glu Ala Thr Ile Met Ser Tyr Ser
                260                 265                 270

Glu Gln Arg Gly Val Gly Trp Leu Ala Trp Ser Trp Lys Gly Asn Gly
                275                 280                 285

Pro Glu Trp Glu Tyr Leu Asp Leu Ser Asn Asp Trp Ala Gly Asn Asn
                290                 295                 300

Leu Thr Ala Trp Gly Asn Thr Ile Val Asn Gly Pro Tyr Gly Leu Arg
305                 310                 315                 320

Glu Thr Ser Arg Leu Ser Thr Val Phe Thr Gly Gly Ser Asp Gly
                325                 330                 335

Gly Thr Ser Pro Thr Thr Leu Tyr Asp Phe Glu Gly Ser Met Gln Gly
                340                 345                 350

Trp Thr Gly Ser Ser Leu Ser Gly Gly Pro Trp Ala Val Thr Glu Trp
                355                 360                 365

Ser Ser Lys Gly Ser His Ser Leu Lys Ala Asp Ile Gln Leu Ser Ser
370                 375                 380

Asn Ser Gln His Tyr Leu His Val Ile Gln Asn Thr Ser Leu Gln Gln
385                 390                 395                 400

Asn Ser Arg Ile Gln Ala Thr Val Lys His Ala Asn Trp Gly Ser Val
                405                 410                 415

Gly Asn Gly Met Thr Ala Arg Leu Tyr Val Lys Thr Gly His Gly Tyr
                420                 425                 430

Thr Trp Tyr Ser Gly Ser Phe Val Pro Ile Asn Gly Ser Ser Gly Thr
                435                 440                 445

Thr Leu Ser Leu Asp Leu Ser Asn Val Gln Asn Leu Ser Gln Val Arg
450                 455                 460

Glu Ile Gly Val Gln Phe Gln Ser Ala Ser Asp Ser Ser Gly Gln Thr
```

|     | 465 |     |     | 470 |     |     | 475 |     |     | 480 |     |
| --- | --- | --- | --- | --- | --- | --- | --- | --- | --- | --- | --- |
| Ser | Ile | Tyr | Ile | Asp | Asn | Val | Ile | Val | Glu |     |     |
|     |     |     |     | 485 |     |     |     |     | 490 |     |     |

<210> SEQ ID NO 3
<211> LENGTH: 1438
<212> TYPE: DNA
<213> ORGANISM: Bacillus sp. I633

<400> SEQUENCE: 3

```
gcaaattccg gattttatgt aagcggtacc actctatacg atgccaatgg aaacccattt      60
gtaatgagag ggattaacca tgggcacgca tggtataaag accaggcaac tactgcaatt     120
gaagggattg caaataccgg tgctaatacg gtccggattg tgttatctga tgggggacaa     180
tggacaaaag atgacatcca tacagtaaga aaccttatct ctttagcgga agataatcat     240
ttggttgctg ttcctgaagt tcatgatgct accggttatg attccattgc ttcgctcaat     300
cgtgctgttg attattggat tgaaatgaga agtgctttaa ttggaaagga agataccgtc     360
attattaata ttgcgaatga atggtttggt tcgtgggaag gggatgcttg ggctgacggg     420
tataaacaag caatcccgcg attgcgtaac gccggtctaa accataccct tgatggtagat   480
gctgcggggt ggggacaatt tccacaatcg attcatgatt atgaagaga agtttttaat     540
gctgacccte aacgaaatac aatgttttcg attcatatgt atgaatatgc aggtggtaat     600
gcatcgcaag ttcgtactaa tattgaccga gttcttaatc aagacctcgc attagtcatt     660
ggtgaatttg acaccgtca tacaaatggt gacgtcgatg aagcaacgat tatgagctat     720
tctgaacaaa gaggagttgg gtggttggcg tggtcatgga agggaacggg cccagaatgg     780
gagtatttag acctttcgaa tgattgggct ggaaataacc ttacagcttg gggaaataca     840
atagtgaatg gtccatatgg tttaagagaa acttcgagat taagcaccgt ttttacagct     900
agcccggaac caacaccaga gccgaccgca aatacaccgg tatcaggcaa tttgaaggtt     960
gaattctaca cagcaatcc ttcagatact actaactcaa tcaatcctca gttcaaggtt    1020
actaataccg gaagcagtgc aattgatttg tccaaactca cattgagata ttattataca    1080
gtagacggac agaaagatca gaccttctgg tgtgaccatg ctgcaataat cggcagtaac    1140
ggcagctaca acggaattac ttcaaatgta aaaggaacat ttgtaaaaat gagttcctca    1200
acaaataacg cagacaccta ccttgaaata agctttacag gcggaactct tgaaccgggt    1260
gcacatgttc agatacaagg tagatttgca agaatgact ggagtaacta tacacagtca    1320
aatgactact cattcaagtc tcgttcacag tttgttgaat gggatcaggt aacagcatac    1380
ttgaacggtg ttcttgtatg gggtaaagaa cccggtggca gtgtagtata gcggccgc    1438
```

<210> SEQ ID NO 4
<211> LENGTH: 476
<212> TYPE: PRT
<213> ORGANISM: Bacillus

<400> SEQUENCE: 4

| Ala | Asn | Ser | Gly | Phe | Tyr | Val | Ser | Gly | Thr | Thr | Leu | Tyr | Asp | Ala | Asn |
| --- | --- | --- | --- | --- | --- | --- | --- | --- | --- | --- | --- | --- | --- | --- | --- |
| 1   |     |     |     | 5   |     |     |     |     | 10  |     |     |     |     | 15  |     |

| Gly | Asn | Pro | Phe | Val | Met | Arg | Gly | Ile | Asn | His | Gly | His | Ala | Trp | Tyr |
| --- | --- | --- | --- | --- | --- | --- | --- | --- | --- | --- | --- | --- | --- | --- | --- |
|     |     |     | 20  |     |     |     |     | 25  |     |     |     |     | 30  |     |     |

| Lys | Asp | Gln | Ala | Thr | Thr | Ala | Ile | Glu | Gly | Ile | Ala | Asn | Thr | Gly | Ala |
| --- | --- | --- | --- | --- | --- | --- | --- | --- | --- | --- | --- | --- | --- | --- | --- |
|     |     |     | 35  |     |     |     |     | 40  |     |     |     |     | 45  |     |     |

| Asn | Thr | Val | Arg | Ile | Val | Leu | Ser | Asp | Gly | Gly | Gln | Trp | Thr | Lys | Asp |
| --- | --- | --- | --- | --- | --- | --- | --- | --- | --- | --- | --- | --- | --- | --- | --- |

-continued

```
            50                  55                  60
Asp Ile His Thr Val Arg Asn Leu Ile Ser Leu Ala Glu Asp Asn His
 65                  70                  75                  80

Leu Val Ala Val Pro Glu Val His Asp Ala Thr Gly Tyr Asp Ser Ile
                 85                  90                  95

Ala Ser Leu Asn Arg Ala Val Asp Tyr Trp Ile Glu Met Arg Ser Ala
            100                 105                 110

Leu Ile Gly Lys Glu Asp Thr Val Ile Ile Asn Ile Ala Asn Glu Trp
            115                 120                 125

Phe Gly Ser Trp Glu Gly Asp Ala Trp Ala Asp Gly Tyr Lys Gln Ala
130                 135                 140

Ile Pro Arg Leu Arg Asn Ala Gly Leu Asn His Thr Leu Met Val Asp
145                 150                 155                 160

Ala Ala Gly Trp Gly Gln Phe Pro Gln Ser Ile His Asp Tyr Gly Arg
                165                 170                 175

Glu Val Phe Asn Ala Asp Pro Gln Arg Asn Thr Met Phe Ser Ile His
                180                 185                 190

Met Tyr Glu Tyr Ala Gly Gly Asn Ala Ser Gln Val Arg Thr Asn Ile
                195                 200                 205

Asp Arg Val Leu Asn Gln Asp Leu Ala Leu Val Ile Gly Glu Phe Gly
                210                 215                 220

His Arg His Thr Asn Gly Asp Val Asp Glu Ala Thr Ile Met Ser Tyr
225                 230                 235                 240

Ser Glu Gln Arg Gly Val Gly Trp Leu Ala Trp Ser Trp Lys Gly Asn
                245                 250                 255

Gly Pro Glu Trp Glu Tyr Leu Asp Leu Ser Asn Asp Trp Ala Gly Asn
                260                 265                 270

Asn Leu Thr Ala Trp Gly Asn Thr Ile Val Asn Gly Pro Tyr Gly Leu
                275                 280                 285

Arg Glu Thr Ser Arg Leu Ser Thr Val Phe Thr Ala Ser Pro Glu Pro
                290                 295                 300

Thr Pro Glu Pro Thr Ala Asn Thr Pro Val Ser Gly Asn Leu Lys Val
305                 310                 315                 320

Glu Phe Tyr Asn Ser Asn Pro Ser Asp Thr Thr Asn Ser Ile Asn Pro
                325                 330                 335

Gln Phe Lys Val Thr Asn Thr Gly Ser Ser Ala Ile Asp Leu Ser Lys
                340                 345                 350

Leu Thr Leu Arg Tyr Tyr Tyr Thr Val Asp Gly Gln Lys Asp Gln Thr
                355                 360                 365

Phe Trp Cys Asp His Ala Ala Ile Ile Gly Ser Asn Gly Ser Tyr Asn
                370                 375                 380

Gly Ile Thr Ser Asn Val Lys Gly Thr Phe Val Lys Met Ser Ser Ser
385                 390                 395                 400

Thr Asn Asn Ala Asp Thr Tyr Leu Glu Ile Ser Phe Thr Gly Gly Thr
                405                 410                 415

Leu Glu Pro Gly Ala His Val Gln Ile Gln Gly Arg Phe Ala Lys Asn
                420                 425                 430

Asp Trp Ser Asn Tyr Thr Gln Ser Asn Asp Tyr Ser Phe Lys Ser Arg
                435                 440                 445

Ser Gln Phe Val Glu Trp Asp Gln Val Thr Ala Tyr Leu Asn Gly Val
                450                 455                 460

Leu Val Trp Gly Lys Glu Pro Gly Gly Ser Val Val
465                 470                 475
```

-continued

<210> SEQ ID NO 5
<211> LENGTH: 1482
<212> TYPE: DNA
<213> ORGANISM: Bacillus agaradhaerens

<400> SEQUENCE: 5

```
atgaaaaaaa agttatcaca gatttatcat ttaattattt gcacacttat ataagtgtg       60
ggaataatgg ggattacaac gtccccatca gcagcaagta caggcttta tgttgatggc      120
aatacgttat atgacgcaaa tgggcagcca tttgtcatga gaggtattaa ccatggacat     180
gcttggtata agacaccgc ttcaacagct attcctgcca ttgcagagca aggcgccaac      240
acgattcgta ttgttttatc agatggcggt caatgggaaa aagacgacat tgacaccatt     300
cgtgaagtca ttgagcttgc ggagcaaaat aaaatggtgg ctgtcgttga agttcatgat     360
gccacgggtc gcgattcgcg cagtgattta aatcgagccg ttgattattg atagaaatg     420
aaagatgcgc ttatcggtaa agaagatacg gttattatta acattgcaaa cgagtggtat     480
gggagttggg atggctcagc ttgggccgat ggctatattg atgtcattcc gaagcttcgc    540
gatgccggct taacacacac cttaatggtt gatgcagcag gatgggggca atatccgcaa    600
tctattcatg attacggaca agatgtgttt aatgcagatc cgttaaaaaa tacgatgttc    660
tccatccata tgtatgagta tgctggtggt gatgctaaca ctgttagatc aaatattgat    720
agagtcatag atcaagacct tgctctcgta ataggtgaat tcggtcatag acatactgat    780
ggtgatgttg atgaagatac aatccttagt tattctgaag aaactggcac agggtggctc    840
gcttggtctt ggaaaggcaa cagtaccgaa tgggactatt tagaccttc agaagactgg    900
gctggtcaac atttaactga ttgggggaat agaattgtcc acggggccga tggcttacag    960
gaaacctcca aaccatccac cgtatttaca tgatgataacg gtggtcaccc tgaaccgcca  1020
actgctacta ccttgtatga ctttgaagga agcacacaag ggtggcatgg aagcaacgtg   1080
accggtggcc cttggtccgt aacagaatgg ggtgcttcag gtaactactc tttaaaagcc   1140
gatgtaaatt taacctcaaa ttcttcacat gaactgtata gtgaacaaag tcgtaatcta  1200
cacggatact ctcagctcaa cgcaaccgtt cgccatgcca attggggaaa tcccggtaat  1260
ggcatgaatg caagactta cgtgaaaacg ggctctgatt atacatggca tagcggtcct  1320
tttacacgta tcaatagctc caactcagga acaacgttat cttttgattt aaacaacatc  1380
gaaaatagtc atcatgttag ggaaataggc gtgcaatttt cagcggcaga taatagcagt  1440
ggtcaaactg ctctatacgt tgataacgtt actttaagat ag                      1482
```

<210> SEQ ID NO 6
<211> LENGTH: 493
<212> TYPE: PRT
<213> ORGANISM: Bacillus

<400> SEQUENCE: 6

```
Met Lys Lys Leu Ser Gln Ile Tyr His Leu Ile Ile Cys Thr Leu
1               5                   10                  15

Ile Ile Ser Val Gly Ile Met Gly Ile Thr Thr Ser Pro Ser Ala Ala
            20                  25                  30

Ser Thr Gly Phe Tyr Val Asp Gly Asn Thr Leu Tyr Asp Ala Asn Gly
        35                  40                  45

Gln Pro Phe Val Met Arg Gly Ile Asn His Gly His Ala Trp Tyr Lys
    50                  55                  60
```

-continued

```
Asp Thr Ala Ser Thr Ala Ile Pro Ala Ile Ala Glu Gln Gly Ala Asn
 65                  70                  75                  80

Thr Ile Arg Ile Val Leu Ser Asp Gly Gly Gln Trp Glu Lys Asp Asp
                 85                  90                  95

Ile Asp Thr Ile Arg Glu Val Ile Glu Leu Ala Glu Gln Asn Lys Met
            100                 105                 110

Val Ala Val Val Glu Val His Asp Ala Thr Gly Arg Asp Ser Arg Ser
            115                 120                 125

Asp Leu Asn Arg Ala Val Asp Tyr Trp Ile Glu Met Lys Asp Ala Leu
130                 135                 140

Ile Gly Lys Glu Asp Thr Val Ile Ile Asn Ile Ala Asn Glu Trp Tyr
145                 150                 155                 160

Gly Ser Trp Asp Gly Ser Ala Trp Ala Asp Gly Tyr Ile Asp Val Ile
                165                 170                 175

Pro Lys Leu Arg Asp Ala Gly Leu Thr His Thr Leu Met Val Asp Ala
            180                 185                 190

Ala Gly Trp Gly Gln Tyr Pro Gln Ser Ile His Asp Tyr Gly Gln Asp
            195                 200                 205

Val Phe Asn Ala Asp Pro Leu Lys Asn Thr Met Phe Ser Ile His Met
210                 215                 220

Tyr Glu Tyr Ala Gly Gly Asp Ala Asn Thr Val Arg Ser Asn Ile Asp
225                 230                 235                 240

Arg Val Ile Asp Gln Asp Leu Ala Leu Val Ile Gly Glu Phe Gly His
                245                 250                 255

Arg His Thr Asp Gly Asp Val Asp Glu Asp Thr Ile Leu Ser Tyr Ser
            260                 265                 270

Glu Glu Thr Gly Thr Gly Trp Leu Ala Trp Ser Trp Lys Gly Asn Ser
            275                 280                 285

Thr Glu Trp Asp Tyr Leu Asp Leu Ser Glu Asp Trp Ala Gly Gln His
            290                 295                 300

Leu Thr Asp Trp Gly Asn Arg Ile Val His Gly Ala Asp Gly Leu Gln
305                 310                 315                 320

Glu Thr Ser Lys Pro Ser Thr Val Phe Thr Asp Asn Gly Gly His
                325                 330                 335

Pro Glu Pro Pro Thr Ala Thr Thr Leu Tyr Asp Phe Glu Gly Ser Thr
            340                 345                 350

Gln Gly Trp His Gly Ser Asn Val Thr Gly Gly Pro Trp Ser Val Thr
            355                 360                 365

Glu Trp Gly Ala Ser Gly Asn Tyr Ser Leu Lys Ala Asp Val Asn Leu
            370                 375                 380

Thr Ser Asn Ser Ser His Glu Leu Tyr Ser Glu Gln Ser Arg Asn Leu
385                 390                 395                 400

His Gly Tyr Ser Gln Leu Asn Ala Thr Val Arg His Ala Asn Trp Gly
                405                 410                 415

Asn Pro Gly Asn Gly Met Asn Ala Arg Leu Tyr Val Lys Thr Gly Ser
            420                 425                 430

Asp Tyr Thr Trp His Ser Gly Pro Phe Thr Arg Ile Asn Ser Ser Asn
            435                 440                 445

Ser Gly Thr Thr Leu Ser Phe Asp Leu Asn Asn Ile Glu Asn Ser His
            450                 455                 460

His Val Arg Glu Ile Gly Val Gln Phe Ser Ala Ala Asp Asn Ser Ser
465                 470                 475                 480

Gly Gln Thr Ala Leu Tyr Val Asp Asn Val Thr Leu Arg
```

<210> SEQ ID NO 7
<211> LENGTH: 1407
<212> TYPE: DNA
<213> ORGANISM: Bacillus agaradhaerens

<400> SEQUENCE: 7

```
atgaaaaaaa agttatcaca gatttatcat ttaattattt gcacacttat aataagtgtg      60
ggaataatgg ggattacaac gtccccatca gcagcaagta caggcttta tgttgatggc     120
aatacgttat atgacgcaaa tgggcagcca tttgtcatga gaggtattaa ccatggacat     180
gcttggtata agacaccgc ttcaacagct attcctgcca ttgcagagca aggcgccaac     240
acgattcgta ttgttttatc agatggcggt caatgggaaa agacgacat tgacaccatt     300
cgtgaagtca ttgagcttgc ggagcaaaat aaaatggtgg ctgtcgttga agttcatgat     360
gccacgggtc gcgattcgcg cagtgattta atcgagccg ttgattattg gatagaaatg     420
aaagatgcgc ttatcggtaa agaagatacg gttattatta acattgcaaa cgagtggtat     480
gggagttggg atggctcagc ttgggccgat ggctatattg atgtcattcc gaagcttcgc     540
gatgccggct taacacacac cttaatggtt gatgcagcag gatggggca atatccgcaa     600
tctattcatg attacggaca agatgtgttt aatgcagatc cgttaaaaaa tacgatgttc     660
tccatccata tgtatgagta tgctggtggt gatgctaaca ctgttagatc aaatattgat     720
agagtcatag atcaagacct tgctctcgta ataggtgaat tcggtcatag acatactgat     780
ggtgatgttg atgaagatac aatccttagt tattctgaag aaactggcac agggtggctc     840
gcttggtctt ggaaaggcaa cagtaccgaa tgggactatt tagacctttc agaagactgg     900
gctggtcaac atttaactga ttgggggaat agaattgtcc acggggccga tggcttacag     960
gaaacctcca aaccatccac cgtatttaca gatgataacg tggtcaccc tgaaccgcca    1020
actgctacta ccttgtatga ctttgaagga agcacacaag ggtggcatgg aagcaacgtg    1080
accggtggcc cttggtccgt aacagaatgg ggtgcttcag gtaactactc tttaaaagcc    1140
gatgtaaatt taacctcaaa ttcttcacat gaactgtata gtgaacaaag tcgtaatcta    1200
cacggatact ctcagctcaa cgcaaccgtt cgccatgcca attggggaaa tcccggtaat    1260
ggcatgaatg caagactta cgtgaaaacg ggctctgatt atacatggca tagcggtcct    1320
tttacacgta tcaatagctc caactcagga acaacgttat cttttgattt aaacaacatc    1380
gaaaatatca tcatgttagg gaaatag                                        1407
```

<210> SEQ ID NO 8
<211> LENGTH: 468
<212> TYPE: PRT
<213> ORGANISM: Bacillus agaradhaerens

<400> SEQUENCE: 8

Met Lys Lys Lys Leu Ser Gln Ile Tyr His Leu Ile Ile Cys Thr Leu
1               5                   10                  15

Ile Ile Ser Val Gly Ile Met Gly Ile Thr Thr Ser Pro Ser Ala Ala
            20                  25                  30

Ser Thr Gly Phe Tyr Val Asp Gly Asn Thr Leu Tyr Asp Ala Asn Gly
        35                  40                  45

Gln Pro Phe Val Met Arg Gly Ile Asn His Gly His Ala Trp Tyr Lys
    50                  55                  60

Asp Thr Ala Ser Thr Ala Ile Pro Ala Ile Ala Glu Gln Gly Ala Asn

```
                65                  70                  75                  80
Thr Ile Arg Ile Val Leu Ser Asp Gly Gly Gln Trp Glu Lys Asp Asp
                        85                  90                  95
Ile Asp Thr Ile Arg Glu Val Ile Glu Leu Ala Glu Gln Asn Lys Met
                100                 105                 110
Val Ala Val Val Glu Val His Asp Ala Thr Gly Arg Asp Ser Arg Ser
            115                 120                 125
Asp Leu Asn Arg Ala Val Asp Tyr Trp Ile Glu Met Lys Asp Ala Leu
        130                 135                 140
Ile Gly Lys Glu Asp Thr Val Ile Ile Asn Ile Ala Asn Glu Trp Tyr
145                 150                 155                 160
Gly Ser Trp Asp Gly Ser Ala Trp Ala Asp Gly Tyr Ile Asp Val Ile
                165                 170                 175
Pro Lys Leu Arg Asp Ala Gly Leu Thr His Thr Leu Met Val Asp Ala
                180                 185                 190
Ala Gly Trp Gly Gln Tyr Pro Gln Ser Ile His Asp Tyr Gly Gln Asp
            195                 200                 205
Val Phe Asn Ala Asp Pro Leu Lys Asn Thr Met Phe Ser Ile His Met
        210                 215                 220
Tyr Glu Tyr Ala Gly Gly Asp Ala Asn Thr Val Arg Ser Asn Ile Asp
225                 230                 235                 240
Arg Val Ile Asp Gln Asp Leu Ala Leu Val Ile Gly Glu Phe Gly His
                245                 250                 255
Arg His Thr Asp Gly Asp Val Asp Glu Asp Thr Ile Leu Ser Tyr Ser
                260                 265                 270
Glu Glu Thr Gly Thr Gly Trp Leu Ala Trp Ser Trp Lys Gly Asn Ser
            275                 280                 285
Thr Glu Trp Asp Tyr Leu Asp Leu Ser Glu Asp Trp Ala Gly Gln His
        290                 295                 300
Leu Thr Asp Trp Gly Asn Arg Ile Val His Gly Ala Asp Gly Leu Gln
305                 310                 315                 320
Glu Thr Ser Lys Pro Ser Thr Val Phe Thr Asp Asn Gly Gly His
                325                 330                 335
Pro Glu Pro Pro Thr Ala Thr Thr Leu Tyr Asp Phe Glu Gly Ser Thr
            340                 345                 350
Gln Gly Trp His Gly Ser Asn Val Thr Gly Gly Pro Trp Ser Val Thr
        355                 360                 365
Glu Trp Gly Ala Ser Gly Asn Tyr Ser Leu Lys Ala Asp Val Asn Leu
370                 375                 380
Thr Ser Asn Ser Ser His Glu Leu Tyr Ser Glu Gln Ser Arg Asn Leu
385                 390                 395                 400
His Gly Tyr Ser Gln Leu Asn Ala Thr Val Arg His Ala Asn Trp Gly
                405                 410                 415
Asn Pro Gly Asn Gly Met Asn Ala Arg Leu Tyr Val Lys Thr Gly Ser
            420                 425                 430
Asp Tyr Thr Trp His Ser Gly Pro Phe Thr Arg Ile Asn Ser Ser Asn
        435                 440                 445
Ser Gly Thr Thr Leu Ser Phe Asp Leu Asn Asn Ile Glu Asn Ile Ile
    450                 455                 460
Met Leu Gly Lys
465

<210> SEQ ID NO 9
```

<211> LENGTH: 1761
<212> TYPE: DNA
<213> ORGANISM: Bacillus halodurans

<400> SEQUENCE: 9

```
atgaaaagta taaagaaatt ggtagtcgtt tgcatggcat ttctattaat ttttccatcg      60
acgtcatttg cttttctgg  aagcgtttca gcttcaggtc aagagcttaa aatgacagat     120
caaaacgcat ctcaatatac aaaagagttg tttgccttt  tacgtgatgt aagtggtaaa    180
caagttttat ttggtcaaca acacgcaact gatgagggat aacacttag  aggaacaggt    240
aaccgaattg gttcaacaga atcagaagtg aaaaatgctg ttggtgatta tcctgctgtt    300
tttggttggg atacaaacag tctagatggt agagaaaagc ccggtaatga tgaaccgagt    360
caagaacaaa gaatcttaaa tacagcagct tcaatgaagg cagctcacga cttaggtggg    420
attatcacac taagtatgca tcctgataac tttgtaacag gaggggctta tggcgataca    480
actggaaatg ttgtacaaga aattcttcct ggtggatcaa agcatgaaga attcaatgca    540
tggttggata acctagcggc tttagctcac gaattaaagg atgacaacgg gaaacacatt    600
ccaattattt tccgtccttt ccatgagcaa acaggttctt ggttctggtg gggagcaagc    660
acaacaactc cagaacagta taagctatt  tacagatata cggttgaata cttacgtgac    720
gtaaaaggag caaacaactt cttatacggt ttttctcctg gtgcaggtcc agctggcgat    780
ttaaatcgtt atatggaaac ttaccctggt gatgattatg tcgatatctt tggtattgat    840
aactatgaca taaatcaaa  tgctggatca gaagcttgga tacaaggtgt tgtaaccgat    900
ttagctatgc ttgttgattt agctgaagaa aaaggaaaga ttgctgcgtt taccgagtat    960
ggttacagtg caacaggtat gaatcgtact ggtaacacat tggattggta tactcgttta   1020
cttaatgcaa taaagaaga  tccaaaagca agtaagattt cttacatgct tacatgggca   1080
aactttggtt tccctaacaa tatgtatgtt ccttacaaag acattcacgg tgatttaggt   1140
ggagatcatg aactccttcc agatttcatc aaatttttg  aagatgatta ctcagctttc   1200
acaggagata tcaagggaaa tgtgtatgat acaggaatta aatatactgt agcaccacat   1260
gaacgtttaa tgtatgtgct ttcgcctatt actggaacaa cgataacaga tactgttaca   1320
ttacgagcta agtattaaa  cgatgataac gcagttgtta cgtacagggt tgaaggttct   1380
gacgttgaac atgaaatgac gttagctgac tcgggatact acacagctaa gtattctccg   1440
acggcagaag taaatggtgg atcagttgat ttaacagtta cgtactggtc tggagaagaa   1500
aaagtacaag atgaagtgat tagactttat gtaaaggctt cagaaatctc actttacaag   1560
cttacgtttg atgaggatat taatggaatt aagtcgaatg gcacttggcc tgaagatggt   1620
attacatctg acgtttctca tgtcagtttt gacggaaatg ggaaattgaa gtttgcagtt   1680
aatggaatgt catccgaaga gtggtggcaa gaacttaaat tagaattaac agatctttct   1740
gatgtgaatt tagccaagta a                                              1761
```

<210> SEQ ID NO 10
<211> LENGTH: 586
<212> TYPE: PRT
<213> ORGANISM: Bacillus halodurans

<400> SEQUENCE: 10

Met Lys Ser Ile Lys Lys Leu Val Val Cys Met Ala Phe Leu Leu
1               5                   10                  15

Ile Phe Pro Ser Thr Ser Phe Ala Phe Ser Gly Ser Val Ser Ala Ser
                20                  25                  30

-continued

```
Gly Gln Glu Leu Lys Met Thr Asp Gln Asn Ala Ser Gln Tyr Thr Lys
             35                  40                  45
Glu Leu Phe Ala Phe Leu Arg Asp Val Ser Gly Lys Gln Val Leu Phe
         50                  55                  60
Gly Gln Gln His Ala Thr Asp Glu Gly Leu Thr Leu Arg Gly Thr Gly
 65                  70                  75                  80
Asn Arg Ile Gly Ser Thr Glu Ser Glu Val Lys Asn Ala Val Gly Asp
                 85                  90                  95
Tyr Pro Ala Val Phe Gly Trp Asp Thr Asn Ser Leu Asp Gly Arg Glu
                100                 105                 110
Lys Pro Gly Asn Asp Glu Pro Ser Gln Glu Gln Arg Ile Leu Asn Thr
            115                 120                 125
Ala Ala Ser Met Lys Ala Ala His Asp Leu Gly Gly Ile Ile Thr Leu
130                 135                 140
Ser Met His Pro Asp Asn Phe Val Thr Gly Gly Ala Tyr Gly Asp Thr
145                 150                 155                 160
Thr Gly Asn Val Val Gln Glu Ile Leu Pro Gly Gly Ser Lys His Glu
                165                 170                 175
Glu Phe Asn Ala Trp Leu Asp Asn Leu Ala Ala Leu Ala His Glu Leu
            180                 185                 190
Lys Asp Asp Asn Gly Lys His Ile Pro Ile Ile Phe Arg Pro Phe His
        195                 200                 205
Glu Gln Thr Gly Ser Trp Phe Trp Trp Gly Ala Ser Thr Thr Thr Pro
    210                 215                 220
Glu Gln Tyr Lys Ala Ile Tyr Arg Tyr Thr Val Glu Tyr Leu Arg Asp
225                 230                 235                 240
Val Lys Gly Ala Asn Asn Phe Leu Tyr Gly Phe Ser Pro Gly Ala Gly
                245                 250                 255
Pro Ala Gly Asp Leu Asn Arg Tyr Met Glu Thr Tyr Pro Gly Asp Asp
            260                 265                 270
Tyr Val Asp Ile Phe Gly Ile Asp Asn Tyr Asp Asn Lys Ser Asn Ala
        275                 280                 285
Gly Ser Glu Ala Trp Ile Gln Gly Val Val Thr Asp Leu Ala Met Leu
    290                 295                 300
Val Asp Leu Ala Glu Glu Lys Gly Lys Ile Ala Ala Phe Thr Glu Tyr
305                 310                 315                 320
Gly Tyr Ser Ala Thr Gly Met Asn Arg Thr Gly Asn Thr Leu Asp Trp
                325                 330                 335
Tyr Thr Arg Leu Leu Asn Ala Ile Lys Glu Asp Pro Lys Ala Ser Lys
            340                 345                 350
Ile Ser Tyr Met Leu Thr Trp Ala Asn Phe Gly Phe Pro Asn Asn Met
        355                 360                 365
Tyr Val Pro Tyr Lys Asp Ile His Gly Asp Leu Gly Gly Asp His Glu
    370                 375                 380
Leu Leu Pro Asp Phe Ile Lys Phe Phe Glu Asp Tyr Ser Ala Phe
385                 390                 395                 400
Thr Gly Asp Ile Lys Gly Asn Val Tyr Asp Thr Gly Ile Glu Tyr Thr
                405                 410                 415
Val Ala Pro His Glu Arg Leu Met Tyr Val Leu Ser Pro Ile Thr Gly
            420                 425                 430
Thr Thr Ile Thr Asp Thr Val Thr Leu Arg Ala Lys Val Leu Asn Asp
        435                 440                 445
```

```
Asp Asn Ala Val Val Thr Tyr Arg Val Glu Gly Ser Asp Val Glu His
    450                 455                 460

Glu Met Thr Leu Ala Asp Ser Gly Tyr Tyr Thr Ala Lys Tyr Ser Pro
465                 470                 475                 480

Thr Ala Glu Val Asn Gly Gly Ser Val Asp Leu Thr Val Thr Tyr Trp
                485                 490                 495

Ser Gly Glu Glu Lys Val Gln Asp Glu Val Ile Arg Leu Tyr Val Lys
                500                 505                 510

Ala Ser Glu Ile Ser Leu Tyr Lys Leu Thr Phe Asp Glu Asp Ile Asn
            515                 520                 525

Gly Ile Lys Ser Asn Gly Thr Trp Pro Glu Asp Gly Ile Thr Ser Asp
            530                 535                 540

Val Ser His Val Ser Phe Asp Gly Asn Gly Lys Leu Lys Phe Ala Val
545                 550                 555                 560

Asn Gly Met Ser Ser Glu Glu Trp Trp Gln Glu Leu Lys Leu Glu Leu
                565                 570                 575

Thr Asp Leu Ser Asp Val Asn Leu Ala Lys
                580                 585
```

<210> SEQ ID NO 11
<211> LENGTH: 995
<212> TYPE: DNA
<213> ORGANISM: Bacillus sp. AAI12

<400> SEQUENCE: 11

```
gtgtataagc ttacccatac gtattttgtt gcgttaattt gttctatttt gatctttgct      60
ggggttttaa atacttcttc ttcacaagca gaagcccatc acagtgggtt ccatgttaat     120
ggtacaacat tatatgatgc aaatggaaac ccttttgtta tgagagggat taatcatgga     180
catgcttggt ttaaacaaga actagaaaca tccatgagag ggattagtca acaggggca     240
aatacgattc gtgtcgtttt gtctaatggg caaagatggc aaaaagatga tcgaaacatg     300
gtagcttcgg ttatttcttt ggcagagcag catcaaatga ttgccgtttt agaagttcat     360
gatgctactg gtagcaataa tttctccgat ctgcaagctg ctgtggacta ttggattgag     420
atgaaggat ttttgcaggg gaaagaggac atagtgatca ttaatatcgc aatgaatgg      480
tacggtgctt gggacggagg cgcatgggca cgagggtatc agaatgcgat acgtcagctt     540
cgaaatgcag gcttgtcaca tacatttatg gttgacgctg ccggttatgg ccagtaccct     600
caatcggtag ttgattatgg tcaagaagta ttaaatgctg accccagag aaacacaatg      660
ttttctgttc atatgtatga atatgcaggc ggagatgcta atacagtaag acgaaacatt     720
gactcgatct taagccagaa cttagctctt gtcattggtg aattcgggca ttggcattat     780
gacggtgatg ttgatgagga caccatttta agctattcac agcaaagaaa tgtgggatgg     840
ttggcgtgga gctggcatgg caatagtgaa ggggtcgaat atcttgattt atcgaatgac     900
tttgctggta atcgactgac atggtggggt gatcgaatag taaacggtcc gaatgggatt     960
cgtcaaacct ctaaaagaag cagtgtgttt caata                                995
```

<210> SEQ ID NO 12
<211> LENGTH: 331
<212> TYPE: PRT
<213> ORGANISM: Bacillus sp.AAI12

<400> SEQUENCE: 12

```
Val Tyr Lys Leu Thr His Thr Tyr Phe Val Ala Leu Ile Cys Ser Ile
1               5                   10                  15
```

-continued

```
Leu Ile Phe Ala Gly Val Leu Asn Thr Ser Ser Gln Ala Glu Ala
            20                  25                  30

His His Ser Gly Phe His Val Asn Gly Thr Thr Leu Tyr Asp Ala Asn
        35                  40                  45

Gly Asn Pro Phe Val Met Arg Gly Ile Asn His Gly His Ala Trp Phe
 50                  55                  60

Lys Gln Glu Leu Glu Thr Ser Met Arg Gly Ile Ser Gln Thr Gly Ala
 65                  70                  75                  80

Asn Thr Ile Arg Val Val Leu Ser Asn Gly Gln Arg Trp Gln Lys Asp
                85                  90                  95

Asp Arg Asn Met Val Ala Ser Val Ile Ser Leu Ala Glu Gln His Gln
            100                 105                 110

Met Ile Ala Val Leu Glu Val His Asp Ala Thr Gly Ser Asn Asn Phe
        115                 120                 125

Ser Asp Leu Gln Ala Ala Val Asp Tyr Trp Ile Glu Met Lys Asp Val
130                 135                 140

Leu Gln Gly Lys Glu Asp Ile Val Ile Ile Asn Ile Ala Asn Glu Trp
145                 150                 155                 160

Tyr Gly Ala Trp Asp Gly Gly Ala Trp Ala Arg Gly Tyr Gln Asn Ala
                165                 170                 175

Ile Arg Gln Leu Arg Asn Ala Gly Leu Ser His Thr Phe Met Val Asp
            180                 185                 190

Ala Ala Gly Tyr Gly Gln Tyr Pro Gln Ser Val Val Asp Tyr Gly Gln
        195                 200                 205

Glu Val Leu Asn Ala Asp Pro Gln Arg Asn Thr Met Phe Ser Val His
210                 215                 220

Met Tyr Glu Tyr Ala Gly Gly Asp Ala Asn Thr Val Arg Arg Asn Ile
225                 230                 235                 240

Asp Ser Ile Leu Ser Gln Asn Leu Ala Leu Val Ile Gly Glu Phe Gly
                245                 250                 255

His Trp His Tyr Asp Gly Asp Val Asp Glu Asp Thr Ile Leu Ser Tyr
            260                 265                 270

Ser Gln Gln Arg Asn Val Gly Trp Leu Ala Trp Ser Trp His Gly Asn
        275                 280                 285

Ser Glu Gly Val Glu Tyr Leu Asp Leu Ser Asn Asp Phe Ala Gly Asn
290                 295                 300

Arg Leu Thr Trp Trp Gly Asp Arg Ile Val Asn Gly Pro Asn Gly Ile
305                 310                 315                 320

Arg Gln Thr Ser Lys Arg Ser Ser Val Phe Gln
                325                 330
```

<210> SEQ ID NO 13
<211> LENGTH: 1464
<212> TYPE: DNA
<213> ORGANISM: Humicola insolens

<400> SEQUENCE: 13

| | | |
|---|---|---|
| atggcaaagg ctctgaagta ctttgcctgg ggccttgctg ccctggcctc gggcgctgtt | 60 |
| gccgctcctt actgtgctcc ccagccgtcg acaacctctc aggagcctac gagcactccg | 120 |
| tcgcctgtgc ccgtccgcg gaccttcgaa gcggaggatg ccatcctcac gggcacgagg | 180 |
| gttgagtcga gcctcgccgg ctactctggt accggatatg tagcgggctt cgacgagccc | 240 |
| agtgacaaga tcacgttcca cgtggacagc gagaccacac ggctgtacga cctcaccatc | 300 |

-continued

```
cgcgtggccg ccatctatgg cgagaagcgc accaccgtcg tgctcaataa cggcgcggca        360
agtgaggtct acttcccggc aggcgattcg ttcgtcgaca tcgctgccgg ccaggtcctg        420
ctgaaccagg gcgacaacac catcgacatt gtcaacaact ggggatggta cctgatcgac        480
tccatcacca tcacccccctc cgccccgcga ccccctcacc aaatcaaccc ttcccccgtc       540
aaccctgccg ccgacgacaa cgcgcgggcg ttgtacgcat acctccgctc catctacggc        600
aagaaaatcc tttccggcca gcaggagctt tcctgggcga actggatcgc caacagacg        660 ggcaaaactc ccgcgctggt gtccgtcgat atgatggatt attcccctag tcgggtggaa       720
agaggcactg tcgggtctgc cgtcgaggag gccatcgagc atcaccggcg cggcggcatt       780
gtctcggtgt tgtggcactg gaacgcgccc acggggctgt acgacacgcc cgagcgccgg       840
tggtggagcg ggttctacac ggacgcgacc gactttgacg tcgcgcgggc gctggcggat       900
acgacgaatg ccaactacac gctgctgatc cgggatatcg acgcgatcgc ggtgcagctc       960
aagaggttgc gggacgcggg cgtgccggtg ctttggcgcc cgctgcacga ggccgagggc      1020
ggttggtttt ggtggggagc gaagggcccg gaggcataca agaagctgtg ggggattctg      1080
tatgaccgac tcacgaacta ccatgggctg aataacctgc tgtgggtgtg gaactcgatc      1140
ctacccgagt ggtatcccgg agacgaaaca gtagacattg tcagcgcgga cgtgtacgcg      1200
cagggtaatg ggcccatgtc gacgcagtat aaccagctca tcgagctggg caaggacaag      1260
aagatgatcg cggcgactga ggtcggggcc gcgccgctgc cggacctgtt gcaggcctat      1320
gaggctcact ggttgtggtt cgctgtttgg ggagacacgt tcatcaacaa ccctcagtgg      1380
aactcgatcg agaccttgaa gacgatctac aatagcgact atgttctcac tctcgatgag      1440
attcaggggt ggaggaacgc gcaa                                              1464
```

<210> SEQ ID NO 14
<211> LENGTH: 488
<212> TYPE: PRT
<213> ORGANISM: Humicola insolens

<400> SEQUENCE: 14

```
Met Ala Lys Ala Leu Lys Tyr Phe Ala Trp Gly Leu Ala Ala Leu Ala
1               5                   10                  15

Ser Gly Ala Val Ala Ala Pro Tyr Cys Ala Pro Gln Pro Ser Thr Thr
            20                  25                  30

Ser Gln Glu Pro Thr Ser Thr Pro Ser Pro Val Pro Gly Pro Arg Thr
        35                  40                  45

Phe Glu Ala Glu Asp Ala Ile Leu Thr Gly Thr Arg Val Glu Ser Ser
    50                  55                  60

Leu Ala Gly Tyr Ser Gly Thr Gly Tyr Val Ala Gly Phe Asp Glu Pro
65                  70                  75                  80

Ser Asp Lys Ile Thr Phe His Val Asp Ser Glu Thr Thr Arg Leu Tyr
                85                  90                  95

Asp Leu Thr Ile Arg Val Ala Ala Ile Tyr Gly Glu Lys Arg Thr Thr
            100                 105                 110

Val Val Leu Asn Asn Gly Ala Ala Ser Glu Val Tyr Phe Pro Ala Gly
        115                 120                 125

Asp Ser Phe Val Asp Ile Ala Ala Gly Gln Val Leu Leu Asn Gln Gly
    130                 135                 140

Asp Asn Thr Ile Asp Ile Val Asn Asn Trp Gly Trp Tyr Leu Ile Asp
145                 150                 155                 160

Ser Ile Thr Ile Thr Pro Ser Ala Pro Arg Pro Pro His Gln Ile Asn
```

```
                165                 170                 175
Pro Ser Pro Val Asn Pro Ala Ala Asp Asp Asn Ala Arg Ala Leu Tyr
            180                 185                 190
Ala Tyr Leu Arg Ser Ile Tyr Gly Lys Lys Ile Leu Ser Gly Gln Gln
            195                 200                 205
Glu Leu Ser Trp Ala Asn Trp Ile Ala Gln Gln Thr Gly Lys Thr Pro
            210                 215                 220
Ala Leu Val Ser Val Asp Met Met Asp Tyr Ser Pro Ser Arg Val Glu
225                 230                 235                 240
Arg Gly Thr Val Gly Ser Ala Val Glu Glu Ala Ile Glu His His Arg
                245                 250                 255
Arg Gly Gly Ile Val Ser Val Leu Trp His Trp Asn Ala Pro Thr Gly
                260                 265                 270
Leu Tyr Asp Thr Pro Glu Arg Arg Trp Trp Ser Gly Phe Tyr Thr Asp
                275                 280                 285
Ala Thr Asp Phe Asp Val Ala Arg Ala Leu Ala Asp Thr Thr Asn Ala
                290                 295                 300
Asn Tyr Thr Leu Leu Ile Arg Asp Ile Asp Ala Ile Ala Val Gln Leu
305                 310                 315                 320
Lys Arg Leu Arg Asp Ala Gly Val Pro Val Leu Trp Arg Pro Leu His
                325                 330                 335
Glu Ala Glu Gly Gly Trp Phe Trp Trp Gly Ala Lys Gly Pro Glu Ala
                340                 345                 350
Tyr Lys Lys Leu Trp Gly Ile Leu Tyr Asp Arg Leu Thr Asn Tyr His
                355                 360                 365
Gly Leu Asn Asn Leu Leu Trp Val Trp Asn Ser Ile Leu Pro Glu Trp
            370                 375                 380
Tyr Pro Gly Asp Glu Thr Val Asp Ile Val Ser Ala Asp Val Tyr Ala
385                 390                 395                 400
Gln Gly Asn Gly Pro Met Ser Thr Gln Tyr Asn Gln Leu Ile Glu Leu
                405                 410                 415
Gly Lys Asp Lys Lys Met Ile Ala Ala Thr Glu Val Gly Ala Ala Pro
                420                 425                 430
Leu Pro Asp Leu Leu Gln Ala Tyr Glu Ala His Trp Leu Trp Phe Ala
                435                 440                 445
Val Trp Gly Asp Thr Phe Ile Asn Asn Pro Gln Trp Asn Ser Ile Glu
            450                 455                 460
Thr Leu Lys Thr Ile Tyr Asn Ser Asp Tyr Val Leu Thr Leu Asp Glu
465                 470                 475                 480
Ile Gln Gly Trp Arg Asn Ala Gln
                485

<210> SEQ ID NO 15
<211> LENGTH: 1107
<212> TYPE: DNA
<213> ORGANISM: Bacillus sp. AA349

<400> SEQUENCE: 15
atgagaagta tgaagctttt atttgctatg tttattttag ttttttcctc ttttactttt    60
aacttagtag ttgcgcaagc tagtggacat gggcaaatgc ataaagtacc ttgggcacca   120
caagctgaag cacctggaaa aacggctgaa aatggagtct gggataaagt tcgaaataat   180
cctggaaaag ccaatcctcc agcaggaaaa gtcaatggtt tttatataga tggaacaacc   240
ttatatgatg caaatggtaa gccatttgtg atgcgtggaa ttaaccacgg tcattcatgg   300
```

```
tacaagcctc acatagaaac cgcgatggag gcaattgctg atactggagc aaactccatt    360
cgtgtagttc tctcagatgg acaacagtgg accaaagatg atgttgacga agtagcaaaa    420
attatatctt tagcagaaaa acattcttta gttgctgctc ttgaggtaca tgatgcactc    480
ggaacagatg atattgaacc attacttaaa acagttgatt actggattga gatcaaagat    540
gctttaatcg gaaagagga caaagtaatt attaacattt ctaatgaatg gtttggttct    600
tggagcagtg aaggttgggc agatggatat aaaaaagcaa ttcctttact aagagaggcg    660
ggtctaaaac atacacttat ggttgacgca gctgggtggg acaatttcc tagatctat     720 catgaaaaag gattagaagt ttttaactca gacccattaa agaatacaat gttttccatt    780
catatgtatg aatgggcagc gggtaatcct caacaagtaa aagacaatat tgacggtgtt    840
cttgaaaaga atttagctgt agtaattggt gagttcggtc atcatcacta cggaagagat    900
gttgctgttg atacaatctt aagtcattct gagaagtatg atgtaggttg gcttgcttgg    960
tcttggcacg gaaatagtgg tggtgtagag tatcttgact tagcaacaga tttctcaggg   1020
acacaactaa ctgaatgggg agaaagaatt gtacacggtc cgaatggttt aaaagaaact   1080
tctgaaatcg ttagtgtata caaaaaa                                       1107
```

<210> SEQ ID NO 16
<211> LENGTH: 369
<212> TYPE: PRT
<213> ORGANISM: Bacillus sp.

<400> SEQUENCE: 16

```
Met Arg Ser Met Lys Leu Leu Phe Ala Met Phe Ile Leu Val Phe Ser
 1               5                  10                  15

Ser Phe Thr Phe Asn Leu Val Val Ala Gln Ala Ser Gly His Gly Gln
            20                  25                  30

Met His Lys Val Pro Trp Ala Pro Gln Ala Glu Ala Pro Gly Lys Thr
        35                  40                  45

Ala Glu Asn Gly Val Trp Asp Lys Val Arg Asn Asn Pro Gly Lys Ala
    50                  55                  60

Asn Pro Pro Ala Gly Lys Val Asn Gly Phe Tyr Ile Asp Gly Thr Thr
65                  70                  75                  80

Leu Tyr Asp Ala Asn Gly Lys Pro Phe Val Met Arg Gly Ile Asn His
                85                  90                  95

Gly His Ser Trp Tyr Lys Pro His Ile Glu Thr Ala Met Glu Ala Ile
            100                 105                 110

Ala Asp Thr Gly Ala Asn Ser Ile Arg Val Val Leu Ser Asp Gly Gln
        115                 120                 125

Gln Trp Thr Lys Asp Asp Val Asp Glu Val Ala Lys Ile Ile Ser Leu
    130                 135                 140

Ala Glu Lys His Ser Leu Val Ala Ala Leu Glu Val His Asp Ala Leu
145                 150                 155                 160

Gly Thr Asp Asp Ile Glu Pro Leu Leu Lys Thr Val Asp Tyr Trp Ile
                165                 170                 175

Glu Ile Lys Asp Ala Leu Ile Gly Lys Glu Asp Lys Val Ile Ile Asn
            180                 185                 190

Ile Ser Asn Glu Trp Phe Gly Ser Trp Ser Ser Glu Gly Trp Ala Asp
        195                 200                 205

Gly Tyr Lys Lys Ala Ile Pro Leu Leu Arg Glu Ala Gly Leu Lys His
    210                 215                 220
```

```
Thr Leu Met Val Asp Ala Ala Gly Trp Gly Gln Phe Pro Arg Ser Ile
225                 230                 235                 240

His Glu Lys Gly Leu Glu Val Phe Asn Ser Asp Pro Leu Lys Asn Thr
            245                 250                 255

Met Phe Ser Ile His Met Tyr Glu Trp Ala Ala Gly Asn Pro Gln Gln
                260                 265                 270

Val Lys Asp Asn Ile Asp Gly Val Leu Glu Lys Asn Leu Ala Val Val
            275                 280                 285

Ile Gly Glu Phe Gly His His His Tyr Gly Arg Asp Val Ala Val Asp
290                 295                 300

Thr Ile Leu Ser His Ser Glu Lys Tyr Asp Val Gly Trp Leu Ala Trp
305                 310                 315                 320

Ser Trp His Gly Asn Ser Gly Gly Val Glu Tyr Leu Asp Leu Ala Thr
                325                 330                 335

Asp Phe Ser Gly Thr Gln Leu Thr Glu Trp Gly Glu Arg Ile Val His
                340                 345                 350

Gly Pro Asn Gly Leu Lys Glu Thr Ser Glu Ile Val Ser Val Tyr Lys
                355                 360                 365

Lys
```

<210> SEQ ID NO 17
<211> LENGTH: 915
<212> TYPE: DNA
<213> ORGANISM: Bacillus sp.

<400> SEQUENCE: 17

```
atctcaacac tcagaaatgc cggtattcgc aatacaatcg ttgtggatgc atcggggtgg     60
ggacaaaatt catcgccaat taaagcttat ggcaacgaag tgttaaacca tgatccgcag    120
cgcaatgtta tgttctccat acacatgtac ggttcctgga ataatcagtc gcgaatcggc    180
agcgaattgc aggccatcaa agaccttggt cttgctgtca tgattggtga attcggatac    240
aactacaaca acggcaataa caacttgggg agtcaggtta acgcccagga aatcatgaat    300
caggcgcaag caaaaggaat cggctacatg ccgtggtcgt ggactggcaa tgacgcggct    360
aactcttggt tggatatgac aacaaacgat tggcaaacac ttacatcatg ggggaatcta    420
gttgtaaatg gaaccaacgg cattcgagct acgtctgtcc cagcaactgt atttaataca    480
caaacaacaa tttatgattt tgaaggcggc aatgcccagg gctggtcagg ttccggtttg    540
agcgggggc cttggtctgt taatgaatgg gcggcgagcg gtagttattc tctcaaagcg     600
aatatatctc taggcgccac tcaaaaagct ttgcaaacca cagcgtccca taatttcagc    660
ggccggtcta cattatccgt aagagtaaag catgcagcat ggggaaatca cggcagcggt    720
atgcaagcca gttatatgt gaaaacaggg gccggttacg cctggtatga tggcggcact     780
gtaaacatca cagctcggg caacacattg acgctaaacc tggcaggcat tcctaatctg     840
aacgacgtca gagaactcgg aattgaattt ataacacctg caaattcgag tggttctttc    900
gcaatttatg ttgac                                                     915
```

<210> SEQ ID NO 18
<211> LENGTH: 305
<212> TYPE: PRT
<213> ORGANISM: Bacillus sp.

<400> SEQUENCE: 18

```
Ile Ser Thr Leu Arg Asn Ala Gly Ile Arg Asn Thr Ile Val Val Asp
1               5                   10                  15
```

```
Ala Ser Gly Trp Gly Gln Asn Ser Ser Pro Ile Lys Ala Tyr Gly Asn
            20                  25                  30

Glu Val Leu Asn His Asp Pro Gln Arg Asn Val Met Phe Ser Ile His
        35                  40                  45

Met Tyr Gly Ser Trp Asn Asn Gln Ser Arg Ile Gly Ser Glu Leu Gln
    50                  55                  60

Ala Ile Lys Asp Leu Gly Leu Ala Val Met Ile Gly Glu Phe Gly Tyr
65                  70                  75                  80

Asn Tyr Asn Asn Gly Asn Asn Asn Leu Gly Ser Gln Val Asn Ala Gln
                85                  90                  95

Glu Ile Met Asn Gln Ala Gln Ala Lys Gly Ile Gly Tyr Met Pro Trp
            100                 105                 110

Ser Trp Thr Gly Asn Asp Ala Ala Asn Ser Trp Leu Asp Met Thr Thr
        115                 120                 125

Asn Asp Trp Gln Thr Leu Thr Ser Trp Gly Asn Leu Val Val Asn Gly
    130                 135                 140

Thr Asn Gly Ile Arg Ala Thr Ser Val Pro Ala Thr Val Phe Asn Thr
145                 150                 155                 160

Gln Thr Thr Ile Tyr Asp Phe Glu Gly Gly Asn Ala Gln Gly Trp Ser
                165                 170                 175

Gly Ser Gly Leu Ser Gly Gly Pro Trp Ser Val Asn Glu Trp Ala Ala
            180                 185                 190

Ser Gly Ser Tyr Ser Leu Lys Ala Asn Ile Ser Leu Gly Ala Thr Gln
        195                 200                 205

Lys Ala Leu Gln Thr Thr Ala Ser His Asn Phe Ser Gly Arg Ser Thr
210                 215                 220

Leu Ser Val Arg Val Lys His Ala Ala Trp Gly Asn His Gly Ser Gly
225                 230                 235                 240

Met Gln Ala Lys Leu Tyr Val Lys Thr Gly Ala Gly Tyr Ala Trp Tyr
                245                 250                 255

Asp Gly Gly Thr Val Asn Ile Asn Ser Ser Gly Asn Thr Leu Thr Leu
            260                 265                 270

Asn Leu Ala Gly Ile Pro Asn Leu Asn Asp Val Arg Glu Leu Gly Ile
        275                 280                 285

Glu Phe Ile Thr Pro Ala Asn Ser Ser Gly Ser Phe Ala Ile Tyr Val
    290                 295                 300

Asp
305

<210> SEQ ID NO 19
<211> LENGTH: 397
<212> TYPE: DNA
<213> ORGANISM: Bacillus clausii

<400> SEQUENCE: 19
atctctcagg gcttggtagg agtcattatt ctcttataca tggcatttag tcaagagaga      60
ggattggcgc aaactggatt tcaagtaaca gggacccagt tgcttgatgg agagggcaat     120
ccgtatgtga tgcgtggagt caatcacgga cattcatggt tcaaacaaga ccttgataca     180
gcaataccag ctattgcagc gactggcgct aatacggtga gaatcgtttt atcgaatggc     240
caacaatggg agcgagatac cgtagcggaa gttgaaagag tgcttgcagt taccgaagag     300
gaaggcttga cggctgtact tgaagttcat gatgcgacgg gaagtgatga tccaaacgat     360
ttgtttactg cagtggagta ttggtcagag agaggat                              397
```

<210> SEQ ID NO 20
<211> LENGTH: 132
<212> TYPE: PRT
<213> ORGANISM: Bacillus clausii

<400> SEQUENCE: 20

```
Ile Ser Gln Gly Leu Val Gly Val Ile Ile Leu Leu Tyr Met Ala Phe
1               5                   10                  15

Ser Gln Glu Arg Gly Leu Ala Gln Thr Gly Phe Gln Val Thr Gly Thr
            20                  25                  30

Gln Leu Leu Asp Gly Glu Gly Asn Pro Tyr Val Met Arg Gly Val Asn
        35                  40                  45

His Gly His Ser Trp Phe Lys Gln Asp Leu Asp Thr Ala Ile Pro Ala
    50                  55                  60

Ile Ala Ala Thr Gly Ala Asn Thr Val Arg Ile Val Leu Ser Asn Gly
65                  70                  75                  80

Gln Gln Trp Glu Arg Asp Thr Val Ala Glu Val Arg Val Leu Ala
                85                  90                  95

Val Thr Glu Glu Glu Gly Leu Thr Ala Val Leu Glu Val His Asp Ala
                100                 105                 110

Thr Gly Ser Asp Asp Pro Asn Asp Leu Phe Thr Ala Val Glu Tyr Trp
            115                 120                 125

Ser Glu Arg Gly
    130
```

<210> SEQ ID NO 21
<211> LENGTH: 960
<212> TYPE: DNA
<213> ORGANISM: Bacillus sp.

<400> SEQUENCE: 21

| | | | | |
|---|---|---|---|---|
| atgaatcgta agcggttaca atgggttgga gcactagtgg tggtgttggt tttgtttgta | 60 |
| tacagtagcg gtttagcatc tgcacaaagc ggctttcacg taaaggtac agagttgttg | 120 |
| gacaaaaatg gcgatcctta cgttatgcgt ggcgtcaacc atggacattc ttggtttaaa | 180 |
| caagatttag aggaggcaat ccctgccata gcagaaacag gggcgaacac agtgagaatc | 240 |
| gtcttatcca atggacagca atgggaaaaa gatgatgcct ctgagcttgc ccgtgtgctt | 300 |
| gctgccacag aaacatatgg gttgacaacc gtgctggaag tccacgatgc acaggaagt | 360 |
| gataatcccg atgatttaga taaagcagtc gattactgga tcgaaatggc tgatgttcta | 420 |
| aaggggacag aagaccgggt aatcattaac attgccaatg aatggtatgg ggcgtggagg | 480 |
| agtgacgttt gggcagaggc atacgcacaa gcgatcccgc gcttgcgcag tgctggcctc | 540 |
| gcccatacgt taatagttga tgcggcaggt tggggacagt accctgcctc tatccatgag | 600 |
| cggggagccg acgtatttgc ctccgatcca ttaaaaaaca caatgttttc catccatatg | 660 |
| tacgaatatg caggagcgga tagggcgaca gtttctgaaa acatcgacgg tgtacttgct | 720 |
| gaaaatcttg ctgtggtaat cggtgaattt ggccataggc atcatgatgg cgatgtcgat | 780 |
| gaagatgcga ttttggccta tacagcagag cggcaagtgg gctggcttgc ctggtcatgg | 840 |
| tatggcaata gcgggggtgt tgaatacttg gatttaactg aaggcccatc aggtccatta | 900 |
| acgagttggg gcgaacggat tgtctatggg gaaatgggct aaaagtaat tgatcacttg | 960 |

<210> SEQ ID NO 22
<211> LENGTH: 320

<212> TYPE: PRT
<213> ORGANISM: Bacillus sp.

<400> SEQUENCE: 22

Met Asn Arg Lys Arg Leu Gln Trp Val Gly Ala Leu Val Val Leu
1               5                   10                  15

Val Leu Phe Val Tyr Ser Ser Gly Leu Ala Ser Ala Gln Ser Gly Phe
            20                  25                  30

His Val Lys Gly Thr Glu Leu Leu Asp Lys Asn Gly Asp Pro Tyr Val
            35                  40                  45

Met Arg Gly Val Asn His Gly His Ser Trp Phe Lys Gln Asp Leu Glu
    50                  55                  60

Glu Ala Ile Pro Ala Ile Ala Glu Thr Gly Ala Asn Thr Val Arg Ile
65                  70                  75                  80

Val Leu Ser Asn Gly Gln Gln Trp Glu Lys Asp Asp Ala Ser Glu Leu
                85                  90                  95

Ala Arg Val Leu Ala Ala Thr Glu Thr Tyr Gly Leu Thr Thr Val Leu
            100                 105                 110

Glu Val His Asp Ala Thr Gly Ser Asp Asn Pro Asp Asp Leu Asp Lys
            115                 120                 125

Ala Val Asp Tyr Trp Ile Glu Met Ala Asp Val Leu Lys Gly Thr Glu
130                 135                 140

Asp Arg Val Ile Ile Asn Ile Ala Asn Glu Trp Tyr Gly Ala Trp Arg
145                 150                 155                 160

Ser Asp Val Trp Ala Glu Ala Tyr Ala Gln Ala Ile Pro Arg Leu Arg
                165                 170                 175

Ser Ala Gly Leu Ala His Thr Leu Ile Val Asp Ala Ala Gly Trp Gly
            180                 185                 190

Gln Tyr Pro Ala Ser Ile His Glu Arg Gly Ala Asp Val Phe Ala Ser
            195                 200                 205

Asp Pro Leu Lys Asn Thr Met Phe Ser Ile His Met Tyr Glu Tyr Ala
210                 215                 220

Gly Ala Asp Arg Ala Thr Val Ser Glu Asn Ile Asp Gly Val Leu Ala
225                 230                 235                 240

Glu Asn Leu Ala Val Val Ile Gly Glu Phe Gly His Arg His His Asp
                245                 250                 255

Gly Asp Val Asp Glu Asp Ala Ile Leu Ala Tyr Thr Ala Glu Arg Gln
            260                 265                 270

Val Gly Trp Leu Ala Trp Ser Trp Tyr Gly Asn Ser Gly Gly Val Glu
            275                 280                 285

Tyr Leu Asp Leu Thr Glu Gly Pro Ser Gly Pro Leu Thr Ser Trp Gly
        290                 295                 300

Glu Arg Ile Val Tyr Gly Glu Met Gly Leu Lys Val Ile Asp His Leu
305                 310                 315                 320

<210> SEQ ID NO 23
<211> LENGTH: 564
<212> TYPE: DNA
<213> ORGANISM: Bacillus sp.

<400> SEQUENCE: 23
atgaatcgta agcggttaca atgggttgga gcactagtgg cggtgttggt tttgtttgta      60
tacagtagcg gtttagcatc tgcacaaagc ggctttcacg taaaaggtac agagttgttg     120
gacaaaaatg gcgatcctta cgttatgcgt ggcgtcaacc atggacattc ttggtttaaa     180

-continued

```
caagatttag aggaggcaat ccctgccata gcagaaacag gggcgaacac agtgagaatc      240
gtcttatcca atggacagca atgggaaaaa gatgatgcct ctgagcttgc ccgtgtgctt      300
gctgccacag aaacatatgg gttgacaacc gtgctggaag tccacgatgc tacaggaagt      360
gataatcccg atgatttaga taaagcagtc gattactgga tcgaaatggc tgatgttcta      420
aaggggacag aagaccgggt aatcattaac attgccaatg aatggtatgg ggcgtggagg      480
agtgaccttt gggcaaaagc atacgcacaa gcgatcccgc gcttgcgcag tgctggcctc      540
gcccatacgt taataattga tgcc                                              564
```

<210> SEQ ID NO 24
<211> LENGTH: 188
<212> TYPE: PRT
<213> ORGANISM: Bacillus sp.

<400> SEQUENCE: 24

Met Asn Arg Lys Arg Leu Gln Trp Val Gly Ala Leu Val Ala Val Leu
1               5                   10                  15

Val Leu Phe Val Tyr Ser Ser Gly Leu Ala Ser Ala Gln Ser Gly Phe
            20                  25                  30

His Val Lys Gly Thr Glu Leu Leu Asp Lys Asn Gly Asp Pro Tyr Val
        35                  40                  45

Met Arg Gly Val Asn His Gly His Ser Trp Phe Lys Gln Asp Leu Glu
    50                  55                  60

Glu Ala Ile Pro Ala Ile Ala Glu Thr Gly Ala Asn Thr Val Arg Ile
65                  70                  75                  80

Val Leu Ser Asn Gly Gln Gln Trp Glu Lys Asp Asp Ala Ser Glu Leu
                85                  90                  95

Ala Arg Val Leu Ala Ala Thr Glu Thr Tyr Gly Leu Thr Thr Val Leu
            100                 105                 110

Glu Val His Asp Ala Thr Gly Ser Asp Asn Pro Asp Asp Leu Asp Lys
        115                 120                 125

Ala Val Asp Tyr Trp Ile Glu Met Ala Asp Val Leu Lys Gly Thr Glu
    130                 135                 140

Asp Arg Val Ile Ile Asn Ile Ala Asn Glu Trp Tyr Gly Ala Trp Arg
145                 150                 155                 160

Ser Asp Leu Trp Ala Lys Ala Tyr Ala Gln Ala Ile Pro Arg Leu Arg
                165                 170                 175

Ser Ala Gly Leu Ala His Thr Leu Ile Ile Asp Ala
            180                 185

<210> SEQ ID NO 25
<211> LENGTH: 2445
<212> TYPE: DNA
<213> ORGANISM: Bacillus sp.

<400> SEQUENCE: 25

```
atgaacaaac aaccgttaaa gactgcattt attatgttgt tatgtagcgt gtttatgttt       60
caaagcctac cttactatgt gaacgctatc aatgaaggcg agagagaagc ttttgcatcc      120
gcagggagat atgatgctga acaggcgact acgacaggaa atgccgtatt cacgaccgag      180
cctgttgagg acggcgagta cgccggtccg ggctacattt ccttcttttc tgaagattcc      240
tcgccacctt cttcatcgac aacctttcac attcaggccg ataaaacgga gctctatcat      300
ttatctatcg gatactatgc tccatacgga aacaaggaa ccacaattct ggtgaacggt      360
gcaggtaacg gagagtttat gttgccagcg cccgaggacg gggcagtctc cgccgaagtg      420
```

-continued

```
gaaattagca aaatcctgct cgaagaagga aataatacga ttacattcac aagaggctgg    480
ggttattacg gcattgaata tattcgggtc gagccggtta atccaacgtt accgactata    540
tttattgaag cagaagaaga ttacgaagcg actggaaatg ttagcgttac caatgaaatc    600
gaaggttatt ccggagcagg ctatttgttc aaccaagagg ggacaattca ttggaatgta    660
acctcaccgg aaacctctat atatgaagta atcgttgcct atgcagctcc ttatggcgac    720
aaacaaacaa atctgacagt gaatggacag ggtaccgtca atcttgactt gaaagagaca    780
gaagtcttcg tggagttgaa tgtcggcatc gtaagtctca atgaaggcga aaacacacta    840
acactccata gtggttgggg atggtacaat atcgattata tcaagcttgt acctgtggtc    900
agttcggatc ccgaaccgca tcaggtcgaa aaaacactgg tgaatccgga cgcctcacct    960
gaggcaagag cgctaattaa ttatctcgta gaccagtacg ggaacaaaat tctatcaggt   1020
caaaccgagt tgaaagacgc caggtggatc catgaacagg tgggcaaata tcctgccggtt  1080 atggcagttg attttatgga ctacagcccg tcccgcgtag tgcatggcgc aactggaact   1140
gcggttgagg aagcgattga gtgggcagag atgggtggga tcattacctt ccactggcat   1200
tggaacgcgc caaaggacct gcttaatgta cccggcaatg agtggtggtc cggttttttat  1260 acccgtgcca acgtttga tgtggagtac gctttagaga accgggaatc tgaggatttc    1320
caattgttga ttagcgacat ggatgtgatc gccgagcaat gaagcggct gcaggcagag    1380 aacatccctg tgttatggag accgcttcat gaggcggaag gcggctggtt ctggtggggc    1440
gccaaaggtc cagaggcggc aatagagctc tacaggctga tgtacgatcg ttacaccaat   1500
caccataaac taaacaattt gatatggatg tggaattcgg aagcggaaga atggtatccg   1560
ggcgatgatg tcgtggacat gatcagtacc gatatttata atcctgtcgg agatttcagt   1620
cccagcatca acaagtatga gcatctaaag gaattggtac aggataagaa gctggttgcc   1680
ttgcctgaaa ccggcattat tccggatccc gatcagcttc agctgttcaa tgcgaactgg   1740
agttggttcg ccacctggac tggagactat atcagggacg gcatctccaa ccctatagaa    1800
cacctgcaaa aggtgtttca tcatgactac gtcatcaccc tggatgaatt gccggagaac    1860
ctgtcccgtt acggattatc tgaaggagtc tggaagagcg acgccgatct atccgtaaaa    1920
acgaggacga cctccgaaat tacagtgaac tggtcaaatg ccattcaata tgattccgtt    1980
aatggctata aattaattaa agatggtgta gagaccgttt cagttgaagg cggcgtgcaa    2040
gagtatacct tcacaaattt attgccgggc acgcagtata cgataaaagt agaggcactg    2100
gaccaggatg accgatggac cgccgacgga ccggtcgccg ttgtatctac attatccaac    2160
gctccgatat cctatcctcc ggctgtcact cctgatgagc cgaatgaaga actgtcggaa    2220
ggagagtata cgctcttggc agatgactta tccagccagg atggtgttct ggaagtaagt    2280
cttgagccga cagttacgaa gctcattatt ccttctgcac tagccggcac attagacgga    2340
gacttgagaa tcggttatgg ggacgtctgg atcgtcatcc cacacgaaca gcttggggt    2400 gacgagcagc aatccggcag cgcgtatgag ttagtgctgg agatc                    2445
```

<210> SEQ ID NO 26
<211> LENGTH: 815
<212> TYPE: PRT
<213> ORGANISM: Bacillus sp.

<400> SEQUENCE: 26

```
Met Asn Lys Gln Pro Leu Lys Thr Ala Phe Ile Met Leu Leu Cys Ser
1               5                  10                  15
```

-continued

```
Val Phe Met Phe Gln Ser Leu Pro Tyr Tyr Val Asn Ala Ile Asn Glu
             20                  25                  30
Gly Glu Arg Glu Ala Phe Ala Ser Ala Gly Arg Tyr Asp Ala Glu Gln
             35                  40                  45
Ala Thr Thr Thr Gly Asn Ala Val Phe Thr Thr Glu Pro Val Glu Asp
             50                  55                  60
Gly Glu Tyr Ala Gly Pro Gly Tyr Ile Ser Phe Phe Ser Glu Asp Ser
 65                  70                  75                  80
Ser Pro Pro Ser Ser Thr Thr Phe His Ile Gln Ala Asp Lys Thr
                 85                  90                  95
Glu Leu Tyr His Leu Ser Ile Gly Tyr Tyr Ala Pro Tyr Gly Asn Lys
                100                 105                 110
Gly Thr Thr Ile Leu Val Asn Gly Ala Gly Asn Gly Glu Phe Met Leu
                115                 120                 125
Pro Ala Pro Glu Asp Gly Ala Val Ser Ala Glu Val Glu Ile Ser Lys
                130                 135                 140
Ile Leu Leu Glu Glu Gly Asn Asn Thr Ile Thr Phe Thr Arg Gly Trp
145                 150                 155                 160
Gly Tyr Tyr Gly Ile Glu Tyr Ile Arg Val Glu Pro Val Asn Pro Thr
                165                 170                 175
Leu Pro Thr Ile Phe Ile Glu Ala Glu Asp Tyr Glu Ala Thr Gly
                180                 185                 190
Asn Val Ser Val Thr Asn Glu Ile Glu Gly Tyr Ser Gly Ala Gly Tyr
                195                 200                 205
Leu Phe Asn Gln Glu Gly Thr Ile His Trp Asn Val Thr Ser Pro Glu
                210                 215                 220
Thr Ser Ile Tyr Glu Val Ile Ala Tyr Ala Ala Pro Tyr Gly Asp
225                 230                 235                 240
Lys Gln Thr Asn Leu Thr Val Asn Gly Gln Gly Thr Val Asn Leu Asp
                245                 250                 255
Leu Lys Glu Thr Glu Val Phe Val Glu Leu Asn Val Gly Ile Val Ser
                260                 265                 270
Leu Asn Glu Gly Glu Asn Thr Leu Thr Leu His Ser Gly Trp Gly Trp
                275                 280                 285
Tyr Asn Ile Asp Tyr Ile Lys Leu Val Pro Val Val Ser Ser Asp Pro
                290                 295                 300
Glu Pro His Gln Val Glu Lys Thr Leu Val Asn Pro Asp Ala Ser Pro
305                 310                 315                 320
Glu Ala Arg Ala Leu Ile Asn Tyr Leu Val Asp Gln Tyr Gly Asn Lys
                325                 330                 335
Ile Leu Ser Gly Gln Thr Glu Leu Lys Asp Ala Arg Trp Ile His Glu
                340                 345                 350
Gln Val Gly Lys Tyr Pro Ala Val Met Ala Val Asp Phe Met Asp Tyr
                355                 360                 365
Ser Pro Ser Arg Val Val His Gly Ala Thr Gly Thr Ala Val Glu Glu
                370                 375                 380
Ala Ile Glu Trp Ala Glu Met Gly Gly Ile Ile Thr Phe His Trp His
385                 390                 395                 400
Trp Asn Ala Pro Lys Asp Leu Leu Asn Val Pro Gly Asn Glu Trp Trp
                405                 410                 415
Ser Gly Phe Tyr Thr Arg Ala Thr Thr Phe Asp Val Glu Tyr Ala Leu
                420                 425                 430
```

```
Glu Asn Arg Glu Ser Glu Asp Phe Gln Leu Leu Ile Ser Asp Met Asp
            435                 440                 445

Val Ile Ala Glu Gln Leu Lys Arg Leu Gln Ala Glu Asn Ile Pro Val
    450                 455                 460

Leu Trp Arg Pro Leu His Glu Ala Glu Gly Gly Trp Phe Trp Trp Gly
465                 470                 475                 480

Ala Lys Gly Pro Glu Ala Ala Ile Glu Leu Tyr Arg Leu Met Tyr Asp
                485                 490                 495

Arg Tyr Thr Asn His His Lys Leu Asn Asn Leu Ile Trp Met Trp Asn
            500                 505                 510

Ser Glu Ala Glu Glu Trp Tyr Pro Gly Asp Asp Val Val Asp Met Ile
            515                 520                 525

Ser Thr Asp Ile Tyr Asn Pro Val Gly Asp Phe Ser Pro Ser Ile Asn
    530                 535                 540

Lys Tyr Glu His Leu Lys Glu Leu Val Gln Asp Lys Lys Leu Val Ala
545                 550                 555                 560

Leu Pro Glu Thr Gly Ile Ile Pro Asp Pro Asp Gln Leu Gln Leu Phe
                565                 570                 575

Asn Ala Asn Trp Ser Trp Phe Ala Thr Trp Thr Gly Asp Tyr Ile Arg
            580                 585                 590

Asp Gly Ile Ser Asn Pro Ile Glu His Leu Gln Lys Val Phe His His
            595                 600                 605

Asp Tyr Val Ile Thr Leu Asp Glu Leu Pro Glu Asn Leu Ser Arg Tyr
    610                 615                 620

Gly Leu Ser Glu Gly Val Trp Lys Ser Asp Ala Asp Leu Ser Val Lys
625                 630                 635                 640

Thr Arg Thr Thr Ser Glu Ile Thr Val Asn Trp Ser Asn Ala Ile Gln
                645                 650                 655

Tyr Asp Ser Val Asn Gly Tyr Lys Leu Ile Lys Asp Gly Val Glu Thr
            660                 665                 670

Val Ser Val Glu Gly Gly Val Gln Glu Tyr Thr Phe Thr Asn Leu Leu
            675                 680                 685

Pro Gly Thr Gln Tyr Thr Ile Lys Val Glu Ala Leu Asp Gln Asp Asp
    690                 695                 700

Arg Trp Thr Ala Asp Gly Pro Val Ala Val Ser Thr Leu Ser Asn
705                 710                 715                 720

Ala Pro Ile Ser Tyr Pro Pro Ala Val Thr Pro Asp Glu Pro Asn Glu
                725                 730                 735

Glu Leu Ser Glu Gly Glu Tyr Thr Leu Leu Ala Asp Asp Leu Ser Ser
            740                 745                 750

Gln Asp Gly Val Leu Glu Val Ser Leu Glu Pro Thr Val Thr Lys Leu
            755                 760                 765

Ile Ile Pro Ser Ala Leu Ala Gly Thr Leu Asp Gly Asp Leu Arg Ile
    770                 775                 780

Gly Tyr Gly Asp Val Trp Ile Val Ile Pro His Glu Gln Leu Gly Gly
785                 790                 795                 800

Asp Glu Gln Gln Ser Gly Ser Ala Tyr Glu Leu Val Leu Glu Ile
                805                 810                 815

<210> SEQ ID NO 27
<211> LENGTH: 1488
<212> TYPE: DNA
<213> ORGANISM: Bacillus sp.

<400> SEQUENCE: 27
```

-continued

```
atgaggaatg aaaaaatcag gccatttact aaaataaagg caagtgttgt tactagtgtt     60
ttactattaa ctatttccct aattttcact ataggaaata tagcaaatgc tgaatctgag    120
gtaagaatat ttgaagctga agatgctatt ttaaatgggc tgactattaa aaattctgaa    180
ccaggttttt ctggtaccgg atatgtaggt gactttgaaa atagctctca gagtgtgacg    240
tttcaaattg aggctcctaa agccggttta tacaacttaa atattggata tggcgcgatt    300
tatggaagtg gaaaagtagc taatgttatt gtaaatggag agaagctaag tactttttaca   360
atgggaagtg gctttggtaa agcgtcagca ggaaaggtat tacttaattc aggcttaaat    420
actatctcga ttactcctaa ttggacatgg tttaccattg attatattga agttatacat    480
gcaccggaac cggaaaacca taatgtagaa aagacgttaa ttaacccaaa tgcaacggat    540
gaagccaaag ctttaataag ctatctagtt gataactttg gtgagaaaat tcttgcaggg    600
caacatgatt atccaaatac acgaccacga gatttagaat atatttatga aactactggg    660
aagtatcctg ctgttttagg tttagacttt attgataaca gtccttctag agttgagcgc    720
ggagcctctg ctgatgaaac accagtagct attgactggt ggaataaagg gggaattgtt    780
actttcacct ggcattggaa tgctcccaaa gatttattag atgaaccagg aaatgaatgg    840
tggagtggtt tttatacgag agcaacaact tttgacgtag aatatgcttt aaaacatccg    900
aagtcggagg actacatgct tctaatacgt gatattgatg taatagctgg tgaactaaag    960
aaattgcagg aagcaaatgt tcctgtttta tggaggccac ttcatgaggc tgaaggcggg   1020
tggttctggt gggggcaaa aggtcctgaa tcaaccaagg agctatggag attaatgtat   1080
gatagaatga cgaactacca taacttaaat aatttaatat gggtatggaa ttccattgaa   1140
gaggattggt atcctggaga tgagtatgtc gatattgtaa gcttcgattc atatccaggt   1200
gaatataact atagtccaat gagccgtgag tatgaagcac ttaaagagtt gtctagtaac   1260
aagaaactta tagcaatagc agaaaatgga ccaataccag atcctgattt actacaactt   1320
taccatgcta actatagttg gtttgctaca tggaatggag atatattaag aaatcaaaat   1380
agcgaagagc acctaagaaa agtatataat catgattatg tgattaccct aaataaatta   1440
cctaacctta aaacatatag gggaagatgc acttatacag acactatc                1488
```

<210> SEQ ID NO 28
<211> LENGTH: 496
<212> TYPE: PRT
<213> ORGANISM: Bacillus sp.

<400> SEQUENCE: 28

Met Arg Asn Glu Lys Ile Arg Pro Phe Thr Lys Ile Lys Ala Ser Val
1               5                   10                  15

Val Thr Ser Val Leu Leu Leu Thr Ile Ser Leu Ile Phe Thr Ile Gly
            20                  25                  30

Asn Ile Ala Asn Ala Glu Ser Glu Val Arg Ile Phe Glu Ala Glu Asp
        35                  40                  45

Ala Ile Leu Asn Gly Leu Thr Ile Lys Asn Ser Glu Pro Gly Phe Ser
    50                  55                  60

Gly Thr Gly Tyr Val Gly Asp Phe Glu Asn Ser Ser Gln Ser Val Thr
65                  70                  75                  80

Phe Gln Ile Glu Ala Pro Lys Ala Gly Leu Tyr Asn Leu Asn Ile Gly
            85                  90                  95

Tyr Gly Ala Ile Tyr Gly Ser Gly Lys Val Ala Asn Val Ile Val Asn
            100                 105                 110

```
Gly Glu Lys Leu Ser Thr Phe Thr Met Gly Ser Gly Phe Gly Lys Ala
        115                 120                 125

Ser Ala Gly Lys Val Leu Leu Asn Ser Gly Leu Asn Thr Ile Ser Ile
130                 135                 140

Thr Pro Asn Trp Thr Trp Phe Thr Ile Asp Tyr Ile Glu Val Ile His
145                 150                 155                 160

Ala Pro Glu Pro Glu Asn His Asn Val Glu Lys Thr Leu Ile Asn Pro
                165                 170                 175

Asn Ala Thr Asp Glu Ala Lys Ala Leu Ile Ser Tyr Leu Val Asp Asn
            180                 185                 190

Phe Gly Glu Lys Ile Leu Ala Gly Gln His Asp Tyr Pro Asn Thr Arg
        195                 200                 205

Pro Arg Asp Leu Glu Tyr Ile Tyr Glu Thr Thr Gly Lys Tyr Pro Ala
    210                 215                 220

Val Leu Gly Leu Asp Phe Ile Asp Asn Ser Pro Ser Arg Val Glu Arg
225                 230                 235                 240

Gly Ala Ser Ala Asp Glu Thr Pro Val Ala Ile Asp Trp Trp Asn Lys
                245                 250                 255

Gly Gly Ile Val Thr Phe Thr Trp His Trp Asn Ala Pro Lys Asp Leu
            260                 265                 270

Leu Asp Glu Pro Gly Asn Glu Trp Trp Ser Gly Phe Tyr Thr Arg Ala
        275                 280                 285

Thr Thr Phe Asp Val Glu Tyr Ala Leu Lys His Pro Lys Ser Glu Asp
    290                 295                 300

Tyr Met Leu Leu Ile Arg Asp Ile Asp Val Ile Ala Gly Glu Leu Lys
305                 310                 315                 320

Lys Leu Gln Glu Ala Asn Val Pro Val Leu Trp Arg Pro Leu His Glu
                325                 330                 335

Ala Glu Gly Gly Trp Phe Trp Trp Gly Ala Lys Gly Pro Glu Ser Thr
            340                 345                 350

Lys Glu Leu Trp Arg Leu Met Tyr Asp Arg Met Thr Asn Tyr His Asn
        355                 360                 365

Leu Asn Asn Leu Ile Trp Val Trp Asn Ser Ile Glu Glu Asp Trp Tyr
    370                 375                 380

Pro Gly Asp Glu Tyr Val Asp Ile Val Ser Phe Asp Ser Tyr Pro Gly
385                 390                 395                 400

Glu Tyr Asn Tyr Ser Pro Met Ser Arg Glu Tyr Glu Ala Leu Lys Glu
                405                 410                 415

Leu Ser Ser Asn Lys Lys Leu Ile Ala Ile Ala Glu Asn Gly Pro Ile
            420                 425                 430

Pro Asp Pro Asp Leu Leu Gln Leu Tyr His Ala Asn Tyr Ser Trp Phe
        435                 440                 445

Ala Thr Trp Asn Gly Asp Ile Leu Arg Asn Gln Asn Ser Glu Glu His
    450                 455                 460

Leu Arg Lys Val Tyr Asn His Asp Tyr Val Ile Thr Leu Asn Lys Leu
465                 470                 475                 480

Pro Asn Leu Lys Thr Tyr Arg Gly Arg Cys Thr Tyr Thr Asp Thr Ile
                485                 490                 495
```

<210> SEQ ID NO 29
<211> LENGTH: 1086
<212> TYPE: DNA
<213> ORGANISM: Bacillus licheniformis

```
<400> SEQUENCE: 29
atgtacaaaa aatttggaat ctctttattg cttgctttat taatcgtttc agctttctcg      60
cagacggcat ctgctcatac agtgaatccg gtgaaccaaa atgcccagtc gacaacgaag     120
gagctgatga attggcttgc tcatctgccg aaccgatcgg aaaatcgcgt actgtcaggt     180
gcattcggcg gatattctaa tgcgacgttt tctatgaaag aagccaatcg aatcaaagat     240
gctacagggc agtcacctgt cgtgtatgct tgtgattatt cgagaggatg gctggagaca     300
gctcatattg ctgatgcgat cgattatagc tgtaacagcg atctaatctc tcattggaag     360
agcggaggca tacctcagat cagcatgcat cttcctaacc ctgcgtttca atccggcaat     420
tacaaaacaa agatctcaaa cagtcagtat gaaaaaatct tagactcatc aaccacagaa     480
ggcaaacgat tggatgctgt actgagcaag gttgcagatg gccttcagca gttaaaaaat     540
gaaggcgttc cagttctttt cagacctctt cacgaaatga acggagaatg gttctggtgg     600
gggcttaccg gctataacca aaaggatagc gagcgaatat cactatacaa acagctttac     660
caaaaaatct atcattatat gaccgataca agaggattgg acaacttgat ttgggtttat     720
gcaccagacg ccaaccgcga ctttaagaca gacttttatc ctggggattc atatgttgat     780
attgtcggat tagacgcgta tttctcagat gcttattcga tcaaaggata tgacgagtta     840
acggcgctta ataagccatt tgcctttaca gaagtcggtc cgcaaacaac aaacggcagc     900
ctggattatt ctcaatttat caatgcagtt aaacaaaaat atccgaaaac catttatttc     960
ttagcttggg atgagggttg gagccctgcg gctaatcagg tgcctttaa tctctataat     1020 gacagttgga cgctgaataa gggagagcta tgggaaggca gctcacttac accggcagcc    1080
gaataa                                                               1086

<210> SEQ ID NO 30
<211> LENGTH: 361
<212> TYPE: PRT
<213> ORGANISM: Bacillus licheniformis

<400> SEQUENCE: 30

Met Tyr Lys Lys Phe Gly Ile Ser Leu Leu Ala Leu Leu Ile Val
 1               5                  10                  15

Ser Ala Phe Ser Gln Thr Ala Ser Ala His Thr Val Asn Pro Val Asn
                20                  25                  30

Gln Asn Ala Gln Ser Thr Thr Lys Glu Leu Met Asn Trp Leu Ala His
            35                  40                  45

Leu Pro Asn Arg Ser Glu Asn Arg Val Leu Ser Gly Ala Phe Gly Gly
    50                  55                  60

Tyr Ser Asn Ala Thr Phe Ser Met Lys Glu Ala Asn Arg Ile Lys Asp
65                  70                  75                  80

Ala Thr Gly Gln Ser Pro Val Val Tyr Ala Cys Asp Tyr Ser Arg Gly
                85                  90                  95

Trp Leu Glu Thr Ala His Ile Ala Asp Ala Ile Asp Tyr Ser Cys Asn
                100                 105                 110

Ser Asp Leu Ile Ser His Trp Lys Ser Gly Gly Ile Pro Gln Ile Ser
            115                 120                 125

Met His Leu Pro Asn Pro Ala Phe Gln Ser Gly Asn Tyr Lys Thr Lys
        130                 135                 140

Ile Ser Asn Ser Gln Tyr Glu Lys Ile Leu Asp Ser Ser Thr Thr Glu
145                 150                 155                 160

Gly Lys Arg Leu Asp Ala Val Leu Ser Lys Val Ala Asp Gly Leu Gln
```

```
                165                 170                 175
Gln Leu Lys Asn Glu Gly Val Pro Val Leu Phe Arg Pro Leu His Glu
                180                 185                 190

Met Asn Gly Glu Trp Phe Trp Trp Gly Leu Thr Gly Tyr Asn Gln Lys
        195                 200                 205

Asp Ser Glu Arg Ile Ser Leu Tyr Lys Gln Leu Tyr Gln Lys Ile Tyr
    210                 215                 220

His Tyr Met Thr Asp Thr Arg Gly Leu Asp Asn Leu Ile Trp Val Tyr
225                 230                 235                 240

Ala Pro Asp Ala Asn Arg Asp Phe Lys Thr Asp Phe Tyr Pro Gly Asp
                245                 250                 255

Ser Tyr Val Asp Ile Val Gly Leu Asp Ala Tyr Phe Ser Asp Ala Tyr
            260                 265                 270

Ser Ile Lys Gly Tyr Asp Glu Leu Thr Ala Leu Asn Lys Pro Phe Ala
        275                 280                 285

Phe Thr Glu Val Gly Pro Gln Thr Thr Asn Gly Ser Leu Asp Tyr Ser
    290                 295                 300

Gln Phe Ile Asn Ala Val Lys Gln Lys Tyr Pro Lys Thr Ile Tyr Phe
305                 310                 315                 320

Leu Ala Trp Asp Glu Gly Trp Ser Pro Ala Ala Asn Gln Gly Ala Phe
                325                 330                 335

Asn Leu Tyr Asn Asp Ser Trp Thr Leu Asn Lys Gly Glu Leu Trp Glu
            340                 345                 350

Gly Ser Ser Leu Thr Pro Ala Ala Glu
        355                 360

<210> SEQ ID NO 31
<211> LENGTH: 3041
<212> TYPE: DNA
<213> ORGANISM: Caldocellulosiruptor sp.

<400> SEQUENCE: 31
caatgggctt gaagattggt attcactggg gtgctgattt tgtaatagcc aatatcaagg      60
ttgaagaggt aactcagtaa aagaggcttt ttgctggtga gcacaccgct gaagagaaaa    120
gtaaggttat gttaaagaag cggtgtgccc accggcttta aaaaaataaa aaggggaga    180 gtgccaggat tatgagaaag ggcttaaaga ttacatcttt aatagtgagc cttgtatttt    240
tacttgggct tttgccgaca ggaatttttg gtgctgttga cacatctgtt caaagctatg    300
ttttcgactt tgaagatggc accacaatga cattcggtga ggcttgggga gactcattaa    360
aatgtatcaa aaaggtgtca gtttctactg atttgcagcg acctggtaac aagtatgcgc    420
tcaggcttga tgttgagttc aacgagaaca atggatggga ccagggcgac cttggtgcat    480
ggataggtgg tgttgtcgaa gggcagtttg actttacaaa ctacaagtct gttgagtttg    540
aaatgtttgt tccatacgac gagtttgcaa aagcaaaagg tggctttgct tacaaggttg    600
tattgaatga tggatggaaa gaacttgaa gcgaatttag cattacagta aatgctggca    660
aaaaggtgaa gataaacggc aaggactata tggtcattca aaggcgtttt gcaattccag    720
atgattttag aaccaaaaag cgtgcacagc ttgtgttcca atttgcaggt caaaactgca    780
actacaaagg acctatctac cttgacaata taagagtaag acctgaggat gcgtcaaacc    840
tctcaaaaga agactatgga agtagcgaag aagaggaaat ttctgaggac ttttttcacag    900 gggttaccct tgtgtatcca caggaaggca aaaactttgt gtacaatttt gaaaagaca    960 caatgggatt ttataaatac tcgggtgatg gatttgcaaa gaaaacaaag tcaatggaat  1020
```

-continued

```
tttcacagga cttgaagaca tcaacaaatg caggcagcct caaactcaat gctaatttcc    1080
agggtactgc gttttgaagaa atgaacattg ctgtaaagct cacagacaaa gaaggaaaac    1140
tttttgacct tggcaaatac tccgcacttg agtatacaat ctacattcca aatccagaca    1200
aagttgcggg gaaaatcatg tctgcaagtg ctgtggacag tccatggaag ataatcaaag    1260
actttacact tcttaactac aaagataaga caacatggaa agagataaac ggaaagactt    1320
atgcggtcat aaagtgcaag gataatcttt acaatgtaaa agaaaaagca ggtgtattgg    1380
ttttgaggat tgcgggtct tatgtaaagt atacaggccc catctacatt gataacgtaa      1440
cattaattgc tggaaagaag gttgcaccaa aggtggagag aatatcactt ccaaatccaa    1500
agacatacta taaagttaag attgaagctg agagtgcaag tgatggctgg gcttacagcg    1560
ttgagaaaga aaatgcaaag ttttctggga aaggctatgt acttttgttt gggaacaaca    1620
tgggcaatac cctttataac atcaaggttc gaagacagg acattacatc ttcactcttg      1680
caatctcaac ccttgggctt gtaaaggatg gtagcattga tatctggata gacggtgatt    1740
tgaaaggtgg ggcaaaggtt ccaaacgtaa agggcaagtt ccaggaagtt gttgtcagaa    1800
aaaagattta tttaacagcg ggtgagcaca caatatcact gcaaaaatct ggcggataca    1860
caattgcagt tgactatttt gtgatagaag agcttgttgc ggcaaataaa tcaaagcttt    1920
cggtttcttc aaagttagtg accccaaatc cacaccccaa tgcccaaagg ctcataaatt    1980
atttgtcaag catttcggt gaaaagattt tgtctggtca gcagagcagc ggtgaaggca      2040
aagaggttca gatgatttt gatgtcacaa agagatatcc agctgttaga agctttgatt      2100
tcatggacta ctcaccaagc agagtgcagc atggtacaaa aggtacagat gttgatgagg    2160
caataaagtg gtggaagagc ggcggcatag ttgcattttg ctggcactgg aacgcaccaa    2220
caggtcttat tgaccagccg ggcaaagagt ggtggagagg tttttacaca gaggctacaa    2280
catttgacct caagaaagcc atggacaatc caaattctga gaatataaa ctcatttga      2340 gagatataga cgctattgct gagcagctca aaaaattgca ggctgaaggt gtgccagttc    2400
ttttcagacc gcttcacgag gcctctggcg gctggttctg gtggggtgca aaaggtccag    2460
agccgtatat aaagctttgg aagctcatgt ttgacaggct tgtaaactat cacaaaatca    2520
acaacctaat atgggtatgg aacggtcagg atgctgcctg gtatccgggt gaccagtatg    2580
ttgatataat tgcagaagat atatatgagg aaaaagctca gtactcacca tatacagaga    2640
ggttcgtgaa agctctcaag tacacaaatg caaacaagat gatagcactt tctgagtgcg    2700
gaactattcc tgacccggct gtgctaaaac aagaaggtgt ttcgtggctg tggttttctg    2760
tatgggcagg aagctatgtc atgacaggca gcaagtacaa cgatgaatgg aacgacaatc    2820
acatgctaag aaagatttac aacaatgact atgtaataac aaaagatgaa ctacctgata    2880
taaagagcat tccactcaaa tagaatgaga tatattttgg aatatccaaa atcaactgtc    2940
agcctgtgag aggagagaag ttcaaaaaag acctcctccc ttttggttc ttgcaaaata      3000 atcaattttt ggttttgaca tctcaaacat gttaattaaa a                        3041
```

<210> SEQ ID NO 32
<211> LENGTH: 903
<212> TYPE: PRT
<213> ORGANISM: Caldocellulosiruptor sp.

<400> SEQUENCE: 32

```
Met Arg Lys Gly Leu Lys Ile Thr Ser Leu Ile Val Ser Leu Val Phe
1               5                   10                  15
```

-continued

```
Leu Leu Gly Leu Leu Pro Thr Gly Ile Phe Gly Ala Val Glu Thr Ser
             20                  25                  30

Val Gln Ser Tyr Val Phe Asp Phe Glu Asp Gly Thr Thr Met Thr Phe
         35                  40                  45

Gly Glu Ala Trp Gly Asp Ser Leu Lys Cys Ile Lys Lys Val Ser Val
     50                  55                  60

Ser Thr Asp Leu Gln Arg Pro Gly Asn Lys Tyr Ala Leu Arg Leu Asp
65                  70                  75                  80

Val Glu Phe Asn Glu Asn Asn Gly Trp Asp Gln Gly Asp Leu Gly Ala
                 85                  90                  95

Trp Ile Gly Gly Val Val Glu Gly Gln Phe Asp Phe Thr Asn Tyr Lys
                100                 105                 110

Ser Val Glu Phe Glu Met Phe Val Pro Tyr Asp Glu Phe Ala Lys Ala
            115                 120                 125

Lys Gly Gly Phe Ala Tyr Lys Val Val Leu Asn Asp Gly Trp Lys Glu
        130                 135                 140

Leu Gly Ser Glu Phe Ser Ile Thr Val Asn Ala Gly Lys Lys Val Lys
145                 150                 155                 160

Ile Asn Gly Lys Asp Tyr Met Val Ile His Lys Ala Phe Ala Ile Pro
                165                 170                 175

Asp Asp Phe Arg Thr Lys Lys Arg Ala Gln Leu Val Phe Gln Phe Ala
            180                 185                 190

Gly Gln Asn Cys Asn Tyr Lys Gly Pro Ile Tyr Leu Asp Asn Ile Arg
        195                 200                 205

Val Arg Pro Glu Asp Ala Ser Asn Leu Ser Lys Glu Asp Tyr Gly Ser
    210                 215                 220

Ser Glu Glu Glu Glu Ile Ser Glu Asp Phe Phe Thr Gly Val Thr Leu
225                 230                 235                 240

Val Tyr Pro Gln Glu Gly Lys Asn Phe Val Tyr Asn Phe Glu Lys Asp
                245                 250                 255

Thr Met Gly Phe Tyr Lys Tyr Ser Gly Asp Gly Phe Ala Lys Lys Thr
            260                 265                 270

Lys Ser Met Glu Phe Ser Gln Asp Leu Lys Thr Ser Thr Asn Ala Gly
        275                 280                 285

Ser Leu Lys Leu Asn Ala Asn Phe Gln Gly Thr Ala Phe Glu Glu Met
    290                 295                 300

Asn Ile Ala Val Lys Leu Thr Asp Lys Glu Gly Lys Leu Phe Asp Leu
305                 310                 315                 320

Gly Lys Tyr Ser Ala Leu Glu Tyr Thr Ile Tyr Ile Pro Asn Pro Asp
                325                 330                 335

Lys Val Ala Gly Lys Ile Met Ser Ala Ser Ala Val Asp Ser Pro Trp
            340                 345                 350

Lys Ile Ile Lys Asp Phe Thr Leu Leu Asn Tyr Lys Asp Lys Thr Thr
        355                 360                 365

Trp Lys Glu Ile Asn Gly Lys Thr Tyr Ala Val Ile Lys Cys Lys Asp
    370                 375                 380

Asn Leu Tyr Asn Val Lys Glu Lys Ala Gly Val Leu Val Leu Arg Ile
385                 390                 395                 400

Ala Gly Ser Tyr Val Lys Tyr Thr Gly Pro Ile Tyr Ile Asp Asn Val
                405                 410                 415

Thr Leu Ile Ala Gly Lys Lys Val Ala Pro Lys Val Glu Arg Ile Ser
            420                 425                 430

Leu Pro Asn Pro Lys Thr Tyr Tyr Lys Val Lys Ile Glu Ala Glu Ser
```

-continued

```
              435                 440                 445
Ala Ser Asp Gly Trp Ala Tyr Ser Val Glu Lys Glu Asn Ala Lys Phe
            450                 455                 460

Ser Gly Lys Gly Tyr Val Leu Leu Phe Gly Asn Asn Met Gly Asn Thr
465                 470                 475                 480

Leu Tyr Asn Ile Lys Val Pro Lys Thr Gly His Tyr Ile Phe Thr Leu
                485                 490                 495

Ala Ile Ser Thr Leu Gly Leu Val Lys Asp Gly Ser Ile Asp Ile Trp
            500                 505                 510

Ile Asp Gly Asp Leu Lys Gly Gly Ala Lys Val Pro Asn Val Lys Gly
            515                 520                 525

Lys Phe Gln Glu Val Val Arg Lys Lys Ile Tyr Leu Thr Ala Gly
530                 535                 540

Glu His Thr Ile Ser Leu Gln Lys Ser Gly Tyr Thr Ile Ala Val
545                 550                 555                 560

Asp Tyr Phe Val Ile Glu Glu Leu Val Ala Ala Asn Lys Ser Lys Leu
                565                 570                 575

Ser Val Ser Ser Lys Leu Val Thr Pro Asn Pro His Pro Asn Ala Gln
            580                 585                 590

Arg Leu Ile Asn Tyr Leu Ser Ser Ile Tyr Gly Glu Lys Ile Leu Ser
            595                 600                 605

Gly Gln Gln Ser Ser Gly Glu Gly Lys Glu Val Gln Met Ile Phe Asp
610                 615                 620

Val Thr Lys Arg Tyr Pro Ala Val Arg Ser Phe Asp Phe Met Asp Tyr
625                 630                 635                 640

Ser Pro Ser Arg Val Gln His Gly Thr Lys Gly Thr Asp Val Asp Glu
            645                 650                 655

Ala Ile Lys Trp Trp Lys Ser Gly Gly Ile Val Ala Phe Cys Trp His
            660                 665                 670

Trp Asn Ala Pro Thr Gly Leu Ile Asp Gln Pro Gly Lys Glu Trp Trp
            675                 680                 685

Arg Gly Phe Tyr Thr Glu Ala Thr Thr Phe Asp Leu Lys Lys Ala Met
            690                 695                 700

Asp Asn Pro Asn Ser Glu Glu Tyr Lys Leu Ile Leu Arg Asp Ile Asp
705                 710                 715                 720

Ala Ile Ala Glu Gln Leu Lys Lys Leu Gln Ala Glu Gly Val Pro Val
            725                 730                 735

Leu Phe Arg Pro Leu His Glu Ala Ser Gly Gly Trp Phe Trp Trp Gly
            740                 745                 750

Ala Lys Gly Pro Glu Pro Tyr Ile Lys Leu Trp Lys Leu Met Phe Asp
            755                 760                 765

Arg Leu Val Asn Tyr His Lys Ile Asn Asn Leu Ile Trp Val Trp Asn
770                 775                 780

Gly Gln Asp Ala Ala Trp Tyr Pro Gly Asp Gln Tyr Val Asp Ile Ile
785                 790                 795                 800

Ala Glu Asp Ile Tyr Glu Glu Lys Ala Gln Tyr Ser Pro Tyr Thr Glu
                805                 810                 815

Arg Phe Val Lys Ala Leu Lys Tyr Thr Asn Ala Asn Lys Met Ile Ala
            820                 825                 830

Leu Ser Glu Cys Gly Thr Ile Pro Asp Pro Ala Val Leu Lys Gln Glu
            835                 840                 845

Gly Val Ser Trp Leu Trp Phe Ser Val Trp Ala Gly Ser Tyr Val Met
850                 855                 860
```

Thr Gly Ser Lys Tyr Asn Asp Glu Trp Asn Asp Asn His Met Leu Arg
865                 870                 875                 880

Lys Ile Tyr Asn Asn Asp Tyr Val Ile Thr Lys Asp Glu Leu Pro Asp
            885                 890                 895

Ile Lys Ser Ile Pro Leu Lys
            900

<210> SEQ ID NO 33
<211> LENGTH: 1450
<212> TYPE: RNA
<213> ORGANISM: Bacillus sp. I633

<400> SEQUENCE: 33

| | | | | | |
|---|---|---|---|---|---|
| gcucccugau | guuagcggcg | gacggguagag | uaacacgugg | gcaaccugcc | cuguagacug | 60 |
| ggauaacauc | gagaaaucgg | ugcuaauacc | ggauaauaga | uggaauugca | uaauucuauu | 120 |
| uuaaaagaug | gcuccggcua | ucacuacagg | augggcccgc | ggcgcauuag | cuaguuggua | 180 |
| agguaacggc | uuaccaaggc | gacgaugcgu | agccgaccug | agagggugau | cggccacacu | 240 |
| gggacugaga | cacggcccag | acuccuacgg | gaggcagcag | uagggaaucu | uccgcaaugg | 300 |
| acgaaagucu | gacggagcaa | cgccgcguga | gcgaugaagg | ccuucggguu | guaaagcucu | 360 |
| guuguuaggg | aagaacaagu | gccauucaaa | uaggguggca | ccuugacggu | accuaaccag | 420 |
| aaagccacgg | cuaacuacgu | gccagcagcc | gcgguaauac | guagguggca | agcguugucc | 480 |
| ggaauuauug | ggcguaaagc | gcgcgcaggc | gguucuuaa | gucugaugug | aaagcccccg | 540 |
| gcucaaccgg | ggagggucau | uggaaacugg | gagacuugag | uacagaagag | gagaguggaa | 600 |
| uuccacgugu | agcggugaaa | ugcguagaua | uguggaggaa | caccaguggc | gaaggcgacu | 660 |
| cucuggucug | uaacugacgc | ugaggcgcga | aagcguggggg | agcaaacagg | auuagauacc | 720 |
| cugguagucc | acgccguaaa | cgaugagugc | uagguguuaa | ggguucgau | gcccuuagug | 780 |
| ccgaaguuaa | cacaguaagc | acuccgccug | gggaguacgg | ccgcaaggcu | gaaacucaaa | 840 |
| ggaauugacg | ggggcccgca | caagcggugg | agcauguggu | uuaauucgaa | gcaacgcgaa | 900 |
| gaaccuuacc | aggucuugac | auccuuugac | aacccuagag | auagggcguu | ccccuucggg | 960 |
| ggacaaagug | acaguggug | cauguugguc | gucagcucgu | gucgugagau | guggguuaa | 1020 |
| gucccgcaac | gagcgcaacc | cuugaucuua | guugccagca | uuuaguuggg | cacucuaagg | 1080 |
| ugacugccgg | ugacaaaccg | gaggaaggug | gggaugacgu | caaaucauca | ugccccuuau | 1140 |
| gaccugggcu | acacacgugc | uacaauggau | gguacaaagg | gcagcaaaac | cgcgaggucg | 1200 |
| agccaauccc | auaaaaccau | ucucaguucg | gauguaggc | ugcaaucgc | cuacaugaag | 1260 |
| ccggaaucgc | uaguaaucgc | ggaucagcau | gccgcgguga | auacguuccc | gggccuugua | 1320 |
| cacaccgccc | gucacaccac | gagaguuugu | aacacccgaa | gucggugggg | uaaccuuuug | 1380 |
| gagccagccg | ccuaaggugg | gacagaugau | uggggugaag | ucguaacaag | guagccguau | 1440 |
| cggaaggugc | | | | | | 1450 |

<210> SEQ ID NO 34
<211> LENGTH: 1508
<212> TYPE: RNA
<213> ORGANISM: Bacillus sp. AAI12

<400> SEQUENCE: 34

| | | | | | |
|---|---|---|---|---|---|
| gacgaacgcu | ggcggcgugc | cuaauacaug | caagucgagc | ggacauuuag | gagcuugcuc | 60 |
| cuaauguua | gcggcggacg | ggugaguaac | acgugggcaa | ccugcccugu | agacugggau | 120 |

| | |
|---|---|
| aacaucgaga aaucggugcu aauaccggau aaucuugagg auugcauaau ccucuuguaa | 180 |
| aagauggcuc cggcuaucac uacgggaugg gcccgcggcg cauuagcuag uugguaaggu | 240 |
| aacggcuuac caaggcgacg augcguagcc gaccugagag ggugaucggc cacacuggga | 300 |
| cugagacacg gcccagacuc cuacgggagg cagcaguagg gaaucuuccg caauggacga | 360 |
| aagucugacg gagcaacgcc gcgugaguga ugaaggguuu cggcucguaa agcucuguug | 420 |
| uuagggaaga acaagugccg uucaaauagg gcggccaccuu gacgguaccu aaccagaaag | 480 |
| ccacggcuaa cuacgugcca gcagccgcgg uaauacguag guggcaagcg uuguccggaa | 540 |
| uuauugggcg uaaagcgcgc gcaggcgguc uuuuaagucu gaugugaaau cucggggcuc | 600 |
| aaccccgagc ggucauugga aacgggaga cuugaguaca aagaggaga uggaauucc | 660 |
| acguguagcg gugaaaugcg uagauaugug gaggaacacc aguggcgaag gcgacucucu | 720 |
| ggucuguaac ugacgcugag gcgcgaaagc gugggagca acaggauua gauacccugg | 780 |
| uaguccacgc cguaaacgau gagugcuagg uguuaggggu uucgaugccc uuagugccga | 840 |
| aguuaacaca uuaagcacuc cgccugggga guacgaccgc aagguugaaa ucaaaggaa | 900 |
| uugacggggg cccgcacaag caguggagca ugugguuuaa uucgaagcaa cgcgaagaac | 960 |
| cuuaccaggu cuugacaucc uuaugaccuc ccuagagaua gggauuuccc uucggggaca | 1020 |
| uaagugacag guggugcaug uugucguca gcucgugucg ugagauguug gguuaagucc | 1080 |
| cgcaacgagc gcaacccuug aucuuaguug ccagcauuua guugggcacu cuaaggugac | 1140 |
| ugccggugau aaaccggagg aaggugggga ugacgucaaa ucaucaugcc ccuuaugacc | 1200 |
| ugggcuacac acgugcuaca auggauggua caaagagcag caaaaccgcg aggucgagcc | 1260 |
| aaucucauaa agccauucuc aguucggauu guaggcugca acucgccuac augaagccgg | 1320 |
| aauugcuagu aaucgcggau cagcaugccg cggugaauac guucccgggc cuuguacaca | 1380 |
| ccgcccguca caccacgaga guuuguaaca cccgaagucg guggaguaac ccuuacggga | 1440 |
| gcuagccgcc uaaggugggga cagaugauug gggugaaguc guaacaaggu agccguaucg | 1500 |
| gaaggugc | 1508 |

```
<210> SEQ ID NO 35
<211> LENGTH: 42
<212> TYPE: DNA
<213> ORGANISM: Artificial Sequence
<220> FEATURE:
<223> OTHER INFORMATION: Primer

<400> SEQUENCE: 35
```

| | |
|---|---|
| gtcgccgggg cggccgctat caattggtaa ctgtatctca gc | 42 |

```
<210> SEQ ID NO 36
<211> LENGTH: 64
<212> TYPE: DNA
<213> ORGANISM: Artificial Sequence
<220> FEATURE:
<223> OTHER INFORMATION: Primer

<400> SEQUENCE: 36
```

| | |
|---|---|
| gtcgcccggg agctctgatc aggtaccaag cttgtcgacc tgcagaatga ggcagcaaga | 60 |
| agat | 64 |

```
<210> SEQ ID NO 37
<211> LENGTH: 61
<212> TYPE: DNA
```

```
<213> ORGANISM: Artificial Sequence
<220> FEATURE:
<223> OTHER INFORMATION: Primer

<400> SEQUENCE: 37
gtcggcggcc gctgatcacg taccaagctt gtcgacctgc agaatgaggc agcaagaaga      60
t                                                                     61

<210> SEQ ID NO 38
<211> LENGTH: 35
<212> TYPE: DNA
<213> ORGANISM: Artificial Sequence
<220> FEATURE:
<223> OTHER INFORMATION: Primer

<400> SEQUENCE: 38
gtcggagctc tatcaattgg taactgtatc tcagc                                 35

<210> SEQ ID NO 39
<211> LENGTH: 35
<212> TYPE: DNA
<213> ORGANISM: Artificial Sequence
<220> FEATURE:
<223> OTHER INFORMATION: Primer

<400> SEQUENCE: 39
aacagctgat cacgactgat cttttagctt ggcac                                 35

<210> SEQ ID NO 40
<211> LENGTH: 37
<212> TYPE: DNA
<213> ORGANISM: Artificial Sequence
<220> FEATURE:
<223> OTHER INFORMATION: Primer

<400> SEQUENCE: 40
aactgcagcc gcggcacatc ataatgggac aaatggg                               37

<210> SEQ ID NO 41
<211> LENGTH: 45
<212> TYPE: DNA
<213> ORGANISM: Artificial Sequence
<220> FEATURE:
<223> OTHER INFORMATION: Primer

<400> SEQUENCE: 41
gttgagaaag cggccgcctt ttttctattc tacaatcaca ttatc                      45

<210> SEQ ID NO 42
<211> LENGTH: 46
<212> TYPE: DNA
<213> ORGANISM: Artificial Sequence
<220> FEATURE:
<223> OTHER INFORMATION: Primer

<400> SEQUENCE: 42
gacgacgtac aagcggccgc tcactacgga gaagttcctc catcag                     46

<210> SEQ ID NO 43
<211> LENGTH: 41
<212> TYPE: DNA
<213> ORGANISM: Artificial Sequence
<220> FEATURE:
<223> OTHER INFORMATION: Primer

<400> SEQUENCE: 43
```

```
cattctgcag ccgcggcaaa ttccggattt tatgtaagcg g                41

<210> SEQ ID NO 44
<211> LENGTH: 45
<212> TYPE: DNA
<213> ORGANISM: Artificial Sequence
<220> FEATURE:
<223> OTHER INFORMATION: Primer

<400> SEQUENCE: 44
gttgagaaag cggccgcctt ttttctattc tacaatcaca ttatc           45

<210> SEQ ID NO 45
<211> LENGTH: 41
<212> TYPE: DNA
<213> ORGANISM: Artificial Sequence
<220> FEATURE:
<223> OTHER INFORMATION: Primer

<400> SEQUENCE: 45
cattctgcag ccgcggcaaa ttccggattt tatgtaagcg g                41

<210> SEQ ID NO 46
<211> LENGTH: 35
<212> TYPE: DNA
<213> ORGANISM: Artificial Sequence
<220> FEATURE:
<223> OTHER INFORMATION: Primer

<400> SEQUENCE: 46
catcatgcta gctgtaaaaa cggtgcttaa tctcg                      35

<210> SEQ ID NO 47
<211> LENGTH: 44
<212> TYPE: DNA
<213> ORGANISM: Artificial Sequence
<220> FEATURE:
<223> OTHER INFORMATION: Primer

<400> SEQUENCE: 47
cattctgcag ccgcggcagc aagtacaggc ttttatgttg atgg            44

<210> SEQ ID NO 48
<211> LENGTH: 49
<212> TYPE: DNA
<213> ORGANISM: Artificial Sequence
<220> FEATURE:
<223> OTHER INFORMATION: Primer

<400> SEQUENCE: 48
gacgacgtac aagcggccgc gctatttccc taacatgatg atattttcg       49

<210> SEQ ID NO 49
<211> LENGTH: 10
<212> TYPE: PRT
<213> ORGANISM: Artificial Sequence
<220> FEATURE:
<223> OTHER INFORMATION: Synthetic

<400> SEQUENCE: 49

Ala Ser Pro Glu Pro Thr Pro Glu Pro Thr
1               5                   10

<210> SEQ ID NO 50
<211> LENGTH: 38
<212> TYPE: DNA
```

```
<213> ORGANISM: Artificial Sequence
<220> FEATURE:
<223> OTHER INFORMATION: Primer

<400> SEQUENCE: 50
cattctgcag ccgcggcatt ttctggaagc gtttcagc                            38

<210> SEQ ID NO 51
<211> LENGTH: 38
<212> TYPE: DNA
<213> ORGANISM: Artificial Sequence
<220> FEATURE:
<223> OTHER INFORMATION: Primer

<400> SEQUENCE: 51
cagcagtagc ggccgccact tcctgctggt acatatgc                            38

<210> SEQ ID NO 52
<211> LENGTH: 37
<212> TYPE: DNA
<213> ORGANISM: Artificial Sequence
<220> FEATURE:
<223> OTHER INFORMATION: Primer

<400> SEQUENCE: 52
cattctgcag ccgcggcaca tcacagtggg ttccatg                             37

<210> SEQ ID NO 53
<211> LENGTH: 46
<212> TYPE: DNA
<213> ORGANISM: Artificial Sequence
<220> FEATURE:
<223> OTHER INFORMATION: Primer

<400> SEQUENCE: 53
gcgttgagac gcgcggccgc ttattgaaac acactgcttc ttttag                   46

<210> SEQ ID NO 54
<211> LENGTH: 37
<212> TYPE: DNA
<213> ORGANISM: Artificial Sequence
<220> FEATURE:
<223> OTHER INFORMATION: Primer

<400> SEQUENCE: 54
cattctgcag ccgcggcaag tggacatggg caaatgc                             37

<210> SEQ ID NO 55
<211> LENGTH: 47
<212> TYPE: DNA
<213> ORGANISM: Artificial Sequence
<220> FEATURE:
<223> OTHER INFORMATION: primer

<400> SEQUENCE: 55
gcgttgagac gcgcggccgc ttattttttg tatacactaa cgatttc                  47
```

MANNANASES

This application is a provisional of 60/106,054 filed Oct. 28, 1998 which is a provisional of 60/105,970 filed Oct. 28, 1998 which is a provisional of 60/123,543 filed Mar. 9, 1999 which is a provisional of 60/123,623 filed Mar. 10, 1999 which is a provisional of 60/123,641 filed Mar. 10, 1999 which is a provisional of 60/123,642 filed Mar. 10, 1999 and a con of Ser. No. 09/111,256, filed Jun. 10, 1998 now abandoned and a con of PCT/USDK99/00314 Jun. 10, 1998.

The present invention relates to microbial mannanases, more specifically to microbial enzymes exhibiting mannanase activity as their major enzymatic activity in the neutral and alkaline pH ranges; to a method of producing such enzymes; and to methods for using such enzymes in the paper and pulp, textile, oil drilling, cleaning, laundering, detergent and cellulose fiber processing industries.

BACKGROUND OF THE INVENTION

Mannan containing polysaccharides are a major component of the hemicellulose fraction in woods and endosperm in many leguminous seeds and in some mature seeds of non-leguminous plants. Essentially unsubstituted linear beta-1,4-mannan is found in some non-leguminous plants. Unsubstituted beta-1,4-mannan which is present e.g. in ivory nuts resembles cellulose in the conformation of the individual polysaccharide chains, and is water-insoluble. In leguminous seeds, water-soluble galactomannan is the main storage carbohydrate comprising up to 20% of the total dry weight. Galactomannans have a linear beta-1,4-mannan backbone substituted with single alpha-1,6-galactose, optionally substituted with acetyl groups. Mannans are also found in several monocotyledonous plants and are the most abundant polysaccharides in the cell wall material in palm kernel meal. Glucomannans are linear polysaccharides with a backbone of beta-1,4-linked mannose and glucose alternating in a more or less regular manner, the backbone optionally being substituted with galactose and/or acetyl groups. Mannans, galactomannans, glucomannans and galactoglucomannans (i.e. glucomannan backbones with branched galactose) contribute to more than 50% of the softwood hemicellulose. Moreover, the cellulose of many red algae contains a significant amount of mannose.

Mannanases have been identified in several Bacillus organisms. For example, Talbot et al., Appl. Environ. Microbiol., Vol.56, No. 11, pp. 3505–3510 (1990) describes a beta-mannanase derived from *Bacillus stearothermophilus* in dimer form having molecular weight of 162 kDa and an optimum pH of 5.5–7.5. Mendoza et al., World J. Microbiol. Biotech., Vol. 10, No. 5, pp. 551–555 (1994) describes a beta-mannanase derived from *Bacillus subtilis* having a molecular weight of 38 kDa, an optimum activity at pH 5.0 and 55° C. and a pI of 4.8. JP-A-03047076 discloses a beta-mannanase derived from Bacillus sp., having a molecular weight of 37±3 kDa measured by gel filtration, an optimum pH of 8–10 and a pI of 5.3–5.4. JP-A-63056289 describes the production of an alkaline, thermostable beta-mannanase which hydrolyses beta-1,4-D-mannopyranoside bonds of e.g. mannans and produces manno-oligosaccharides. JP-A-63036775 relates to the Bacillus microorganism FERM P-8856 which produces beta-mannanase and beta-mannosidase at an alkaline pH. JP-A-08051975 discloses alkaline beta-mannanases from alkalophilic Bacillus sp. AM-001 having molecular weights of 43±3 kDa and 57±3 kDa and optimum pH of 8–10. A purified mannanase from *Bacillus amyloliquefaciens* useful in the bleaching of pulp and paper and a method of preparation thereof is disclosed in WO 97/11164. WO 91/18974 describes a hemicellulase such as a glucanase, xylanase or mannanase active at an extreme pH and temperature. WO 94/25576 discloses an enzyme from *Aspergillus aculeatus*, CBS 101.43, exhibiting mannanase activity which may be useful for degradation or modification of plant or algae cell wall material. WO 93/24622 discloses a mannanase isolated from *Trichoderma reseei* useful for bleaching lignocellulosic pulps.

WO 95/35362 discloses cleaning compositions containing plant cell wall degrading enzymes having pectinase and/or hemicellulase and optionally cellulase activity for the removal of stains of vegetable origin and further discloses an alkaline mannanase from the strain C11SB.G17.

It is an object of the present invention to provide a novel and efficient enzyme exhibiting mannanase activity also in the alkaline pH range, e.g. when applied in cleaning compositions or different industrial processes.

SUMMARY OF THE INVENTION

The inventors have now found novel enzymes having substantial mannanase activity, i.e. enzymes exhibiting mannanase activity which may be obtained from a bacterial strain of the genus Bacillus and have succeeded in identifying DNA sequences encoding such enzymes. The DNA sequences are listed in the sequence listing as SEQ ID No. 1, 5, 9, 11, 13, 15, 17, 19, 21, 23, 25, 27, 29 and 31; and the deduced amino acid sequences are listed in the sequence listing as SEQ ID No. 2, 6, 10, 12, 14, 16, 18, 20, 22, 24, 26, 28, 30 and 32, respectively. It is believed that the novel enzymes will be classified according to the Enzyme Nomenclature in the Enzyme Class EC 3.2.1.78.

In a first aspect, the present invention relates to a mannanase which is i) a polypeptide produced by Bacillus sp. I633, ii) a polypeptide comprising an amino acid sequence as shown in positions 32–330 of SEQ ID NO:2, or iii) an analogue of the polypeptide defined in i) or ii) which is at least 65% homologous with said polypeptide, is derived from said polypeptide by substitution, deletion or addition of one or several amino acids, or is immunologically reactive with a polyclonal antibody raised against said polypeptide in purified form.

Within one aspect, the present invention provides an isolated polynucleotide molecule selected from the group consisting of (a) polynucleotide molecules encoding a polypeptide having mannanase activity and comprising a sequence of nucleotides as shown in SEQ ID NO: 1 from nucleotide 94 to nucleotide 990; (b) species homologs of (a); (c) polynucleotide molecules that encode a polypeptide having mannanase activity that is at least 65% identical to the amino acid sequence of SEQ ID NO: 2 from amino acid residue 32 to amino acid residue 330; (d) molecules complementary to (a), (b) or (c); and (e) degenerate nucleotide sequences of (a), (b), (c) or (d).

The plasmid pBXM3 comprising the polynucleotide molecule (the DNA sequence) encoding a mannanase of the present invention has been transformed into a strain of the *Escherichia coli* which was deposited by the inventors according to the Budapest Treaty on the International Recognition of the Deposit of Microorganisms for the Purposes of Patent Procedure at the Deutsche Sammlung von Mikroorganismen und Zellkulturen GmbH, Mascheroder Weg 1b, D-38124 Braunschweig, Federal Republic of Germany, on May 29, 1998 under the deposition number DSM 12197.

Within another aspect of the invention there is provided an expression vector comprising the following operably linked elements: a transcription promoter; a DNA segment selected from the group consisting of (a) polynucleotide molecules encoding a polypeptide having mannanase activity and comprising a sequence of nucleotides as shown in SEQ ID NO: 1 from nucleotide 94 to nucleotide 990; (b) species homologs of (a); (c) polynucleotide molecules that encode a polypeptide having mannanase activity that is at least 65% identical to the amino acid sequence of SEQ ID NO: 2 from amino acid residue 32 to amino acid residue 330; and (d) degenerate nucleotide sequences of (a), (b), or (c); and a transcription terminator.

Within yet another aspect of the present invention there is provided a cultured cell into which has been introduced an expression vector as disclosed above, wherein said cell expresses the polypeptide encoded by the DNA segment.

Further aspects of the present invention provide an isolated polypeptide having mannanase activity selected from the group consisting of (a) polypeptide molecules comprising a sequence of amino acid residues as shown in SEQ ID NO:2 from amino acid residue 32 to amino acid residue 330; (b) species homologs of (a); and a fusion protein having mannanase activity comprising a first polypeptide part exhibiting mannanase activity and a second polypeptide part exhibiting cellulose binding function, the second polypeptide preferably being a cellulose binding domain (CBD), such as a fusion protein represented by SEQ ID NO:4.

Within another aspect of the present invention there is provided a composition comprising a purified polypeptide according to the invention in combination with other polypeptides.

Within another aspect of the present invention there are provided methods for producing a polypeptide according to the invention comprising culturing a cell into which has been introduced an expression vector as disclosed above, whereby said cell expresses a polypeptide encoded by the DNA segment and recovering the polypeptide.

The novel enzyme of the present invention is useful for the treatment of cellulosic material, especially cellulose-containing fiber, yarn, woven or non-woven fabric, treatment of mechanical paper-making pulps, kraft pulps or recycled waste paper, and for retting of fibres. The treatment can be carried out during the processing of cellulosic material into a material ready for manufacture of paper or of garment or fabric, the latter e.g. in the desizing or scouring step; or during industrial or household laundering of such fabric or garment.

Accordingly, in further aspects the present invention relates to a cleaning or detergent composition comprising the enzyme of the invention; and to use of the enzyme of the invention for the treatment, e.g. cleaning, of cellulose-containing fibers, yarn, woven or non-woven fabric, as well as synthetic or partly synthetic fabric.

It is contemplated that the enzyme of the invention is useful in an enzymatic scouring process and/or desizing (removal of mannan size) in the preparation of cellulosic material e.g. for proper response in subsequent dyeing operations. The enzyme is also useful for removal of mannan containing print paste. Further, detergent compositions comprising the novel enzyme are capable of removing or bleaching certain soils or stains present on laundry, especially soils and spots resulting from mannan containing food, plants, and the like. Further, treatment with cleaning or detergent compositions comprising the novel enzyme can improve whiteness as well as prevent binding of certain soils to the cellulosic material.

Accordingly, the present invention also relates to cleaning compositions, including laundry, dishwashing, hard surface cleaner, personal cleansing and oral/dental compositions, comprising the mannanase of the invention. Further, the present invention relates to such cleaning compositions comprising a mannanase and an enzyme selected from cellulases, proteases, lipases, amylases, pectin degrading enzymes and xyloglucanases, such compositions providing superior cleaning performance, i.e. superior stain removal, dingy cleaning or whiteness maintenance.

DEFINITIONS

Figure 1:
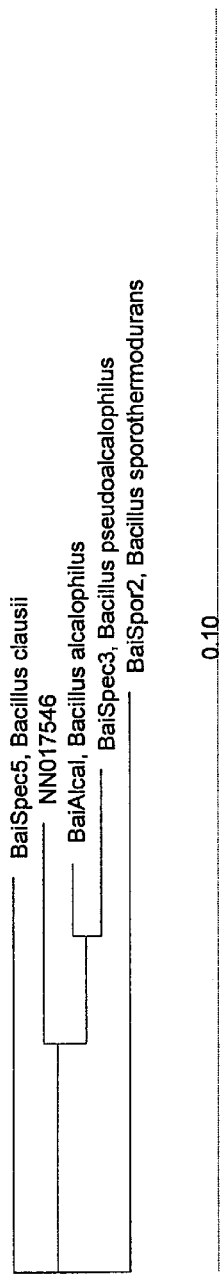
FIG. 1 shows a phylogenic tree generated from ARP program relating closest species to Bacillus sp. I633.

Prior to discussing this invention in further detail, the following terms will first be defined.

The term "ortholog" (or "species homolog") denotes a polypeptide or protein obtained from one species that has homology to an analogous polypeptide or protein from a different species.

The term "paralog" denotes a polypeptide or protein obtained from a given species that has homology to a distinct polypeptide or protein from that same species.

The term "expression vector" denotes a DNA molecule, linear or circular, that comprises a segment encoding a polypeptide of interest operably linked to additional segments that provide for its transcription. Such additional segments may include promoter and terminator sequences, and may optionally include one or more origins of replication, one or more selectable markers, an enhancer, a polyadenylation signal, and the like. Expression vectors are generally derived from plasmid or viral DNA, or may contain elements of both. The expression vector of the invention may be any expression vector that is conveniently subjected to recombinant DNA procedures, and the choice of vector will often depend on the host cell into which the vector is to be introduced. Thus, the vector may be an autonomously replicating vector, i.e. a vector which exists as an extrachromosomal entity, the replication of which is independent of chromosomal replication, e.g. a plasmid. Alternatively, the vector may be one which, when introduced into a host cell, is integrated into the host cell genome and replicated together with the chromosome(s) into which it has been integrated.

The term "recombinant expressed" or "recombinantly expressed" used herein in connection with expression of a polypeptide or protein is defined according to the standard definition in the art. Recombinantly expression of a protein is generally performed by using an expression vector as described immediately above.

The term "isolated", when applied to a polynucleotide molecule, denotes that the polynucleotide has been removed from its natural genetic milieu and is thus free of other extraneous or unwanted coding sequences, and is in a form suitable for use within genetically engineered protein production systems. Such isolated molecules are those that are separated from their natural environment and include cDNA and genomic clones. Isolated DNA molecules of the present invention are free of other genes with which they are ordinarily associated, but may include naturally occurring 5' and 3' untranslated regions such as promoters and terminators. The identification of associated regions will be evident to one of ordinary skill in the art (see for example, Dynan and Tijan, *Nature* 316:774–78, 1985). The term "an isolated polynucleotide" may alternatively be termed "a cloned polynucleotide".

When applied to a protein/polypeptide, the term "isolated" indicates that the protein is found in a condition other than its native environment. In a preferred form, the isolated protein is substantially free of other proteins, particularly other homologous proteins (i.e. "homologous impurities" (see below)). It is preferred to provide the protein in a greater than 40% pure form, more preferably greater than 60% pure form.

Even more preferably it is preferred to provide the protein in a highly purified form, i.e., greater than 80% pure, more preferably greater than 95% pure, and even more preferably greater than 99% pure, as determined by SDS-PAGE.

The term "isolated protein/polypeptide may alternatively be termed "purified protein/polypeptide".

The term "homologous impurities" means any impurity (e.g. another polypeptide than the polypeptide of the invention) which originate from the homologous cell where the polypeptide of the invention is originally obtained from.

The term "obtained from" as used herein in connection with a specific microbial source, means that the polynucleotide and/or polypeptide is produced by the specific source (homologous expression), or by a cell in which a gene from the source have been inserted (heterologous expression).

The term "operably linked", when referring to DNA segments, denotes that the segments are arranged so that they function in concert for their intended purposes, e.g. transcription initiates in the promoter and proceeds through the coding segment to the terminator.

The term "polynucleotide" denotes a single- or double-stranded polymer of deoxyribonucleotide or ribonucleotide bases read from the 5' to the 3' end. Polynucleotides include RNA and DNA, and may be isolated from natural sources, synthesized in vitro, or prepared from a combination of natural and synthetic molecules.

The term "complements of polynucleotide molecules" denotes polynucleotide molecules having a complementary base sequence and reverse orientation as compared to a reference sequence. For example, the sequence 5' ATG-CACGGG 3' is complementary to 5' CCCGTGCAT 3'.

The term "degenerate nucleotide sequence" denotes a sequence of nucleotides that includes one or more degenerate codons (as compared to a reference polynucleotide molecule that encodes a polypeptide). Degenerate codons contain different triplets of nucleotides, but encode the same amino acid residue (i.e., GAU and GAC triplets each encode Asp).

The term "promoter" denotes a portion of a gene containing DNA sequences that provide for the binding of RNA polymerase and initiation of transcription. Promoter sequences are commonly, but not always, found in the 5' non-coding regions of genes.

The term "secretory signal sequence" denotes a DNA sequence that encodes a polypeptide (a "secretory peptide") that, as a component of a larger polypeptide, directs the larger polypeptide through a secretory pathway of a cell in which it is synthesized. The larger peptide is commonly cleaved to remove the secretory peptide during transit through the secretory pathway.

The term "enzyme core" denotes a single domain enzyme which may or may not have been modified or altered, but which has retained its original activity; the catalytic domain as known in the art has remained intact and functional.

By the term "linker" or "spacer" is meant a polypeptide comprising at least two amino acids which may be present between the domains of a multidomain protein, for example an enzyme comprising an enzyme core and a binding domain such as a cellulose binding domain (CBD) or any other enzyme hybrid, or between two proteins or polypeptides expressed as a fusion polypeptide, for example a fusion protein comprising two core enzymes. For example, the fusion protein of an enzyme core with a CBD is provided by fusing a DNA sequence encoding the enzyme core, a DNA sequence encoding the linker and a DNA sequence encoding the CBD sequentially into one open reading frame and expressing this construct.

The term "mannanase" or "galactomannanase" denotes a mannanase enzyme defined according to the art as officially being named mannan endo-1,4-beta-mannosidase and having the alternative names beta-mannanase and endo-1,4-mannanase and catalysing hydrolyses of 1,4-beta-D-mannosidic linkages in mannans, galactomannans, glucomannans, and galactoglucomannans which enzyme is classified according to the Enzyme Nomenclature as EC 3.2.1.78.

DETAILED DESCRIPTION OF THE INVENTION

HOW TO USE A SEQUENCE OF THE INVENTION TO GET OTHER RELATED SEQUENCES: The disclosed sequence information herein relating to a polynucleotide sequence encoding a mannanase of the invention can be used as a tool to identify other homologous mannanases. For instance, polymerase chain reaction (PCR) can be used to amplify sequences encoding other homologous mannanases from a variety of microbial sources, in particular of different Bacillus species.

Assay for Activity Test

A polypeptide of the invention having mannanase activity may be tested for mannanase activity according to standard test procedures known in the art, such as by applying a solution to be tested to 4 mm diameter holes punched out in agar plates containing 0.2% AZCL galactomannan (carob), i.e. substrate for the assay of endo-1,4-beta-D-mannanase available as CatNo.I-AZGMA from the company Megazyme.

Polynucleotides

Within preferred embodiments of the invention an isolated polynucleotide of the invention will hybridize to similar sized regions of SEQ ID NO: 1, or a sequence complementary thereto, under at least medium stringency conditions.

In particular polynucleotides of the invention will hybridize to a denatured double-stranded DNA probe comprising either the full sequence shown in SEQ ID NO:1 or a partial sequence comprising the segment shown in positions 91–990 of SEQ ID NO:1 which segment encodes for the catalytically active domain or enzyme core of the mannanase of the invention or any probe comprising a subsequence shown in positions 91–990 of SEQ ID NO:1 which subsequence has a length of at least about 100 base pairs under at least medium stringency conditions, but preferably at high stringency conditions as described in detail below. Suitable experimental conditions for determining hybridization at medium, or high stringency between a nucleotide probe and a homologous DNA or RNA sequence involves presoaking of the filter containing the DNA fragments or RNA to hybridize in 5×SSC (Sodium chloride/Sodium citrate, Sambrook et al. 1989) for 10 min, and prehybridization of the filter in a solution of 5×SSC, 5×Denhardt's solution (Sambrook et al. 1989), 0.5% SDS and 100 µg/ml of denatured sonicated salmon sperm DNA (Sambrook et al. 1989), followed by hybridization in the same solution containing a concentration of 10 ng/ml of a random-primed (Feinberg, A. P. and Vogelstein, B. (1983) Anal. Biochem. 132:6–13), 32P-dCTP-labeled (specific activity higher than $1 \times 10^9$ cpm/µg) probe for 12 hours at ca. 45° C. The filter is then washed twice for 30 minutes in 2×SSC, 0.5% SDS at least 60° C. (medium stringency), still more preferably at least 65° C. (medium/high stringency), even more preferably at least 70° C. (high stringency), and even more preferably at least 75° C. (very high stringency).

Molecules to which the oligonucleotide probe hybridizes under these conditions are detected using a x-ray film.

Other useful isolated polynucleotides are those which will hybridize to similar sized regions of SEQ ID NO: 5, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29 or SEQ ID NO: 31, respectively, or a sequence complementary thereto, under at least medium stringency conditions.

Particularly useful are polynucleotides which will hybridize to a denatured double-stranded DNA probe comprising either the full sequence shown in SEQ ID NO:5 or a partial sequence comprising the segment shown in positions 94–1032 of SEQ ID NO:5 which segment encodes for the catalytically active domain or enzyme core of the mannanase of the invention or any probe comprising a subsequence shown in positions 94–1032 of SEQ ID NO:5 which subsequence has a length of at least about 100 base pairs under at least medium stringency conditions, but preferably at high stringency conditions as described in detail above; as well as polynucleotides which will hybridize to a denatured double-stranded DNA probe comprising either the full sequence shown in SEQ ID NO:9 or a partial sequence comprising the segment shown in positions 94–1086 of SEQ ID NO:9 which segment encodes for the catalytically active domain or enzyme core of the mannanase of the invention or any probe comprising a subsequence shown in positions 94–1086 of SEQ ID NO:9 which subsequence has a length of at least about 100 base pairs under at least medium stringency conditions, but preferably at high stringency conditions as described in detail above; as well as polynucleotides which will hybridize to a denatured double-stranded DNA probe comprising either the full sequence shown in SEQ ID NO:11 or a partial sequence comprising the segment shown in positions 97–993 of SEQ ID NO:11 which segment encodes for the catalytically active domain or enzyme core of the mannanase of the invention or any probe comprising a subsequence shown in positions 97–993 of SEQ ID NO:11 which subsequence has a length of at least about 100 base pairs under at least medium stringency conditions, but preferably at high stringency conditions as described in detail above; as well as polynucleotides which will hybridize to a denatured double-stranded DNA probe comprising either the full sequence shown in SEQ ID NO:13 or a partial sequence comprising the segment shown in positions 498–1464 of SEQ ID NO:13 which segment encodes for the catalytically active domain or enzyme core of the mannanase of the invention or any probe comprising a subsequence shown in positions 498–1464 of SEQ ID NO:13 which subsequence has a length of at least about 100 base pairs under at least medium stringency conditions, but preferably at high stringency conditions as described in detail above; as well as polynucleotides which will hybridize to a denatured double-stranded DNA probe comprising either the full sequence shown in SEQ ID NO:15 or a partial sequence comprising the segment shown in positions 204–1107 of SEQ ID NO:15 which segment encodes for the catalytically active domain or enzyme core of the mannanase of the invention or any probe comprising a subsequence shown in positions 204–1107 of SEQ ID NO:15 which subsequence has a length of at least about 100 base pairs under at least medium stringency conditions, but preferably at high stringency conditions as described in detail above; as well as polynucleotides which will hybridize to a denatured double-stranded DNA probe comprising either the sequence shown in SEQ ID NO:17 or any probe comprising a subsequence of SEQ ID NO:17 which subsequence has a length of at least about 100 base pairs under at least medium stringency conditions, but preferably at high stringency conditions as described in detail above; as well as polynucleotides which will hybridize to a denatured double-stranded DNA probe comprising either the sequence shown in SEQ ID NO:19 or any probe comprising a subsequence of SEQ ID NO:19 which subsequence has a length of at least about 100 base pairs under at least medium stringency conditions, but preferably at high stringency conditions as described in detail above; as well as polynucleotides which will hybridize to a denatured double-stranded DNA probe comprising either the full sequence shown in SEQ ID NO:21 or a partial sequence comprising the segment shown in positions 88–960 of SEQ ID NO:21 which segment encodes for the catalytically active domain or enzyme core of the mannanase of the invention or any probe comprising a subsequence shown in positions 88–960 of SEQ ID NO:21 which subsequence has a length of at least about 100 base pairs under at least medium stringency conditions, but preferably at high stringency conditions as described in detail above; as well as polynucleotides which will hybridize to a denatured double-stranded DNA probe comprising either the full sequence shown in SEQ ID NO:23 or any probe comprising a subsequence of SEQ ID NO:23 which subsequence has a length of at least about 100 base pairs under at least medium stringency conditions, but preferably at high stringency conditions as described in detail above; as well as polynucleotides which will hybridize to a denatured double-stranded DNA probe comprising either the full sequence shown in SEQ ID NO:25 or a partial sequence comprising the segment shown in positions 904–1874 of SEQ ID NO:25 which segment encodes for the catalytically active domain or enzyme core of the mannanase of the invention or any probe comprising a subsequence shown in positions 904–1874 of SEQ ID NO:25 which subsequence has a length of at least about 100 base pairs under at least medium stringency conditions, but preferably at high stringency conditions as described in detail above; as well as polynucleotides which will hybridize to a denatured double-stranded DNA probe comprising either the full sequence shown in SEQ ID NO:27 or a partial sequence comprising the segment shown in positions 498–1488 of SEQ ID NO:27 which segment encodes for the catalytically active domain or enzyme core of the mannanase of the invention or any probe comprising a subsequence shown in positions 498–1488 of SEQ ID NO:27 which subsequence has a length of at least about 100 base pairs under at least medium stringency conditions, but preferably at high stringency conditions as described in detail above; as well as polynucleotides which will hybridize to a denatured double-stranded DNA probe comprising either the full sequence shown in SEQ ID NO:29 or a partial sequence comprising the segment shown in positions 79–1083 of SEQ ID NO:29 which segment encodes for the catalytically active domain or enzyme core of the mannanase of the invention or any probe comprising a subsequence shown in positions 79–1083 of SEQ ID NO:29 which subsequence has a length of at least about 100 base pairs under at least medium stringency conditions, but preferably at high stringency conditions as described in detail above; as well as polynucleotides which will hybridize to a denatured double-stranded DNA probe comprising either the full sequence shown in SEQ ID NO:31 or a partial sequence comprising the segment shown in positions 1779–2709 of SEQ ID NO:31 which segment encodes for the catalytically active domain or enzyme core of the mannanase of the invention or any probe comprising a subsequence shown in positions 1779–2709 of SEQ ID NO:31 which subsequence has a length of at least about 100 base pairs under at least medium stringency conditions, but preferably at high stringency conditions as described in detail above.

As previously noted, the isolated polynucleotides of the present invention include DNA and RNA. Methods for isolating DNA and RNA are well known in the art. DNA and RNA encoding genes of interest can be cloned in Gene Banks or DNA libraries by means of methods known in the art.

Polynucleotides encoding polypeptides having mannanase activity of the invention are then identified and isolated by, for example, hybridization or PCR.

The present invention further provides counterpart polypeptides and polynucleotides from different bacterial strains (orthologs or paralogs). Of particular interest are mannanase polypeptides from gram-positive alkalophilic strains, including species of Bacillus such as Bacillus sp., *Bacillus agaradhaerens, Bacillus halodurans, Bacillus clausii* and *Bacillus licheniformis;* and mannanase polypeptides from Thermoanaerobacter group, including species of Caldicellulosiruptor. Also mannanase polypeptides from the fungus Humicola or Scytalidium, in particular the species *Humicola insolens* or *Scytalidium thermophilum,* are of interest.

Species homologues of a polypeptide with mannanase activity of the invention can be cloned using information and compositions provided by the present invention in combination with conventional cloning techniques. For example, a DNA sequence of the present invention can be cloned using chromosomal DNA obtained from a cell type that expresses the protein. Suitable sources of DNA can be identified by probing Northern or Southern blots with probes designed from the sequences disclosed herein. A library is then prepared from chromosomal DNA of a positive cell line. A DNA sequence of the invention encoding an polypeptide having mannanase activity can then be isolated by a variety of methods, such as by probing with probes designed from the sequences disclosed in the present specification and claims or with one or more sets of degenerate probes based on the disclosed sequences. A DNA sequence of the invention can also be cloned using the polymerase chain reaction, or PCR (Mullis, U.S. Pat. No. 4,683,202), using primers designed from the sequences disclosed herein. Within an additional method, the DNA library can be used to transform or transfect host cells, and expression of the DNA of interest can be detected with an antibody (mono-clonal or polyclonal) raised against the mannanase cloned from B.sp, expressed and purified as described in Materials and Methods and Example 1, or by an activity test relating to a polypeptide having mannanase activity.

The mannanase encoding part of the DNA sequence (SEQ ID NO:1) cloned into plasmid pBXM3 present in *Escherichia coli* DSM 12197 and/or an analogue DNA sequence of the invention may be cloned from a strain of the bacterial species Bacillus sp. I633, or another or related organism as described herein.

The mannanase encoding part of the polynucleotide molecule (the DNA sequence of SEQ ID NO:5) was transformed a strain of the *Escherichia coli* which was deposited by the inventors according to the Budapest Treaty on the International Recognition of the Deposit of Microorganisms for the Purposes of Patent Procedure at the Deutsche Sammlung von Mikroorganismen und Zellkulturen GmbH, Mascheroder Weg 1b, D-38124 Braunschweig, Federal Republic of Germany, on May 18, 1998 under the deposition number DSM 12180; this mannanase encoding part of the polynucleotide molecule (the DNA sequence of SEQ ID NO:5) and/or an analogue DNA sequence thereof may be cloned from a strain of the bacterial species *Bacillus agaradhaerens,* for example from the type strain DSM 8721, or another or related organism as described herein.

The mannanase encoding part of the polynucleotide molecule (the DNA sequence of SEQ ID NO:9) was transformed a strain of the *Escherichia coli* which was deposited by the inventors according to the Budapest Treaty on the International Recognition of the Deposit of Microorganisms for the Purposes of Patent Procedure at the Deutsche Sammlung von Mikroorganismen und Zellkulturen GmbH, Mascheroder Weg 1b, D-38124 Braunschweig, Federal Republic of Germany, on Oct. 7, 1998 under the deposition number DSM 12433; this mannanase encoding part of the polynucleotide molecule (the DNA sequence of SEQ ID NO:9) and/or an analogue DNA sequence thereof may be cloned from a strain of the bacterial species Bacillus sp. AAI12 or another or related organism as described herein.

The mannanase encoding part of the polynucleotide molecule (the DNA sequence of SEQ ID NO:11) was transformed a strain of the *Escherichia coli* which was deposited by the inventors according to the Budapest Treaty on the International Recognition of the Deposit of Microorganisms for the Purposes of Patent Procedure at the Deutsche Sammlung von Mikroorganismen und Zellkulturen GmbH, Mascheroder Weg 1b, D-38124 Braunschweig, Federal Republic of Germany, on Oct. 9, 1998 under the deposition number DSM 12441; this mannanase encoding part of the polynucleotide molecule (the DNA sequence of SEQ ID NO:11) and/or an analogue DNA sequence thereof may be cloned from a strain of the bacterial species *Bacillus halodurans* or another or related organism as described herein.

The mannanase encoding part of the polynucleotide molecule (the DNA sequence of SEQ ID NO:13) was transformed a strain of the *Escherichia coli* which was deposited by the inventors according to the Budapest Treaty on the International Recognition of the Deposit of Microorganisms for the Purposes of Patent Procedure at the Deutsche Sammlung von Mikroorganismen und Zellkulturen GmbH, Mascheroder Weg 1b, D-38124 Braunschweig, Federal Republic of Germany, on May 11, 1995 under the deposition number DSM 9984; this mannanase encoding part of the polynucleotide molecule (the DNA sequence of SEQ ID NO:13) and/or an analogue DNA sequence thereof may be cloned from a strain of the fungal species *Humicola insolens* or another or related organism as described herein.

The mannanase encoding part of the polynucleotide molecule (the DNA sequence of SEQ ID NO:15) was transformed a strain of the *Escherichia coli* which was deposited by the inventors according to the Budapest Treaty on the International Recognition of the Deposit of Microorganisms for the Purposes of Patent Procedure at the Deutsche Sammlung von Mikroorganismen und Zellkulturen GmbH, Mascheroder Weg 1b, D-38124 Braunschweig, Federal Republic of Germany, on Oct. 5, 1998 under the deposition number DSM 12432; this mannanase encoding part of the polynucleotide molecule (the DNA sequence of SEQ ID NO:15) and/or an analogue DNA sequence thereof may be cloned from a strain of the bacterial species Bacillus sp. AA349 or another or related organism as described herein.

The mannanase encoding part of the polynucleotide molecule (the DNA sequence of SEQ ID NO:17) was transformed a strain of the *Escherichia coli* which was deposited by the inventors according to the Budapest Treaty on the International Recognition of the Deposit of Microorganisms for the Purposes of Patent Procedure at the Deutsche Sammlung von Mikroorganismen und Zellkulturen GmbH, Mascheroder Weg 1b, D-38124 Braunschweig, Federal Republic of Germany, on Jun. 4, 1999 under the deposition number DSM 12847; this mannanase encoding part of the polynucleotide molecule (the DNA sequence of SEQ ID NO:17) and/or an analogue DNA sequence thereof may be cloned from a strain of the bacterial species Bacillus sp. or another or related organism as described herein.

The mannanase encoding part of the polynucleotide molecule (the DNA sequence of SEQ ID NO:19) was transformed a strain of the *Escherichia coli* which was deposited by the inventors according to the Budapest Treaty on the International Recognition of the Deposit of Microorganisms for the Purposes of Patent Procedure at the Deutsche Sammlung von Mikroorganismen und Zellkulturen GmbH, Mascheroder Weg 1b, D-38124 Braunschweig, Federal Republic of Germany, on Jun. 4, 1999 under the deposition number DSM 12848; this mannanase encoding part of the polynucleotide molecule (the DNA sequence of SEQ ID NO:19) and/or an analogue DNA sequence thereof may be cloned from a strain of the bacterial species Bacillus sp. or another or related organism as described herein.

The mannanase encoding part of the polynucleotide molecule (the DNA sequence of SEQ ID NO:21) was transformed a strain of the *Escherichia coli* which was deposited by the inventors according to the Budapest Treaty on the International Recognition of the Deposit of Microorganisms for the Purposes of Patent Procedure at the Deutsche Sammlung von Mikroorganismen und Zellkulturen GmbH, Mascheroder Weg 1b, D-38124 Braunschweig, Federal Republic of Germany, on Jun. 4, 1999 under the deposition number DSM 12849; this mannanase encoding part of the polynucleotide molecule (the DNA sequence of SEQ ID NO:21) and/or an analogue DNA sequence thereof may be cloned from a strain of the bacterial species *Bacillus clausii* or another or related organism as described herein.

The mannanase encoding part of the polynucleotide molecule (the DNA sequence of SEQ ID NO:23) was transformed a strain of the *Escherichia coli* which was deposited by the inventors according to the Budapest Treaty on the International Recognition of the Deposit of Microorganisms for the Purposes of Patent Procedure at the Deutsche Sammlung von Mikroorganismen und Zellkulturen GmbH, Mascheroder Weg 1b, D-38124 Braunschweig, Federal Republic of Germany, on Jun. 4, 1999 under the deposition number DSM 12850; this mannanase encoding part of the polynucleotide molecule (the DNA sequence of SEQ ID NO:23) and/or an analogue DNA sequence thereof may be cloned from a strain of the bacterial species Bacillus sp. or another or related organism as described herein.

The mannanase encoding part of the polynucleotide molecule (the DNA sequence of SEQ ID NO:25) was transformed a strain of the *Escherichia coli* which was deposited by the inventors according to the Budapest Treaty on the International Recognition of the Deposit of Microorganisms for the Purposes of Patent Procedure at the Deutsche Sammlung von Mikroorganismen und Zellkulturen GmbH, Mascheroder Weg 1b, D-38124 Braunschweig, Federal Republic of Germany, on Jun. 4, 1999 under the deposition number DSM 12846; this mannanase encoding part of the polynucleotide molecule (the DNA sequence of SEQ ID NO:25) and/or an analogue DNA sequence thereof may be cloned from a strain of the bacterial species Bacillus sp. or another or related organism as described herein.

The mannanase encoding part of the polynucleotide molecule (the DNA sequence of SEQ ID NO:27) was transformed a strain of the *Escherichia coli* which was deposited by the inventors according to the Budapest Treaty on the International Recognition of the Deposit of Microorganisms for the Purposes of Patent Procedure at the Deutsche Sammlung von Mikroorganismen und Zellkulturen GmbH, Mascheroder Weg 1b, D-38124 Braunschweig, Federal Republic of Germany, on Jun. 4, 1999 under the deposition number DSM 12851; this mannanase encoding part of the polynucleotide molecule (the DNA sequence of SEQ ID NO:27) and/or an analogue DNA sequence thereof may be cloned from a strain of the bacterial species Bacillus sp. or another or related organism as described herein.

The mannanase encoding part of the polynucleotide molecule (the DNA sequence of SEQ ID NO:29) was transformed a strain of the *Escherichia coli* which was deposited by the inventors according to the Budapest Treaty on the International Recognition of the Deposit of Microorganisms for the Purposes of Patent Procedure at the Deutsche Sammlung von Mikroorganismen und Zellkulturen GmbH, Mascheroder Weg 1b, D-38124 Braunschweig, Federal Republic of Germany, on Jun. 4, 1999 under the deposition number DSM 12852; this mannanase encoding part of the polynucleotide molecule (the DNA sequence of SEQ ID NO:29) and/or an analogue DNA sequence thereof may be cloned from a strain of the bacterial species *Bacillus licheniformis* or another or related organism as described herein.

The mannanase encoding part of the polynucleotide molecule (the DNA sequence of SEQ ID NO:31) was transformed a strain of the *Escherichia coli* which was deposited by the inventors according to the Budapest Treaty on the International Recognition of the Deposit of Microorganisms for the Purposes of Patent Procedure at the Deutsche Sammlung von Mikroorganismen und Zellkulturen GmbH, Mascheroder Weg 1b, D-38124 Braunschweig, Federal Republic of Germany, on Oct. 5, 1998 under the deposition number DSM 12436; this mannanase encoding part of the polynucleotide molecule (the DNA sequence of SEQ ID NO:31) and/or an analogue DNA sequence thereof may be cloned from a strain of the bacterial species Caldicellulosiruptor sp. or another or related organism as described herein.

Alternatively, the analogous sequence may be constructed on the basis of the DNA sequence obtainable from the plasmid present in *Escherichia coli* DSM 12197 (which is believed to be identical to the attached SEQ ID NO:1), the plasmid present in *Escherichia coli* DSM 12180 (which is believed to be identical to the attached SEQ ID NO:5), the plasmid present in *Escherichia coli* DSM 12433 (which is believed to be identical to the attached SEQ ID NO:9), the plasmid present in *Escherichia coli* DSM 12441 (which is believed to be identical to the attached SEQ ID NO:11), the plasmid present in *Escherichia coli* DSM 9984 (which is believed to be identical to the attached SEQ ID NO:13), the plasmid present in *Escherichia coli* DSM 12432 (which is believed to be identical to the attached SEQ ID NO:15), the plasmid present in *Escherichia coli* DSM 12847 (which is believed to be identical to the attached SEQ ID NO:17), the plasmid present in *Escherichia coli* DSM 12848 (which is believed to be identical to the attached SEQ ID NO:19), the plasmid present in *Escherichia coli* DSM 12849 (which is believed to be identical to the attached SEQ ID NO:21), the plasmid present in *Escherichia coli* DSM 12850 (which is believed to be identical to the attached SEQ ID NO:23), the plasmid present in *Escherichia coli* DSM 12846 (which is believed to be identical to the attached SEQ ID NO:25), the plasmid present in *Escherichia coli* DSM 12851 (which is believed to be identical to the attached SEQ ID NO:27), the plasmid present in *Escherichia coli* DSM 12852 (which is believed to be identical to the attached SEQ ID NO:29) or the plasmid present in *Escherichia coli* DSM 12436 (which is believed to be identical to the attached SEQ ID NO:31), e.g. be a subsequence thereof, and/or by introduction of nucleotide substitutions which do not give rise to another amino acid sequence of the mannanase encoded by the DNA sequence, but which corresponds to the codon usage of the host organism intended for production of the enzyme, or by introduction of nucleotide substitutions which may give rise to a different amino acid sequence (i.e. a variant of the mannan degrading enzyme of the invention).

Polypeptides

The sequence of amino acids in positions 32–490 of SEQ ID NO: 2 is a mature mannanase sequence. The sequence of amino acids nos. 1–31 of SEQ ID NO: 2 is the signal peptide. It is believed that the subsequence of amino acids in positions 32–330 of SEQ ID NO:2 is the catalytic domain of the mannanase enzyme and that the mature enzyme additionally comprises a linker in positions 331–342 and at least one C-terminal domain of unknown function in positions 343–490. Since the object of the present invention is to obtain a polypeptide which exhibits mannanase activity, the present invention relates to any mannanase enzyme comprising the sequence of amino acids nos. 32–330 of SEQ ID NO: 2, i.e. a catalytical domain, optionally operably linked, either N-terminally or C-terminally, to one or two or more than two other domains of a different functionality. The domain having the subsequence of amino acids nos. 343–490 of SEQ ID NO: 2 is a domain of the mannanase enzyme of unknown function, this domain being highly homologous with similar domains in known mannanases, cf. example 1.

The sequence of amino acids in positions 32–494 of SEQ ID NO:6 is a mature mannanase sequence. The sequence of amino acids nos. 1–31 of SEQ ID NO:6 is the signal peptide. It is believed that the subsequence of amino acids in positions 32–344 of SEQ ID NO:6 is the catalytic domain of the mannanase enzyme and that the mature enzyme additionally comprises at least one C-terminal domain of unknown function in positions 345–494. Since the object of the present invention is to obtain a polypeptide which exhibits mannanase activity, the present invention relates to any mannanase enzyme comprising the sequence of amino acids nos. 32–344 of SEQ ID NO:6, ie a catalytical domain, optionally operably linked, either N-terminally or C-terminally, to one or two or more than two other domains of a different functionality.

The sequence of amino acids in positions 32–586 of SEQ ID NO:10 is a mature mannanase sequence. The sequence of amino acids nos. 1–31 of SEQ ID NO:10 is the signal peptide. It is believed that the subsequence of amino acids in positions 32–362 of SEQ ID NO:10 is the catalytic domain of the mannanase enzyme and that the mature enzyme additionally comprises at least one C-terminal domain of unknown function in positions 363–586.

Since the object of the present invention is to obtain a polypeptide which exhibits mannanase activity, the present invention relates to any mannanase enzyme comprising the sequence of amino acids nos. 32-326 of SEQ ID NO: 10, ie a catalytical domain, optionally operably linked, either N-terminally or C-terminally, to one or two or more than two other domains of a different functionality.

The sequence of amino acids in positions 33-331 of SEQ ID NO:12 is a mature mannanase sequence. The sequence of amino acids nos. 1-32 of SEQ ID NO:12 is the signal peptide. It is believed that the subsequence of amino acids in positions 33-331 of SEQ ID NO:12 is the catalytic domain of the mannanase enzyme. This mannanase enzyme core comprising the sequence of amino acids nos. 33-331 of SEQ ID NO: 12, ie a catalytical domain, may or may not be operably linked, either N-terminally or C-terminally, to one or two or more than two other domains of a different functionality, ie being part of a fusion protein.

The sequence of amino acids in positions 22-488 of SEQ ID NO:14 is a mature mannanase sequence. The sequence of amino acids nos. 1-21 of SEQ ID NO:14 is the signal peptide. It is believed that the subsequence of amino acids in positions 166-488 of SEQ ID NO:14 is the catalytic domain of the mannanase enzyme and that the mature enzyme additionally comprises at least one N-terminal domain of unknown function in positions 22-164. Since the object of the present invention is to obtain a polypeptide which exhibits mannanase activity, the present invention relates to any mannanase enzyme comprising the sequence of amino acids nos. 166-488 of SEQ ID NO:14, ie a catalytical domain, optionally operably linked, either N-terminally or C-terminally, to one or two or more than two other domains of a different functionality.

The sequence of amino acids in positions 26-369 of SEQ ID NO:16 is a mature mannanase sequence. The sequence of amino acids nos. 1-25 of SEQ ID NO:16 is the signal peptide. It is believed that the subsequence of amino acids in positions 68-369 of SEQ ID NO:16 is the catalytic domain of the mannanase enzyme and that the mature enzyme additionally comprises at least one N-terminal domain of unknown function in positions 26-67. Since the object of the present invention is to obtain a polypeptide which exhibits mannanase activity, the present invention relates to any mannanase enzyme comprising the sequence of amino acids nos. 68-369 of SEQ ID NO:16, ie a catalytical domain, optionally operably linked, either N-terminally or C-terminally, to one or two or more than two other domains of a different functionality.

The sequence of amino acids of SEQ ID NO:18 is a partial sequence forming part of a mature mannanase sequence. The present invention relates to any mannanase enzyme comprising the sequence of amino acids nos. 1-305 of SEQ ID NO:18.

The sequence of amino acids of SEQ ID NO:20 is a partial sequence forming part of a mature mannanase sequence. The present invention relates to any mannanase enzyme comprising the sequence of amino acids nos. 1-132 of SEQ ID NO:20.

The sequence of amino acids in positions 29-320 of SEQ ID NO:22 is a mature mannanase sequence. The sequence of amino acids nos. 1-28 of SEQ ID NO:22 is the signal peptide. It is believed that the subsequence of amino acids in positions 29-320 of SEQ ID NO:22 is the catalytic domain of the mannanase enzyme. This mannanase enzyme core comprising the sequence of amino acids nos. 29-320 of SEQ ID NO:22, ie a catalytic domain, may or may not be operably linked, either N-terminally or C-terminally, to one or two or more than two other domains of a different functionality, ie being part of a fusion protein.

The sequence of amino acids of SEQ ID NO:24 is a partial sequence forming part of a mature mannanase sequence. The present invention relates to any mannanase enzyme comprising the sequence of amino acids nos. 29-188 of SEQ ID NO:24.

The sequence of amino acids in positions 30-815 of SEQ ID NO:26 is a mature mannanase sequence. The sequence of amino acids nos. 1-29 of SEQ ID NO:26 is the signal peptide. It is believed that the subsequence of amino acids in positions 301-625 of SEQ ID NO:26 is the catalytic domain of the mannanase enzyme and that the mature enzyme additionally comprises at least two N-terminal domain of unknown function in positions 44-166 and 195-300, respectively, and a C-terminal domain of unknown function in positions 626-815. Since the object of the present invention is to obtain a polypeptide which exhibits mannanase activity, the present invention relates to any mannanase enzyme comprising the sequence of amino acids nos. 301-625 of SEQ ID NO:26, ie a catalytical domain, optionally operably linked, either N-terminally or C-terminally, to one or two or more than two other domains of a different functionality.

The sequence of amino acids in positions 38-496 of SEQ ID NO:28 is a mature mannanase sequence. The sequence of amino acids nos. 1-37 of SEQ ID NO:28 is the signal peptide. It is believed that the subsequence of amino acids in positions 166-496 of SEQ ID NO:28 is the catalytic domain of the mannanase enzyme and that the mature enzyme additionally comprises at least one N-terminal domain of unknown function in positions 38-165. Since the object of the present invention is to obtain a polypeptide which exhibits mannanase activity, the present invention relates to any mannanase enzyme comprising the sequence of amino acids nos. 166-496 of SEQ ID NO:28, ie a catalytical domain, optionally operably linked, either N-terminally or C-terminally, to one or two or more than two other domains of a different functionality.

The sequence of amino acids in positions 26-361 of SEQ ID NO:30 is a mature mannanase sequence. The sequence of amino acids nos. 1-25 of SEQ ID NO:30 is the signal peptide. It is believed that the subsequence of amino acids in positions 26-361 of SEQ ID NO:30 is the catalytic domain of the mannanase enzyme. This mannanase enzyme core comprising the sequence of amino acids nos. 26-361 of SEQ ID NO:30, ie a catalytical domain, may or may not be optionally operably linked, either N-terminally or C-terminally, to one or two or more than two other domains of a different functionality.

The sequence of amino acids in positions 23-903 of SEQ ID NO:32 is a mature mannanase sequence. The sequence of amino acids nos. 1-22 of SEQ ID NO:32 is the signal peptide. It is believed that the subsequence of amino acids in positions 593-903 of SEQ ID NO:32 is the catalytic domain of the mannanase enzyme and that the mature enzyme additionally comprises at least three N-terminally domains of unknown function in positions 23-214, 224-424 and 434-592, respectively. Since the object of the present invention is to obtain a polypeptide which exhibits mannanase activity, the present invention relates to any mannanase enzyme comprising the sequence of amino acids nos. 593-903 of SEQ ID NO:32, ie a catalytical domain, optionally operably linked, either N-terminally or C-terminally, to one or two or more than two other domains of a different functionality.

The present invention also provides mannanase polypeptides that are substantially homologous to the polypeptides of SEQ ID NO:2, SEQ ID NO:6, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30 and SEQ ID NO:32, respectively, and species homologs (paralogs or orthologs) thereof. The term "substantially homologous" is used herein to denote polypeptides having 65%, preferably at least 70%, more preferably at least 75%, more preferably at least 80%, more preferably at least 85%, and even more preferably at least 90%, sequence identity to the sequence shown in amino acids nos. 32-330 or nos. 32-490 of SEQ ID NO:2 or their orthologs or paralogs; or to the sequence shown in amino acids nos. 32-344 or nos. 32-494 of SEQ ID NO:6 or their orthologs or paralogs; or to the sequence shown in amino acids nos. 32-362 or nos. 32-586 of SEQ ID NO:10 or their orthologs or paralogs; or to the sequence shown in amino acids nos. 33-331 of SEQ ID NO:12 or its orthologs or paralogs; or to the sequence shown in amino acids nos. 166-488 or nos. 22-488 of SEQ ID NO:14 or their orthologs or paralogs; or to the sequence shown in amino acids nos. 68-369 or nos. 32 -369 of SEQ ID NO:16 or their orthologs or paralogs; or to the sequence shown in amino acids nos. 1-305 of SEQ ID NO:18 or its orthologs or paralogs; or to the sequence shown in amino acids nos. 1-132 of SEQ ID NO:20 or its orthologs or paralogs; or to the sequence shown in amino acids nos. 29-320 of SEQ ID NO:22 or its orthologs or paralogs; or to the sequence shown in amino acids nos. 29-188 of SEQ ID NO:24 or its orthologs or paralogs; or to the sequence shown in amino acids nos. 301-625 or nos. 30-625 of SEQ ID NO:26 of their orthologs or paralogs; or to the sequence shown in amino acids nos. 166-496 or nos. 38-496 of SEQ ID NO:28 or their orthologs or paralogs; or to the sequences shown in amino acids nos. 26-361 of SEQ ID NO:30 or its orthologs or paralogs; or to the sequence shown in amino acids nos. 593-903 or nos. 23-903 of SEQ ID NO:32 or their orthologs or paralogs.

Such polypeptides will more preferably be at least 95% identical, and most preferably 98% or more identical to the sequence shown in amino acids nos. 32-330 or nos. 32-490 of SEQ ID NO:2 or its orthologs or paralogs; or to the sequence shown in amino acids nos. 32-344 or nos. 32-494 of SEQ ID NO:6 or its orthologs or paralogs; or to the sequence shown in amino acids nos. 32-362 or nos. 32-586 of SEQ ID NO:10 or its orthologs or paralogs; or to the sequence shown in amino acids nos. 33-331 of SEQ ID NO:12 or its orthologs or paralogs; or to the sequence shown in amino acids nos. 166-488 or nos. 22-488 of SEQ ID NO:14 or its orthologs or paralogs; or to the sequence shown in amino acids nos. 68-369 or nos. 32-369 of SEQ ID NO:16 or its orthologs or paralogs; or to the sequence shown in amino acids nos. 1-305 of SEQ ID NO:18 or its orthologs or paralogs; or to the sequence shown in amino acids nos. 1-132 of SEQ ID NO:20 or its orthologs or paralogs; or to the sequence shown in amino acids nos. 29-320 of SEQ ID NO:22 or its orthologs or paralogs; or to the sequence shown in amino acids nos. 29-188 of SEQ ID NO:24 or its orthologs or paralogs; or to the sequence shown in amino acids nos. 301-625 or nos. 30-625 of SEQ ID NO:26 or its orthologs or paralogs; or to the sequence shown in amino acids nos. 166-496 or nos. 38-496 of SEQ ID NO:28 or its orthologs or paralogs; or to the sequence shown in amino acids nos. 26-361 of SEQ ID NO:30 or its orthologs or paralogs; or to the sequence shown in amino acids nos. 593-903 or nos. 23-903 of SEQ ID NO:32 or its orthologs or paralogs.

Percent sequence identity is determined by conventional methods, by means of computer programs known in the art such as GAP provided in the GCG program package (Program Manual for the Wisconsin Package, Version 8, August 1994, Genetics Computer Group, 575 Science Drive, Madison, Wis., USA 53711) as disclosed in Needleman, S. B. and Wunsch, C. D., (1970), Journal of Molecular Biology, 48, 443–453, which is hereby incorporated by reference in its entirety. GAP is used with the following settings for polypeptide sequence comparison: GAP creation penalty of 3.0 and GAP extension penalty of 0.1.

Sequence identity of polynucleotide molecules is determined by similar methods using GAP with the following settings for DNA sequence comparison: GAP creation penalty of 5.0 and GAP extension penalty of 0.3.

The enzyme preparation of the invention is preferably derived from a microorganism, preferably from a bacterium, an archea or a fungus, especially from a bacterium such as a bacterium belonging to Bacillus, preferably to a Bacillus strain which may be selected from the group consisting of the species Bacillus sp. and highly related Bacillus species in which all species preferably are at least 95%, even more preferably at least 98%, homologous to Bacillus sp. I633, Bacillus halodurans or Bacillus sp. AAI12 based on aligned 16 S rDNA sequences.

These species are claimed based on phylogenic relationships identifed from aligned 16 S rDNA sequences from RDP (Ribosomal Database Project) (Bonne L. Maidak, Neils Larson, Michael J. McCaughey, Ross Overbeek, Gary J. Olsen, Karl Fogel, James Blandy, and Carl R. Woese, Nucleic Acids Reasearch, 1994, Vo. 22, No17, p. 3485–3487, The Ribosomal Database Project). The alignment was based on secondary structure. Calculation of sequence similarities were established using the "Full matrix calculation" with default settings of the neighbor joining method integrated in the ARB program package (Oliver Strunk and Wolfgang Ludwig, Technical University of Munich, Germany).

Information derived from table II are the basis for the claim for all family 5 mannanases from the highly related Bacillus species in which all species over 93% homologous to Bacillus sp. I633 are claimed. These include: *Bacillus sporothermodurans, Bacillus acalophilus, Bacillus pseudoalcalophilus* and *Bacillus clausii*. See FIG. 1: Phylogenic tree generated from ARP program relating closest species to Bacillus sp. I633. The 16 S RNA is shown in SEQ ID NO:33.

TABLE II

| 16S ribosomal RNA homology index for select Bacillus species | | | | |
|---|---|---|---|---|
| | BaiSpor2 | BaiAlcal | BaiSpec3 | BaiSpec5 | B.sp.I633 |
| BaiSpor2 | | 92.75% | 92.98% | 92.41% | 93.43% |
| BaiAlcal | | | 98.11% | 94.69% | 97.03% |
| BaiSpec3 | | | | 94.49% | 96.39% |
| BaiSpec5 | | | | | 93.67% |

BaiSpor2 = *B sporothermodurans*, u49079
BaiAlcal = *B. B. alcalophilus*, x76436
BaiSpec3 = *B. pseudoalcalophilus*, x76449
BaiSpec5 = *B clausii*, x76440

Figure 2:
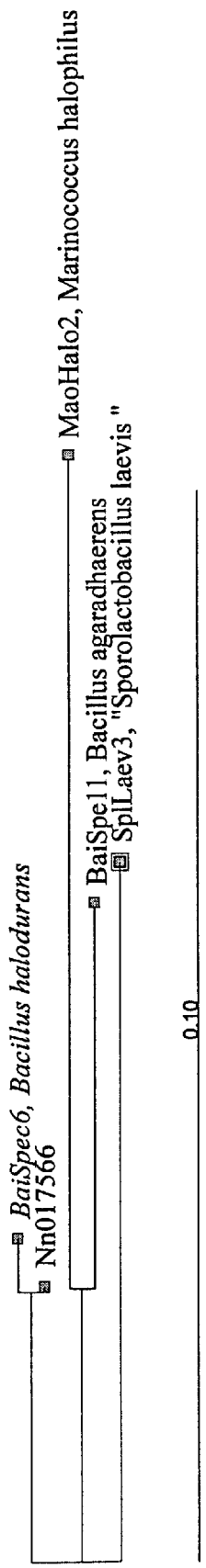
FIG. 2 shows a phylogenic tree generated from ARP program relating closest species to *Bacillus halodurans*.

Other useful family 5 mannanases are those derived from the highly related Bacillus species in which all species show more than 93% homology to *Bacillus halodurans* based on aligned 16 S sequences. These Bacillus species included: *Sporolactobacillus laevis, Bacillus agaradhaerens* and *Marinococcus halophilus*. See FIG. 2: Phylogenic tree generated from ARP program relating closest species to *Bacillus halodurans*.

TABLE III

| 16S ribosomal RNA homology index for selected Bacillus species | | | | |
|---|---|---|---|---|
| | SplLaev3 | BaiSpec6 | BaiSpe11 | MaoHalo2 | NN |
| SplLaev3 | | 90.98% | 87.96% | 85.94% | 91.32% |
| BaiSpec6 | | | 91.63% | 87.96% | 99.46% |
| BaiSpe11 | | | | 89.04% | 92.04% |
| MaoHalo2 | | | | | 88.17% |
| NN | | | | | |

SplLaev3 = *Sporolactobacillus laevis*, D16287
BaiSpec6 = *B. halodurans*, X76442
BaiSpe11 = *B. agaradhaerens*, X76445
MaoHalo2 = *Marinococcus halophilus*, X62171
NN = donor organism of the invention (*B. halodurans*)

Other useful family 5 mannanases are those derived from a strain selected from the group consisting of the species *Bacillus agaradhaerens* and highly related Bacillus species in which all species preferably are at least 95%, even more preferably at least 98%, homologous to *Bacillus agaradhaerens*, DSM 8721, based on aligned 16 S rDNA sequences.

Figure 3:
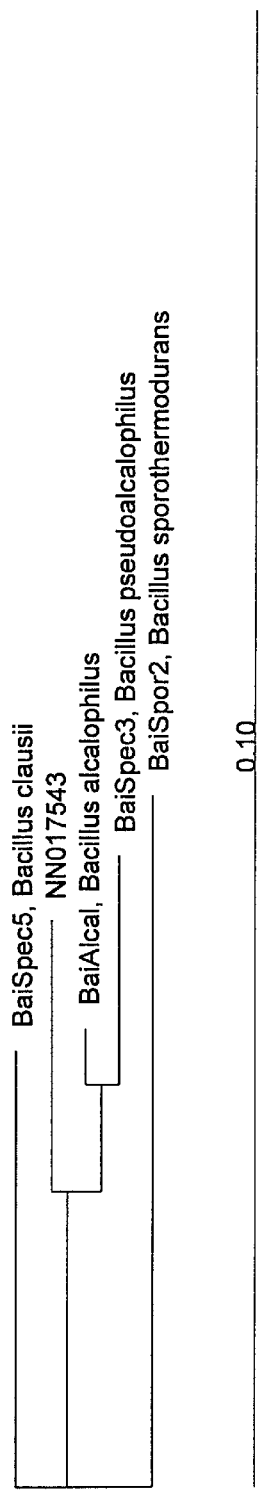
FIG. 3 shows a phylogenic tree generated from ARP program relating closest species to Bacillus sp. AAI 12.

Useful family 26 mannanases are for example those derived from the highly related Bacillus species in which all species over 93% homologous to Bacillus sp. AAI12 are claimed. These included: *Bacillus sporothermodurans, Bacillus acalophilus, Bacillus pseudoalcalophilus* and *Bacillus clausii*. See FIG. 3: Phylogenic tree generated from ARP program relating closest species to Bacillus sp. AAI 12. The 16 S RNA is shown in SEQ ID NO:34.

TABLE IV

| 16S ribosomal RNA homology index for selected Bacillus species | | | | |
|---|---|---|---|---|
| | BaiSpor2 | BaiAlcal | BaiSpec3 | BaiSpec5 | B.sp.AAI12 |
| BaiSpor2 | | 92.75% | 92.98% | 92.41% | 92.24% |
| BaiAlcal | | | 98.11% | 94.69% | 97.28% |
| BaiSpec3 | | | | 94.49% | 96.10% |
| BaiSpec5 | | | | | 93.83% |

BaiSpor2 = *B sporothermodurans*, u49079
BaiAlcal = *B. B. alcalophilus*, x76436
BaiSpec3 = *B. pseudoalcalophilus*, x76449
BaiSpec5 = *B clausii*, x76440

Other useful family 26 mannanases are those derived from a strain selected from the group consisting of the species *Bacillus licheniformis* and highly related Bacillus species in which all species preferably are at least 95%, even more preferably at least 98%, homologous to *Bacillus licheniformis* based on aligned 16 S rDNA sequences.

Substantially homologous proteins and polypeptides are characterized as having one or more amino acid substitutions, deletions or additions. These changes are preferably of a minor nature, that is conservative amino acid substitutions (see Table 2) and other substitutions that do not significantly affect the folding or activity of the protein or polypeptide; small deletions, typically of one to about 30 amino acids; and small amino- or carboxyl-terminal extensions, such as an amino-terminal methionine residue, a small linker peptide of up to about 20–25 residues, or a small extension that facilitates purification (an affinity tag), such as a poly-histidine tract, protein A (Nilsson et al., *EMBO J.* 4:1075, 1985; Nilsson et al., *Methods Enzymol.* 198:3, 1991. See, in general Ford et al., *Protein Expression and Purification* 2: 95–107, 1991, which is incorporated herein by reference. DNAs encoding affinity tags are available from commercial suppliers (e.g., Pharmacia Biotechs, Piscataway, N.J.; New England Biolabs, Beverly, Mass.).

However, even though the changes described above preferably are of a minor nature, such changes may also be of a larger nature such as fusion of larger polypeptides of up to 300 amino acids or more both as amino- or carboxyl-terminal extensions to a Mannanase polypeptide of the invention.

TABLE 1

Conservative amino acid substitutions

| | |
|---|---|
| Basic: | arginine |
| | lysine |
| | histidine |
| Acidic: | glutamic acid |
| | aspartic acid |
| Polar: | glutamine |
| | asparagine |
| Hydrophobic: | leucine |
| | isoleucine |
| | valine |
| Aromatic: | phenylalanine |
| | tryptophan |
| | tyrosine |
| Small: | glycine |
| | alanine |
| | serine |
| | threonine |
| | methionine |

In addition to the 20 standard amino acids, non-standard amino acids (such as 4-hydroxyproline, 6-N-methyl lysine, 2-aminoisobutyric acid, isovaline and a-methyl serine) may be substituted for amino acids residues of a polypeptide according to the invention. A limited number of non-conservative amino acids, amino acids that are not encoded by the genetic code, and unnatural amino acids may be substituted for amino acid residues. "Unnatural amino acids" have been modified after protein synthesis, and/or have a chemical structure in their side chain(s) different from that of the standard amino acids. Unnatural amino acids can be chemically synthesized, or preferably, are commercially available, and include pipecolic acid, thiazolidine carboxylic acid, dehydroproline, 3- and 4-methylproline, and 3,3-dimethylproline.

Essential amino acids in the mannanase polypeptides of the present invention can be identified according to procedures known in the art, such as site-directed mutagenesis or alanine-scanning mutagenesis (Cunningham and Wells, *Science* 244: 1081–1085, 1989). In the latter technique, single alanine mutations are introduced at every residue in the molecule, and the resultant mutant molecules are tested for biological activity (i.e mannanase activity) to identify amino acid residues that are critical to the activity of the molecule. See also, Hilton et al., *J. Biol. Chem.* 271:4699–4708, 1996. The active site of the enzyme or other biological interaction can also be determined by physical analysis of structure, as determined by such techniques as nuclear magnetic resonance, crystallography, electron diffraction or photoaffinity labeling, in conjunction with mutation of putative contact site amino acids. See, for example, de Vos et al., *Science* 255:306–312, 1992; Smith et al., *J. Mol. Biol.* 224:899–904, 1992; Wlodaver et al., *FEBS lett.* 309:59–64, 1992. The identities of essential amino acids can also be inferred from analysis of homologies with polypeptides which are related to a polypeptide according to the invention.

Multiple amino acid substitutions can be made and tested using known methods of mutagenesis, recombination and/or shuffling followed by a relevant screening procedure, such as those disclosed by Reidhaar-Olson and Sauer (*Science* 241:53–57, 1988), Bowie and Sauer (*Proc. Natl. Acad. Sci. USA* 86: 2152–2156, 1989), WO95/17413, or WO 95/22625. Briefly, these authors disclose methods for simultaneously randomizing two or more positions in a polypeptide, or recombination/shuffling of different mutations (WO95/17413, WO95/22625), followed by selecting for functional a polypeptide, and then sequencing the mutagenized polypeptides to determine the spectrum of allowable substitutions at each position. Other methods that can be used include phage display (e.g., Lowman et al., *Biochem.* 30:10832–10837, 1991; Ladner et al., U.S. Pat. No. 5,223,409; Huse, WIPO Publication WO 92/06204) and region-directed mutagenesis (Derbyshire et al., *Gene* 46:145, 1986; Ner et al., *DNA* 7:127, 1988).

Mutagenesis/shuffling methods are disclosed above can be combined with high-throughput, automated screening methods to detect activity of cloned, mutagenized polypeptides in host cells. Mutagenized DNA molecules that encode active polypeptides can be recovered from the host cells and rapidly sequenced using modern equipment. These methods allow the rapid determination of the importance of individual amino acid residues in a polypeptide of interest, and can be applied to polypeptides of unknown structure.

Using the methods discussed above, one of ordinary skill in the art can identify and/or prepare a variety of polypeptides that are substantially homologous to residues 32–330 or 32–490 of SEQ ID NO:2; or to residues 32–344 or 32–494 of SEQ ID NO:6; or to residues 32–362 or 32–586 of SEQ ID NO:10; or to residues 33–331 of SEQ ID NO:12; or to residues 166–488 or 22–488 of SEQ ID NO:14, or to residues 68–369 or 32–369 of SEQ ID NO:16; or to residues 1–305 of SEQ ID NO:18; or to residues 1–132 of SEQ ID NO:20; or to residues 29–320 of SEQ ID NO:22; or to residues 29–188 of SEQ ID NO:24; or to residues 301–625 or 30–625 of SEQ ID NO:26; or to residues 166–496 or 38–496 of SEQ ID NO:28; or to residues 26–361 of SEQ ID NO:30; or to residues 593–903 or 23–903 of SEQ ID NO:32 and retain the mannanase activity of the wild-type protein.

The mannanase enzyme of the invention may, in addition to the enzyme core comprising the catalytically domain, also comprise a cellulose binding domain (CBD), the cellulose binding domain and enzyme core (the catalytically active domain) of the enzyme being operably linked. The cellulose binding domain (CBD) may exist as an integral part of the encoded enzyme, or a CBD from another origin may be introduced into the mannan degrading enzyme thus creating an enzyme hybrid. In this context, the term "cellulose-binding domain" is intended to be understood as defined by Peter Tomme et al. "Cellulose-Binding Domains: Classification and Properties" in "Enzymatic Degradation of Insoluble Carbohydrates", John N. Saddler and Michael H. Penner (Eds.), ACS Symposium Series, No. 618, 1996. This definition classifies more than 120 cellulose-binding domains into 10 families (I-X), and demonstrates that CBDs are found in various enzymes such as cellulases, xylanases, mannanases, arabinofuranosidases, acetyl esterases and chitinases. CBDs have also been found in algae, e.g. the red alga *Porphyra purpurea* as a non-hydrolytic polysaccharide-binding protein, see Tomme et al., op.cit. However, most of the CBDs are from cellullases and yxlanases, CBDs are found at the N and C termini of proteins or are internal. Enzyme hybrids are known in the art, see e.g. WO 90/00609 and WO 95/16782, and may be prepared by transforming into a host cell a DNA construct comprising at least a fragment of DNA encoding the cellulose-binding domain ligated, with or without a linker, to a DNA sequence encoding the mannan degrading enzyme and growing the host cell to express the fused gene. Enzyme hybrids may be described by the following formula:

CBD-MR-X wherein CBD is the N-terminal or the C-terminal region of an amino acid sequence corresponding to at least the cellulose-binding domain; MR is the middle region (the linker), and may be a bond, or a short linking group preferably of from about 2 to about 100 carbon atoms, more preferably of from 2 to 40 carbon atoms; or is preferably from about 2 to to about 100 amino acids, more preferably of from 2 to 40 amino acids; and X is an N-terminal or C-terminal region of the mannanase of the invention. SEQ ID NO:4 discloses the amino acid sequence of an enzyme hybrid of a mannanase enzyme core and a CBD.

Preferably, the mannanase enzyme of the present invention has its maximum catalytic activity at a pH of at least 7, more preferably of at least 8, more preferably of at least 8.5, more preferably of at least 9, more preferably of at least 9.5, more preferably of at least 10, even more preferably of at least 10.5, especially of at least 11; and preferably the maximum activity of the enzyme is obtained at a temperature of at least 40° C., more preferably of at least 50° C., even more preferably of at least 55° C.

Preferably, the cleaning composition of the present invention provides, eg when used for treating fabric during a washing cycle of a machine washing process, a washing solution having a pH typically between about 8 and about 10.5. Typically, such a washing solution is used at temperatures between about 20° C. and about 95° C., preferably between about 20° C. and about 60° C., preferably between about 20° C. and about 50° C.

Protein Production

The proteins and polypeptides of the present invention, including full-length proteins, fragments thereof and fusion proteins, can be produced in genetically engineered host cells according to conventional techniques. Suitable host cells are those cell types that can be transformed or transfected with exogenous DNA and grown in culture, and include bacteria, fungal cells, and cultured higher eukaryotic cells. Bacterial cells, particularly cultured cells of gram-positive organisms, are preferred. Gram-positive cells from the genus of Bacillus are especially preferred, such as from the group consisting of *Bacillus subtilis, Bacillus lentus, Bacillus clausii, Bacillus agaradhaerens, Bacillus brevis, Bacillus stearothermophilus, Bacillus alkalophilus, Bacillus amyloliquefaciens, Bacillus coagulans, Bacillus circulans, Bacillus lautus, Bacillus thuringiensis, Bacillus licheniformis,* and Bacillus sp., in particular Bacillus sp. I633, Bacillus sp. AAI12, *Bacillus clausii, Bacillus agaradhaerens* and *Bacillus licheniformis.*

In another preferred embodiment, the host cell is a fungal cell. "Fungi" as used herein includes the phyla Ascomycota, Basidiomycota, Chytridiomycota, and Zygomycota (as defined by Hawksworth et al., In, *Ainsworth and Bisby's Dictionary of The Fungi,* 8 th edition, 1995, CAB International, University Press, Cambridge, UK) as well as the Oomycota (as cited in Hawksworth et al., 1995, supra, page 171) and all mitosporic fungi (Hawksworth et al., 1995, supra). Representative groups of Ascomycota include, e.g., Neurospora, Eupenicillium (=Penicillium), Emericella (=Aspergillus), Eurotium (=Aspergillus), and the true yeasts listed above. Examples of Basidiomycota include mushrooms, rusts, and smuts. Representative groups of Chytridiomycota include, e.g., Allomyces, Blastocladiella, Coelomomyces, and aquatic fungi. Representative groups of Oomycota include, e.g., Saprolegniomycetous aquatic fungi (water molds) such as Achlya. Examples of mitosporic fungi include Aspergillus, Penicilluim, Candida, and Alternaria. Representative groups of Zygomycota include, e.g., Rhizopus and Mucor.

In yet another preferred embodiment, the fungal host cells is a filamentous fungal cell. "Filamentous fungi" include all filamentous forms of the subdivision Eumycota and Oomycota (as defined by Hawksworth et al., 1995, supra). In a more preferred embodiment, the filamentous fungal host cell is a cell of a species of, but not limited to, Acremonium, Aspergillus, Fusarium, Humicola, Mucor, Myceliophthora, Neurospora, Penicillium, Thielavia, Tolypocladium, and Trichoderma or a teleomorph or synonym thereof.

In particular, the cell may belong to a species of Trichoderma, preferably *Trichoderma harzianum* or *Trichoderma reesei,* or a species of Aspergillus, most preferably *Aspergillus oryzae* or *Aspergillus niger,* or a species of Fusarium, most preferably a Fusarium sp. having the identifying characteristic of Fusarium ATCC 20334, as further described in PCT/US/95/07743.

Fungal cells may be transformed by a process involving protoplast formation, transformation of the protoplasts, and regeneration of the cell wall in a manner known per se. Suitable procedures for transformation of Aspergillus host cells are described in EP 238 023 and Yelton et al., 1984, *Proceedings of the National Academy of Sciences USA* 81:1470–1474. A suitable method of transforming Fusarium species is described by Malardier et al., 1989, *Gene* 78:147–156 or in copending U.S. Ser. No. 08/269,449. Yeast may be transformed using the procedures described by Becker and Guarente, In Abelson, J. N. and Simon, M. I., editors, *Guide to Yeast Genetics and Molecular Biology,* Methods in Enzymology, Volume 194, pp 182–187, Academic Press, Inc., New York; Ito et al., 1983, *Journal of Bacteriology* 153:163; and Hinnen et al., 1978, *Proceedings of the National Academy of Sciences USA* 75:1920. Mammalian cells may be transformed by direct uptake using the calcium phosphate precipitation method of Graham and Van der Eb (1978, *Virology* 52:546).

Techniques for manipulating cloned DNA molecules and introducing exogenous DNA into a variety of host cells are disclosed by Sambrook et al., *Molecular Cloning: A Laboratory Manual,* 2 nd ed., Cold Spring Harbor Laboratory Press, Cold Spring Harbor, N.Y., 1989; Ausubel et al. (eds.), *Current Protocols in Molecular Biology,* John Wiley and Sons, Inc., N.Y. 1987; and "Bacillus subtilis and Other Gram-Positive Bacteria", Sonensheim et al., 1993, American Society for Microbiology, Washington D.C., which are incorporated herein by reference.

In general, a DNA sequence encoding a mannanase of the present invention is operably linked to other genetic elements required for its expression, generally including a transcription promoter and terminator within an expression vector. The vector will also commonly contain one or more selectable markers and one or more origins of replication, although those skilled in the art will recognize that within certain systems selectable markers may be provided on separate vectors, and replication of the exogenous DNA may be provided by integration into the host cell genome. Selection of promoters, terminators; selectable markers, vectors and other elements is a matter of routine design within the level of ordinary skill in the art. Many such elements are described in the literature and are available through commercial suppliers.

To direct a polypeptide into the secretory pathway of a host cell, a secretory signal sequence (also known as a leader sequence, prepro sequence or pre sequence) is provided in the expression vector. The secretory signal sequence may be that of the polypeptide, or may be derived from another secreted protein or synthesized de novo. Numerous suitable secretory signal sequences are known in the art and reference is made to "Bacillus subtillis and Other Gram-Positive Bacteria", Sonensheim et al., 1993, American Society for Microbiology, Washington D.C.; and Cutting, S. M. (eds.) "Molecular Biological Methods for Bacillus", John Wiley and Sons, 1990, for further description of suitable secretory signal sequences especially for secretion in a Bacillus host cell. The secretory signal sequence is joined to the DNA sequence in the correct reading frame. Secretory signal sequences are commonly positioned 5' to the DNA sequence encoding the polypeptide of interest, although certain signal sequences may be positioned elsewhere in the DNA sequence of interest (see, e.g., Welch et al., U.S. Pat. No. 5,037,743; Holland et al., U.S. Pat. No. 5,143,830).

The expression vector of the invention may be nay expression vector that is conveniently subjected to recombinant DNA procedures, and the choice of vector will often depend on the host cell into which the vector it is to be introduced. Thus, the vector may be an autonomously replicating vector, i.e. a vector which exists as an extrachromosomal entity, the replication of which is independent of chromosomal replication, e.g. a plasmid, Alternatively, the vector may be one which, when introduced into a host cell, is integrated into the host cell genome and replicated together with the chromosome(s) into which it has been integrated.

Examples of suitable promoters for use in filamentous fungus host cells are, e.g. the ADH3 promoter (McKnight et al., *The EMBO J.* 4 (1985), 2093–2099) or the tpiA promoter. Examples of other useful promoters are those derived from the gene encoding *Aspergillus oryzae* TAKA amylase, *Rhizomucor miehei* aspartic proteinase, *Aspergillus niger* neutral a-amylase, *Aspergillus niger* acid stable a-amylase, *Aspergillus niger* or *Aspergillus awamori* glucoamylase (gluA), *Rhizomucor miehei* lipase, *Aspergillus oryzae* alkaline protease, *Aspergillus oryzae* triose phosphate isomerase or *Aspergillus nidulans* acetamidase.

Transformed or transfected host cells are cultured according to conventional procedures in a culture medium containing nutrients and other components required for the growth of the chosen host cells. A variety of suitable media, including defined media and complex media, are known in the art and generally include a carbon source, a nitrogen source, essential amino acids, vitamins and minerals. Media may also contain such components as growth factors or serum, as required. The growth medium will generally select for cells containing the exogenously added DNA by, for example, drug selection or deficiency in an essential nutrient which is complemented by the selectable marker carried on the expression vector or co-transfected into the host cell.

Protein Isolation

When the expressed recombinant polypeptide is secreted the polypeptide may be purified from the growth media. Preferably the expression host cells are removed from the media before purification of the polypeptide (e.g. by centrifugation).

When the expressed recombinant polypeptide is not secreted from the host cell, the host cell are preferably disrupted and the polypeptide released into an aqueous "extract" which is the first stage of such purification technique. Preferably the expression host cells are collected from the media before the cell disruption (e.g. by centrifugation).

The cell disruption may be performed by conventional techniques such as by lysozyme digestion or by forcing the cells through high pressure. See (Robert K. Scobes, Protein Purification, Second edition, Springer-Verlag) for further description of such cell disruption techniques.

Whether or not the expressed recombinant polypeptides (or chimeric polypeptides) is secreted or not it can be purified using fractionation and/or conventional purification methods and media.

Ammonium sulfate precipitation and acid or chaotrope extraction may be used for fractionation of samples. Exemplary purification steps may include hydroxyapatite, size exclusion, FPLC and reverse-phase high performance liquid chromatography. Suitable anion exchange media include derivatized dextrans, agarose, cellulose, polyacrylamide, specialty silicas, and the like. PEI, DEAE, QAE and Q derivatives are preferred, with DEAE Fast-Flow Sepharose (Pharmacia, Piscataway, N.J.) being particularly preferred. Exemplary chromatographic media include those media derivatized with phenyl, butyl, or octyl groups, such as Phenyl-Sepharose FF (Pharmacia), Toyopearl butyl 650 (Toso Haas, Montgomerville, Pa.), Octyl-Sepharose (Pharmacia) and the like; or polyacrylic resins, such as Amberchrom CG 71 (Toso Haas) and the like. Suitable solid supports include glass beads, silica-based resins, cellulosic resins, agarose beads, cross-linked agarose beads, polystyrene beads, cross-linked polyacrylamide resins and the like that are insoluble under the conditions in which they are to be used. These supports may be modified with reactive groups that allow attachment of proteins by amino groups, carboxyl groups, sulfhydryl groups, hydroxyl groups and/or carbohydrate moieties. Examples of coupling chemistries include cyanogen bromide activation, N-hydroxysuccinimide activation, epoxide activation sulfhydryl activation, hydrazide activation, and carboxyl and amino derivatives for carbodiimide coupling chemistries. These and other solid media are well known and widely used in the art, and are available from commercial suppliers.

Selection of a particular method is a matter of routine design and is determined in part by the properties of the chosen support. See, for example, *Affinity Chromatography: Principles& Methods*, Pharmacia LKB Biotechnology, Uppsala, Sweden, 1988.

Polypeptides of the invention or fragments thereof may also be prepared through chemical synthesis. Polypeptides of the invention may be monomers or multimers; glycosylated or non-glycosylated; pegylated or non-pegylated; and may or may not include an initial methionine amino acid residue.

Based on the sequence information disclosed herein a full length DNA sequence encoding a mannanase of the invention and comprising the DNA sequence shown in SEQ ID NO 1, at least the DNA sequence from position 94 to position 990, or, alternatively, the DNA sequence from position 94 to position 1470, may be cloned. Likewise may be cloned a full length DNA sequence encoding a mannanase of the invention and comprising the DNA sequence shown in SEQ ID No 5, at least the DNA sequence from position 94 to position 1032, or, alternatively, the DNA sequence from position 94 to position 1482; and a full length DNA sequence encoding a mannanase of the invention and comprising the DNA sequence shown in SEQ ID No 9, at least the DNA sequence from position 94 to position 1086, or, alternatively, the DNA sequence from position 94 to position 1761; and a full length DNA sequence encoding a mannanase of the invention and comprising the DNA sequence shown in SEQ ID No 11, at least the DNA sequence from position 97 to position 993; and a full length DNA sequence encoding a mannanase of the invention and comprising the DNA sequence shown in SEQ ID No 13, at least the DNA sequence from position 498 to position 1464, or, alternatively, the DNA sequence from position 64 to position 1464; and a full length DNA sequence encoding a mannanase of the invention and comprising the DNA sequence shown in SEQ. ID No 15, at least the DNA sequence from position 204 to position 1107, or, alternatively, the DNA sequence from position 76 to position 1107; and a DNA sequence partially encoding a mannanase of the invention and comprising the DNA sequence shown in SEQ ID No 17; and a DNA sequence partially encoding a mannanase of the invention and comprising the DNA sequence shown in SEQ ID No 19; and a full length DNA sequence encoding a mannanase of the invention and comprising the DNA sequence shown in SEQ ID No 21, at least the DNA sequence from position 88 to position 960; and a DNA sequence partially encoding a mannanase of the invention and comprising the DNA sequence shown in SEQ ID No 23; and a full length DNA sequence encoding a mannanase of the invention and comprising the DNA sequence shown in SEQ ID No 25, at least the DNA sequence from position 904 to position 1875, or, alternatively, the DNA sequence from position 88 to position 2445; and a full length DNA sequence encoding a mannanase of the invention and comprising the DNA sequence shown in SEQ ID No 27, at least the DNA sequence from position 498 to position 1488, or, alternatively, the DNA sequence from position 112 to position 1488; and a full length DNA sequence encoding a mannanase of the invention and comprising the DNA sequence shown in SEQ ID No 29, at least the DNA sequence from position 79 to position 1083; and a full length DNA sequence encoding a mannanase of the invention and comprising the DNA sequence shown in SEQ ID No 31, at least the DNA sequence from position 1779 to position 2709, or, alternatively, the DNA sequence from position 67 to position 2709.

Cloning is performed by standard procedures known in the art such as by, preparing a genomic library from a Bacillus strain especially a strain selected from B. sp. I633, B. sp. AAI12, B. sp. AA349. *Bacillus agaradhaerens, Bacillus halodurans, Bacillus calusii* and *Bacillus licheniformis*, or from a fungal strain, especially the strain *Humicola insolens;* plating such a library on suitable substrate plates;

identifying a clone comprising a polynucleotide sequence of the invention by standard hybridization techniques using a probe based on any of the sequences SEQ ID Nos. 1, 5, 9, 11, 13, 15, 17, 19, 21, 23, 25, 27, 29 or 31; or by identifying a clone from said genomic library by an Inverse PCR strategy using primers based on sequence information from SEQ ID No 1, 5, 9, 11, 13, 15, 17, 19, 21, 23, 25, 27, 29 or 31. Reference is made to M. J. MCPherson et al. ("PCR A practical approach" Information Press Ltd. Oxford England) for further details relating to Inverse PCR.

Based on the sequence information disclosed herein (SEQ ID Nos. 1, 2, 5, 6, 9, 10, 11, 12, 13, 14, 15, 16, 17, 18, 19, 20, 21, 22, 23, 24, 25, 26, 27, 28, 29, 30, 31, 32) is it routine work for a person skilled in the art to isolate homologous polynucleotide sequences encoding homologous mannanase of the invention by a similar strategy using genomic libraries from related microbial organisms, in particular from genomic libraries from other strains of the genus Bacillus such as alkalophilic species of Bacillus sp., or from fungal strains such as species of Humicola.

Alternatively, the DNA encoding the mannan or galactomannan-degrading enzyme of the invention may, in accordance with well-known procedures, conveniently be cloned from a suitable source, such as any of the above mentioned organisms, by use of synthetic ologonucleotide probes prepared on the basis of the DNA sequence obtainable from the plasmid present any of the strains *Escherichia coli* DSM 12197, DSM 12180, DSM 12433, DSM 12441, DSM 9984, DSM 12432, DSM 12436, DSM 12846, DSM 12847, DSM 12848, DSM 12849, DSM 12850, DSM 12851 and DSM 12852.

Accordingly, the polynucleotide molecule of the invention may be isolated from any of *Escherichia coli*, DSM 12197, DSM 12180, DSM 12433, DSM 12441, DSM 9984, DSM 12432, DSM 12436, DSM 12846, DSM 12847, DSM 12848, DSM 12849, DSM 12850, DSM 12851 and DSM 12852, in which the plasmid obtained by cloning such as described above is deposited. Also, the present invention relates to an isolated substantially pure biological culture of any of the strains *Escherichia coli*, DSM 12197, DSM 12180, DSM 12433, DSM 12441, DSM 9984, DSM 12432, DSM 12436, DSM 12846, DSM 12847, DSM 12848, DSM 12849, DSM 12850, DSM 12851and DSM 12852.

In the present context, the term "enzyme preparation" is intended to mean either a conventional enzymatic fermentation product, possibly isolated and purified, from a single species of a microorganism, such preparation usually comprising a number of different enzymatic activities; or a mixture of monocomponent enzymes, preferably enzymes derived from bacterial or fungal species by using conventional recombinant techniques, which enzymes have been fermented and possibly isolated and purified separately and which may originate from different species, preferably fungal or bacterial species or the fermentation product of a microorganism which acts as a host cell for expression of a recombinant mannanase, but which microorganism simultaneously produces other enzymes, e.g. pectin degrading enzymes, proteases, or cellulases, being naturally occurring fermentation products of the microorganism, i.e. the enzyme complex conventionally produced by the corresponding naturally occurring microorganism.

The mannanase preparation of the invention may further comprise one or more enzymes selected from the group consisting of proteases, cellulases (endo-β-1,4-glucanases), β-glucanases (endo-β-1,3 (4)-glucanases), lipases, cutinases, peroxidases, laccases, amylases, glucoamylases, pectinases, reductases, oxidases, phenoloxidases, ligninases, pullulanases, hemicellulases, pectate lyases, xyloglucanases, xylanases, pectin acetyl esterases, rhamnogalacturonan acetyl esterases, polygalacturonases, rhamnogalacturonases, pectin lyases, pectin methylesterases, cellobiohydrolases, transglutaminanses; or mixtures thereof. In a preferred embodiment, one or more of all enzymes in the preparation is produced by using recombinant techniques, i.e. the enzymes(s) is/are monocomponent enzyme(s) which is/are mixed with the other enzyme(s) to form an enzyme preparation with the desired enzyme blend.

In another aspect, the present invention also relates to a method of producing the enzyme preparation of the invention, the method comprising culturing a microorganism, eg a wild-type strain, capable of producing the mannanase under conditions permitting the production of the enzyme, and recovering the enzyme from the culture. Culturing may be carried out using conventional fermentation techniques, e.g. culturing in shake flasks or fermentors with agitation to ensure sufficient aeration on a growth medium inducing production of the mannanase enzyme. The growth medium may contain a conventional N-source such as peptone, yeast extract or casamino acids, a reduced amount of a conventional C-source such as dextrose or sucrose, and an inducer such as guar gum or locust beam gum. The recovery may be carried out using conventional techniques, e.g. separation of bio-mass and supernatant by centrifugation or filtration, recovery of the supernatant or disruption of cells if the enzyme of interest is intracellular, perhaps followed by further purification as described in EP 0 406 314 or by crystallization as described in WO 97/15660.

Examples of useful bacteria producing the enzyme or the enzyme preparation of the invention are Gram positive bacteria, preferably from the Bacillus/Lactobacillus subdivision, preferably a strain from the genus Bacillus, more preferably a strain of Bacillus sp.

In yet another aspect, the present invention relates to an isolated mannanase having the properties described above and which is free from homologous impurities, and is produced using conventional recombinant techniques.

Immunological Cross-Reactivity

Polyclonal antibodies to be used in determining immunological cross-reactivity may be prepared by use of a purified mannanase enzyme. More specifically, antiserum against the mannanase of the invention may be raised by immunizing rabbits (or other rodents) according to the procedure described by N. Axelsen et al. in: A Manual of Quantitative Immunoelectrophoresis, Blackwell Scientific Publications, 1973, Chapter 23, or A. Johnstone and R. Thorpe, Immunochemistry in Practice, Blackwell Scientific Publications, 1982 (more specifically p. 27–31). Purified immunoglobulins may be obtained from the antisera, for example by salt precipitation ($(NH_4)_2\ SO_4$), followed by dialysis and ion exchange chromatography, e.g. on DEAE-Sephadex. Immunochemical characterization of proteins may be done either by Outcherlony double-diffusion analysis (O. Ouchterlony in: Handbook of Experimental Immunology (D. M. Weir, Ed.), Blackwell Scientific Publications, 1967, pp. 655–706), by crossed immunoelectrophoresis (N. Axelsen et al., supra, Chapters 3 and 4), or by the rocket immunoelectrophoresis (N. Axelsen et al., Chapter 2).

Use in the detergent industry

In further aspects, the present invention relates to a detergent composition comprising the mannanase or mannanase preparation of the invention, to a process for machine treatment of fabrics comprising treating fabric during a washing cycle of a machine washing process with a washing solution containing the mannanase or mannanase preparation of the invention, and to cleaning compositions, including laundry, dishwashing, hard surface cleaner, personal cleansing and oral/dental compositions, comprising a mannanase and optionally another enzyme selected among cellulases, amylases, pectin degrading enzymes and xyloglucanases and providing superior cleaning performance, i.e. superior stain removal, dingy cleaning and whiteness maintenance.

Without being bound to this theory, it is believed that the mannanase of the present invention is capable of effectively degrading or hydrolysing any soiling or spots containing galactomannans and, accordingly, of cleaning laundry comprising such soilings or spots.

The cleaning compositions of the invention must contain at least one additional detergent component. The precise nature of these additional components, and levels of incorporation thereof will depend on the physical form of the composition, and the nature of the cleaning operation for which it is to be used.

The cleaning compositions of the present invention preferably further comprises a detergent ingredient selected from a selected surfactant, another enzyme, a builder and/or a bleach system.

The cleaning compositions according to the invention can be liquid, paste, gels, bars, tablets, spray, foam, powder or granular. Granular compositions can also be in "compact" form and the liquid compositions can also be in a "concentrated" form.

The compositions of the invention may for example, be formulated as hand and machine dishwashing compositions, hand and machine laundry detergent compositions including laundry additive compositions and compositions suitable for use in the soaking and/or pretreatment of stained fabrics, rinse added fabric softener compositions, and compositions for use in general household hard surface cleaning operations. Compositions containing such carbohydrases can also be formulated as sanitization products, contact lens cleansers and health and beauty care products such as oral/dental care and persona cleaning compositions.

When formulated as compositions for use in manual dishwashing methods the compositions of the invention preferably contain a surfactant and preferably other detergent compounds selected from organic polymeric compounds, suds enhancing agents, group II metal ions, solvents, hydrotropes and additional enzymes.

When formulated as compositions suitable for use in a laundry machine washing method, the compositions of the invention preferably contain both a surfactant and a builder compound and additionally one or more detergent components preferably selected from organic polymeric compounds, bleaching agents, additional enzymes, suds suppressors, dispersants, lime-soap dispersants, soil suspension and anti-redeposition agents and corrosion inhibitors. Laundry compositions can also contain softening agents, as additional detergent components. Such compositions containing carbohydrase can provide fabric cleaning, stain removal, whiteness maintenance, softening, colour appearance, dye transfer inhibition and sanitization when formulated as laundry detergent compositions.

The compositions of the invention can also be used as detergent additive products in solid or liquid form. Such additive products are intended to supplement or boost the performance of conventional detergent compositions and can be added at any stage of the cleaning process.

If needed the density of the laundry detergent compositions herein ranges from 400 to 1200 g/litre, preferably 500 to 950 g/litre of composition measured at 20° C.

The "compact" form of the compositions herein is best reflected by density and, in terms of composition, by the amount of inorganic filler salt, inorganic filler salts are conventional ingredients of the detergent compositions in powder form; in conventional detergent compositions, the filler salts are present in substantial amounts, typically 17–35% by weight of the total composition. In the compact compositions, the filler salt is present in amounts not exceeding 15% of the total composition, preferably not exceeding 10%, most preferably not exceeding 5% by weight of the composition. The inorganic filler salts, such as meant in the present compositions are selected from the alkali and alkaline-earth-metal salts of sulphates and chlorides. A preferred filler salt is sodium sulphate.

Liquid detergent compositions according to the present invention can also be in a "concentrated form", in such case, the liquid detergent compositions according the present invention will contain a lower amount of water, compared to conventional liquid detergents. Typically the water content of the concentrated liquid detergent is preferably less than 40%, more preferably less than 30%, most preferably less than 20% by weight of the detergent composition.

Cleaning compositions Surfactant system

The cleaning or detergent compositions according to the present invention comprise a surfactant system, wherein the surfactant can be selected from nonionic and/or anionic and/or cationic and/or ampholytic and/or zwitterionic and/or semi-polar surfactants.

The surfactant is typically present at a level from 0.1% to 60% by weight. The surfactant is preferably formulated to be compatible with enzyme hybrid and enzyme components present in the composition. In liquid or gel compositions the surfactant is most preferably formulated in such a way that it promotes, or at least does not degrade, the stability of any enzyme hybrid or enzyme in these compositions.

Suitable systems for use according to the present invention comprise as a surfactant one or more of the nonionic and/or anionic surfactants described herein.

Polyethylene, polypropylene, and polybutylene oxide conden-sates of alkyl phenols are suitable for use as the nonionic surfactant of the surfactant systems of the present invention, with the polyethylene oxide condensates being preferred. These compounds include the condensation products of alkyl phenols having an alkyl group containing from about 6 to about 14 carbon atoms, preferably from about 8 to about 14 carbon atoms, in either a straight chain or branched-chain configuration with the alkylene oxide. In a preferred embodiment, the ethylene oxide is present in an amount equal to from about 2 to about 25 moles, more preferably from about 3 to about 15 moles, of ethylene oxide per mole of alkyl phenol. Commercially available nonionic surfactants of this type include Igepal™ CO-630, marketed by the GAF Corporation; and Triton™ X-45, X-114, X-100 and X-102, all marketed by the Rohm & Haas Company. These surfactants are commonly referred to as alkylphenol alkoxylates (e.g., alkyl phenol ethoxylates).

The condensation products of primary and secondary aliphatic alcohols with about 1 to about 25 moles of ethylene oxide are suitable for use as the nonionic surfactant of the nonionic surfactant systems of the present invention. The alkyl chain of the aliphatic alcohol can either be straight or branched, primary or secondary, and generally contains from about 8 to about 22 carbon atoms. Preferred are the condensation products of alcohols having an alkyl group containing from about 8 to about 20 carbon atoms, more preferably from about 10 to about 18 carbon atoms, with from about 2 to about 10 moles of ethylene oxide per mole of alcohol. About 2 to about 7 moles of ethylene oxide and most preferably from 2 to 5 moles of ethylene oxide per mole of alcohol are present in said condensation products. Examples of commercially available nonionic surfactants of this type include Tergitol™ 15-S-9. (The condensation product of $C_{11}$–$C_{15}$ linear alcohol with 9 moles ethylene oxide), Tergitol™ 24-L-6 NMW (the condensation product of $C_{12}$–$C_{14}$ primary alcohol with 6 moles ethylene oxide with a narrow molecular weight distribution), both marketed by Union Carbide Corporation; Neodol™ 45-9 (the condensation product of $C_{14}$–$C_{15}$ linear alcohol with 9 moles of ethylene oxide), Neodol™ 23-3 (the condensation product of $C_{12}$–$C_{13}$ linear alcohol with 3.0 moles of ethylene oxide), Neodol™ 45-7 (the condensation product of $C_{14}$–$C_{15}$ linear alcohol with 7 moles of ethylene oxide), Neodol™ 45-5 (the condensation product of $C_{14}$–$C_{15}$ linear alcohol with 5 moles of ethylene oxide) marketed by Shell Chemical Company, Kyro™ EOB (the condensation product of $C_{13}$–$C_{15}$ alcohol with 9 moles ethylene oxide), marketed by The Procter & Gamble Company, and Genapol LA 050 (the condensation product of $C_{12}$–$C_{14}$ alcohol with 5 moles of ethylene oxide) marketed by Hoechst. Preferred range of HLB in these products is from 8–11 and most preferred from 8–10.

Also useful as the nonionic surfactant of the surfactant systems of the present invention are alkylpolysaccharides disclosed in U.S. Pat. No. 4,565,647, having a hydrophobic group containing from about 6 to about 30 carbon atoms, preferably from about 10 to about 16 carbon atoms and a polysaccharide, e.g. a polyglycoside, hydrophilic group containing from about 1.3 to about 10, preferably from about 1.3 to about 3, most preferably from about 1.3 to about 2.7 saccharide units. Any reducing saccharide containing 5 or 6 carbon atoms can be used, e.g., glucose, galactose and galactosyl moieties can be substituted for the glucosyl moieties (optionally the hdyrophobic group is attached at the 2-, 3-, 4-, etc. positions thus giving a glucose or galactose as opposed to a glucoside or galactoside). The intersaccharide bonds can be, e.g., between the one position of the additional saccharide units and the 2-, 3-, 4-, and/or 6-positions on the preceding saccharide units.

The preferred alkylpolyglycosides have the formula

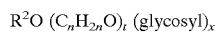

$$R^2O\,(C_nH_{2n}O)_t\,(\text{glycosyl})_x$$

wherein $R^2$ is selected from the group consisting of alkyl, alkylphenyl, hydroxyalkyl, hydroxyalkylphenyl, and mixtures thereof in which the alkyl groups contain from about 10 to about 18, preferably from about 12 to about 14, carbon atoms; n is 2 or 3, preferably 2; to is from 0 to about 10, pre-ferably 0; and x is from about 1.3 to about 10, preferably from about 1.3 to about 3, most preferably from about 1.3 to about 2.7. The glycosyl is preferably derived from glucose. To prepare these compounds the alcohol or alkylpolyethoxy alcohol is formed first and then reacted with glucose, or a source of glucose, to form the glucoside (attachment at the 1-position). The additional glycosyl units can then be attached between their 1-position and the preceding glycosyl units 2-, 3-, 4-, and/or 6-position, preferably predominantly the 2-position.

The condensation products of ethylene oxide with a hydrophobic base formed by the condensation of propylene oxide with propylene glycol are also suitable for use as the additional nonionic surfactant systems of the present invention. The hydrophobic portion of these compounds will preferably have a molecular weight from about 1500 to about 1800 and will exhibit water insolubility. The addition of polyoxyethylene moieties to this hydrophobic portion tends to increase the water solubility of the molecule as a whole, and the liquid character of the product is retained up to the point where the polyoxyethylene content is about 50% of the total weight of the condensation product, which corresponds to condensation with up to about 40 moles of ethylene oxide. Examples of compounds of this type include certain of the commercially available Pluronic™ surfactants, marketed by BASF.

Also suitable for use as the nonionic surfactant of the nonionic surfactant system of the present invention, are the condensation products of ethylene oxide with the product resulting from the reaction of propylene oxide and ethylenediamine. The hydrophobic moiety of these products consists of the reaction product of ethylenediamine and excess propylene oxide, and generally has a molecular weight of from about 2500 to about 3000. This hdyrophobic moiety is condensed with ethylene oxide to the extent that the condensation product contains from about 40% to about 80% by weight of polyoxyethylene and has a molecular weight of from about 5,000 to about 11,000. Examples of this type of nonionic surfactant include certain of the commercially available Tetronic™ compounds, marketed by BASF.

Preferred for use as the nonionic surfactant of the surfactant systems of the present invention are polyethylene oxide condensates of alkyl phenols, condensation products of primary and secondary aliphatic alcohols with from about 1 to about 25 moles of ethyleneoxide, alkylpolysaccharides, and mixtures hereof. Most preferred are $C_8$–$C_{14}$ alkyl phenol ethoxylates having from 3 to 15 ethoxy groups and $C_8$–$C_{18}$ alcohol ethoxylates (preferably $C_{10}$ avg.) having from 2 to 10 ethoxy groups, and mixtures thereof.

Highly preferred nonionic surfactants are polyhydroxy fatty acid amide surfactants of the formula

wherein $R^1$ is H, or $R^1$ is $C_{1-4}$ hydrocarbyl, 2-hydroxyethyl, 2-hydroxypropyl or a mixture thereof, $R^2$ is $C_{5-31}$ hydrocarbyl, and Z is a polyhydroxyhydrocarbyl having a linear hydrocarbyl chain with at least 3 hydroxyls directly connected to the chain, or an alkoxylated derivative thereof. Preferably, $R^1$ is methyl, $R^2$ is straight $C_{11-15}$ alkyl or $C_{16-18}$ alkyl or alkenyl chain such as coconut alkyl or mixtures thereof, and Z is derived from a reducing sugar such as glucose, fructose, maltose or lactose, in a reductive amination reaction.

Highly preferred anionic surfactants include alkyl alkoxylated sulfate surfactants. Examples hereof are water soluble salts or acids of the formula RO(A)$_m$SO3M where R is an unsubstituted $C_{10}$–C—$_{24}$ alkyl or hydroxyalkyl group having a $C_{10}$–$C_{24}$ alkyl component, preferably a $C_{12}$–$C_{20}$ alkyl or hydro-xyalkyl, more preferably $C_{12}$–$C_{18}$ alkyl or hydroxyalkyl, A is an ethoxy or propoxy unit, m is grater then zero, typically between about 0.5 and about 6, more preferably between about 0.5 and about 3, and M is H or a cation which can be, for example, a metal cation (e.g., sodium potassium, lithium, calcium, magnesium, etc.), ammonium or substituted-ammonium cation. Alkyl ethoxylated sulfates as well as alkyl propoxylated sulfates are contemplated herein. Specific examples of substituted ammonium cations include methyl-, dimethyl, trimethyl-ammonium cations and quaternary ammonium cations such as tetramethyl-ammonium and dimethyl piperdinium cations and those derived from alkylamines such as ethylamine, diethylamine, triethylamine, mixtures thereof, and the like. Exemplary surfactants are $C_{12}$–$C_{18}$ alkyl polyethoxylate (1.0) sulfate ($C_{12}$–$C_{18}$E(1.0)M, $C_{12}$–$C_{18}$ alkyl polyethoxylate (2.25) sulfate ($C_{12}$–$C_{18}$ (2.25)M, and $C_{12}$–$C_{18}$ alkyl polyethoxylate (3.0) sulfate ($C_{12}$–$C_{18}$E(3.0)M), and $C_{12}$–$C_{18}$ alkyl polyethoxylate (4.0) sulfate ($C_{12}$–$C_{18}$E(4.0) M), wherein M is conveniently selected from sodium and potassium.

Suitable anionic surfactants to be used are alkyl ester sulfonate surfactants including linear esters of $C_8$–$C_{20}$ carboxylic acids (i.e., fatty acids) which are sulfonated with gaseous $SO_3$ according to the "The Journal of the American Oil Chemist Society", 52 (1975), pp. 323–329. Suitable starting materials would include natural fatty substances as derived from tallow, palm oil, etc.

The preferred alkyl ester sulfonate surfactant, especially for laundry applications, comprise alkyl ester sulfonate surfactants of the structural formula:

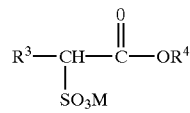

wherein $R^3$ is a $C_8$–$C_{20}$ hydrocarbyl, preferably an alkyl, or combination thereof, $R^4$ is a $C_1$–$C_6$ hydrocarbyl, preferably an alkyl, or combination thereof, and M is a cation which forms a water soluble salt with the alkyl ester sulfonate. Suitable salt-forming cations include metals such as sodium, potassium, and lithium, and substituted or unsubstituted ammonium cations, such as monoethanolamine, diethonolamine, and triethanolamine. Preferably, $R^3$ is $C_{10}$–$C_{16}$ alkyl, and $R^4$ is methyl, ethyl or isopropyl. Especially preferred are the methyl ester sulfonates where $R^3$ is $C_{10}$–$C_{16}$ alkyl.

Other suitable anionic surfactants include the alkyl sulfate surfactants which are water soluble salts or acids of the formula ROSO$_3$M wherein R preferably is a $C_{10}$–$C_{24}$ hydrocarbyl, preferably an alkyl or hydroxyalkyl having a $C_{10}$–$C_{20}$ alkyl component, more preferably a $C_{12}$–$C_{18}$ alkyl or hydroxyalkyl, and M is H or a cation, e.g., an alkali metal cation (e.g. sodium, potassium, lithium), or ammonium or substituted ammonium (e.g. methyl-, dimethyl-, and trimethyl ammonium cations and quaternary ammonium cations such as tetramethyl-ammonium and dimethyl piperdinium cations and quaternary ammonium cations derived from alkylamines such as ethylamine, diethylamine, triethylamine, and mixtures thereof, and the like). Typically, alkyl chains of $C_{12}$–$C_{16}$ are preferred for lower wash temperatures (e.g. below about 50° C.) and $C_{16}$–$C_{18}$ alkyl chains are preferred for higher wash temperatures (e.g. above about 50° C.).

Other anionic surfactants useful for detersive purposes can also be included in the laundry detergent compositions of the present invention. Theses can include salts (including, for example, sodium, potassium, ammonium, and substituted ammonium salts such as mono- di- and triethanolamine salts) of soap, $C_8$–$C_{22}$ primary or secondary alkanesulfonates, $C_8$–$C_{24}$ olefinsulfonates, sulfonated polycarboxylic acids prepared by sulfonation of the pyrolyzed product of alkaline earth metal citrates, e.g., as described in British patent specification No. 1,082,179, $C_8$–$C_{24}$ alkylpolyglycolethersulfates (containing up to 10 moles of ethylene oxide); alkyl glycerol sulfonates, fatty acyl glycerol sulfonates, fatty oleyl glycerol sulfates, alkyl phenol ethylene oxide ether sulfates, paraffin sulfonates, alkyl phosphates, isethionates such as the acyl isethionates, N-acyl taurates, alkyl succinamates and sulfosuccinates, monoesters of sulfosuccinates (especially saturated and unsaturated $C_{12}$–$C_{18}$ monoesters) and diesters of sulfosuccinates (especially saturated and unsaturated $C_6$–$C_{12}$ diesters), acyl sarcosinates, sulfates of alkylpolysaccharides such as the sulfates of alkylpolyglucoside (the nonionic nonsulfated compounds being described below), branched primary alkyl sulfates, and alkyl polyethoxy carboxylates such as those of the formula RO $(CH_2CH_2O)_k$—$CH_2COO$—M+to wherein R is a $C_8$–$C_{22}$ alkyl, k is an integer from 1 to 10, and M is a soluble salt forming cation. Resin acids and hydrogenated resin acids are also suitable, such as rosin, hydrogenated rosin, and resin acids and hydrogenated resin acids present in or derived from tall oil.

Alkylbenzene sulfonates are highly preferred. Especially preferred are linear (straight-chain) alkyl benzene sulfonates (LAS) wherein the alkyl group preferably contains from 10 to 18 carbon atoms.

Further examples are described in "Surface Active Agents and Detergents" (Vol. I and II by Schwartz, Perrry and Berch). A variety of such surfactants are also generally disclosed in U.S. Pat. No. 3,929,678, (Column 23, line 58 through Column 29, line 23, herein incorporated by reference).

When included therein, the laundry detergent compositions of the present invention typically comprise from about 1% to about 40%, preferably from about 3% to about 20% weight of such anionic surfactants.

The cleaning or laundry detergent compositions of the present invention may also contain cationic, ampholytic, zwitterionic, and semi-polar surfactants, as well as the nonionic and/or anionic surfactants other than those already described herein.

Cationic detersive surfactants suitable for use in the laundry detergent compositions of the present invention are those having one long-chain hydrocarbyl group. Examples of such cationic surfactants include the ammonium surfactants such as alkyltrimethylammonium halogenides, and those surfactants having the formula:

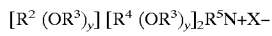

[$R^2$ $(OR^3)_y$] [$R^4$ $(OR^3)_y$]$_2 R^5 N+X-$ wherein $R^2$ is an alkyl or alkyl benzyl group having from about 8 to about 18 carbon atoms in the alkyl chain, each $R^3$ is selected form the group consisting of —$CH_2CH_2$—, —$CH_2CH$ $(CH_3)$—, —$CH_2CH$ $(CH_2OH)$—, —$CH_2CH_2CH_2$—, and mixtures thereof; each $R^4$ is selected from the group consisting of $C_1$–$C_4$ alkyl, $C_1$–$C_4$ hydroxyalkyl, benzyl ring structure formed by joining the two $R^4$ groups, —$CH_2CHOHCHOHCOR^6CHOHCH_2OH$, wherein $R^6$ is any hexose or hexose polymer having a molecular weight less than about 1000, and hydrogen when y is not 0; $R^5$ is the same as $R^4$ or is an alkyl chain, wherein the total number of carbon atoms or $R^2$ plus $R^5$ is not more than about 18; each y is from 0 to about 10, and the sum of the y values is from 0 to about 15; and X is any compatible anion.

Highly preferred cationic surfactants are the water soluble quaternary ammonium compounds useful in the present composition having the formula:

$R_1 R_2 R_3 R_4 N^+ X^-$     (i)

wherein $R_1$ is $C_8$–$C_{16}$ alkyl, each of $R_2$, $R_3$ and $R_4$ is independently $C_1$–$C_4$ alkyl, $C_1$–$C_4$ hydroxy alkyl, benzyl, and —$(C_2H_{40})_x H$ where x has a value from 2 to 5, and X is an anion. Not more than one of $R_2$, $R_3$ or $R_4$ should be benzyl.

The preferred alkyl chain length for $R_1$ is $C_{12}$–$C_{15}$, particularly where the alkyl group is a mixture of chain lengths derived from coconut or palm kernel fat or is derived synthetically by olefin build up to OXO alcohols synthesis.

Preferred groups for $R_2 R_3$ and $R_4$ are methyl and hydroxyethyl groups and the anion X may be selected from halide, methosulphate, acetate and phosphate ions.

Examples of suitable quaternary ammonium compounds of formulae (i) for use herein are:

coconut trimethyl ammonium chloride or bromide;

coconut methyl dihydroxyethyl ammonium chloride or bromide;

decyl triethyl ammonium chloride;

decyl dimethyl hydroxyethyl ammonium chloride or bromide;

$C_{12}$–$C_{15}$ dimethyl hydroxyethyl ammonium chloride or bromide;

coconut dimethyl hydroxyethyl ammonium chloride or bromide;

myristyl trimethyl ammonium methyl sulphate;

lauryl dimethyl benzyl ammonium chloride or bromide;

lauryl dimethyl (ethenoxy)$_4$ ammonium chloride or bromide;

choline esters (compounds of formula (i) where $R_1$ is

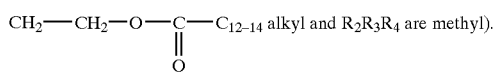

$CH_2$—$CH_2$—O—C—$C_{12-14}$ alkyl and $R_2 R_3 R_4$ are methyl).
‖
O di-alkyl imidazolines [compounds of formula (i)].

Other cationic surfactants useful herein are also described in U.S. Pat. No. 4,228,044 and in EP 000 224.

When included therein, the laundry detergent compositions of the present invention typically comprise from 0.2% to about 25%, preferably from about 1% to about 8% by weight of such cationic surfactants.

Ampholytic surfactants are also suitable for use in the laundry detergent compositions of the present invention. These surfactants can be broadly described as aliphatic derivatives of secondary or tertiary amines, or aliphatic derivatives of heterocyclic secondary and tertiary amines in which the aliphatic radical can be straight- or branched-chain. One of the aliphatic substituents contains at least about 8 carbon atoms, typically from about 8 to about 18 carbon atoms, and at least one contains an anionic water-solubilizing group, e.g. carboxy, sulfonate, sulfate. See U.S. Pat. No. 3,929,678 (column 19, lines 18–35) for examples of ampholytic surfactants.

When included therein, the laundry detergent compositions of the present invention typically comprise from 0.2% to about 15%, preferably from about 1% to about 10% by weight of such ampholytic surfactants.

Zwitterionic surfactants are also suitable for use in laundry detergent compositions. These surfactants can be broadly described as derivatives of secondary and tertiary amines, derivatives of heterocyclic secondary and tertiary amines, or derivatives of quaternary ammonium, quaternary phosphonium or tertiary sulfonium compounds. See U.S. Pat. No. 3,929,678 (column 19, line 38 through column 22, line 48) for examples of zwitterionic surfactants.

When included therein, the laundry detergent compositions of the present invention typically comprise from 0.2% to about 15%, preferably from about 1% to about 10% by weight of such zwitterionic surfactants.

Semi-polar nonionic surfactants are a special category of nonionic surfactants which include water-soluble amine oxides containing one alkyl moiety of from about 10 to about 18 carbon atoms and 2 moieties selected from the group consisting of alkyl groups and hydroxyalkyl groups containing from about 1 to about 3 carbon atoms; water-soluble phosphine oxides containing one alkyl moiety of from about 10 to about 18 carbon atoms and 2 moieties selected from the group consisting of alkyl groups and hydroxyalkyl groups containing from about 1 to about 3 carbon atoms; and water-soluble sulfoxides containing one alkyl moiety from about 10 to about 18 carbon atoms and a moiety selected from the group consisting of alkyl and hydroxyalkyl moieties of from about 1 to about 3 carbon atoms.

Semi-polar nonionic detergent surfactants include the amine oxide surfactants having the formula:

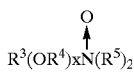

wherein $R^3$ is an alkyl, hydroxyalkyl, or alkyl phenyl group or mixtures thereof containing from about 8 to about 22 carbon atoms; $R^4$ is an alkylene or hydroxyalkylene group containing from about 2 to about 3 carbon atoms or mixtures thereof; x is from 0 to about 3: and each $R^5$ is an alkyl or hydroxyalkyl group containing from about 1 to about 3 carbon atoms or a polyethylene oxide group containing from about 1 to about 3 ethylene oxide groups. The $R^5$ groups can be attached to each other, e.g., through an oxygen or nitrogen atom, to form a ring structure.

These amine oxide surfactants in particular include $C_{10}$–$C_{18}$ alkyl dimethyl amine oxides and $C_8$–$C_{12}$ alkoxy ethyl dihydroxy ethyl amine oxides.

When included therein, the laundry detergent compositions of the present invention typically comprise from 0.2% to about 15%, preferably from about 1% to about 10% weight of such semi-polar nonionic surfactants.

Builder system

The compositions according to the present invention may further comprise a builder system. Any conventional builder system is suitable for use herein including aluminosilicate materials, silicates, polycarboxylates and fatty acids, materials such as ethylenediamine tetraacetate, metal ion sequestrants such aminopolyphosphonates, particularly ethylenediamine tetramethylene phosphonic acid and diethylene triamine pentamethylenephosphonic acid. Though less preferred for obvious environmental reasons, phosphate builders can also be used herein.

Suitable builders can be an inorganic ion exchange material, commonly an inorganic hydrated aluminosilicate material, more particularly a hydrated synthetic zeolite such as hydrated zeolite A, X, B, HS or MAP.

Another suitable inorganic builder material is layered silicate, e.g. SKS-6 (Hoechst). SKS-6 is a crystalline layered silicate consisting of sodium silicate ($Na_2Si_2O_5$).

Suitable polycarboxylates containing one carboxy group include lactic acid, glycolic acid and ether derivatives thereof as disclosed in Belgian Pat. Nos. 831,368, 821,369 and 821,370. Polycarboxylates containing two carboxy groups include the water-soluble salts of succinic acid, malonic acid, (ethylenedioxy) diacetic acid, maleic acid, diglycollic acid, tartaric acid, tartronic acid and fumaric acid, as well as the ether carboxylates described in German Offenle-enschrift 2,446,686, and 2,446,487, U.S. Pat. No. 3,935,257 and the sulfinyl carboxylates described in Belgian Pat. No. 840,623. Polycarboxylates containing three carboxy groups include, in particular, water-soluble citrates, aconitrates and citraconates as well as succinate derivatives such as the carboxymethyloxysuccinates described in British Patent No. 1,379,241, lactoxysuccinates described in Netherlands Application 7205873, and the oxypolycarboxylate materials such as 2-oxa-1,1,3-propane tricarboxylates described in British Pat. No. 1,387,447.

Polycarboxylates containing four carboxy groups include oxydisuccinates disclosed in British Patent No. 1,261,829, 1,1,2,2,-ethane tetracarboxylates, 1,1,3,3-propane tetracarboxylates containing sulfo substituents include the sulfosuccinate derivatives disclosed in British Patent Nos. 1,398,421 and 1,398,422 and in U.S. Pat. No. 3,936,448, and the sulfonated pyrolysed citrates described in British Patent No. 1,082,179; while polycarboxylates containing phosphone substituents are disclosed in British Patent No. 1,439,000.

Alicyclic and heterocyclic polycarboxylates include cyclopentane-cis, cis-cis-tetracarboxylates, cyclopentadienide pentacarboxylates, 2,3,4,5-tetrahydro-furan-cis, cis, cis-tetracarboxylates, 2,5-tetrahydro-furan-cis, discarboxylates, 2,2,5,5,-tetrahydrofuran-tetracarboxylates, 1,2,3,4,5,6-hexane-hexacarboxylates and carboxymethyl derivatives of polyhydric alcohols such as sorbitol, mannitol, and xylitol. Aromatic polycarboxylates include mellitic acid, pyromellitic acid and the phthalic acid derivatives disclosed in British Patent No. 1,425,343.

Of the above, the preferred polycarboxylates are hydroxy-carboxylates containing up to three carboxy groups per molecule, more particularly citrates.

Preferred builder systems for use in the present compositions include a mixture of water-insoluble aluminosilicate builder such as zeolite A or of a layered silicate (SKS-6), and a water-soluble carboxylate chelating agent such as citric acid.

A suitable chelant for inclusion in the detergent compositions in accordance with the invention is ethylenediamine-N,N'-disuccinic acid (EDDS) or the alkali metal, alkaline earth metal, ammonium, or substituted ammonium salts thereof, or mixtures thereof. Preferred EDDS compounds are the free acid form and the sodium or magnesium salt thereof. Examples of such preferred sodium salts of EDDS include $Na_2EDDS$ and $Na_4EDDS$. Examples of such preferred magnesium salts of EDDS include MgEDDS and $Mg_2EDDS$. The magnesium salts are the most preferred for inclusion in compositions in accordance with the invention.

Preferred builder systems include a mixture of a water-insoluble aluminosilicate builder such as zeolite A, and a water soluble carboxylate chelating agent such as citric acid.

Other builder materials that can form part of the builder system for use in granular compositions include inorganic materials such as alkali metal carbonates, bicarbonates, silicates, and organic materials such as the organic phosphonates, amino polyalkylene phosphonates and amino polycarboxylates.

Other suitable water-soluble organic salts are the homo- or co-polymeric acids or their salts, in which the polycarboxylic acid comprises at least two carboxy radicals separated form each other by not more than two carbon atoms.

Polymers of this type are disclosed in GB-A-1,596,756. Examples of such salts are polyacrylates of MW 2000–5000 and their copolymers with maleic anhydride, such copolymers having a molecular weight of from 20,000 to 70,000, especially about 40,000.

Detergency builder salts are normally included in amounts of from 5% to 80% by weight of the composition. Preferred levels of builder for liquid detergents are from 5% to 30%.

Enzymes

Mannanase is incorporated into the cleaning or detergent compositions in accordance with the invention preferably at a level of from 0.0001% to 2%, more preferably from 0.0005% to 0.5%, most preferred from 0.001% to 0.1% pure enzyme by weight of the composition.

The cleaning compositions of the present invention may further comprise as an essential element a carbohydrase selected from the group consisting of cellulases, amylases, pectin degrading enzymes and xyloglucanases. Preferably, the cleaning compositions of the present invention will comprise a mannanase, an amylase and another bioscouring-type of enzyme selected from the group consisting of cellulases, pectin degrading enzymes and xyloglucanases.

The cellulases usable in the present invention include both bacterial or fungal cellulases. Preferably, they will have a pH optimum of between 5 and 12 and a specific activity above 50 CEVU/mg (Cellulose Viscosity Unit). Suitable cellulases are disclosed in U.S. Pat. No. 4,435,307, J61078384 and WO96/02653 which discloses fungal cellulase produced from Humicola insolens, Trichoderma, Thielavia and Sporotrichum, respectively, EP 739 982 describes cellulases isolated from novel Bacillus species. Suitable cellulases are also disclosed in GB-A-2075028; GB-A-2095275; DE-OS-22 47 832 and WO95/26398.

Examples of such cellulases are cellulases produced by a strain of Humicola insolens (Humicola grisea var. thermoidea), particularly the strain Humicola insolens, DSM 1800. Other suitable cellulases are cellulases originated from Humicola insolens having a molecular weight of about 50 kD, an isoelectric point of 5.5 and containing 415 amino acids; and a ⁻43 kD endo-beta-1,4-glucanase derived from Humicola insolens, DSM 1800; a preferred cellulase has the amino acid sequence disclosed in PCT Patent Application No. WO 91/17243. Also suitable cellulases are the EGIII cellulases from Trichoderma longibrachiatum described in WO94/21801. Especially suitable cellulases are the cellulases having color care benefits. Examples of such cellulases are the cellulases described in WO96/29397, EP-A-0495257, WO 91/17243, WO91/17244 and WO91/21801. Other suitable cellulases for fabric care and/or cleaning properties are described in WO96/34092, WO96/17994 and WO95/24471.

Said cellulases are normally incorporated in the detergent composition at levels from 0.0001% to 2% of pure enzyme by weight of the detergent composition.

Preferred cellulases for the purpose of the present invention are alkaline cellulases, i.e. enzyme having at least 25%, more preferably at least 40% of their maximum activity at a pH ranging from 7 to 12. More preferred cellulases are enzymes having their maximum activity at a pH ranging from 7 to 12. A preferred alkaline cellulase is the cellulase sold under the tradename Carezyme® by Novo Nordisk A/S.

Amylases (α and/or β) can be included for removal of carbohydrate-based stains. WO94/02597, Novo Nordisk A/S published Feb. 03, 1994, describes cleaning compositions which incorporate mutant amylases. See also WO95/10603, Novo Nordisk A/S, published Apr. 20, 1995. Other amylases known for use in cleaning compositions include both α- and β-amylases. α-Amylases are known in the art and include those disclosed in U.S. Pat. No. 5,003,257; EP 252,666; WO/91/00353; FR 2,676,456; EP 285,123; EP 525,610; EP 368,341; and British Patent specification no. 1,296,839 (Novo). Other suitable amylases are stability-enhanced amylases described in WO94/18314, published Aug. 18, 1994 and WO96/05295, Genecor, published Feb. 22, 1996 and amylase variants having additional modification in the immediate parent available from Novo Nordisk A/S, disclosed in WO 95/10603, published April 1995. Also suitable are amylases described in EP 277 216, WO95/26397 and WO96/23873 (all by Novo Nordisk).

Examples of commercial α-amylases products are Purafect Ox Am® from Genecor and Termamyl®, Ban®, Fungamyl® and Duramyl®, all available from Novo Nordisk A/S Denmark. WO95/26397 describes other suitable amylases: α- amylases characterised by having a specific activity at least 25% higher than the specific activity of Termamyl® at a temperature range of 25° C. to 55° C. and at a pH value in the range of 8 to 10, measured by the Phadebas ® α-amylase activity assay. Suitable are variants of the above enzymes, described in WO96/23873 (Novo Nordisk). Other amylolytic enzymes with improved properties with respect to the activity level and the combination of thermostability and a higher activity level are described in WO 95/35382.

Preferred amylases for the purpose of the present invention are the amylases sold under the tradename Termamyl, Duramyl and Maxamyl and or the α-amylase variant demonstrating increased thermostability disclosed as SEQ ID NO: 2 in WO96/23873.

Preferred amylases for specific applications are alkaline amylases, ie enzymes having an enzymatic activity of at least 10%, preferably at least 25%, more preferably at least 40% of their maximum activity at a pH ranging from 7 to 12. More preferred amylases are enzymes having their maximum activity at a pH range from 7 to 12.

The amylolytic enzymes are incorporated in the detergent compositions of the present invention a level of from 0.0001% to 2%, preferably from 0.00018% to 0.06%, more preferably from 0.00024% to 0.048% pure enzyme by weight of the composition.

The term "pectin degrading enzyme" is intended to encompass arabinanase (EC 3.2.1.99), galactanases (EC 3.2.1.89), polygalacturonase (EC 3.2.1.15) exo-polygalacturonase (EC 3.2.1.67), exo-poly-alpha-galacturonidase (EC 3.2.1.82), pectin lyase (EC 4.2.2.10), pectin esterase (EC 3.2.1.11), pectate lyase (EC 4.2.2.2), exo-polygalacturonate lyase (EC 4.2.2.9) and hemicellulases such as endo-1,3-β-xylosidase (EC 3.2.1.32), xylan-1, 4-β-xylosidase (EC 3.2.1.37) and α-L-arabinofuranosidase (EC 3.2.1.55). The pectin degrading enzymes are natural mixtures of the above mentioned enzymatic activities. Pectin enzymes therefore include the pectin methylesterases which hdyrolyse the pectin methyl ester linkages, polygalacturonases which cleave the glycosidic bonds between galacturonic acid molecules, and the pectin transeliminases or lyases which act on the pectic acids to bring about non-hydrolytic cleavage of α-1→4 glycosidic linkages to form unsaturated derivatives of galacturonic acid.

Pectin degrading enzymes are incorporated into the compositions in accordance with the invention preferably at a level of from 0.0001% to 2%, more preferably from 0.0005% to 0.5%, most preferred from 0.001% to 0.1% pure enzyme by weight of the total composition.

Preferred pectin degrading enzymes for specific applications are alkaline pectin degrading enzymes, ie enzymes having an enzymatic activity of at least 10%, preferably at least 25%, more preferably at least 40% of their maximum activity at a pH ranging from 7 to 12. More preferred pectin degrading enzymes are enzymes having their maximum activity at a pH ranging from 7 to 12. Alkaline pectin degrading enzymes are produced by alkalophilic microorganisms e.g. bacterial, fungal and yeast microorganisms such as Bacillus species. Preferred microorganisms are Bacillus firmus, Bacillus circulans, and Bacillus subtilis as described in JP 56131376 and JP 56068393. Alkaline pectin decomposing enzymes include galacturn-1,4-α-galacturonase (EC 3.2.1.67), poly-galacturonase activities (EC 3.2.1.15, pectin esterase (EC 3.1.1.11), pectate lyase (EC 4.2.2.2) and their iso enzymes and they can be produced by the Erwinia species. Preferred are E. chrysanthemi, E. carotovora, E. amylovora, E. herbicola, E. dissolvens as described in JP 59066588, JP 63042988 and in World J. Microbiol. Microbiotechnol. (8, 2, 115–120) 1992. Said alkaline pectin enzymes can also be produced by Bacillus species as disclosed in JP 73006557 and Agr. Biol. Chem. (1972), 36 (2) 285–93.

The term xyloglucanase encompasses the family of enzymes described by Vincken and Voragen at Wageningen University [Vincken et al (1994) Plant Physiol., 104, 99–107] and are able to degrade xyloglucans as described in Hayashi et al (1989) Plant. Physiol. Plant Mol. Biol., 40, 139–168. Vincken et al demonstrated the removal of xyloglucan coating from cellulose of the isolated apple cell wall by a xyloglucanase purified from *Trichoderma viride* (endo-IV-glucanase). This enzyme enhances the enzymatic degradation of cell wall-embedded cellulose and work in synergy with pectic enzymes. Rapidase LIQ+ from Gist-Brocades contains an xyloglucanase activity.

This xyloglucanase is incorporated into the cleaning compositions in accordance with the invention preferably at a level of from 0.0001% to 2%, more preferably from 0.0005% to 0.5%, most preferred from 0.001% to0.1% pure enzyme by weight of the composition.

Preferred xyloglucanases for specific applications are alkaline xyloglucanases, ie enzymes having an enzymatic activity of at least 10%, preferably at lest 25%, more preferably at least 40% of their maximum activity at a pH ranging from 7 to 12. More preferred xyloglucanases are enzymes having their maximum activity at a pH ranging from 7 to 12.

The above-mentioned enzymes may be of any suitable origin, such as vegetable, animal, bacterial, fungal and yeast origin. Origin can further be mesophilic or extremophilic (psychrophilic, psychrotrophic, thermophilic, barophilic, alkalophilic, acidophilic, halophilic, etc.). Purified or non-purified forms of these enzymes may be used. Nowadays, it is common practice to modify wild-type enzymes via protein/genetic engineering techniques in order to optimise their performance efficiency in the cleaning compositions of the invention. For example, the variants may be designed such that the compatibility of the enzyme to commonly encountered ingredients of such compositions is increased. Alternatively, the variant may be designed such that the optimal pH, bleach or chelant stability, catalytic activity and the like, of the enzyme variant is tailored to suit the particular cleaning application.

In particular, attention should be focused on amino acids sensitive to oxidation in the case of bleach stability and on surface charges for the surfactant compatibility. The isoelectric point of such enzymes may be modified by the substitution of some charged amino acids, e.g. an increase in isoelectric point may help to improve compatibility with anionic surfactants. The stability of the enzymes may be further enhanced by the creation of e.g. additional salt bridges and enforcing metal binding sites to increase chelant stability.

Bleaching agents:

Additional optional detergent ingredients that can be included in the detergent compositions of the present invention include bleaching agents such as PB1, PB4 and percarbonate with a particle size of 400–800 microns. These bleaching agent components can include one or more oxygen bleaching agents and, depending upon the bleaching agent chosen, one or more bleach activators. When present oxygen bleaching compounds will typically be present at levels of from about 1% to about 25%. In general, bleaching compounds are optional added components in non-liquid formulations, e.g. granular detergents.

A bleaching agent component for use herein can be any of the bleaching agents useful for detergent compositions including oxygen bleaches, as well as others known in the art.

A bleaching agent suitable for the present invention can be an activated or non-activated bleaching agent.

One category of oxygen bleaching agent that can be used encompasses percarboxylic acid bleaching agents and salts thereof. Suitable examples of this class of agents include magnesium monoperoxyphthalate hexahydrate, the magnesium salt of meta-chloro perbenzoic acid, 4-nonylamino-4-oxoperoxybutyric acid and diperoxydodecanedioic acid. Such bleaching agents are disclosed in U.S. Pat. No. 4,483, 781, U.S. 740,446, EP 0 133 354 and U.S. Pat. No. 4,412, 934. Highly preferred bleaching agents also include 6-nonylamino-6-oxoperoxycarproic acid as described in U.S. Pat. No. 4,634,551.

Another category of bleaching agents that can be used encompasses the halogen bleaching agents. Examples of hypohalite bleaching agents, for example, include trichloro isocyanuric acid and the sodium and potassium dichloroisocyanurates and N-chloro and N-bromo alkane sulphonamides. Such materials are normally added at 0.5–10% by weight of the finished product, preferably 1–5% by weight.

The hydrogen peroxide releasing agents can be used in combination with bleach activators such as tetra-acetylethylenediamine (TAED), nonanoyloxybenzene-sulfonate (NOBS, described in U.S. Pat. No. 4,412,934), 3,5-trimethyl-hexsanoloxybenzenesulfonate (ISONOBS, described in EP 120 591) or pentaacetylglucose (PAG), which are perhydrolyzed to form a peracid as the active bleaching species, leading to improved bleaching effect. In addition, very suitable are the bleach activators C8(6-octanamido-caproyl) oxybenzene-sulfonate, C9(6-nonanamido caproyl) oxybenzenesulfonate and C10 (6-decanamido caproyl) oxybenzenesulfonate or mixtures thereof. Also suitable activators are acylated citrate esters such as disclosed in European Patent Application No. 91870207.7.

Useful bleaching agents, including peroxyacids and bleaching systems comprising bleach activators and peroxygen bleaching compounds for use in cleaning compositions according to the invention are described in U.S. application Ser. No. 08/136,626.

The hydrogen peroxide may also be present by adding an enzymatic system (i.e. an enzyme and a substrate therefore) which is capable of generation of hydrogen peroxide at the beginning or during the washing and/or rinsing process. Such enzymatic systems are disclosed in European Patent Application EP 0 537 381.

Bleaching agents other than oxygen bleaching agents are also known in the art and can be utilized herein. One type of non-oxygen bleaching agent of particular interest includes photoactivated bleaching agents such as the sulfonated zinc and/or aluminium phthalocyanines. These materials can be deposited upon the substrate during the washing process. Upon irradiation with light, in the presence of oxygen, such as by hanging clothes out to dry in the daylight, the sulfonated zinc phthalocyanine is activated and, consequently, the substrate is bleached. Preferred zinc phthalocyanine and a photoactivated bleaching process are described in U.S. Pat. No. 4,033,718. Typically, detergent composition will contain about 0.025% to about 1.25%, by weight, of sulfonated zinc phthalocyanine.

Bleaching agents may also comprise a maganese catalyst. The manganese catalyst may, e.g., be one of the compounds described in "Efficient manganese catalysts for low-temperature bleaching", Nature 369, 1994, pp. 637–639.

Suds Suppressors:

Another optional ingredient is a suds suppressor, exemplified by silicones, and silica-silicone mixtures. Silicones can generally be represented by alkylated polysiloxane materials, while silica is normally used in finely divided forms exemplified by silica aerogels and xerogels and hydrophobic silicas of various types. Theses materials can be incorporated as particulates, in which the suds suppressor is advantageously releasably, incorporated in a water-soluble or water-dispersible, substantially non surface-active detergent impermeable carrier. Alternatively the suds suppressor can be dissolved or dispersed in a liquid carrier and applied by spraying on to one or more of the other components.

A preferred silicone suds controlling agent is disclosed in U.S. Pat. No. 3,933,672. Other particularly useful suds suppressors are the self-emulsifying silicone suds suppressors, described in German Patent Application DTOS 2,646,126. An example of such a compound is DC-544, commercially available from Dow Corning, which is a siloxane-glycol copolymer. Especially preferred suds controlling agent are the suds suppressor system comprising a mixture of silicone oils and 2-alkyl-alkanols. Suitable 2-alkyl-alkanols are 2-butyl-octanol which are commercially available under the trade name Isofol 12 R.

Such suds suppressor system are described in European Patent Application EP 0 593 841.

Especially preferred silicone suds controlling agents are described in European Patent Application No. 92201649.8. Said compositions can comprise a silicone/silica mixture in combination with fumed nonporous silica such as Aerosil®.

The suds suppressors described above are normally employed at levels of from 0.001% to 2% by weight of the composition, preferably from 0.01% to 1% by weight.

Other components:

Other components used in detergent compositions may be employed, such as soil-suspending agents, soil-releasing agents, optical brighteners, abrasives, bactericides, tarnish inhibitors, coloring agents, and/or encapsulated or nonencapsulated perfumes.

Especially suitable encapsulating materials are water soluble capsules which consist of a matrix of polysaccharide and polyhydroxy compounds such as described in GB 1,464,616.

Other suitable water soluble encapsulating materials comprise dextrins derived from ungelatinized starch acid esters of substituted dicarboxylic acids such as described in U.S. Pat. No. 3,455,838. These acid-ester dextrins are, preferably, prepared from such starches as waxy maize, waxy sorghum, sago, tapioca and potato. Suitable examples of said encapsulation materials include N-Lok manufactured by National Starch. The N-Lok encapsulating material consists of a modified maize starch and glucose. The starch is modified by adding monofunctional substituted groups such as octenyl succinic acid anhydride.

Antiredeposition and soil suspension agents suitable herein include cellulose derivatives such as methylcellulose, carboxymethylcellulose and hydroxyethylcellulose, and homo- or co-polymeric polycarboxylic acids or their salts.. Polymers of this type include the polyacrylates and maleic anhydride-acrylic acid copolymers previously mentioned as builders, as well as copolymers of maleic anhydride with ethylene, methylvinyl ether or methacrylic acid, the maleic anhydride constituting at least 20 mole percent of the copolymer. These materials are normally used at levels of from 0.5% to 10% by weight, more preferably form 0.75% to 8%, most preferably from 1% to 6% by weight of the composition.

Preferred optical brighteners are anionic in character, examples of which are disodium 4,4'-bis-(2-diethanolamino-4-anilino -s- triazin-6-ylamino)stilbene-2:2' disulphonate, disodium 4, - 4'-bis-(2-morpholino-4-anilino-s-triazin-6-ylamino-stilbene-2:2' -disulphonate, disodium 4,4' -bis-(2, 4-dianilino-s-triazin-6-ylamino)stilbene-2:2' -disulphonate, monosodium 4',4" - bis-(2,4-dianilino-s-tri-azin-6 ylamino) stilbene-2-sulphonate, disodium 4,4' -bis-(2-anilino-4-(N-methyl-N-2-hydroxyethylamino)-s-triazin-6-ylamino) stilbene-2,2' - disulphonate, di-sodium 4,4' -bis-(4-phenyl-2,1,3-triazol-2-yl)-stilbene-2,2' disulphonate, di-so-dium 4,4'bis(2-anilino-4-(1-methyl-2-hydroxyethylamino)-s-triazin-6-ylamino)stilbene-2,2'disulphonate, sodium 2(stilbyl-4"-(naphtho-1',2':4,5)-1,2,3, - triazole-2"- sulphonate and 4,4'-bis(2-sulphostyryl)biphenyl.

Other useful polymeric materials are the polyethylene glycols, particularly those of molecular weight 1000–10000, more particularly 2000 to 8000 and most preferably about 4000. These are used at levels of from 0.20% to 5% more preferably from 0.25% to 2.5% by weight. These polymers and the previously mentioned homo- or co-polymeric polycarboxylate salts are valuable for improving whiteness maintenance, fabric ash deposition, and cleaning performance on clay, proteinaceous and oxidizable soils in the presence of transition metal impurities.

Soil release agents useful in compositions of the present invention are conventionally copolymers or terpolymers of terephthalic acid with ethylene glycol and/or propylene glycol units in various arrangements. Examples of such polymers are disclosed in U.S. Pat. Nos. 4,116,885 and 4,711,730 and EP 0 272 033. A particular preferred polymer in accordance with EP 0 272 033 has the formula:

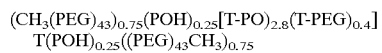

where PEG is —(OC$_2$H$_4$)O—, PO is (OC$_3$H$_6$O) and T is (pOOC$_6$H$_4$CO).

Also very useful are modified polyesters as random copolymers of dimethyl terephthalate, dimethyl sulfoisophthalate, ethylene glycol and 1,2-propanediol, the end groups consisting primarily of sulphobenzoate and secondarily of mono esters of ethylene glycol and/or 1,2-propanediol. The target is to obtain a polymer capped at both end by sulphobenzoate groups, "primarily", in the present context most of said copolymers herein will be endcapped by sulphobenzoate groups. However, some copolymers will be less than fully capped, and therefore their end groups may consist of monoester of ethylene glycol and/or 1,2-propanediol, thereof consist "secondarily" of such species.

The selected polyesters herein contain about 46% by weight of dimethyl terephthalic acid, about 16% by weight of 1,2-propanediol, about 10% by weight ethylene glycol, about 13% by weight of dimethyl sulfobenzoic acid and about 15% by weight of sulfoisophthalic acid, and have a molecular weight of about 3.000. The polyesters and their method of preparation are described in detail in EP 311 342.

Softening agents:

Fabric softening agents can also be incorporated into laundry detergent compositions in accordance with the present invention. These agents may be inorganic or organic in type. Inorganic softening agents are exemplified by the smectite clays disclosed in GB-A-1 400898 and U.S. Pat.

No. 5,019,292. Organic fabric softening agents include the water insoluble tertiary amines as disclosed in GB-A1 514 276 and EP 0 011 340 and their combination with mono $C_{12}$–$C_{14}$ quaternary ammonium salts are disclosed in EP-B 0 026 528 and di-long-chain amides as disclosed in EP- 0 242 919. Other useful organic ingredients of fabric softening systems include high molecular weight polyethylene oxide materials as disclosed in EP 0 299 575 and 0 313 146.

Levels of smectite clay are normally in the range from 5% to 14%, more preferably from 8% to 12% by weight, with the material being added as a dry mixed component to the remainder of the formulation. Organic fabric softening agents such as the water-insoluble tertiary amines or dilong chain amide materials are incorporated at levels of from 0.5% to 5% by weight, normally from 1% to 3% by weight whilst the high molecular weight polyethylene oxide materials and the water soluble cationic materials are added at levels of from 0.1% to 2%, normally from 0.15% to 1.5% by weight. These materials are normally added to the spray dried portion of the composition, although in some instances it may be more convenient to add them as a dry mixed particulate, or spray them as molten liquid on to other solid components of the composition.

Polymeric dye-transfer inhibiting agents:

The detergent compositions according to the present invention may also comprise from 0.001% to 10%, more preferably from 0.01% to 2%, more preferably form 0.05% to 1% by weight of polymeric dye- transfer inhibiting agents. Said polymeric dye-transfer inhibiting agents are normally incorporated into detergent compositions in order to inhibit the transfer of dyes from colored fabrics onto fabrics washed therewith. These polymers have the ability of complexing or adsorbing the fugitive dyes washed out of dyed fabrics before the dyes have the opportunity to become attached to other articles in the wash.

Especially suitable polymeric dye-transfer inhibiting agents are polyamine N-oxide polymers, copolymers of N-vinyl-pyrrolidone and N-vinylimidazole, polyvinylpyrrolidone polymers, polyvinyloxazolidones and polyvinylimidazoles or mixtures thereof.

Addition of such polymers also enhances the performance of the enzymes according the invention.

Use in the Paper Pulp Industry

Further, it is contemplated that the mannanase of the present invention is useful in chlorine-free bleaching processes for paper pulp (chemical pumps, semichemical pumps, mechanical pulps or kraft pulps) in order to increase the brightness thereof, thus decreasing or eliminating the need for hydrogen peroxide in the bleaching process.

Use in the Textile and Cellulosic Fiber Processing Industries

The mannanase of the present invention can be used in combination with other carbohydrate degrading enzymes (for instance xyloglucanase, xylanase, various pectinases) for preparation of fibers or for cleaning of fibers in combination with detergents.

In the present context, the term "cellulosic material" is intended to mean fibers, sewn and unsewn fabrics, including knits, wovens, denims, yarns, and toweling, made from cotton, cotton blends or natural or manmade cellulosics (e.g. originating from xylan-containing cellulose fibers such as from wood pulp) or blends thereof. Examples of blends are blends of cotton or rayon/viscose with one or more companion material such as wool, synthetic fibers (e.g. polyamide fibers, acrylic fibers, polyester fibers, polyvinyl alcohol fibers, polyvinyl chloride fibers, polyvinylidene chloride fibers, polyurethane fibers, polyurea fibers, aramid fibers), and cellulose-containing fibers (e.g. rayon/viscose, ramie, hemp, flax-linen, jute, cellulose acetate fibers, lyocell).

The processing of cellulosic material for the textile industry, as for example cotton fiber, into a material ready for garment manufacture involves several steps: spinning of the fiber into a yarn; construction of woven or knit fabric from the yarn and subsequent preparation, dyeing and finishing operations. Woven goods are constructed by weaving a filling yarn between a series of warp yarns; the yarns could be two different types.

Desizing: polymeric size like e.g. mannan, starch, CMC or PVA is added before weaving in order to increase the warp speed; This material must be removed before further processing. The enzyme of the invention is useful for removal of mannan containing size.

Degradation of Thickeners

Galactomannans such as guar gum and locust bean gum are widely used as thickening agents e.g. in food and print paste for textile printing such as prints on T-shirts. The enzyme or enzyme preparation according to the invention can be used for reducing the viscosity of eg residual food in processing equipment and thereby facilitate cleaning after processing. Further, it is contemplated that the enzyme or enzyme preparation is useful for reducing viscosity of print paste, thereby facilitating wash out of surplus print paste after textile printins.

Degradation or Modification of Plant Material

The enzyme or enzyme preparation according to the invention is preferably used as an agent for degradation or modification of mannan, galactomannan, glucomannan or galactoglucomannan containing material originating from plants. Examples of such material is guar gum and locust bean gum.

The mannanase of the invention may be used in modifying the physical-chemical properties of plant derived material such as the viscosity. For instance, the mannanase may be used to reduce the viscosity of feed or food which contain mannan and to promote processing of viscous mannan containing material.

Coffee Extraction

The enzymes or enzyme preparation of the invention may also be used for hydrolysing galactomannans present in a liquid coffee extract, preferably in order to inhibit gel formation during freeze drying of the (instant) coffee. Preferably, the mannanase of the invention is immobilized in order to reduce enzyme consumption and avoid contamination of the coffee. This use is further disclosed in EP-A-676 145.

Use in the Fracturing of a Subterranean Formation (Oil Drilling)

Further, it is contemplated that the enzyme of the present invention is useful as an enzyme breaker as disclosed in U.S. Pat. Nos. 5,806,597, 5,562,160, 5,201,370 and 5,067,566 to BJ Services Company (Houston, Tex., U.S.A.), all of which are hereby incorporated by reference.

Accordingly, the mannanase of the present invention is useful in a method of fracturing a subterranean formation in a well bore in which a gellable fracturing fluid is first formed by blending together an aqueous fluid, a hydratable polymer, a suitable cross-linking agent for cross-linking the hydratable polymer to form a polymer gel and an enzyme breaker, ie the enzyme of the invention. The cross-linked polymer gel is pumped into the well bore under sufficient pressure to fracture the surrounding formation. The enzyme breaker is allowed to degrade the cross-linked polymer with time to reduce the viscosity of the fluid so that the fluid can be pumped from the formation back to the well surface.

The enzyme breaker may be an ingredient of a fracturing fluid or a breaker-crosslinker-polymer complex which further comprises a hydratable polymer and a crosslinking agent. The fracturing fluid or complex may be a gel or may be gellable. The complex is useful in a method for using the complex in a fracturing fluid to fracture a subterranean formation that surrounds a well bore by pumping the fluid to a desired location within the well bore under sufficient pressure to fracture the surrounding subterranean formation. The complex may be maintained in a substantially non-reactive state by maintaining specific conditions of pH and temperature, until a time at which the fluid is in place in the well bore and the desired fracture is completed. Once the fracture is completed, the specific conditions at which the complex is inactive are no longer maintained. When the conditions change sufficiently, the complex becomes active and the breaker begins to catalyze polymer degradation causing the fracturing fluid to become sufficiently fluid to be pumped from the subterranean formation to the well surface.

MATERIALS AND METHODS

Assay for activity test

A polypeptide of the invention having mannanase activity may be tested for mannanase activity according to standard test procedures known in the art, such as by applying a solution to be tested to 4 mm diameter holes punched out in agar plates containing 0.2% AZCL galactomannan (carob), i.e. substrate for the assay of endo-1,4-beta-D-mannanase available as CatNo.I-AZGMA from the company Megazyme.

Determination of catalytic activity (ManU) of mannanase Colorimetric Assay

Substrate: 0.2% AZCL-Galactomannan (Megazyme, Australia) from carob in 0.1 M Glycin buffer, pH 10.0.

The assay is carried out in an Eppendorf Micro tube 1.5 ml on a thermomixer with stirring and temperature control of 40° C. Incubation of 0.750 ml substrate with 0.05 ml enzyme for 20 min, stop by centrifugation for 4 minutes at 15000 rpm. The colour of the supernatant is measured at 600 nm in a 1 cm cuvette.

One ManU (Mannanase units) gives 0.24 abs in 1 cm.

Strains and donor organism

The Bacillus sp. I633 mentioned above comprises the beta-1,4-mannanase encoding DNA sequence shown in SEQ.ID.NO: 1.

E.coli DSM 12197 comprises the plasmid containing the DNA encoding the beta-1,4-mannanase of the invention (SEQ.ID.NO: 1).

The Bacillus agaradhaerens NCIMB 40482 mentioned above comprises the beta-1,4-mannanase encoding DNA sequence shown in SEQ.ID.NO: 5.

E.coli DSM 12180 comprises the plasmid containing the DNA encoding the beta-1,4-mannanase of the invention (SEQ.ID.NO: 5).

The Bacillus sp. AAI12 mentioned above comprises the beta-1,4-mannanase encoding DNA sequence shown in SEQ.ID.NO: 9.

E.coli DSM 12433 comprises the plasmid containing the DNA encoding the beta-1,4-mannanase of the invention (SEQ.ID.NO: 9).

The Bacillus halodurans mentioned above comprises the beta-1,4-mannanase encoding DNA sequence shown in SEQ.ID.NO: 11.

E.coli DSM 12441 comprises the plasmid containing the DNA encoding the beta-1,4-mannanase of the invention (SEQ.ID.NO: 11).

The Humicola insolens mentioned above comprises the beta-1,4-mannanase encoding DNA sequence shown in SEQ.ID.NO: 13.

E.coli DSM 9984 comprises the plasmid containing the DNA encoding the beta-1,4-mannanase of the invention (SEQ.ID.NO.: 13).

The Bacillus sp. AA349 mentioned above comprises the beta-1,4-mannanase encoding DNA sequence shown in SEQ.ID.NO: 15.

E.coli DSM 12432 comprises the plasmid containing the DNA encoding the beta-1,4-mannanase of the invention (SEQ.ID.NO: 15).

E.coli DSM 12847 comprises the plasmid containing the DNA encoding the beta-1,4-mannanase of the invention (SEQ.ID.NO: 17).

E.coli DSM 12848 comprises the plasmid containing the DNA encoding the beta-1,4-mannanase of the invention (SEQ.ID.NO: 19).

The Bacillus clausii mentioned above comprises the beta-1,4-mannanase encoding DNA sequence shown in SEQ.ID.NO: 21.

E.coli DSM 12849 comprises the plasmid containing the DNA encoding the beta-1,4-mannanase of the invention (SEQ.ID.NO: 21).

E.coli DSM 12850 comprises the plasmid containing the DNA encoding the beta-1,4-mannanase of the invention (SEQ.ID.NO: 23).

Bacillus sp. comprises the beta-1,4-mannanase encoding DNA sequence shown in SEQ.ID.NO.: 25.

E.coli DSM 12846 comprises the plasmid containing the DNA encoding the beta-1,4-mannanase of the invention (SEQ.ID.NO:25).

Bacillus sp. comprises the beta-1,4-mannanase encoding DNA sequence shown in SEQ.ID.NO: 27.

E.coli DSM 12851 comprises the plasmid containing the DNA encoding the beta-1,4-mannanase of the invention (SEQ.ID.NO: 27).

The Bacillus licheniformis mentioned above comprises the beta-1,4-mannanase encoding DNA sequence shown in SEQ.ID.NO: 29.

E.coli DSM 12852 comprises the plasmid containing the DNA encoding the beta-1,4-mannanase of the invention (SEQ.ID.NO: 29).

Bacillus sp. comprises the beta-1,4-mannanase encoding DNA sequence shown in SEQ.ID.NO: 31.

E.coli DSM 12436 comprises the plasmid containing the DNA encoding the beta-1,4-mannanase of the invention (SEQ.ID.NO: 31).

E. coli strain: Cells of E. coli SJ2 (Diderichsen, B., Wedsted, U., Hedegaard, L., Jensen, B. R., Sjøholm, C. (1990) Cloning of aldB, which encodes alpha-acetolactate decarboxylase, an exoenzyme from Bacillus brevis. J. Bacteriol., 172, 4315–4321), were prepared for and transformed by electroporation using a Gene Pulser™ electroporator from BIO-RAD as described by the supplier.

B.subtilis PL2306. This strain is the B.subtilis DN1885 with disrupted apr and npr genes (Diderichsen, B., Wedsted, U., Hedegaard, L., Jensen, B. R., Sjøholm, C. (1990) Cloning of aldB, which encodes alpha-acetolactate decarboxylase, an exoenzyme from Bacillus brevis. J. Bacteriol., 172, 4315–4321) disrupted in the transcriptional unit of the known *Bacillus subtilis* cellulase gene, resulting in cellulase negative cells. The disruption was performed essentially as described in (Eds. A. L. Sonenshein, J. A. Hoch and Richard Losick (1993) *Bacillus subtilis* and other Gram-Positive Bacteria, American Society for microbiology, p.618).

Competent cells were prepared and transformed as described by Yasbin, R. E., Wilson, G. A. and Young, F. E. (1975) Transformation and transfection in lysogenic strains of *Bacillus subtilis*: evidence for selective induction of prophage in competent cells. J. Bacteriol, 121: 296–304.

General Molecular Biology Methods

Unless otherwise stated all the DNA manipulations and transformations were performed using standard methods of molecular biology (Sambrook et al. (1989) Molecular cloning: A laboratory manual, Cold Spring Harbor lab., Cold Spring Harbor, N.Y.; Ausubel, F. M. et al. (eds.) "Current protocols in Molecular Biology". John Wiley and Sons, 1995; Harwood, C. R., and Cutting, S. M. (eds.) "Molecular Biological Methods for Bacillus". John Wiley and Sons, 1990).

Enzymes for DNA manipulations were used according to the manufacturer's instructions (e.g. restriction endonucleases, ligases etc. are obtainable from New England Biolabs, Inc.).

Plasmids pSJ1678: (see International Patent Application published as WO 94/19454).

pBK-CMV (Stratagene inc., La Jolla Calif.)

pMOL944. This plasmid is a pUB110 derivative essentially containing elements making the plasmid propagatable in *Bacillus subtilis*, kanamycin resistance gene and having a strong promoter and signal peptide cloned from the amyL of *B.licheniformis* ATCC14580. The signal peptide contains a SacII site making it convenient to clone the DNA encoding the mature part of a protein in-fusion with the signal peptide. This results in the expression of a Pre-protein which is directed towards the exterior of the cell.

The plasmid was constructed by means of ordinary genetic engineering and is briefly described in the following.

Construction of pMOL944

The pUB110 plasmid (McKenzie, T. et al., 1986, Plasmid 15: 93–103) was digested with the unique restriction enzymes NciI. A PCR fragment amplified from the amyL promoter encoded on the plasmid pDN1981 (P. L. Jørgensen et al.,1990, Gene, 96, p.37–41.) was digested with NciI and inserted in the NciI digested pUB110 to give the plasmid pSJ2624.

The two PCR primers used have the following sequences:
LWN5494 5'-GTCGCCGGGGCGGCCGCTATCAA TTGGTAACTGTATCTCAGC-3' (SEQ ID NO: 35)
LWN5495 5'-GTCGCCCGGGAGCTCTGATCAG GTACCAAGCTTGTCGACCTGCAGAATGAG GCAGCAAGAAGAT-3' (SEQ ID NO: 36)

The primer #LWN5494 inserts a NotI site in the plasmid.

The plasmid pSJ2624 was then digested with SacI and NotI and a new PCR fragment amplified on amyL promoter encoded on the pDN1981 was digested with SacI and NotI and this DNA fragment was inserted in the SacI-NotI digested pSJ2624 to give the plasmid pSJ2670.

This cloning replaces the first amyL promoter cloning with the same promoter but in the opposite direction. The two primers used for PCR amplification have the following sequences:

LWN5938 5'-GTCGGCGGCCGCTGATCACGTAC CAAGCTTGTCGACCTGCAGAATGAGGCAG CAAGAAGAT-3' (SEQ ID NO: 37)
LWN5939 5'-GTCGGAGCTCTATCAATTGGTAA CTGTATCTCAGC-3' (SEQ ID NO: 38)

The plasmid pSJ2670 was digested with the restriction enzymes PstI and BclI and a PCR fragment amplified from a cloned DNA sequence encoding the alkaline amylase SP722 (Patent # WO 9526397-A1) was digested with PstI and BclI and inserted to give the plasmid pMOL944. The two primers used for PCR amplification have the following sequence:

LWN7864 5'-AACAGCTGATCACGACTGATCTT TTAGCTTGGCAC-3' (SEQ ID NO: 39)
LWN7901 5'-AACTGCAGCCGCGGCACATCATA ATGGGACAAATGGG-3' (SEQ ID NO: 40)

The primer #LWN7901 inserts a SacII site in the plasmid.

Cultivation of Donor strains and Isolation of Genomic DNA

The relevant strain of Bacillus, eg Bacillus sp. I633, was grown in TY with pH adjusted to approximately pH 9.7 by the addition of 50 ml of 1M Sodium-Sesquicarbonat per 500 ml TY. After 24 hours incubation at 30° C. and 300 rpm, the cells were harvested, and genomic DNA was isolated by the method described by Pitcher et al. [Pitcher, D. G., Saunders, N. A., Owen, R. J; Rapid extraction of bacterial genomic DNA with guanidium thiocyanate; *Lett Appl Microbiol* 1989 8 151–156].

Media

TY (as described in Ausubel, F. M. et al. (eds.) "Current protocols in Molecular Biology". John Wiley and Sons, 1995).

LB agar (as described in Ausubel, F. M. et al. (eds.) "Current protocols in Molecular Biology". John Wiley and Sons, 1995).

LBPG is LB agar supplemented with 0.5% Glucose and 0.05 M potassium phosphate, pH 7.0

AZCL-galactomannan is added to LBPG-agar to 0.5% AZCL-galactomannan is from Megazyme, Australia.

BPX media is described in EP 0 506 780 (WO 91/09129).

NZY agar (per liter) 5 of NaCl, 2 g of MgSO4, 5 g of yeast extract, 10 g of NZ amine (casein hydrolysate), 15 g of agar; add deionized water to 1 liter, adjust pH with NaOH to pH 7.5 and autoclave NZY broth (per liter) 5 g of NaCl, 2 g of MgSO4, 5 g of yeast extract, 10 g of NZ amine (casein hydrolysate); add deionized water to 1 liter, adjust pH with NaOH to pH 7.5 and autoclave NZY Top Agar (per liter) 5 g of NaCl, 2 g of MgSO4, 5 g of yeast extract, 10 g of NZ amine (casein hydrolysate), 0.7% (w/v) agarose; add deionized water to 1 liter, adjust pH with NaOH to pH 7.5 and autoclave.

The following non-limiting examples illustrate the invention.

EXAMPLE 1

Mannanase Derived from Bacillus sp (I633)

Construction of a genomic library from Bacillus sp. I633 in the lambdaZAPExpress vector Genomic DNA of Bacillus sp. I633 was partially digested with restriction enzyme Sau3A, and size-fractionated by electrophoresis on a 0.7% agarose gel (SeaKem agarose, FMC, USA). Fragments between 1.5 and 10 kb in size were isolated and concentrated to a DNA band by running the DNA fragments backwards on a 1.5% agarose gel followed by the extraction of the fragments from the agarose gel slice using the Qiaquick gel extraction kit according to the manufacturer's instructions (Qiagen Inc., USA). To construct a genomic library, ca. 100 ng of purified, fractionated DNA from above was ligated with 1 ug of BamHI-cleaved, dephosphorylated lambdaZAPexpress vector arms (Stratagene, La Jolla Calif., USA) for 24 hours at +4° C. according to the manufacturer's instructions. A 3-ul aliquot of the ligation mixture was packaged directly using the GigaPackIII Gold packaging extract (Stratagene, USA) according to the manufacturers instructions (Stratagene). The genomic lambdaZAPExpress phage library was titered using the E. coli XL1-Blue MRF-strain from Stratagene (La Jolla, USA). The unamplified genomic library comprised of $3 \times 10^7$ plaque-forming units (pfu) with a vector background of less than 1%.

Screening for beta-mannanase clones by functional expression in lambdaZAPExpress Approximately 5000 plaque-forming units (pfu) from the genomic library were plated on NZY-agar plates containing 0.1% AZCL-galactomannan (MegaZyme, Australia, cat. no. I-AZGMA), using E. coli XL1-Blue MRF' (Stratagene, USA) as a host, followed by incubation of the plates at 37° C. for 24 hours. Mannanase-positive lambda clones were identified by the formation of blue hydrolysis halos around the positive phage clones. These were recovered from the screening plates by coring the TOP-agar slices containing the plaques of interest into 500 ul of SM buffer and 20 ul of chloroform. The mannanase-positive lambdaZAPExpress clones were plaque-purified by plating an aliquot of the cored phage stock on NZY plates containing 0.1% AZCL-galactomannan as above. Single, mannanase-positive lambda clones were cored into 500 ul of SM buffer and 20 ul of chloroform, and purified by one more plating round as described above.

Single-clone in vivo excision of the phagemids from the mannanase-positive lambdaZAPExpress clones E. coli XL1-Blue cells (Stratagene, La Jolla, Calif.) were prepared and resuspended in 10 mM MgSO4 as recommended by Stratagene (La Jolla, USA). 250-ul aliquots of the pure phage stocks from the mannase-positive clones were combined in Falcon 2059 tubes with 200 uls of XL1-Blue MRF' cells (OD600=1.0) and >$10^6$ pfus/ml of the ExAssist M13 helper phage (Stratagene), and the mixtures were incubated at 37° C. for 15 minutes. Three mls of NZY broth was added to each tube and the tubes were incubated at 37 C for 2.5 hours. The tubes were heated at 65° C. for 20 minutes to kill the E. coli cells and bacteriophage lambda; the phagemids being resistant to heating. The tubes were spun at 3000 rpm for 15 minutes to remove cellular debris and the supernatants were decanted into clean Falcon 2059 tubes. Aliquots of the supernatants containing the excised single-stranded phagemids were used to infect 200 uls of E. coli XLOLR cells (Stratagene, OD600=1.0 in 10 mM MgSO4) by incubation at 37° C. for 15 minutes. 350 uls of NZY broth was added to the cells and the tubes were incubated for 45 min at 37° C. Aliquots of the cells were plated onto LB kanamycin agar plates and incubated for 24 hours at 37° C. Five excised single colonies were re-streaked onto LB kanamycin agar plates containing 0.1% AZCL-galactomannan (MegaZyme, Australia). The mannanase-positive phagemid clones were characterized by the formation of blue hydrolysis halos around the positive colonies. These were further analysed by restriction enzyme digests of the isolated phagemid DNA (QiaSpin kit, Qiagen, USA) with EcoRI, PstI, EcoRI-PstI, and HindIII followed by agarose gel electrophoresis.

Nucleotide sequence analysis

The nucleotide sequence of the genomic beta-1,4-mannanase clone pBXM3 was determined from both strands by the dideoxy chain-termination method (Sanger, F., Nicklen, S., and Coulson, A. R. (1977) Proc. Natl. Acad. Sci. U. S. A. 74, 5463–5467) using 500 ng of Qiagen-purified template (Qiagen, USA), the Taq deoxy-terminal cycle sequencing kit (Perkin-Elmer, USA), fluorescent labeled terminators and 5 pmol of either pBK-CMV polylinker primers (Stratagene, USA) or synthetic oligonucleotide primers. Analysis of the sequence data was performed according to Devereux et al., 1984 (Devereux, J., Haeberli, P., and Smithies, O. (1984) Nucleic Acids Res. 12, 387–395).

Sequence alignment

A multiple sequence alignment of the glycohydrolase family 5 beta-1,4-mannanase from Bacillus sp. I633 of the present invention (ie SEQ ID NO: 2), *Bacillus circulans* (GenBank/EMBL accession no. 066185), Vibrio sp. (acc. no. O69347), *Streptomyces lividans* (acc. no. P51529), and *Caldicellulosiruptor saccharolyticus* (acc. no. P22533). The multiple sequence alignment was created using the PileUp program of the GCG Wisconsin software package,version 8.1. ; with gap creation penalty 3.00 and gap extension penalty 0.10.

Sequence Similarities

The deduced amino acid sequence of the family 5 beta-1,4-mannanase of the present invention cloned from Bacillus sp. I633 shows 75% similarity and 60.1% sequence identity to the beta-1,4-mannanase of *Bacillus circulans* (GenBank/EMBL accession no. 066185), 64.4% similarity and 44.6% identity to the beta-1,4-mannanase from Vibrio sp. (acc. no. O69347), 63% similarity and 43.2% identity to the beta-1,4-mannanase from *Streptomyces lividans* (acc. no. P51529), 52.5% similarity and 34.4% sequence identity to the beta-1,4-mannanase from *Caldicellulosiruptor saccharolyticus* (acc. no. P2253). The sequences were aligned using the GAP program of the GCG Wisconsin software package,version 8.1.; with gap creation penalty 3.00 and gap extension penalty 0.10.

Cloning of Bacillus sp (I633) mannanase gene

A. Subcloning and expression of a catalytic core mannanase enzyme in *B.subtilis:*

The mannanase encoding DNA sequence of the invention was PCR amplified using the PCR primer set consisting of the following two oligo nucleotides:

BXM2.upper.SacII
5'-GTT GAG AAA G<u>CG GCC G</u>CC TTT TTT CTA TTC TAC AAT CAC ATT ATC-3' (SEQ ID NO: 41)

BXM2.core.lower.NotI
5'-GAC GAC GTA CAA <u>GCG GCC GC</u>T CAC TAC GGA GAA GTT CCT CCA TCA G-3' SEQ ID NO: 42)

Restriction sites SacII and NotI are underlined.

Chromosomal DNA isolated from Bacillus sp. I633 as described above was used as template in a PCR reaction using Amplitaq DNA Polymerase (Perkin Elmer) according to manufacturers instructions. The PCR reaction was set up in PCR buffer (10 mM Tris-HCl, pH 8.3, 50 mM KCl, 1.5 mM $MgCl_2$, 0.01% (w/v) gelatin) containing 200 μm of each dNTP, 2.5 units of AmpliTaq polymerase (Perkin-Elmer, Cetus, USA) and 100 pmol of each primer.

The PCR reactions was performed using a DNA thermal cycler (Landgraf, Germany). One incubation at 94° C. for 1 min followed by thirty cycles of PCR performed using a cycle profile of denaturation at 94° C. for 30 sec, annealing at 60° C. for 1 min, and extension at 72° C. for 2 min. Five-μl aliquots of the amplification product was analysed by electrophoresis in 0.7% agarose gels (NuSieve, FMC). The appearance of a DNA fragment size 1.0 kb indicated proper amplification of the gene segment.

Subcloning of PCR fragment:

Fortyfive-μl aliquots of the PCR products generated as described above were purified using QIAquick PCR purification kit (Qiagen, USA) according to the manufacturer's instructions. The purified DNA was eluted in 50 μm of 10 mM Tris-HCl, pH 8.5. 5 μg of pMOL944 and twentyfive-μl of the purified PCR fragment was digested with SacII and NotI, electrophoresed in 0.8% low gelling temperature agarose (SeaPlaque GTG, FMC) gels, the relevant fragments were excised from the gels, and purified using QIAquick Gel extraction Kit (Qiagen, USA) according to the manufacturer's instructions. The isolated PCR DNA fragment was then ligated to the SacII-NotI digested and purified pMOL944. The ligation was performed overnight at 16° C. using 0.5 μg of each DNA fragment, 1 U of T4 DNA ligase and T4 ligase buffer (Boehringer Mannheim, Germany).

The ligation mixture was used to transform competent B.subtilis PL2306. The transformed cells were plated onto LBPG-10 μg/ml of Kanamycin-agar plates. After 18 hours incubation at 37° C. colonies were seen on plates. Several clones were analyzed by isolating plasmid DNA from overnight culture broth.

One such positive clone was restreaked several times on agar plates as used above, this clone was called MB748. The clone MB748 was grown overnight in TY-10 μg/ml Kanamycin at 37° C., and next day 1 ml of cells were used to isolate plasmid from the cells using the Qiaprep Spin Plasmid Miniprep Kit #27106 according to the manufacturers recommendations for B. subtilis plasmid preparations. This DNA was DNA sequenced and revealed the DNA sequence corresponding to the mature part of the mannanase (corresponding to positions 94–990 of SEQ ID NO: 1 and positions 32–330 of SEQ ID NO: 2) with introduced stop codon replacing the amino acid residue no 331 corresponding to the base pair positions 1201–1203 in SEQ ID NO: 1.

B. Subcloning and expression of mature full length mannanase in B.subtilis.

The mannanase encoding DNA sequence of the invention was PCR amplified using the PCR primer set consisting of these two oligo nucleotides:

BXM2.upper.SacII
    5'-CAT TCT GCA <u>GCC GCG GCA</u> AAT TCC GGA TTT TAT GTA AGC GG-3' (SEQ ID NO: 43)

BXM2.lower.NotI
    5'-GTT GAG AAA <u>GCG GCC GCC</u> TTT TTT CTA TTC TAC AAT CAC ATT ATC-3' (SEQ ID NO: 44)

Restriction sites SacII and NotI are underlined

Chromosomal DNA isolated from Bacillus sp . (I633) as described above was used as template in a PCR reaction using Amplitaq DNA Polymerase (Perkin Elmer) according to manufacturers instructions. The PCR reaction was set up in PCR buffer (10 mM Tris-HCl, pH 8.3, 50 mM KCl, 1.5 mM MgCl$_2$, 0.01% (w/v) gelatin) containing 200 μm of each dNTP, 2.5 units of AmpliTaq polymerase (Perkin-Elmer, Cetus, USA) and 100 pmol of each primer The PCR reactions was performed using a DNA thermal cycler (Landgraf, Germany). One incubation at 94° C. for 1 min followed by thirty cycles of PCR performed using a cycle profile of denaturation of 94° C. for 30 sec, annealing at 60° C. for 1 min, and extension at 72° C. for 2 min. Five-μl aliquots of the amplification product was analysed by electrophoresis in 0.7% agarose gels (NuSieve, FMC). The appearance of a DNA fragment size 1.5 kb indicated proper amplification of the gene segment.

Subcloning of PCR fragment:

Fortyfive-μl aliquots of the PCR products generated as described above were purified using QIAquick PCR purification kit (Qiagen, USA) according to the manufacturer's instructions. The purified DNA was eluted in 50 μl of 10 mM Tris-HCl, pH 8.5. 5 μg of pMOL944 and twentyfive-μl of the purified PCR fragment was digested with SacII and NotI, electrophoreses in 0.8% low gelling temperature agarose (SeaPlague GTG, FMC) gels, the relevant fragments were excised from the gels, and purified using QIAquick Gel extraction Kit (Qiagen, USA) according to the manufacturer's instructions. The isolated PCR DNA fragment was then ligated to the SacII-NotI digested and purified pMOL944. The ligation was performed overnight at 16° C. using 0.5 μg of each DNA fragment, 1 U of T4 DNA ligase and T4 ligase buffer (Boehringer Mannheim, Germany).

The ligation mixture was used to transform competent B. subtilis PL2306. The transformed cells were plated onto LBPG-10 μg/ml of Kanamycin-agar plates. After 18 hours incubation at 37° C. colonies were seen on plates. Several clones were analyzed by isolating plasmid DNA from overnight culture broth.

One such positive clone was restreaked several times on agar plates as used above, this clone was called MB643. The clone MB643 was grown overnight in TY-10 μg/ml Kanamycin at 37° C., and next day 1 ml of cells were used to isolate plasmid from the cells using the Qiaprep Spin Plasmid Miniprep Kit #27106 according to the manufacturers recommendations for B. subtilis plasmid preparations. This DNA was DNA sequenced and revealed the DNA sequence corresponding to the mature part of the mannanase position 317–1693 in SEQ ID NO. 1 and 33–490 in the SEQ ID NO. 2.

The clone MB643 was grown in 25×200 ml BPX media with 10 μg/ml of Kanamycin in 500 ml two baffled shake-flasks for 5 days at 37° C. at 300 rpm.

The DNA sequence encoding the C-terminal domain of unknown function from amino acid residue no. 341 to amino acid residue no. 490 shows high homology to a domain denoted X18 from a known mannanase. This X18 is found in EMBL entry AB007123 from: Yoshida S., Sako Y., Uchida A.: "Cloning, sequence analysis, and expression in *Escherichia coli* of a gene coding for an enzyme from *Bacillus circulans* K-1 that degrades guar gum" in Biosci. Biotechnol. Biochem. 62:514–520 (1998). This gene codes for the signal peptide (aa 1–34), the catalytic core of a family 5 mannanase (aa 35–335), a linker (aa 336–362) and finally the X18 domain of unknown function (aa 363–516).

This X18 domain is also found in *Bacillus subtilis* beta-mannanase Swiss protein database entry P55278 which discloses a gene coding for a signal peptide (aa 1–26), a catalytic core family 26 mannanase (aa 27–360) and this X18 protein domain of unknown function (aa 361–513); (Cloning and sequencing of beta-mannanase gene from *Bacillus subtilis* NM-39, Mendoza NS; Arai M; Sugiomto K; Ueda M; Kawaguchi T; Joson LM, Phillippines. In Biochimica Et Biophysica Acta Vol. 1243, No. 3 pp. 552–554 (1995)).

EXAMPLE 2

Expression, Purification and Characterisation of Mannanase from Bacillus sp. I633

The clone MB748 obtained as described in Example 1 and under Materials and Methods was grown in 25×200 ml BPX media with 10 μg/ml of Kanamycin in 500 ml two baffled shakeflasks for 5 days at 37° C. at 300 rpm.

4500 ml of the shake flask culture fluid of the clone MB748 was collected and pH was adjusted to 5.6. 100 ml of cationic agent (10% C521) and 180 ml of anionic agent (A130) was added during agitation for flocculation. The flocculated material was separated by centrifugation using a Sorval RC 3B centrifuge at 9000 rpm for 20 min at 6° C. The supernatant was clarified using Whatman glass filters GF/D and C and finally concentrated on a filtron with a cut off of 10 kDa.

700 ml of this concentrate was adjusted to pH 7.5 using sodium hydroxide. The clear solution was applied to anion-exchange chromatography using a 1000 ml Q-Sepharose column equilibrated with 50 mmol Tris pH 7.5. The mannanase activity bound was eluted in 1100 ml using a sodium chloride gradient. This was concentrated to 440 ml using a Filtron membrane. For obtaining highly pure mannanase the concentrate was passed over a Superdex 200 column equilibrated with 0.1M sodium acetate, pH 6.0.

The pure enzyme gave a single band in SDS-PAGE with a molecular weight of 34 kDa.

Steady state kinetic using locust bean gum:

The assay was carried out using different amounts of the substrate locust bean gum, incubating for 20 min at 40° C. at pH 10 in 1.0 M Glycine buffer, followed by the determination of formation of reducing sugars. Glucose was used as standard for calculation of micromole formation of reducing sugar during steady state.

The following data was obtained for the highly purified mannanase of the invention:

KCat of 467 per sec with a standard deviation of 13;

kM of 0.7 with a standard deviation of 0.07.

The computer program grafit by Leatherbarrow from Erithacus Software U.K. was used for calculations. Reducing sugar was determined using the PHBAH method (Lever, M. (1972), A new reaction for colormetric determination of carbohydrates. Anal. Biochem. 47, 273–279.)

The following N-terminal sequence of the purified protein was determined: ANSGFYVSGTTLYDANG (amino acids 32–48 of SEQ ID NO:2).

Stability: The mannanase was fully stable between pH 6.0 and 11 after incubation for 2 days at room temperature. The enzyme precipitated at low pH.

The pH activity profile shows that the enzyme is more than 60% active between pH 7.5 and pH 10.

Temperature optimum was found to be 50° C. at pH 10.

DSC differential scanning calometry gave 66° C. as melting point at pH 6.0 in sodium acetate buffer indicating that this mannanase enzyme is thermostable.

Immunological properties: Rabbit polyclonal monospecific serum was raised against the highly purified cloned mannanase using conventional techniques at the Danish company DAKO. The serum formed a nice single precipitate in agarose gels with the crude non purified mannanase of the invention.

EXAMPLE 3

Use of the Enzyme of Example 2 in Detergents

Using commercial detergents instead of buffer and incubation for 20 minutes at 40° C. with 0.2% AZCL-Galactomannan (Megazyme, Australia) from carob degree as described above followed by determination of the formation of blue color, the enzyme obtained as described in example 2 was active in European powder detergent Ariel Futur with 60% relative activity, European liquid detergent Ariel Futur with 80% relative activity, in US Tide powder with 45% relative activity and in US Tide liquid detergent with 37% relative activity to the activity measured in Glycine buffer. In these tests, the detergent concentration was as recommended on the commercial detergent packages and the wash water was tap water having 18 degrees German hardness under European (Ariel Futur) conditions and 9 degree under US conditions (US Tide).

EXAMPLE 4

Construction and Expression of Fusion Protein Between the Mannanase of Bacillus sp. I633 (Example 1 and 2) and a Cellulose Binding Domain (CBD)

The CBD encoding DNA sequence of the CipB gene from *Colstridium thermocellum* strain YS (Poole D M; Morag E; Lamed R; Bayer EA; Hazelwood GP; Gilbert HJ (1992) Identification of the cellulose-binding domain of the cellulosome subunit S1 from *Clostridium thermocellum* YS, Fems Microbiology Letters Vol. 78, No. 2–3 pp. 181–186 had previously been introduced to a vector pMOL1578. Chromosomal DNA encoding the CBD can be obtained as described in Poole DM; Morag E; Lamed R; Bayer EA; Hazelwood GP Gilbert HJ (1992) Identification of the cellulose-binding domain of the cellulosome subunit S1 from *Clostridium thermocellum* YS, Fems Microbiology Letters Vol. 78, No. 2–3 pp. 181–186. A DNA sample encoding the CBD was used as template in a PCR and the CBD was cloned in an apprpopriate plasmid pMB993 based on the pMOL944 vector.

The pMB993 vector contains the CipB CBD with a peptide linker preceeding the CBD. The linker consists of the following peptides sequence ASPEPTPEPT (SEQ ID NO: 49) and is directly followed by the CipB CBD. The AS amino acids are derived from the DNA sequence that constitutes the Restriction Endonuclease site NheI, which in the following is used to clone the mannanase of the invention.

Mannanase.Upper.SacII

5'-CAT TCT GCA GCC GCG GCA AAT TCC GGA TTT TAT GTA AGC GG-3' (SEQ ID NO: 45)

Mannanase.Lower.NehI

5'-CAT CAT GCT AGC TGT AAA AAC GGT GCT TAA TCT CG-3' (SEQ ID NO: 46)

Restriction sites NheI and SacII are underlined. Chromosomal DNA isolated from Bacillus sp. I633 as described above was used as template in a PCR reaction using Amplitaq DNA Polymerase (Perkin Elmer) according to manufacturers instructions. The PCR reaction was set up in PCR buffer (10 mM Tris-HCl, pH 8.3, 50 mM KCl, 1.5 mM MgCl$_2$, 0.01% (w/v) gelatin) containing 200 μM of each dNTP, 2.5 units of AmpliTaq polymerase (Perkin-Elmer, Cetus, USA) and 100 pmol of each primer.

The PCR reactions was performed using a DNA thermal cycler (Landgraf, Germany). One incubation at 94° C. for 1 min followed by thirty cycles of PCR performed using a cycle profile of denaturation at 94° C. for 30 sec, annealing at 60° C. for 1 min, and extension at 72° C. for 2 min. Five-μl aliquots of the amplification product was analysed by electrophoresis in 0.7% agarose gels (NuSieve, FMC). The appearance of a DNA fragment size 0.9 kb indicated proper amplification of the gene segment.

Subcloning of PCR fragment:

Fortyfive-μl aliquots of the PCR products generated as described above were purified using QIAquick PCR purification kit (Qiagen, USA) according to the manufacturer's instructions. The purified DNA was eluted in 50 μl of 10 mM Tris-HCl, pH 8.5. 5 μg of pMB993 and twentyfive-μl of the purified PCR fragment was digested with SacII and NheI, electrophoresed in 0.7% low gelling temperature agarose (SeaPlaque GTG, FMC) gels, the relevant fragments were excised from the gels, and purified using QIAquick Gel extraction Kit (Qiagen, USA) according to the manufacturer's instructions. The isolated PCR DNA fragment was then ligated to the SacII-NheI digested and purified pMB993. The ligation was performed overnight at 16° C. using 0.5 μg of each DNA fragment, 1 U of T4 DNA ligase and T4 ligase buffer (Boehringer Mannheim, Germany).

The ligation mixture was used to transform competent *B. subtilis* PL2306. The transformed cells were plated onto LBPG-10 μg/ml of Kanamycin-agar plates. After 18 hours incubation at 37° C. colonies were seen on plates. Several clones were analyzed by isolating plasmid DNA from overnight culture broth.

One such positive clone was restreaked several times on agar plates as used above, this clone was called MB1014. The clone MB1014 was grown overnight in TY-10 μg/ml Kanamycin at 37° C., and next day 1 ml of cells were used to isolate plasmid from the cells using the Qiaprep Spin Plasmid Miniprep Kit #27106 according to the manufacturers recommendations for *B. subtilis* plasmid preparations. This DNA was DNA sequenced and revealed the DNA sequence corresponding to the mature part of the Mannanase-linker-cbd as represented in SEQ ID NO:3 and in the appended protein sequence SEQ ID NO: 4.

Thus the final construction contains the following expression relevant elements: (amyL-promoter)-(amyL-signalpeptide)-mannanase-linker-CBD.

Expression and Detection of Mannanase-CBD Fusion Protein

MB1014 was incubated for 20 hours in TY-medium at 37° C. and 250 rpm. 1 ml of cell-free supernatant was mixed with 200 μl of 10% Avicel (Merck, Darmstadt, Germany) in Millipore H2O. The mixture was left for ½ hour incubation at 0° C. After this binding of BXM2-Linker-CBD fusion protein to Avicel the Avicel with bound protein was spun 5 min at 5000 g. The pellet was resuspended in 100 μl of SDS-page buffer, boiled at 95° C. for 5 min, spun at 5000 g for 5 min and 25 μl was loaded on a 4–20% Laemmli Tris-Glycine, SDS-PAGE NOVEX gel (Novex, USA). The samples were electrophoresed in a Xcell™ Min-Cell (NOVEX, USA) as recommended by the manufacturer, all subsequent handling of gels including staining with comassi, destaining and drying were performed as described by the manufacturer.

The appearance of a protein band of approx. 53 kDa, verified the expression in *B. subtilis* of the full length Mannanase-Linker-CBD fusion encoded on the plasmid pMB1014.

EXAMPLE 5

Mannanase Derived from *Bacillus agaradhaerens* Cloning of the Mannanase Gene from *Bacillus agardherens*

Genomic DNA preparation

Strain *Bacillus agaradherens* NCIMB 40482 was propagated in liquid medium as described in WO94/01532. After 16 hours incubation at 30° C. and 300 rpm, the cells were harvested, and genomic DNA isolated by the method described by Pitcher et al. (Pitcher, D. G., Saunders, N. A., Owen, R. J. (1989). Rapid extraction of bacterial genomic DNA with guanidium thiocyanate. Lett. Appl. Microbiol., 8, 151–156).

Genomic library construction

Genomic DNA was partially digested with restriction enzyme Sau3A, and size-fractionated by electrophoresis on a 0.7% agarose gel. Fragments between 2 and 7 kb in size was isolated by electrophoresis onto DEAE-cellulose paper (Dretzen, G., Bellard, M., Sassone-Corsi, P., Chambon, P. (1981) A reliable method for the recovery of DNA fragments from agarose and acrylamide gels. Anal. Biochem., 112, 295–298).

Isolated DNA fragments were ligated to BamHI digested pSJ1678 plasmid DNA, and the ligation mixture was used to transform *E. coli* SJ2.

Identification of positive clones

A DNA library in *E. coli*, constructed as described above, was screened on LB agar plates containing 0.2% AZCL-galactomannan (Megazyme) and 9 μg/ml Chloramphenicol and incubated overnight at 37° C. Clones expressing mannanase activity appeared with blue diffusion halos. Plasmid DNA from one of these clone was isolated by Qiagen plasmid spin preps on 1 ml of overnight culture broth (cells incubated at 37° C. in TY with 9 μg/ml Chloramphenicol and shaking at 250 rpm).

This clone (MB525) was further characterized by DNA sequencing of the cloned Sau3a DNA fragment. DNA sequencing was carried out by primerwalking, using the Taq deoxy-terminal cycle sequencing kit (Perkin-Elmer, USA), fluorescent labelled terminators and appropriate oligonucleotides as primers.

Analysis of the sequence data was performed according to Devereux et al. (1984) Nucleic Acids Res. 12, 387–395. The sequence encoding the mannanase is shown in SEQ ID No. 5. The derived protein sequence is shown in SEQ ID No.6.

Subcloning and expression of *B. agaradhaerens* mannanase in *B. subtilis*

The mannanase encoding DNA sequence of the invention was PCR amplified using the PCR primer set consisting of these two oligo nucleotides:

Mannanase.upper.ScaII
5'-CAT TCT GCA GCC GCG GCA GCA AGT ACA GGC TTT TAT GTT GAT GG-3' (SEQ ID NO: 47)

Mannanase.lower.NotI
5'-GAC GAC GTA CAA GCG GCC GCG CTA TTT CCC TAA CAT GAT GAT ATT TTC G-3' (SEQ ID NO: 48)

Restriction sites SacII and NotII are underlined. Chromosomal DNA isolated from *B. agaradeherens* NCIMB 40482 as described above was used as template in a PCR reaction using AmpliTaq DNA Polymerase (Perkin Elmer) according to manufacturers instructions. The PCR reaction was set up in PCR buffer (10 mM Tris-HCl, pH 8.3, 50 mM KCl, 1.5 mM $MgCl_2$, 0.01% (w/v) gelatin) containing 200 μM of each dNTP, 2.5 units of AmpliTaq polymerase (Perkin-Elmer, Cetus, USA) and 100 pmol of each primer.

The PCR reaction was performed using a DNA thermal cycler (Landgraf, Germany). One incubation at 94° C. for 1 min followed by thirty cycles of PCR performed using a cycle profile of denaturation at 94° C. for 30 sec, annealing at 60° C. for 1 min, and extension at 72° C. for 2 min. Five-μl aliquots of the amplification product was analysed by electrophoresis in 0.7% agarose gels (NuSieve, FMC). The appearance of a DNA fragment size 1.4 kb indicated proper amplification of the gene segment.

Subcloning of PCR fragment

Fortyfive-μl aliquots of the PCR products generated as described above were purified using QIAquick PCR purification kit (Qiagen, USA) according to the manufacturer's instructions. The purified DNA was eluted in 50 μl of 10 mM Tris-HCl, pH 8.5. 5 μg of pMOL944 and twentyfive-μl of the purified PCR fragment was digested with SacII and NotI, electrophoresed in 0.8% low gelling temperature agarose (SeaPlaque GTG, FMC) gels, the relevant fragments were excised from the gels, and purified using QIAquick Gel extraction kit (Qiagen, USA) according to the manufacturer's instructions. The isolated PCR DNA fragment was then ligated to the SacII-NotI digested and purified pMOL944. The ligation was performed overnight at 16° C. using 0.5 μg of each DNA fragment, 1 U of T4 DNA ligase and T4 ligase buffer (Boehringer Mannheim, Germany).

The ligation mixture was used to transform competent B. subtilis PL2306. The transformed cells were plated onto LBPG-10 μg/ml of Kanamycin plates. After 18 hours incubation at 37° C. colonies were seen on plates. Several clones were analysed by isolating plasmid DNA from overnight culture broth.

One such positive clone was restreaked several times on agar plates as used above, this clone was called MB594. The clone MB594 was grown overnight in TY-10 μg/ml kanamycin at 37° C., an next day 1 ml of cells were used to isolate plasmid from the cells using the Qiaprep Spin Plasmid Miniprep Kit #27106 according to the manufacturers recommendations for B. subtilis plasmid preparations. This DNA was DNA sequenced and revealed the DNA sequence corresponding to the mature part of the mannanase, i.e. positions 94–1404 of the appended SEQ ID NO:7. The derived mature protein is shown in SEQ ID NO:8. It will appear that the 3' end of the mannanse encoded by the sequence of SEQ ID NO:5 was changed to the one shown in SEQ ID NO:7 due to the design of the lower primer used in the PCR. The resulting amino acid sequence is shown in SEQ ID NO:8 and it is apparent that the C terminus of the SEQ ID NO:6 (SHHVREIGVQFSAADN SSGQTALYVDNVTLR) is changed to the C terminus of SEQ ID NO:8 (IIMLGK).

EXAMPLE 6

Expression, Purification and Characterisation of Mannanase from *Bacillus agaradhaerens*

The clone MB 594 obtained as described in example 5 was grown in 25×200 ml BPX media with 10 μg/ml of Kanamycin in 500 ml two baffled shakeflasks for 5 days at 37° C. at 300 rpm.

6500 ml of the shake flask culture fluid of the clone MB 594 (batch #9813) was collected and pH adjusted to 5.5. 146 ml of cationic agent (C521) and 292 ml of anionic agent (A130) was added during agitation for flocculation. The flocculated material was separated by centrifugation using a Sorval RC 3B centrifuge at 9000 rpm for 20 min at 6° C. The supernatant was clarified using Whatman glass filters GF/D and C and finally concentrated on a filtron with a cut off of 10 kDa.

750 ml of this concentrate was adjusted to pH 7.5 using sodium hydroxide. The clear solution was applied to anionexchange chromatography using a 900 ml Q-Sepharose column equilibrated with 50 mmol Tris pH 7.5. The mannanase activity bound was eluted using a sodium chloride gradient.

The pure enzyme gave a single band in SDS-PAGE with a molecular weight of 38 kDa.

The amino acid sequence of the mannanase enzyme, i.e. the translated DNA sequence, is shown in SEQ ID No.6.

Determination of kinetic constants:

Substrate: Locust bean gum (carob) and reducing sugar analysis (PHBAH). Locust bean gum from Sigma (G-0753).

Kinetic determination using different concentrations of locust bean gum and incubation for 20 min at 40° C. at pH 10 gave Kcat: 467 per sec.

$K_m$: 0.08 gram per l

MW: 38 kDa pI (isoelectric point): 4.2

The temperature optimum of the mannanase was found to be 60° C.

The pH activity profile showed maximum activity between pH 8 and 10.

DSC differential scanning calometry gives 77° C. as melting point at pH 7.5 in Tris buffer indicating that this enzyme is very termostable.

Detergent compatibility using 0.2% AZCL-Galactomannan from carob as substrate and incubation as described above at 40° C. shows excellent compability with conventional liquid detergents and good compability with conventional powder detergents.

EXAMPLE 7

Use of the Enzyme of the Invention in Detergents

The purified enzyme obtained as described in example 6 (batch #9813) showed improved cleaning performance when tested at a level of 1 ppm in a miniwash test using a conventional commercial liquid detergent. The test was carried out under conventional North American wash conditions.

EXAMPLE 8

Mannanase derived from Bacillus sp. AAI12

Construction of a genomic library from Bacillus sp. AAI12

Genomic DNA of Bacillus sp. was partially digested with restriction enzyme Sau3A, and size-fractionated by electrophoresis on a 0.7% agarose gel (SeaKem agarose, FMC, USA). Fragments between 1.5 and 10 kb in size were isolated and concentrated to a DNA band by running the DNA fragments backwards on a 1.5% agarose gel followed by extraction of the fragments from the agarose gel slice using the Qiaquick gel extraction kit according to the manufacturer's instructions (Qiagen Inc., USA). To construct a genomic library, ca. 100 ng of purified, fractionated DNA from above was ligated with 1 ug of BamHI-cleaved, dephosphorylated lambdaZAPexpress vector arms (Stratagene, La Jolla Calif., USA) for 24 hours at +4° C. according to the manufacturer's instructions. A 3-ul aliquot of the ligation mixture was packaged directly using the GigaPackIII Gold packaging extract (Stratagene, USA) according to the manufactures instructions (Stratagene). The genomic lambdaZAPExpress phage library was titered using the E. coli XL1-Blue MRF-strain from Stratagene (La Jolla, USA). The unamplified genomic library comprised of 7.8× 107 plaque-forming units (pfu) with a vector background of less than 1%.

Screening for beta-mannanase clones by functional expression in lambdaZAPExpress Approximately 5000 plaque-forming units (pfu) from the genomic library were plated on NZY-agar plates containing 0.1% AZCL-galactomannan (MegaZyme, Australia, cat. no. I-AZGMA), using *E. coli* XL1-Blue MRF' (Stratagene, USA) as a host, followed by incubation of the plates at 37°

C. for 24 hours. Mannanase-positive lambda clones were identified by the formation of blue hydrolysis halos around the positive phage clones. These were recovered from the screening plates by coring the TOP-agar slices containing the plaques of interest into 500 ul of SM buffer and 20 ul of chloroform. The mannanase-positive lambdaZAPExpress clones were plaque-purified by plating an aliquot of the cored phage stock on NZY plates containing 0.1% AZCL-galactomannan as above. Single, mannanase-positive lambda clones were cored into 500 ul of SM buffer and 20 ul of chloroform, and purified by one more plating round as described above.

Single-clone in vivo excision of the phagemids from the mannanase-positive lambdaZAPExpress clones E. coli XL1-Blue cells (Stratagene, La Jolla Calif.) were prepared and resuspended in 10 mM MgSO4 as recommended by Stratagene (La Jolla, USA). 250-ul aliquots of the pure phage stocks from the mannase-positive clones were combined in Falcon 2059 tubes with 200 uls of XL1-Blue MRF' cells (OD600=1.0) and >106 pfus/ml of the ExAssist M13 helper phage (Stratagene), and the mixtures were incubated at 37 C for 15 minutes. Three mls of NZY broth was added to each tube and the tubes were incubated at 37 C for 2.5 hours. The tubes were heated at 65 C for 20 minutes to kill the E. coli cells and bacteriophage lambda; the phagemids being resistant to heating. The tubes were spun at 3000 rpm for 15 minutes to remove cellular debris and the supernatants were decanted into clean Falcon 2059 tubes. Aliquots of the supernatants containing the excised single-stranded phagemids were used to infect 200 uls of E. coli XLOLR cells (Stratagene, OD600=1.0 in 10 mM MgSO4) by incubation at 37° C. for 15 minutes. 350 uls of NZY broth was added to the cells and the tubes were incubated for 45 min at 37° C. Aliquots of the cells were plated onto LB kanamycin agar plates and incubated for 24 hours at 37° C. Five excised single colonies were re-streaked onto LB kanamycin agar plates containing 0.1% AZCL-galactomannan (MegaZyme, Australia). The mannanase-positive phagemid clones were characterized by the formation of blue hydrolysis halos around the positive colonies. These were further analysed by restriction enzyme digests of the isolated plagemid DNA (QiaSpin kit, Qiagen, USA) with EcoRI, PstI, EcoRI-PstI, and HindIII followed by agarose gel electrophoresis.

Nucleotide sequence analysis

The nucleotide sequence of the genomic beta-1,4-mannanase clone pBXM1 was determined from both strands by the dideoxy chain-termination method (Sanger, F., Nicklen, S., and Coulson, A. R. (1977) Proc. Natl. Acad. Sci. U. S. A. 74, 5463–5467) using 500 ng of Qiagen-purified template (Qiagen, USA), the Taq deoxy-terminal cycle sequencing kit (Perkin-Elmer, USA), fluorescent labeled terminators and 5 pmol of either pBK-CMV polylinker primers (Stratagene, USA) or synthetic oligonucleotide primers. Analysis of the sequence data was performed according to Devereux et al. 1984 (Devereux, J., Haeberli, P., and Smithies, O. (1984) Nucleic Acids Res. 12, 387–395).

Sequence alignment

A multiple sequence alignment of the glycohydrolase family 26 beta-1,4-mannanases from Bacillus sp. AAI 12 of the present invention (ie SEQ ID NO: 10), Caldicellulosiruptor saccharolyticus (GenBank/EMBL accession no. P77847), Dictyoglomus thermophilum (acc. no. O30654), Rhodothermus marinus (acc. no. P49425), Piromyces sp. encoded by ManA (acc. no. P55296), Bacillus sp. (acc. no. P91007), Bacillus subtilis (acc. no. O05512) and Pseudomonas fluorescens (acc. no P49424. was created using the PileUp program of the GCG Wisconsin software package, version 8.1. (see above); with gap creation penalty 3.00 and gap extension penalty 0.10.

Sequence Similarities

The deduced amino acid sequence of the family 26 beta-1,4-mannanase of the invention cloned from Bacillus sp. AAI 12 shows 45% sequence similarity and 19.8% sequence identity to the beta-1,4-mannanase from Caldicellulosiruptor saccharolyticus (GenBank/EMBL accession no. P77847), 49% similarity and 25.1.% identity to the beta-1,4-mannanase from Dictyoglomus thermophilum (acc. no. O30654), 48.2% similarity and 26.8% identity to the beta-1,4-mannanase from Rhodothermus marinus (acc. no. P49425), 46% similarity and 19.5% sequence identity to the ManA-encoded beta-1,4-mannanase from Piromyces sp. (acc. no. P55296), 47.2% similarity and 22% identity to the beta-1,4-mannanase from Bacillus sp. (acc. no. P91007), 52.4% similarity and 27.5% sequence identity to the beta-1,4-mannanase from Bacillus subtilis (acc. no. O05512) and 60.6% similarity and 37.4% identity to the beta-1,4-mannanase from Pseudomonas fluorescens (acc. no P49424. The sequences were aligned using the GAP program of the GCG Wisconsin software package,version 8.1.; with gap creation penalty 3.00 and gap extension penalty 0.10.

Cloning of the Bacillus sp (AAI 12) mannanase gene

Subcloning and expression of mannanase in B. subtilis

The mannanase encoding DNA sequence of the invention was PCR amplified using the PCR primer set consisting of these two oligo nucleotides:

BXM1.upper.SacII

5'-CAT TCT GCA GCC GCG GCA TTT TCT GGA AGC GTT TCA GC-3' (SEQ ID NO: 50)

MXM1.lower.NotI

5'-CAG CAG TAG CGG CCG CCA CTT CCT GCT GGT ACA TAT GC-3' (SEQ ID NO: 51)

Restriction sites SacII and NotI are underlined.

Chromosomal DNA isolated from Bacillus sp. AAI 12 as described above was used as template in a PCR reaction using Amplitaq DNA Polymerase (Perkin Elmer) according to manufacturers instructions. The PCR reaction was set up in PCR buffer (10 mM Tris-HCl, pH 8.3, 50 mM KCl, 1.5 mM $MgCl_2$, 0.01% (w/v) gelatin) containing 200 µM of each dNTP, 2.5 units of AmpliTaq polymerase (Perkin-Elmer, Cetus, USA) and 100 pmol of each primer.

The PCR reactions were performed using a DNA thermal cycler (Landgraf, Germany), One incubation at 94° C. for 1 min followed by thirty cycles of PCR performed using a cycle profile of denaturation at 94° C. for 30 sec, annealing at 60° C. for 1 min, and extension at 72° C. for 2 min. Five-µl aliquots of the amplification product was analysed by electrophoresis in 0.7% agarose gels (NuSieve, FMC). The appearance of a DNA fragment size 1.0 kb indicated proper amplification of the gene segment.

Subcloning of PCR fragment

Fortyfive-µl aliquots of the PCR products generated as described above were purified using QIAquick PCR purification kit (Qiagen, USA) according to the manufacturer's instructions. The purified DNA was eluted in 50 µl of 10 mM Tris-HCl, pH 8.5. 5 µg of pMOL944 and twentyfive-µl of the purified PCR fragment was digested with SacII and NotI, electrophoresed in 0.8% low gelling temperature agarose (SeaPlaque GTG, FMC) gels, the relevant fragments were excised from the gels, and purified using QIAquick Gel extraction Kit (Qiagen, USA) according to the manufacturer's instructions. The isolated PCR DNA fragment was then ligated to the SacII-NotI digested and purified pMOL944. The ligation was performed overnight at 16° C. using 0.5 µg of each DNA fragment, 1 U of T4 DNA ligase and T4 ligase buffer (Boehringer Mannheim, Germany).

The ligation mixture was used to transform competent *B. subtilis* PL2306. The transformed cells were plated onto LBPG-10 µg/ml of Kanamycin-agar plates. After 18 hours incubation at 37° C. colonies were seen on plates. Several clones were analyzed by isolating plasmid DNA from overnight culture both.

One such positive clone was restreaked several times on agar plates as used above, this clone was called MB747. The clone MB747 was grown overnight in TY-10 µg/ml Kanamycin at 37° C., and next day 1 ml of cells were used to isolate plasmid from the cells using the Qiaprep Spin Plasmid Miniprep Kit #27106 according to the manufacturers recommendations for *B. subtilis* plasmid preparations. This DNA was DNA sequenced and revealed the DNA sequence corresponding to the mature part of the mannanase in the SEQ ID NO. 9.

Expression, Purification and Characterisation of Mannanase from Bacillus sp. AAI 12

The clone MB747 obtained as described above was grown in 25×200 ml BPX media with 10 µg/ml of Kanamycin in 500 ml two baffled shakeflasks for 5 days at 37° C. at 300 rpm.

4100 ml of the shake flask culture fluid of the clone MB747 was collected, pH was adjusted to 7.0, and EDTA was added to a final concentration of 2 mM. 185 ml of cationic agent (10% C521) and 370 ml of anionic agent (A130) was added during agitation for flocculation. The flocculated material was separated by centrifugation using a Sorval RC 3B centrifuge at 9000 rpm for 20 min at 6° C. The supernatant was clarified using Whatman glass filters GF/D and C and finally concentrated on a filtron with a cut off of 10 kDa.

1500 ml of this concentrate was adjusted to pH 7.5 using sodium hydroxide. The clear solution was applied to anion-exchange chromatography using a 1000 ml Q-Sepharose column equilibrated with 25 mmol Tris pH 7.5. The mannanase activity bound was eluted in 1100 ml using a sodium chloride gradient. This was concentrated to 440 ml using a Filtron membrane. For obtaining highly pure mannanase the concentrate was passed over a Superdex column equilibrated with 0.1M sodium acetate, pH 6.0.

The pure enzyme gave a single bond in SDS-PAGE with a molecular weight of 62 kDa.

The amino acid sequence of the mannanase enzyme, i.e. the translated DNA sequence, is shown in SEQ ID No.10.

The following N-terminal sequence was determined: FSGSVSASGQELKMTDQN.

pI (isoelectric point): 4.5

DSC differential scanning calometry gave 64° C. as melting point at pH 6.0 in sodium acetate buffer indicating that this mannanase enzyme is thermostable.

It was found that the catalytic activity increases with ionic strength indicating that the specific activity of the enzyme may be increased by using salt of phosphate buffer with high ionic strength.

The mannanase activity of the polypeptide of the invention is inhibited by calcium ions.

Immunological properties: Rabbit polyclonal monospecific serum was raised against the highly purified mannanase of the invention using conventional techniques at the Danish company DAKO. The serum formed a nice single precipitate in agarose gels with the crude mannanase of the invention.

EXAMPLE 9

Use of the Enzyme of Example 8 in Detergents

Using commercial detergents instead of buffer and incubation for 20 minutes at 40° C. with 0.2% AZCL-Galactomannan (Megazyme, Australia) from carob degree as described above followed by determination of the formation of blue color, the enzyme obtained as described in example 8 was active in European powder detergent Ariel Futur with 132% relative activity, in US Tide powder with 108% relative activity and in US Tide liquid detergent with 86% relative activity to the activity measured in Glycine buffer. In these tests, the detergent concentration was as recommended on the commercial detergent packages and the wash water was tap water having 18 degrees German hardness under European (Ariel Futur) conditions and 9 degree under US conditions (US Tide).

EXAMPLE 10

Mannanase Derived from *Bacillus halodurans*
Construction of a genomic library from *Bacillus halodurans* in the pSJ1678 vector Genomic DNA of *Bacillus halodurans* was partially digested with restriction enzyme Sau3A, and size-fractionated by electrophoresis on a 0.7% agarose gel (SeaKem agarose, FMC, USA). DNA fragments between 2 and 10 kb in size was isolated by electrophoresis onto DEAE-cellulose paper (Dretzen, G., Bellard, M., Sassone-Corsi, P., Chambon, P. (1981) A reliable method for the recovery of DNA fragments from agarose and acrylamide gels. Anal. Biochem., 112, 295–298). Isolated DNA fragments were ligated to BamHI-digested pSJ1678 plasmid DNA, and the ligation mixture was used to transform *E. coli* SJ2.

Screening for beta-mannanase clones by functional expression in *Escherichia coli*

Approximately 10.000 colony-forming units (cfu) from the genomic library were plated on LB-agar plates containing containing 9 µg/ml chloramphenicol and 0.1% AZCL-galactomannan (MegaZyme, Australia, cat. no. I-AZGMA), using *E. coli* SJ2 as a host, followed by incubation of the plates at 37° C. for 24 hours. Mannanase-positive *E. coli* colonies were identified by the formation of blue hydrolysis halos around the positive plasmid clones. The mannanase-positive clones in pSJ1678 were colony-purified by re-streaking the isolated colonies on LB plates containing 9 µg/ml Chloramphenicol and 0.1% AZCL-galactomannan as above. Single, mannanase-positive plasmid clones were inoculated into 5 ml of LB medium containing containing 9 µg/ml Chloramphenicol, for purification of the plasmid DNA.

Nucleotide sequence analysis

The nucleotide sequence of the genomic beta-1,4-mannanase clone pBXM5 was determined from both strands by the dideoxy chain-termination method (Sanger, F., Nicklen, S., and Coulson, A. R. (1977) Proc. Natl. Acad. Sci. U. S. A. 74, 5463–5467) using 500 ng of Qiagen-purified template (Qiagen, USA), the Taq deoxy-terminal cycle sequencing kit (Perkin-Elmer, USA), fluorescent labeled terminators and 5 pmol of either pBK-CMV polylinker primers (Stratagene, USA) or synthetic oligonucleotide primers. Analysis of the sequence data was performed according to Devereux et al., 1984 (Devereux, J., Haeberli, P., and Smithies, O. (1984) Nucleic Acids Res. 12, 387–395).

Sequence alignment

A multiple sequence alignment of the glycohydrolase family 5 beta-1,4-mannanase from *Bacillus halodurans* of the present invention (ie SEQ ID NO:12), *Bacillus circulans* (GenBank/EMBL accession no. O66185), *Vibrio sp.* (acc. no. O69347), *Streptomyces lividans* (acc. no. P51529), and *Caldicellulosiruptor saccharolyticus* (acc. no. P22533). The multiple sequence alignment was created using the PileUp program of the GCG Wisconsin software package,version 8.1.; with gap creation penalty 3.00 and gap extension penalty 0.10.

Sequence Similarities

The deduced amino acid sequence of the family 5 beta-1,4-mannanase of the present invention cloned from *Bacillus halodurans* shows 77% similarity and 60% sequence identity to the beta-1,4-mannanase of *Bacillus circulans* (GenBank/EMBL accession no. O66185), 64.2% similarity and 46% identity to the beta-1,4-mannanase from *Vibrio sp.* (acc. no. O69347), 63% similarity and 41.8% identity to the beta-1,4-mannanase from *Streptomyces lividans* (acc. no. P51529), 60.3% similarity and 42% sequence identity to the beta-1,4-mannase from *Caldicellulosiruptor saccharolyticus* (acc. no. P2253). The sequences were aligned using the GAP program of the GCG Wisconsin software package, version 8.1.; with gap creation penalty 3.00 and gap extension penalty 0.10.

Cloning of *Bacillus halodurans* mannanase gene
Subcloning and expression of mature full length mannanase in *B. subtilis*

The mannanase encoding DNA sequence of the invention was PCR amplified using the PCR primer set consisting of these two oligo nucleotides:

BXM5.upper.SacII
5'-CAT TCT GCA GCC GCG GCA CAT CAC AGT GGG TTC CAT G-3' (SEQ ID NO: 52)
BXM5.lower.NotI
5'-GCG TTG AGA CGC GCG GCC GCT TAT TGA AAC ACA CTG CTT CTT TTA G-3' (SEQ ID NO: 53)
Restriction sites SacII and NotI are underlined Chromosomal DNA isolated from *Bacillus halodurans* as described above was used as template in a PCR reaction using Amplitaq DNA Polymerase (Perkin Elmer) according to manufacturers instructions. The PCR reaction was set up in PCR buffer (10 mM Tris-HCl, pH 8.3, 50 mM KCl, 1.5 mM MgCl2, 0.01% (w/v) gelatin) containing 200 µM of each dNTP, 2.5 units of AmpliTaq polymerase (Perkin-Elmer, Cetus, USA) and 100 pmol of each primer.

The PCR reactions was performed using a DNA thermal cycler (Landgraf, Germany). One incubation at 94° C. for 1 min followed by thirty cycles of PCR performed using a cycle profile of denaturation at 94° C. for 30 sec, an-nea-ling at 60° C. for 1 min, and extension at 72° C. for 2 min. Five-µl aliquots of the ampli-fication product was analysed by electrophoresis in 0.7% agarose gels (NuSieve, FMC). The appearance of a DNA fragment size 0.9 kb indicated proper amplification of the gene segment.

Subcloning of PCR fragment:

Fortyfive-µl aliquots of the PCR products generated as described above were purified using QIA-quick PCR purification kit (Qiagen, USA) according to the manufacturer's instructions. The purified D-NA was eluted in 50 µl of 10 mM Tris-HCl, pH 8.5.

5 µg of pMOL944 and twentyfive-µl of the purified PCR fragment was digested with SacII and NotI, electrophoresed in 0.8% low gelling temperature agarose (SeaPla-que GTG, FMC) gels, the relevant fragments were excised from the gels, and purified using QIA-quick Gel extraction Kit (Qiagen, USA) according to the manufacturer's instructions. The isolated PCR DNA fragment was then ligated to the SacII-NotI digested and purified pMOL944. The ligation was performed overnight at 16° C. using 0.5 µg of each DNA fragment, 1 U of T4 DNA ligase and T4 ligase buffer (Boehringer Mannheim, Germany).

The ligation mixture was used to transform competent *B. subtilis* PL2306. The transformed cells were plated onto LBPG-10 µg/ml of Kanamycin-agar plates. After 18 hours incubation at 37° C. colonies were seen on plates. Several clones were analyzed by isolating plasmid DNA from overnight culture broth.

One such positive clone was restreaked several times on agar plates as used above, this clone was called MB878. The clone MB878 was grown overnight in TY-10 µg/ml Kanamycin at 37° C., and next day 1 ml of cells were used to isolate plasmid from the cells using the Qiaprep Spin Plasmid Miniprep Kit #27106 according to the manufacturers recommendations for *B. subtilis* plasmid preparations. This DNA was DNA sequenced and revealed the DNA sequence corresponding to the mature part of the mannanase position 97–993 in SEQ ID NO. 11 and 33–331 in the SEQ ID NO. 12.

Expression, Purification and Characterisation of Mannanase from *Bacillus halodurans*

The clone MB878 obtained as described above was grown in 25×200 ml BPX media with 10 µg/ml of Kanamycin in 500 ml two baffled shakeflasks for 5 days at 37° C. at 300 rpm.

5000 ml of the shake flask culture fluid of the clone MB878 was collected and pH was adjusted to 6.0 125 ml of cationic agent (10% C521) and 250 ml of anionic agent (A130) was added during agitation for flocculation. The flocculated material was separated by centrifugation using a Sorval RC 3B centrifuge at 9000 rpm for 20 min at 6° C. The supernatant was adjusted to pH 8.0 using NaOH and clarified using Whatman glass filters GF/D and C. Then 50 g of DEAE A-50 Sephadex was equilibrated with 0.1M Sodium acetate, pH 6.0, and added to the filtrate, the enzyme was bound and left overnight at room temperature. The bound enzyme was eluted with 0.5 M NaCl in the acetate buffer. Then the pH was adjusted to pH 8.0 using sodium hydroxide and then concentrated on a Filtron with a 10 kDa cut off to 450 ml and then stabilized with 20% glycerol, 20% MPG and 2% Berol. The product was used for application trials.

2 ml of this concentrate was adjusted to pH 8.5 using sodium hydroxide. For obtaining highly pure mannanase the concentrate was passed over a Superdex column equilibrated with 0.1M sodium phosphate, pH 8.5.

The pure enzyme gave a single band in SDS-PAGE with a molecular weight of 34 kDa.

The amino acid sequence of the mannanase enzyme, i.e. the translated DNA sequence, is shown in SEQ ID NO:12.

The following N-terminal sequence oft he purified protein was determined: AHHSGFHVNGTTLYDA.

The pH activity profile using the ManU assay (incubation for 20 minutes at 40° C.) shows that the enzyme has a relative activity higher than 50% between pH 7.5 and pH 10.

Temperature optimum was found (using the ManU assay; glycine buffer) to be between 60° C. and 70° C. at pH 10.

Immunological properties: Rabbit polyclonal monospecific serum was raised against the highly purified cloned mannanase using conventional techniques at the Danish company DAKO. The serum formed a nice single precipitate in agarose gels with the crude non purified mannanase of the invention.

EXAMPLE 11

Use of the Mannanase Enzyme of Example 10 in Detergents

Using commercial detergents instead of buffer and incubation for 20 minutes at 40° C. with 0.2% AZCL-Galactomannan (Megazyme, Australia) from carob degree as described above followed by determination of the formation of blue color, the mannanase enzyme obtained as described in example 10 was active with an activity higher than 40% relative to the activity in buffer in European liquid detergent Ariel Futur, in US Tide powder and in US Tide liquid detergent. In these tests, the detergent concentration was as recommended on the commercial detergent packages and the wash water was tap water having 18 degrees German hardness under European (Ariel Futur) conditions and 9 degree under US conditions (US Tide).

EXAMPLE 12

Mannanase Derived from Bacillus sp. AA349

Cloning of Bacillus sp (AA349) mannanase gene

Subcloning and expression of a catalytic core mannanase enzyme in *B. subtilis:*

The mannanase encoding DNA sequence of the invention was PCR amplified using the PCR primer set consisting of the following two oligo nucleotides:

BXM7.upper.SacII
5'-CAT TCT GCA GCC GCG GCA AGT GGA CAT GGG CAA ATG C-3' (SEQ ID NO: 54)
BXM7.lower.NotI
5'-GCG TTG AGA CGC GCG GCC GCT TAT TTT TTG TAT ACA CTA ACG ATT TC-3' (SEQ ID NO: 55)
Restriction sites SacII and NotI are underlined.

Chromosomal DNA isolated from Bacillus sp. AA349 as described above was used as template in a PCR reaction using Amplitaq DNA Polymerase (Perkin Elmer) according to manufacturers instructions. The PCR reaction was set up in PCR buffer (10 mM Tris-HCl, pH 8.3, 50 mM KCl, 1.5 mM $MgCl_2$, 0.01% (w/v) gelatin) containing 200 µM of each dNTP, 2.5 units of AmpliTaq polymerase (Perkin-Elmer, Cetus, USA) and 100 pmol of each primer.

The PCR reactions was performed using a DNA terminal cycler (Landgraf, Germany). One incubation at 94° C. for 1 min followed by thirty cycles of PCR performed using a cycle profile of denaturation at 94° C. for 30 sec. annealing at 60° C. for 1 min, and extension at 72° C. for 2 min. Five-µl aliquots of the amplification product was analysed by electrophoresis in 0.7% agarose gels (NuSieve, FMC). The appearance of a DNA fragment approximate size of 1.0 kb indicated proper amplification of the gene segment.

Subcloning of PCR Fragment

Fortyfive-µl aliquots of the PCR products generated as described above were purified using QIAquick PCR purification kit (Qiagen, USA) according to the manufacturer's instructions. The purified DNA was eluted in 50 µl of 10 mM Tris-HCl, pH 8.5. 5 µg of pMOL944 and twentyfive-µl of the purified PCR fragment was digested with SacII and NotT, electrophoresed in 0.8% low gelling temperature agarose (SeaPlaque GTG, FMC) gels, the relevant fragments were excised from the gels, and purified using QIAquick Gel extraction Kit (Qiagen, USA) according to the manufacturer's instructions. The isolated PCR DNA.fragment was then ligated to the SacII-NotI digested and purified pMOL944. The ligation was performed overnight at 16° C. using 0.5 µg of each DNA fragment, 1 U of T4 DNA ligase and T4 ligase buffer (Boehringer Mannheim, Germany).

The ligation mixture was used to transform competent B.subtillis PL2306. The transformed cells were plated onto LBPG-10 µg/ml of Kanamycin-agar plates. After 18 hours incubation at 37° C. colonies were seen on plates. Several clones were analyzed by isolating plasmid DNA from overnight culture broth.

One such positive clone was restreaked several times on agar plates as used above, this clone was called MB879. The clone MB879 was grown overnight in TY-10 µg/ml Kanamycin at 37° C., and next day 1 ml of cells were used to isolate plasmid from the cells using the Qiaprep Spin Plasmid Miniprep Kit #27106 according to the manufacturers recommendations for B.subtilis plasmid preparations. This DNA was DNA sequenced and revealed the DNA sequence corresponding to the mature part of the mannanase (corresponding to positions 204–1107 in the appended DNA sequence SEQ ID NO:15 and positions 26–369 in the appended protein sequence SEQ ID NO:16.

Expression, Purification and Characterisation of Mannanase from Bacillus sp. AA349

The clone MB879 obtained as described above was grown in 25×200 ml BPX media with 10 µg/ml of Kanamycin in 500 ml two baffled shakeflasks for 5 days at 37° C. at 300 rpm.

400 ml of the shake flask culture fluid of the clone MB879 was collected and pH was 6.5. 19 ml of cationic agent (10% C521) and 38 ml of anionic agent (A130) was added during agitation for flocculation. The flocculated material was separated by centrifugation using a Sorval RC 3 B centrifuge at 5000 rpm for 25 min at 6° C. The then concentrated and washed with water to reduce the conductivity on a Filtron with a 10 kDa cut off to 150 ml. then the pH was adjusted to 4.0 and the liquid applied to S-Sepharose column cromatography in a 50 mM Sodium acetete buffer pH 4.0. The column was first eluted with a NaCl gradient to 0.5 M then the mannase eluted using 0.1 M glycin buffer pH 10. The mannanase active fraction was pooled and they gave a single band in SDS-PAGE with a molecular weight of 38 kDa.

The amino acid sequence of the mannanase enzyme, i.e. the translated DNA sequence, is shown in SEQ ID NO:16.

The pH activity profile using the ManU assay (incubation for 20 minutes at 40° C.) shows that the enzyme has a relative activity higher than 30% between pH 5 and pH 10.

Temperature optimum was found (using the ManU assay; glycine buffer) to be between 60° C. and 70° C. at pH 10.

Immunological properties: Rabbit polyclonal monospecific serum was raised against the highly purified cloned mannanase using conventional techniques at the Danish company DAKO. The serum formed a nice single precipitate in agarose gels with the crude non purified mannanase of the invention.

EXAMPLE 13

Use of the Mannanase Enzyme of Example 12 in Detergents

Using commercial detergents instead of buffer and incubation for 20 minutes at 40° C. with 0.2% AZCL-Galactomannan (Megazyme, Australia) from carob degree as described above followed by determination of the formation of blue color, the mannanase enzyme obtained as described in example 12 was active with an activity higher than 65% relative to the activity in buffer in European liquid detergent Ariel Futur and in U.S. Tide liquid detergent. The mannanase was more than 35% active in powder detergents from Europe, Ariel Futur and in U.S. tide powder. In these tests, the detergent concentration was as recommended on the commercial detergent packages and the wash water was tap water having 18 degrees German hardness under European (Ariel Futur) conditions and 9 degrees under U.S. conditions (U.S. Tide).

EXAMPLE 14

Mannanase derived from the Fungal Strain
*Humicola insolens* DSM 1800

Expression cloning of a family 26 beta-1,4-mannanase from *Humicola insolens*

Fungal strain and cultivation conditions

*Humicola insolens* strain DSM 1800 was fermented as described in WO 97/32014, the mycelium was harvested after 5 days growth at 26° C., immediately frozen in liquid $N_2$, and stored at −80° c.

Preparation of RNase-Free Glassware, Tips and Solutions

All glassware used in RNA isolations were baked at +220° C. for at least 12 h. Eppendorf tubes, pipet tips and plastic columns were treated in 0.1% diethylpyrocarbonate (DEPC) in EtOH for 12 h, and autoclaved. All buffers and water (except Tris-containing buffers) were treated with 0.1% DEPC for 12 h at 37° C., and autoclaved.

Extraction of total RNA

The total RNA was prepared by extraction with guanidinium thiocyanate followed by ultracentrifugation through a 5.7 M CsCl cushion (Chirgwin et al., 1979) using the following modifications. The frozen mycelia was ground in liquid $N_2$ to fine powder with a mortar and a pestle, followed by grinding in a precooled coffee mill, and immediately suspended in 5 vols of RNA extraction buffer (4 M GuSCN, 0.5% Na-laurylsarcosine, 25 mM Na-citrate, pH 7.0, 0.1 M β-mercaptoethanol). The mixture was stirred for 30 min. at RT° and centrifuged (30 min., 5000 rpm, RT°, Heraeus Megafuge 1.0 R) to pellet the cell debris. The supernatant was collected, carefully layered onto a 5.7 M CsCl cushion (5.7 M CsCl, 0.1 EDTA, pH 7.5, 0.1% DEPC; autoclaved prior to use) using 26.5 ml supernatant per 12.0 ml CsCl cushion, and centrifuged to obtain the total RNA (Beckman, SW 28 rotor, 25,000 rpm, RT°, 24 h). After centrifugation the supernatant was carefully removed and the bottom of the tube containing the RNA Pellet was cut off and rinsed with 70% EtOH. The total RNA pellet was transferred into an Eppendorf tube, suspended in 500 ml TE, pH 7.6 (if difficult, heat occasionally for 5 min at 65° C.), phenol extracted and precipitated with ethanol for 12 h at −20° C. (2.5 vols EtOH, 0.1 vol 3 M NaAc, pH 5.2). The RNA was collected by centrifugation, washed in 70% EtOH, and resuspended in a minimum volume of DEPC-DIW. The RNA concentration was determined by measuring $OD_{260/280}$.

Isolation of poly(A) $^+$RNA

The poly (A) $^+$RNAs were isolated by oligo (dT)-cellulose affinity chromatography (Aviv & Leder, 1972). Typically, 0.2 g of oligo (dT) cellulose (Boehringer Mannheim, check for binding capacity) was preswollen in 10 ml of 1×column loading buffer (20 mM Tris-Cl, pH 7.6, 0.5 M NaCl, 1 mM EDTA, 0.1% SDS), loaded onto a DEPC-treated, plugged plastic column (Poly Prep Chromatography Column, Bio Rad), and equilibrated with 20 ml 1×loading buffer. The total RNA was heated at 65° C. for 8 min., quenched on ice for 5 min, and after addition of 1 vol 2× column loading buffer to the RNA sample loaded onto the column. The eluate was collected and reloaded 2–3 times by heating the sample as above and quenching on ice prior to each loading. The oligo (dT) column was washed with 10 vols of 1× loading buffer, then with 3 vols of medium salt buffer (20 mM Tris-Cl, pH 7.6, 0.1 M NaCl, 1 mM EDTA, 0.1% SDS), followed by elution of the poly(A)$^{30}$ RNA with 3 vols of elution buffer (10 mM Tris-Cl, pH 7.6, 1 mM EDTA, 0.05% SDS) preheated to +65° C., by collecting 500 ml fractions. The $OD_{260}$ was read for each collected fraction, and the mRNA containing fractions were pooled and ethanol precipitated at −20° C. for 12 h. The poly(A)$^+$RNA was collected by centrifugation, resuspended in DEPC-DIW and stored in 5–10 mg aliquots at −80° C.

cDNA Synthesis

First Strand Synthesis

Double-stranded cDNA was synthesized from 5 mg of *Humicola insolens* poly(A)$^+$RNA by the RNase H method (Gubler & Hoffman 1983, Sambrook et al., 1989) using the hair-pin modification developed by F. S. Hagen (pers. comm.). The poly (A)$^+$RNA (5 mg in 5 ml of DEPC-treated water) was heated at 70° C. for 8 min., quenched on ice, and combined in a final volume of 50 ml with reverse transcriptase buffer (50 mM Tris-Cl, pH 8.3, 75 mM KCl, 3 mM MgC12, 10 mM DTT, Bethesda Research Laboratories) containing 1 mM each dNTP (Pharmacia), 40 units of human placental ribonuclease inhibitor (RNasin, Promega), 10 mg of oligo (dT)$_{12-18}$ primer (Pharmacia) and 1000 units of SuperScript II RNase H-reverse transcriptase (Bethesda Research Laboratories). First-strand cDNA was synthesized by incubating the reaction mixture at 45° C. for 1 h.

Second Strand Synthesis

After synthesis 30 ml of 10 mM Tris-Cl, pH 7.5, 1 mM EDTA was added, and the mRNA:cDNA hybrids were ethanol precipitated for 12 h at −20° C. by addition of 40 mg glycogen carrier (Boehringer Mannheim) 0.2 vols 10 M $NH_4Ac$ and 2.5 vols 96% EtOH. The hybrids were recovered by centrifugation, washed in 70% EtOH, air dried and resuspended in 250 ml of second strand buffer (20 mM Tris-Cl, pH 7.4, 90 mM KCl, 4.6 mM MgC12, 10 mM $(NH_2)_2SO_4$, 16 mM βNAD$^+$) containing 100 mM each dNTP., 44 units of E. coli DNA polymerase I (Amersham), 6.25 units of RNase H (Bethesda Research Laboratories) and 10.5 units of E. coli DNA ligase (New England Biolabs). Second strand cDNA synthesis was performed by incubating the reaction tube at 16° C. for 3 h, and the reaction was stopped by addition of EDTA to 20 mM final concentration followed by phenol extraction.

Mung Bean Nuclease Treatment

The double-stranded (ds) cDNA was ethanol precipitated at −20° C. for 12 h by addition of 2 vols of 96% EtOH, 0.1 vol 3 M NaAc, pH 5.2, recovered by centrifugation, washed in 70% EtOH, dried (SpeedVac), and resuspended in 30 ml of Mung bean nuclease buffer (30 mM NaAc, pH 4.6, 300 mM NaCl, 1 mM ZnSO4, 0.35 mM DTT, 2% glycerol) containing 36 units of Mung bean nuclease (Bethesda Research Laboratories). The single-stranded hair-pin DNA was clipped by incubating the reaction at 30° C. for 30 min, followed by addition of 70 ml 10 mM Tris-Cl, pH 7.5, 1 mM EDTA, phenol extraction, and ethanol precipitation with 2 vols of 96% EtOH and 0.1 vol 3 M NaAc, pH 5.2 at −20° C. for 12 h.

Blunt-ending with T4 DNA Polymerase

The ds cDNA was blunt-ended with T4 DNA polymerase in 50 ml of T4 DNA polymerase buffer (20 mM Tris-acetate, pH 7.9, 10 mM MgAc, 50 mM KAc, 1 mM DTT) containing 0.5 mM each dNTP and 7.5 units of T4 DNA polymerase (Invitrogen) by incubating the reaction mixture at +37° C. for 15 min. The reaction was stopped by addition of EDTA to 20 mM final concentration, followed by phenol extraction and ethanol precipitation.

Adaptor Ligation and Size Selection

After the fill-in reaction the cDNA was ligated to non-palindromic BstX I adaptors (1 mg/ml, Invitrogen) in 30 ml of ligation buffer (50 mM Tris-C1, pH 7.8, 10 mM MgC12, 10 mM DTT, 1 mM ATP, 25 mg/ml bovine serum albumin) containing 600 pmol BstX I adaptors and 5 units of T4 ligase (Invitrogen) by incubating the reaction mix at +16° C. for 12 h. The reaction was stopped by heating at +70° C. for 5 min, and the adapted cDNA was size-fractionated by agarose gel electrophoresis (0.8% HSB-agarose, FMC) to separate unligated adaptors and small cDNAs. The cDNA was size-selected with a cut-off at 0.7 kb, and the cDNA was electroeluted from the agarose gel in 10 mM Tris-C1, pH 7.5, 1 mM EDTA for 1 h at 100 volts, phenol extracted and ethanol precipitated at −20° C. for 12 h as above.

Construction of the *Humicola insolens* cDNA Library

The adapted, ds cDNAs were recovered by centrifugation, washed in 70% EtOH and resuspended in 25 ml DIW. Prior to large-scale library ligation, four test ligations were carried out in 10 ml of ligation buffer (same as above) each containing 1 ml ds cDNA (reaction tubes #1–#3), 2 units of T4 ligase (Invitrogen) and 50 ng (tube #1), 100 ng (tube #2) and 200 ng (tubes #3 and #4) Bst XI cleaved pYES 2.0 vector (Invitrogen). The ligation reactions were performed by incubation at +16° C. for 12 h, heated at 70° C. for 5 min, and 1 ml of each ligation electroporated (200 W, 2.5 kV, 25 mF) to 40 ml competent E. coli 1061 cells (OD600=0.9 in 1 liter LB-broth, washed twice in cold DIW, once in 20 ml of 10% glycerol, resuspended in 2 ml 10% glycerol). After addition of 1 ml SOC to each transformation mix, the cells were grown at +37° C. for 1 h, 50 ml plated on LB+ampicillin plates (100 mg/ml) and grown at +37° C. for 12 h.

Using the optimal conditions a large-scale ligation was set up in 40 ml of ligation buffer containing 9 units of T4 ligase, and the reaction was incubated at +16° C. for 12 h. The ligation reaction was stopped by heating at 70° C. for 5 min, ethanol precipitated at −20° C. for 12 h, recovered by centrifugation and resuspended in 10 ml DIW. One ml aliquots were transformed into electrocompetent E. coli 1061 cells using the same electroporation conditions as above, and the transformed cells were titered and the library plated on LB+ampicillin plates with 5000–7000 c.f.u./plate. The cDNA library, comprising of 1×10$^6$ recombinant clones, was stored as 1) individual pools (5000–7000 c.f.u./pool) in 20% glycerol at −80° C., 2) cell pellets of the same pools at −20° C., and 3) Qiagen purified plasmid DNA from individual pools at −20° C. (Qiagen Tip 100, Diagen).

Expression Cloning in *Saccharomyces Cerevisiae* of beta-1,4 Mannanase cDNA from *Humicola Insolens*

One ml aliquots of purified plasmid DNA (100 ng/ml) from individual pools were electroporated (200 W, 1.5 kV, 25 mF) into 40 ml of electrocompetent S. cerevisiae W3124 (MATa; ura 3-52; leu 2-3, 112; his 3-D200; pep 4-1137; prc1: :HIS3, prb1: :LEU2; cir+) cells (OD600=1.5 in 500 ml YPD, washed twice in cold DIW, once in cold 1 M sorbitol, resuspended in 0.5 ml 1 M Becker & Guarante, 1991). After addition of 1 ml 1 M cold sorbitol, 80 ml aliquots were plated on SC+glucose−uracil to give 250–400 colony forming units per plate and incubated at 30° C. for 3–5 days. The plates were replicated on SC+galactose−uracil plates, containing AZC1-galactomannan (MegaZyme, Australia) incorporated in the agar plates. In total, ca. 50,000 yeast colonies from the *H. insolens* library were screened for mannanase-positive clones.

The positive clones were identified by the formation of blue hydrolysis halos around the corresponding yeast colonies. The clones were obtained as single colonies, the cDNA inserts were amplified directly from yeast cell lysates using biotinylated pYES 2.0 polylinker primers, purified by magnetic beads (Dynabead M-280, Dynal) system and characterized individually by sequencing the 5'-end of each cDNA clone using the chain-termination method (Sanger et al., 1977) and the Sequenase system (United Sates Biochemical).

The mannanase-positive yeast colonies were incolulated into 20 ml YPD broth in a 50 ml tubes. The tubes were shaken for 2 days at 30° C., and the cells were harvested by centrifugation for 10 min. at 3000 rpm. Total yeast DNA was isolated according to WO 94/14953, dissolved in 50 ml of autoclaved water, and transformed into E. coli by electroporation as above. The insert-containing pYES 2.0 cDNA clones were rescued by plating on LB+ampicillin agar plates, the plasmid DNA was isolated from E. coli using standard procedures, and analyzed by digesting with restriction enzymes.

Necleotide Sequence Analysis

The nucleotide sequence of the full-length *H. insolens* beta-1,4-mannanase cDNA clone pC1M59 was determined from both strands by the dideoxy chain-termination method (Sanger et al. 1977), using 500 ng of Qiagen-purified template (Qiagen, USA) template, the Taq deoxy-terminal cycle sequencing kit (Perkin-Elmer, USA), fluorescent labeled terminators and 5 pmol of the pYES 2.0 polylinker primers (Invitrogen, USA). Analysis of the sequence data were performed according to Deverux et al. (1984).

Heterologous Expression in *Aspergillus Oryzae*

Transformation of *Aspergillus Oryzae*

Transformation of *Aspergillus oryzae* was carried out as described by Christensen et al., (1988), Biotechnology 6, 1419–1422.

Construction of the beta-1,4-Mannanase Expression Cassette for Aspergillus Expression Plasmid DNA was isolated from the mannanase clone pC1M59 using standard procedures and analyzed by restriction enzyme analysis. The cDNA insert was excised using appropriate restriction enzymes and ligated into the Aspergillus expression vector pHD414, which is a derivative of the plasmid p775 (described in EP 238023). The construction of pHD414 is further described in WO 93/11249.

Transformation of *Aspergillus Oryzae* or *Aspergillus Niger*

General procedure: 100 ml of YPD (Sherman et al., Methods in Yeast Genetics, Cold Spring Harbor Laboratory, 1981) is inoculated with spores of A. oryzae or A. niger and incubated with shaking at 37° C. for about 2 days. The mycelium is harvested by filtration through miracloth and washed with 200 ml of 0.6 M MgSO$_4$. The mycelium is suspended in 15 ml of 1.2 M MgSO$_4$. 10 mM NaH$_2$PO$_4$, pH=5.8. The suspension is cooled on ice and 1 ml of buffer containing 120 mg of Novozym® 234 is added. After 5 minutes 1 ml of 12 mg/ml BSA is added and incubation with gentle agitation continued for 1.5–2.5 hours at 37° C. until a large number of protoplasts is visible in a sample inspected under the microscope. The suspension is filtered through miracloth, the filtrate transferred to a sterile tube and overlayered with 5 ml of 0.6 M sorbitol, 100 mM Tris-HCl, pH=7.0. Centriguation is performed for 15 minutes at 100 g and the protoplasts are collected from the top of the MgSO$_4$ cushion. 2 volumes of STC are added to the protoplast suspension and the mixture is centrifugated for 5 minutes at 1000 g. The protoplast pellet is resuspended in 3 ml of STC and repelleted. This is repeated. Finally the protoplasts are resuspended in 0.2–1 ml of STC. 100 μl of protoplast suspension is mixed with 5–25 μg of the appropriate DNA in 10 μl of STC. Protoplasts are mixed with p3SR2 (an A. nidulans amdS gene carrying plasmid). The mixture is left at room temperature for 25 minutes. 0.2 ml of 60% PEG 4000. 10 mM CaCl$_2$ and 10 mM Tris-HCl, pH 7.5 is added and carefully mixed (twice) and finally 0.85 ml of the same solution is added and carefully mixed. The mixture is left at room temperature for 25 minutes, spun at 2500 g for 15 minutes and the pellet is resuspended in 2 ml of 1.2 M sorbitol. After one more sedimentation the protoplasts are spread on the appropriate plates. Protoplasts are spread on minimal plates to inhibit background growth. After incubation for 4–7 days at 37° C. spores are picked and spread for single colonies. This procedure is repeated and spores of a single colony after the second re-isolation is stored as a defined transformant.

Purification of the *Aspergillus Oryzae* Transformants

*Aspergillus oryzae* colonies are purified through conidial spores on AmdS+-plates (+0,01% Triton X-100) and growth in YPM for 3 days at 30° C.

Identification of Mannanase-Positive *Aspergillus Oryzae* Transformants

The supernatants from the *Aspergillus oryzae* transformants were assayed for beta-1,4-mannanase activity on agar plates containing 0.2% AZC1-galactomannan (MegaZyme, Australia) as substrate. Positive transformants were identified by analyzing the plates for blue hydrolysis halos after 24 hours of incubation at 30° C.

SDS-PAGE Analysis

SDS-PAGE analysis of supernatnants from beta-1,4-mannanase producing *Aspergillus oryzae* transformants. The transformants were grown in 5 ml YPM for three days. 10 μl of supernatant was applied to 12% SDS-polyacrylamide gel which was subsequently stained with Coomassie Brilliant Blue.

Purification and Characterisation of the *Humicola Insolens* Mannanse

The gene was transformed into *A. oryzae* ads described above and the transformed strain was grown in a fermentor using standard medium of Maltose syrup, sucrose, MgSO$_4$ Ka$_2$PO$_4$ and K$_2$SO$_4$ and citric acid yeast extract and trace metals. Incubation for 6 days at 34° C. with air.

The fermentation broth (5000 ml) was harvested and the mycelium separated from the liquid by filtration. The clear liquid was concentrated on a filtron to 275 ml.

The mannanase was purified using Cationic chromatography. A S-Spharose column was equilibrated with 25 mM citric acid pH 4.0 and the mannanase bound to the column and was eluted using a sodium chloride gradient (0–0.5 M). The mannanase active fractions was pooled and the pH adjusted to 7.3. The 100 ml pooled mannanase was then concentrated to 5 ml with around 13 mg protein per ml and used for applications trials. For further purification 2 ml was applied to size chromatography on Superdex 200 in sodium acetate buffer pH 6.1. The mannase active fraction showed to equal stained bands in SDS-PAGE with a MW of 45 kDa and 38 kDa, indicating proteolytic degradation of the N-terminal non-catalytic domain.

The amino acid sequence of the mannanase enzyme, i.e. the translated DNA sequence, is shown in SEQ ID NO:14.

The DNA sequence of SEQ ID NO:13 codes for a signal peptide in positions 1 to 21. A domain of unknown function also found in other mannanases is represented in the amino acid sequence SEQ ID NO: 14 in positions 22 to 159 and the catalytic active domain is found in positions 160 to 488 of SEQ ID NO: 14.

Highest sequence homology was found to DICTYOGLOMUS THERMOPHILUM (49% identity); Mannanase sequence EMBL: AF013989 submitted by REEVES R. A., GIBBS M. D., BERGQUIST P. L. submitted in July 1997.

Molecular Weight: 38 kDa.

DSC in sodium acetate buffer pH 6.0 was 65°.

The pH activity profile using the ManU assay (incubation for 20 minutes at 40° C.) shows that the enzyme has optimum activity at pH 8.

Temperature optimum was found (using the ManU assay; Megazyme AZCL locust been gum as substrate) to be 70° C. at pH 10.

Immunological properties: Rabbit polyclonal monospecific serum was raised against the highly purified cloned mannanase using conventional techniques at the Danish company DAKO. The serum formed a nice single precipitate in agarose gels with the crude non purified mannanase of the invention.

EXAMPLE 15

Wash Evaluation of Humicola Insolens Family 26 Mannanase

Wash performance was evaluated by washing locust bean gum coated swatches in a detergent solution with the mannanase of the invention. After wash the effect were visualised by soiling the swatches with iron oxide.

Preparation of locust bean gum swatches: Clean cotton swatches were soaked in a solution of 2 g/l locust bean gum and dried overnight at room temperature. The swatches were prewashed in water and dried again.

Wash: Small circular locust bean gum swatches were placed in a beaker with 6,7 g/l Ariel Futur liquid in 15° dH water and incubated for 30 min at 40° C. with magnetic stirring. The swatches were rinsed in tap water and dried.

Soiling: The swatches were placed in a beaker with 0.25 g/l Fe$_2$O$_3$ and stirred for 3 min. The swatches were rinsed in tap water and dried.

Evaluation: Remission of the swatches was measured at 440 nm using a MacBeth ColorEye 7000 remission spectrophotometer.

The results are expressed as delta remission=$(R_{after\ wash} - R_{before\ wash})_{enzyme} - (R_{after\ wash} - R_{before\ wash})_{control}$, where R is the remission at 440 nm.

The mannanase of this invention is clearly effective on locust bean gum swatches with a wash performance slightly better than the control mannanase from Bacillus sp. I633.

Wash performance of *Humicola insolens* family 26 mannanase compared to the mannanase from Bacillus sp. I633 (examples 1–3) given as delta remission values:

| Enzyme dose in mg/l | *Humicola insolens* mannanase | Bacillus sp. I633 mannanase |
|---|---|---|
| 0 | 0 | 0 |
| 0.01 | 6.6 | 5.0 |
| 0.1 | 9.3 | 8.6 |
| 1.0 | 10.2 | 7.7 |
| 10.0 | 10.5 | 9.7 |

EXAMPLES 16–40

The following examples are meant to exemplify compositions of the present invention, but are not necessarily meant to limit or otherwise define the scope of the invention.

In the detergent compositions, the enzymes levels are expressed by pure enzyme by weight of the total composition and unless otherwise specified, the detergent ingredients are expressed by weight of the total compositions. The abbreviated component identifications therein have the following meanings:

| | |
|---|---|
| LAS | Sodium linear $C_{11-13}$ alkyl benzene sulphonate. |
| TAS | Sodium tallow alkyl sulphate. |
| CxyAS | Sodium $C_{1x}$–$C_{1y}$ alkyl sulfate. |
| CxySAS | Sodium $C_{1x}$–$C_{1y}$ secondary (2, 3) alkyl sulfate. |
| CxyEz | $C_{1x}$–$C_{1y}$ predominantly linear primary alcohol condensed with an average of z moles of ethylene oxide. |
| CxyEzS | $C_{1x}$–$C_{1y}$ sodium alkyl sulfate condensed with an average of z moles of ethylene oxide. |
| QAS | $R_2.N + (CH_3)_2(C_2H_4OH)$ with $R_2 = C_{12}$—$C_{14}$. |
| QAS 1 | $R_2.N + (CH_3)_2(C_2H_4OH)$ with $R_2 = C_8$—$C_{11}$. |
| APA | $C_{8-10}$ amido propyl dimethyl amine. |
| Soap | Sodium linear alkyl carboxylate derived from a 80/20 mixture of tallow and coconut fatty acids. |
| Nonionic | $C_{13}$—$C_{15}$ mixed ethoxylated/propoxylated fatty alcohol with an average degree of ethoxylation of 3.8 and an average degree of propoxylation of 4.5. |
| Neodol 45-13 | C14–C15 linear primary alcohol ethoxylate, sold by Shell Chemical CO. |
| STS | Sodium toluene sulphonate. |
| CFAA | $C_{12}$—$C_{14}$ alkyl N-methyl glucamide. |
| TFAA | $C_{16}$—$C_{18}$ alkyl N-methyl glucamide. |
| TPKFA | $C_{12}$—$C_{14}$ topped whole cut fatty acids. |
| Silicate | Amorphous Sodium Silicate ($SiO_2:Na_2O$ ratio = 1.6–3.2). |
| Metasilicate | Sodium metasilicate ($SiO_2:Na_2O$ ratio = 1.0). |
| Zeolite A | Hydrated Sodium Aluminosilicate of formula $Na_{12}(AlO_2SiO_2)_{12}.27H_2O$ having a primary particle size in the range from 0.1 to 10 micrometers (Weight expressed on an anhydrous basis). |
| Na-SKS-6 | Crystalline layered silicate of formula δ-$Na_2Si_2O_5$. |
| Citrate | Tri-sodium citrate dihydrate of activity 86.4% with a particle size distribution between 425 and 850 micrometres. |
| Citric | Anhydrous citric acid. |
| Borate | Sodium borate |
| Carbonate | Anhydrous sodium carbonate with a particle size between 200 and 900 micrometres. |
| Bicarbonate | Anhydrous sodium hydrogen carbonate with a particle size distribution between 400 and 1200 micrometres. |
| Sulphate | Anhydrous sodium sulphate. |
| Mg Sulphate | Anhydrous magnesium sulfate. |
| STPP | Sodium tripolyphosphate. |
| TSPP | Tetrasodium pyrophosphate. |
| MA/AA | Random copolymer of 4:1 acrylate/maleate, average molecular weight about 70,000–80,000. |
| MA/AA 1 | Random copolymer of 6:4 acrylate/maleate, average molecular weight about 10,000. |
| AA | Sodium polyacrylate polymer of average molecular weight 4,500. |
| PA30 | Polyacrylic acid of average molecular weight of between about 4,500–8,000. |
| 480N | Random copolymer of 7:3 acrylate/methacrylate, average molecular weight about 3,500. |
| Polygel/carbopol | High molecular weight crosslinked polyacrylates. |
| PB1 | Anhydrous sodium perborate monohydrate of nominal formula $NaBO_2.H_2O_2$. |
| PB4 | Sodium perborate tetrahydrate of nominal formula $NaBO_2.3H_2.H_2O_2$. |
| Percarbonate | Anhydrous sodium percarbonate of nominal formula $2Na_2CO_3.3H_2O_2$. |
| NaDCC | Sodium dichloroisocyanurate. |
| TAED | Tetraacetylethylenediamine. |
| NOBS | Nonanoyloxybenzene sulfonate in the form of the sodium salt. |
| NACA-OBS | (6-nonamidocaproyl) oxybenzene sulfonate. |
| DTPA | Diethylene triamine pentaacetic acid. |
| HEDP | 1,1-hydroxyethane diphosphonic acid. |
| DETPMP | Diethyltriamine penta (methylene) phosphonate, marketed by Monsanto under the Trade name Dequest 2060. |
| EDDS | Ethylenediamine-N,N'-disuccinic acid, (S, S) isomer in the form of its sodium salt |
| MnTACN | Manganese 1,4,7-trimethyl-1,4,7-triazacyclononane. |
| Photoactivated Bleach | Sulfonated zinc phtalocyanine encapsulated in dextrin soluble polymer. |
| Photoactivated Bleach 1 | Sulfonated alumino phtalocyanine encapsulated in dextrin soluble polymer. |
| PAAC | Pentaamine acetate cobalt (III) salt. |
| Paraffin | Paraffin oil sold under the tradename Winog 70 by Wintershall. |
| NaBz | Sodium benzoate. |
| BzP | Benzoyl Peroxide. |
| Mannanase | As described herein |
| Protease | Proteolytic enzyme sold under the tradename Savinase, Alcalase, Durazym by Novo Nordisk A/S, Maxacal, Maxapem sold by Gist-Brocades and proteases described in patents WO91/06637 and/or WO95/10591 and/or EP 251 446. |
| Amylase | Amylolytic enzyme sold under the tradename Purafact Ox Am$^R$ described in WO94/18314, WO96/05295 sold by Genencor; Termamyl ®, Fungamyl ® and Duramyl ®, all available from Novo Nordisk A/S and those described in WO95/26397. |
| Lipase | Lipolytic enzyme sold under the tradename Lipolase, Lipolase Ultra by Novo Nordisk A/S and Lipomax by Gist-Brocades. |
| Cellulase | Cellulytic enzyme sold under the tradename Carezyme, Celluzyme and/or Endolase by Novo Nordisk A/S. |
| CMC | Sodium carboxymethyl cellulose. |
| PVP | Polyvinyl polymer, with an average molecular weight of 60,000. |
| PVNO | Polyvinylpyridine-N-Oxide, with an average molecular weight of 50,000. |
| PVPVI | Copolymer of vinylimidazole and vinylpyrrolidone, with an average molecular weight of 20,000. |
| Brightener 1 | Disodium 4,4'-bis(2-sulphostyryl)biphenyl. |
| Brightener 2 | Disodium 4,4'-bis(4-anilino-6-morpholino-1.3.5-triazin-2-yl) stilbene-2:2'-disulfonate. |

-continued

| | |
|---|---|
| Silicone anti-foam | Polydimethylsiloxane foam controller with siloxane-oxyalkylene copolymer as dispersing agent with a ratio of said foam controller to said dispersing agent of 10:1 to 100:1. |
| Suds Suppressor | 12% Silicone/silica, 18% stearyl alcohol, 70% starch in granular form. |
| Opacifier | Water based monostyrene latex mixture, sold by BASF Aktiengesellschaft under the tradename Lytron 621. |
| SRP 1 | Anionically end capped poly esters. |
| SRP 2 | Diethoxylated poly (1,2 propylene terephthalate) short block polymer. |
| QEA | bis(($C_2H_5O$) ($C_2H_4O)_n$) ($CH_3$)—$N^+$—$C_6H_{12}$—$N^+$—($CH_3$) bis(($C_2H_5O$)—($C_2H_4O))_n$, wherein n = from 20 to 30. |
| PEI | Polyethyleneimine with an average molecular weight of 1800 and an average ethoxylation degree of 7 ethyleneoxy residues per nitrogen. |
| SCS | Sodium cumene sulphonate. |
| HMWPEO | High molecular weight polyethylene oxide. |
| PEGx | Polyethylene glycol, of a molecular weight of x. |
| PEO | Polyethylene oxide, with an average molecular weight of 5,000. |
| TEPAE | Tetreaethylenepentaamine ethoxylate. |
| BTA | Benzotriazole. |
| PH | Measured as a 1% solution in distilled water at 20° C. |

EXAMPLE 16

The following high density laundry detergent compositions were prepared according to the present invention:

| | I | II | III | IV | V | VI |
|---|---|---|---|---|---|---|
| LAS | 8.0 | 8.0 | 8.0 | 2.0 | 6.0 | 6.0 |
| TAS | — | 0.5 | — | 0.5 | 1.0 | 0.1 |
| C46(S)AS | 2.0 | 2.5 | — | — | — | — |
| C25AS | — | — | — | 7.0 | 4.5 | 5.5 |
| C68AS | 2.0 | 5.0 | 7.0 | — | — | — |
| C25E5 | — | — | 3.4 | 10.0 | 4.6 | 4.6 |
| C25E7 | 3.4 | 3.4 | 1.0 | — | — | — |
| C25E3S | — | — | — | 2.0 | 5.0 | 4.5 |
| QAS | — | 0.8 | — | — | — | — |
| QAS 1 | — | — | — | 0.8 | 0.5 | 1.0 |
| Zeolite A | 18.1 | 18.0 | 14.1 | 18.1 | 20.0 | 18.1 |
| Citric | — | — | — | 2.5 | — | 2.5 |
| Carbonate | 13.0 | 13.0 | 27.0 | 10.0 | 10.0 | 13.0 |
| Na-SKS-6 | — | — | — | 10.0 | — | 10.0 |
| Silicate | 1.4 | 1.4 | 3.0 | 0.3 | 0.5 | 0.3 |
| Citrate | — | 1.0 | — | 3.0 | — | — |
| Sulfate | 26.1 | 26.1 | 26.1 | 6.0 | — | — |
| Mg sulfate | 0.3 | — | — | 0.2 | — | 0.2 |
| MA/AA | 0.3 | 0.3 | 0.3 | 4.0 | 1.0 | 1.0 |
| CMC | 0.2 | 0.2 | 0.2 | 0.2 | 0.4 | 0.4 |
| PB4 | 9.0 | 9.0 | 5.0 | — | — | — |
| Percarbonate | — | — | — | — | 18.0 | 18.0 |
| TAED | 1.5 | 0.4 | 1.5 | — | 3.9 | 4.2 |
| NACA-OBS | — | 2.0 | 1.0 | — | — | — |
| DETPMP | 0.25 | 0.25 | 0.25 | 0.25 | — | — |
| SRP 1 | — | — | — | 0.2 | — | 0.2 |
| EDDS | — | 0.25 | 0.4 | — | 0.5 | 0.5 |
| CFAA | — | 1.0 | — | 2.0 | — | — |
| HEDP | 0.3 | 0.3 | 0.3 | 0.3 | 0.4 | 0.4 |
| QEA | — | — | — | 0.2 | — | 0.5 |
| Protease | 0.009 | 0.009 | 0.01 | 0.04 | 0.05 | 0.03 |
| Mannanase | 0.05 | 0.009 | 0.03 | 0.009 | 0.03 | 0.009 |
| Amylase | 0.002 | 0.002 | 0.002 | 0.006 | 0.008 | 0.008 |
| Cellulase | 0.0007 | — | — | 0.0007 | 0.0007 | 0.0007 |
| Lipase | 0.006 | — | — | 0.01 | 0.01 | 0.01 |
| Photoactivated bleach (ppm) | 15 | 15 | 15 | — | 20 | 20 |
| PVNO/PVPVI | — | — | — | 0.1 | — | — |
| Brightener 1 | 0.09 | 0.09 | 0.09 | — | 0.09 | 0.09 |
| Perfume | 0.3 | 0.3 | 0.3 | 0.4 | 0.4 | 0.4 |
| Silicone anti-foam | 0.5 | 0.5 | 0.5 | — | 0.3 | 0.3 |
| Density in g/liter | 850 | 850 | 850 | 850 | 850 | 850 |
| Miscellaneous and minors | | | | | | Up to 100% |

EXAMPLE 17

The following granular laundry detergent compositions of particular utility under European machine wash conditions were prepared according to the present invention:

|  | I | II | III | IV | V | VI |
|---|---|---|---|---|---|---|
| LAS | 5.5 | 7.5 | 5.0 | 5.0 | 6.0 | 7.0 |
| TAS | 1.25 | 1.9 | — | 0.8 | 0.4 | 0.3 |
| C24AS/C25AS | — | 2.2 | 5.0 | 5.0 | 5.0 | 2.2 |
| C25E3S | — | 0.8 | 1.0 | 1.5 | 3.0 | 1.0 |
| C45E7 | 3.25 | — | — | — | — | 3.0 |
| TFAA | — | — | 2.0 | — | — | — |
| C25E5 | — | 5.5 | — | — | — | — |
| QAS | 0.8 | — | — | — | — | — |
| QAS 1 | — | 0.7 | 1.0 | 0.5 | 1.0 | 0.7 |
| STPP | 19.7 | — | — | — | — | — |
| Zeolite A | — | 19.5 | 25.0 | 19.5 | 20.0 | 17.0 |
| NaSKS-6/citric acid (79:21) | — | 10.6 | — | 10.6 | — | — |
| Na-SKS-6 | — | — | 9.0 | — | 10.0 | 10.0 |
| Carbonate | 6.1 | 21.4 | 9.0 | 10.0 | 10.0 | 18.0 |
| Bicarbonate | — | 2.0 | 7.0 | 5.0 | — | 2.0 |
| Silicate | 6.8 | — | — | 0.3 | 0.5 | — |
| Citrate | — | — | 4.0 | 4.0 | — | — |
| Sulfate | 39.8 | — | — | 5.0 | — | 12.0 |
| Mg sulfate | — | — | 0.1 | 0.2 | 0.2 | — |
| MA/AA | 0.5 | 1.6 | 3.0 | 4.0 | 1.0 | 1.0 |
| CMC | 0.2 | 0.4 | 1.0 | 1.0 | 0.4 | 0.4 |
| PB4 | 5.0 | 12.7 | — | — | — | — |
| Percarbonate | — | — | — | — | 18.0 | 15.0 |
| TAED | 0.5 | 3.1 | — | — | 5.0 | — |
| NACA-OBS | 1.0 | 3.5 | — | — | — | 2.5 |
| DETPMP | 0.25 | 0.2 | 0.3 | 0.4 | — | 0.2 |
| HEDP | — | 0.3 | — | 0.3 | 0.3 | 0.3 |
| QEA | — | — | 1.0 | 1.0 | 1.0 | — |
| Protease | 0.009 | 0.03 | 0.03 | 0.05 | 0.05 | 0.02 |
| Mannanase | 0.03 | 0.03 | 0.001 | 0.03 | 0.005 | 0.009 |
| Lipase | 0.003 | 0.003 | 0.006 | 0.006 | 0.006 | 0.004 |
| Cellulase | 0.0006 | 0.0006 | 0.0005 | 0.0005 | 0.0007 | 0.0007 |
| Amylase | 0.002 | 0.002 | 0.006 | 0.006 | 0.01 | 0.003 |
| PVNO/PVPVI | — | — | 0.2 | 0.2 | — | — |
| PVP | 0.9 | 1.3 | — | — | — | 0.9 |
| SRP 1 | — | — | 0.2 | 0.2 | 0.2 | — |
| Photoactivated bleach (ppm) | 15 | 27 | — | — | 20 | 20 |
| Photoactivated bleach 1 (ppm) | 15 | — | — | — | — | — |
| Brightener 1 | 0.08 | 0.2 | — | — | 0.09 | 0.15 |
| Brightener 2 | — | 0.04 | — | — | — | — |
| Perfume | 0.3 | 0.5 | 0.4 | 0.3 | 0.4 | 0.3 |
| Silicone anti-foam | 0.5 | 2.4 | 0.3 | 0.5 | 0.3 | 2.0 |
| Density in g/liter | 750 | 750 | 750 | 750 | 750 | 750 |
| Miscellaneous and minors | | | Up to 100% | | | |

EXAMPLE 18

The following detergent compositions of particular utility under European machine wash conditions were prepared according to the present invention:

|  | I | II | III | IV |
|---|---|---|---|---|
| Blown Powder | | | | |
| LAS | 6.0 | 5.0 | 11.0 | 6.0 |
| TAS | 2.0 | — | — | 2.0 |
| Zeolite A | 24.0 | — | — | 20.0 |
| STPP | — | 27.0 | 24.0 | — |
| Sulfate | 4.0 | 6.0 | 13.0 | — |
| MA/AA | 1.0 | 4.0 | 6.0 | 2.0 |
| Silicate | 1.0 | 7.0 | 3.0 | 3.0 |
| CMC | 1.0 | 1.0 | 0.5 | 0.6 |
| Brightener 1 | 0.2 | 0.2 | 0.2 | 0.2 |
| Silicone antifoam | 1.0 | 1.0 | 1.0 | 0.3 |
| DETPMP | 0.4 | 0.4 | 0.2 | 0.4 |
| Spray On | | | | |
| Brightener | 0.02 | — | — | 0.02 |
| C45E7 | — | — | — | 5.0 |
| C45E2 | 2.5 | 2.5 | 2.0 | — |
| C45E3 | 2.6 | 2.5 | 2.0 | — |
| Perfume | 0.5 | 0.3 | 0.5 | 0.2 |
| Silicone antifoam | 0.3 | 0.3 | 0.3 | — |

-continued

|  | I | II | III | IV |
|---|---|---|---|---|
| Dry additives | | | | |
| QEA | — | — | — | 1.0 |
| EDDS | 0.3 | — | — | — |
| Sulfate | 2.0 | 3.0 | 5.0 | 10.0 |
| Carbonate | 6.0 | 13.0 | 15.0 | 14.0 |
| Citric | 2.5 | — | — | 2.0 |
| QAS 1 | 0.5 | — | — | 0.5 |
| Na-SKS-6 | 10.0 | — | — | — |
| Percarbonate | 18.5 | — | — | — |
| PB4 | — | 18.0 | 10.0 | 21.5 |
| TAED | 2.0 | 2.0 | — | 2.0 |
| NACA-OBS | 3.0 | 2.0 | 4.0 | — |
| Protease | 0.03 | 0.03 | 0.03 | 0.03 |
| Mannanase | 0.009 | 0.01 | 0.03 | 0.001 |
| Lipase | 0.008 | 0.008 | 0.008 | 0.004 |
| Amylase | 0.003 | 0.003 | 0.003 | 0.006 |
| Brightener 1 | 0.05 | — | — | 0.05 |
| Miscellaneous and minors | | | Up to 100% | |

EXAMPLE 19

The following granular detergent compositions were prepared according to the present invention:

|  | I | II | III | IV | V | VI |
|---|---|---|---|---|---|---|
| Blown Powder | | | | | | |
| LAS | 23.0 | 8.0 | 7.0 | 9.0 | 7.0 | 7.0 |
| TAS | — | — | — | — | 1.0 | — |
| C45AS | 6.0 | 6.0 | 5.0 | 8.0 | — | — |
| C45AES | — | 1.0 | 1.0 | 1.0 | — | — |
| C45E35 | — | — | — | — | 2.0 | 4.0 |
| Zeolite A | 10.0 | 18.0 | 14.0 | 12.0 | 10.0 | 10.0 |
| MA/AA | — | 0.5 | — | — | — | 2.0 |
| MA/AA 1 | 7.0 | — | — | — | — | — |
| AA | — | 3.0 | 3.0 | 2.0 | 3.0 | 3.0 |
| Sulfate | 5.0 | 6.3 | 14.3 | 11.0 | 15.0 | 19.3 |
| Silicate | 10.0 | 1.0 | 1.0 | 1.0 | 1.0 | 1.0 |
| Carbonate | 15.0 | 20.0 | 10.0 | 20.7 | 8.0 | 6.0 |
| PEG 4000 | 0.4 | 1.5 | 1.5 | 1.0 | 1.0 | 1.0 |
| DTPA | — | 0.9 | 0.5 | — | — | 0.5 |
| Brightener 2 | 0.3 | 0.2 | 0.3 | — | 0.1 | 0.3 |
| Spray On | | | | | | |
| C45E7 | — | 2.0 | — | — | 2.0 | 2.0 |
| C25E9 | 3.0 | — | — | — | — | — |
| C23E9 | — | — | 1.5 | 2.0 | — | 2.0 |
| Perfume | 0.3 | 0.3 | 0.3 | 2.0 | 0.3 | 0.3 |
| Agglomerates | | | | | | |
| C45AS | — | 5.0 | 5.0 | 2.0 | — | 5.0 |
| LAS | — | 2.0 | 2.0 | — | — | 2.0 |
| Zeolite A | — | 7.5 | 7.5 | 8.0 | — | 7.5 |
| Carbonate | — | 4.0 | 4.0 | 5.0 | — | 4.0 |
| PEG 4000 | — | 0.5 | 0.5 | — | — | 0.5 |
| Misc (Water etc.) | — | 2.0 | 2.0 | 2.0 | — | 2.0 |
| Dry additives | | | | | | |
| QAS | — | — | — | — | 1.0 | — |
| Citric | — | — | — | — | 2.0 | — |
| PB4 | — | — | — | — | 12.0 | 1.0 |
| PB1 | 4.0 | 1.0 | 3.0 | 2.0 | — | — |
| Percarbonate | — | — | — | — | 2.0 | 10.0 |
| Carbonate | — | 5.3 | 1.8 | — | 4.0 | 4.0 |
| NOBS | 4.0 | — | 6.0 | — | — | 0.6 |
| Methyl cellulose | 0.2 | — | — | — | — | — |
| Na-SKS-6 | 8.0 | — | — | — | — | — |
| STS | — | — | 2.0 | — | 1.0 | — |
| Culmene sulfonic acid | — | 1.0 | — | — | — | 2.0 |
| Protease | 0.02 | 0.02 | 0.02 | 0.01 | 0.02 | 0.02 |
| Mannanase | 0.009 | 0.01 | 0.03 | 0.009 | 0.01 | 0.001 |
| Lipase | 0.004 | — | 0.004 | — | 0.004 | 0.008 |
| Amylase | 0.003 | — | 0.002 | — | 0.003 | — |
| Cellulase | 0.0005 | 0.0005 | 0.0005 | 0.0007 | 0.0005 | 0.0005 |
| PVPVI | — | — | — | — | 0.5 | 0.1 |
| PVP | — | — | — | — | 0.5 | — |
| PVNO | — | — | 0.5 | 0.3 | — | — |
| QEA | — | — | — | — | 1.0 | — |
| SRP 1 | 0.2 | 0.5 | 0.3 | — | 0.2 | — |
| Silicone antifoam | 0.2 | 0.4 | 0.2 | 0.4 | 0.1 | — |
| Mg sulfate | — | — | 0.2 | — | 0.2 | — |
| Miscellaneous and minors | | | Up to 100% | | | |

EXAMPLE 20

The following nil bleach-containing detergent compositions of particular use in the washing of colored clothing were prepared according to the present invention:

|  | I | II | III |
|---|---|---|---|
| Blown Powder | | | |
| Zeolite A | 15.0 | 15.0 | — |
| Sulfate | — | 5.0 | — |
| LAS | 3.0 | 3.0 | — |
| DETPMP | 0.4 | 0.5 | — |
| CMC | 0.4 | 0.4 | — |
| MA/AA | 4.0 | 4.0 | — |
| Agglomerates | | | |
| C45AS | — | — | 11.0 |
| LAS | 6.0 | 5.0 | — |
| TAS | 3.0 | 2.0 | — |
| Silicate | 4.0 | 4.0 | — |
| Zeolite A | 10.0 | 15.0 | 13.0 |
| CMC | — | — | 0.5 |
| MA/AA | — | — | 2.0 |
| Carbonate | 9.0 | 7.0 | 7.0 |
| Spray-on | | | |
| Perfume | 0.3 | 0.3 | 0.5 |
| C45E7 | 4.0 | 4.0 | 4.0 |
| C25E3 | 2.0 | 2.0 | 2.0 |
| Dry additives | | | |
| MA/AA | — | — | 3.0 |
| Na-SKS-6 | — | — | 12.0 |
| Citrate | 10.0 | — | 8.0 |
| Bicarbonate | 7.0 | 3.0 | 5.0 |
| Carbonate | 8.0 | 5.0 | 7.0 |
| PVPVI/PVNO | 0.5 | 0.5 | 0.5 |
| Protease | 0.03 | 0.02 | 0.05 |
| Mannanase | 0.001 | 0.004 | 0.03 |
| Lipase | 0.008 | 0.008 | 0.008 |
| Amylase | 0.01 | 0.01 | 0.01 |
| Cellulase | 0.001 | 0.001 | 0.001 |
| Silicone antifoam | 5.0 | 5.0 | 5.0 |
| Sulfate | — | 9.0 | — |
| Density (g/liter) | 700 | 700 | 700 |
| Miscellaneous and minors | | Up to 100% | |

EXAMPLE 21

The following detergent compositions were prepared according to the present invention:

|  | I | II | III | IV |
|---|---|---|---|---|
| Base granule | | | | |
| Zeolite A | 30.0 | 22.0 | 24.0 | 10.0 |
| Sulfate | 10.0 | 5.0 | 10.0 | 7.0 |
| MA/AA | 3.0 | — | — | — |
| AA | — | 1.6 | 2.0 | — |
| MA/AA 1 | — | 12.0 | — | 6.0 |
| LAS | 14.0 | 10.0 | 9.0 | 20.0 |
| C45AS | 8.0 | 7.0 | 9.0 | 7.0 |
| C4SAES | — | 1.0 | 1.0 | — |
| Silicate | — | 1.0 | 0.5 | 10.0 |
| Soap | — | 2.0 | — | — |
| Brightener 1 | 0.2 | 0.2 | 0.2 | 0.2 |
| Carbonate | 6.0 | 9.0 | 10.0 | 10.0 |
| PEG 4000 | — | 1.0 | 1.5 | — |
| DTPA | — | 0.4 | — | — |
| Spray On | | | | |
| C25E9 | — | — | — | 5.0 |
| C45E7 | 1.0 | 1.0 | — | — |
| C23E9 | — | 1.0 | 2.5 | — |
| Perfume | 0.2 | 0.3 | 0.3 | — |
| Dry additives | | | | |
| Carbonate | 5.0 | 10.0 | 18.0 | 8.0 |
| PVPVI/PVNO | 0.5 | — | 0.3 | — |
| Protease | 0.03 | 0.03 | 0.03 | 0.02 |
| Mannanase | 0.002 | 0.009 | 0.015 | 0.03 |
| Lipase | 0.008 | — | — | 0.008 |
| Amylase | 0.002 | — | — | 0.002 |
| Cellulase | 0.0002 | 0.0005 | 0.0005 | 0.0002 |
| NOBS | — | 4.0 | — | 4.5 |
| PB1 | 1.0 | 5.0 | 1.5 | 6.0 |
| Sulfate | 4.0 | 5.0 | — | 5.0 |
| SRP 1 | — | 0.4 | — | — |
| Suds suppressor | — | 0.5 | 0.5 | — |
| Miscellaneous and minors | | | | Up to 100% |

EXAMPLE 22

The following granular detergent compositions were prepared according to the present invention:

|  | I | II | III |
|---|---|---|---|
| Blown Powder | | | |
| Zeolite A | 20.0 | — | 15.0 |
| STPP | — | 20.0 | — |
| Sulfate | — | — | 5.0 |
| Carbonate | — | — | 5.0 |
| TAS | — | — | 1.0 |
| LAS | 6.0 | 6.0 | 6.0 |
| C68AS | 2.0 | 2.0 | — |
| Silicate | 3.0 | 8.0 | — |
| MA/AA | 4.0 | 2.0 | 2.0 |
| CMC | 0.6 | 0.6 | 0.2 |
| Brightener 1 | 0.2 | 0.2 | 0.1 |
| DETPMP | 0.4 | 0.4 | 0.1 |
| STS | — | — | 1.0 |
| Spray On | | | |
| C45E7 | 5.0 | 5.0 | 4.0 |
| Silicone antifoam | 0.3 | 0.3 | 0.1 |
| Perfume | 0.2 | 0.2 | 0.3 |
| Dry additives | | | |
| QEA | — | — | 1.0 |
| Carbonate | 14.0 | 9.0 | 10.0 |
| PB1 | 1.5 | 2.0 | — |
| PB4 | 18.5 | 13.0 | 13.0 |
| TAED | 2.0 | 2.0 | 2.0 |
| QAS | — | — | 1.0 |
| Photoactivated bleach | 15 ppm | 15 ppm | 15 ppm |
| Na-SKS-6 | — | — | 3.0 |
| Protease | 0.03 | 0.03 | 0.007 |
| Mannanase | 0.001 | 0.005 | 0.02 |
| Lipase | 0.004 | 0.004 | 0.004 |
| Amylase | 0.006 | 0.006 | 0.003 |
| Cellulase | 0.0002 | 0.0002 | 0.0005 |
| Sulfate | 10.0 | 20.0 | 5.0 |
| Density (g/litre) | 700 | 700 | 700 |
| Miscellaneous and minors | | | Up to 100% |

EXAMPLE 23

The following detergent compositions were prepared according to the present invention:

|  | I | II | III |
|---|---|---|---|
| Blown Powder | | | |
| Zeolite A | 15.0 | 15.0 | 15.0 |
| Sulfate | — | 5.0 | — |
| LAS | 3.0 | 3.0 | 3.0 |
| QAS | — | 1.5 | 1.5 |
| DETPMP | 0.4 | 0.2 | 0.4 |
| EDDS | — | 0.4 | 0.2 |
| CMC | 0.4 | 0.4 | 0.4 |
| MA/AA | 4.0 | 2.0 | 2.0 |
| Agglomerate | | | |
| LAS | 5.0 | 5.0 | 5.0 |
| TAS | 2.0 | 2.0 | 1.0 |
| Silicate | 3.0 | 3.0 | 4.0 |
| Zeolite A | 8.0 | 8.0 | 8.0 |
| Carbonate | 8.0 | 8.0 | 4.0 |
| Spray On | | | |
| Perfume | 0.3 | 0.3 | 0.3 |
| C45E7 | 2.0 | 2.0 | 2.0 |
| C25E3 | 2.0 | — | — |
| Dry Additives | | | |
| Citrate | 5.0 | — | 2.0 |
| Bicarbonate | — | 3.0 | — |
| Carbonate | 8.0 | 15.0 | 10.0 |
| TAED | 6.0 | 2.0 | 5.0 |
| PB1 | 14.0 | 7.0 | 10.0 |
| PEO | — | — | 0.2 |
| Bentonite clay | — | — | 10.0 |
| Protease | 0.03 | 0.03 | 0.03 |
| Mannanase | 0.001 | 0.005 | 0.01 |
| Lipase | 0.008 | 0.008 | 0.008 |
| Cellulase | 0.001 | 0.001 | 0.001 |
| Amylase | 0.01 | 0.01 | 0.01 |
| Silicone antifoam | 5.0 | 5.0 | 5.0 |
| Sulfate | — | 3.0 | — |
| Density (g/litre) | 850 | 850 | 850 |
| Miscellaneous and minors | | | Up to 100% |

EXAMPLE 24

The following detergent compositions were prepared according to the present invention:

|  | I | II | III | IV |
|---|---|---|---|---|
| LAS | 18.0 | 14.0 | 24.0 | 20.0 |
| QAS | 0.7 | 1.0 | — | 0.7 |
| TFAA | — | 1.0 | — | — |
| C23E56.5 | — | — | 1.0 | — |
| C45E7 | — | 1.0 | — | — |
| C45E3S | 1.0 | 2.5 | 1.0 | — |
| STPP | 32.0 | 18.0 | 30.0 | 22.0 |
| Silicate | 9.0 | 5.0 | 9.0 | 8.0 |
| Carbonate | 11.0 | 7.5 | 10.0 | 5.0 |
| Bicarbonate | — | 7.5 | — | — |
| PB1 | 3.0 | 1.0 | — | — |
| PB4 | — | 1.0 | — | — |
| NOBS | 2.0 | 1.0 | — | — |
| DETPMP | — | 1.0 | — | — |
| DTPA | 0.5 | — | 0.2 | 0.3 |
| SRP 1 | 0.3 | 0.2 | — | 0.1 |
| MA/AA | 1.0 | 1.5 | 2.0 | 0.5 |
| CMC | 0.8 | 0.4 | 0.4 | 0.2 |
| PEI | — | — | 0.4 | — |
| Sulfate | 20.0 | 10.0 | 20.0 | 30.0 |
| Mg sulfate | 0.2 | — | 0.4 | 0.9 |
| Mannanase | 0.001 | 0.005 | 0.01 | 0.015 |
| Protease | 0.03 | 0.03 | 0.02 | 0.02 |
| Amylase | 0.008 | 0.007 | — | 0.004 |
| Lipase | 0.004 | — | 0.002 | — |
| Cellulase | 0.0003 | — | — | 0.0001 |
| Photoactivated bleach | 30 ppm | 20 ppm | — | 10 ppm |
| Perfume | 0.3 | 0.3 | 0.1 | 0.2 |
| Brightener ½ | 0.05 | 0.02 | 0.08 | 0.1 |
| Miscellaneous and minors | | | up to 100% | |

EXAMPLE 25

The following liquid detergent formulations were prepared according to the present invention (Levels are given in parts per weight, enzyme are expressed in pure enzyme):

|  | I | II | III | IV | V |
|---|---|---|---|---|---|
| LAS | 11.5 | 8.8 | — | 3.9 | — |
| C25E2.5S | — | 3.0 | 18.0 | — | 16.0 |
| C45E2.25S | 11.5 | 3.0 | — | 15.7 | — |
| C23E9 | — | 2.7 | 1.8 | 2.0 | 1.0 |
| C23E7 | 3.2 | — | — | — | — |
| CFAA | — | — | 5.2 | — | 3.1 |
| TPKFA | 1.6 | — | 2.0 | 0.5 | 2.0 |
| Citric (50%) | 6.5 | 1.2 | 2.5 | 4.4 | 2.5 |
| Ca formate | 0.1 | 0.06 | 0.1 | — | — |
| Na formate | 0.5 | 0.06 | 0.1 | 0.05 | 0.05 |
| SCS | 4.0 | 1.0 | 3.0 | 1.2 | — |
| Borate | 0.6 | — | 3.0 | 2.0 | 2.9 |
| Na hydroxide | 5.8 | 2.0 | 3.5 | 3.7 | 2.7 |
| Ethanol | 1.75 | 1.0 | 3.6 | 4.2 | 2.9 |
| 1,2 Propanediol | 3.3 | 2.0 | 8.0 | 7.9 | 5.3 |
| Monoethanolamine | 3.0 | 1.5 | 1.3 | 2.5 | 0.8 |
| TEPAE | 1.6 | — | 1.3 | 1.2 | 1.2 |
| Mannanase | 0.001 | 0.01 | 0.015 | 0.015 | 0.001 |
| Protease | 0.03 | 0.01 | 0.03 | 0.02 | 0.02 |
| Lipase | — | — | 0.002 | — | — |
| Amylase | — | — | — | 0.002 | — |
| Cellulase | — | — | 0.0002 | 0.0005 | 0.0001 |
| SRP 1 | 0.2 | — | 0.1 | — | — |
| DTPA | — | — | 0.3 | — | — |
| PVNO | — | — | 0.3 | — | 0.2 |
| Brightener 1 | 0.2 | 0.07 | 0.1 | — | — |
| Silicone antifoam | 0.04 | 0.02 | 0.1 | 0.1 | 0.1 |
| Miscellaneous and water | | | | | |

EXAMPLE 26

The following liquid detergent formulations were prepared according to the present invention (Levels are given in parts per weight, enzyme are expressed in pure enzyme):

|  | I | II | III | IV |
|---|---|---|---|---|
| LAS | 10.0 | 13.0 | 9.0 | — |
| C25AS | 4.0 | 1.0 | 2.0 | 10.0 |
| C25E3S | 1.0 | — | — | 3.0 |
| C25E7 | 6.0 | 8.0 | 13.0 | 2.5 |
| TFAA | — | — | — | 4.5 |
| APA | — | 1.4 | — | — |
| TPKFA | 2.0 | — | 13.0 | 7.0 |
| Citric | 2.0 | 3.0 | 1.0 | 1.5 |
| Dodecenyl/tetradecenyl succinic acid | 12.0 | 10.0 | — | — |
| Rapeseed fatty acid | 4.0 | 2.0 | 1.0 | — |
| Ethanol | 4.0 | 4.0 | 7.0 | 2.0 |
| 1,2 Propanediol | 4.0 | 4.0 | 2.0 | 7.0 |
| Monoethanolamine | — | — | — | 5.0 |
| Triethanolamine | — | — | 8.0 | — |
| TEPAE | 0.5 | — | 0.5 | 0.2 |
| DETPMP | 1.0 | 1.0 | 0.5 | 1.0 |
| Mannanase | 0.001 | 0.015 | 0.01 | 0.03 |
| Protease | 0.02 | 0.02 | 0.01 | 0.008 |
| Lipase | — | 0.002 | — | 0.002 |
| Amylase | 0.004 | 0.004 | 0.01 | 0.008 |
| Cellulase | — | — | — | 0.002 |
| SRP 2 | 0.3 | — | 0.3 | 0.1 |
| Boric acid | 0.1 | 0.2 | 1.0 | 2.0 |
| Ca chloride | — | 0.02 | — | 0.01 |
| Brightener 1 | — | 0.4 | — | — |
| Suds suppressor | 0.1 | 0.3 | — | 0.1 |
| Opacifier | 0.5 | 0.4 | — | 0.3 |
| NaOH up to pH | 8.0 | 8.0 | 7.6 | 7.7 |
| Miscellaneous and water | | | | |

EXAMPLE 27

The following liquid detergent compositions were prepared according to the present invention (Levels are given in parts per weight, enzyme are expressed in pure enzyme):

|  | I | II | III | IV |
|---|---|---|---|---|
| LAS | 25.0 | — | — | — |
| C25AS | — | 13.0 | 18.0 | 15.0 |
| C25E3S | — | 2.0 | 2.0 | 4.0 |
| C25E7 | — | — | 4.0 | 4.0 |
| TFAA | — | 6.0 | 8.0 | 8.0 |
| APA | 3.0 | 1.0 | 2.0 | — |
| TPKFA | — | 15.0 | 11.0 | 11.0 |
| Citric | 1.0 | 1.0 | 1.0 | 1.0 |
| Dodecenyl/tetradecenyl succinic acid | 15.0 | — | — | — |
| Rapeseed fatty acid | 1.0 | — | 3.5 | — |
| Ethanol | 7.0 | 2.0 | 3.0 | 2.0 |
| 1,2 Propanediol | 6.0 | 8.0 | 10.0 | 13.0 |
| Monoethanolamine | — | — | 9.0 | 9.0 |
| TEPAE | — | — | 0.4 | 0.3 |
| DETPMP | 2.0 | 1.2 | 1.0 | — |
| Mannanase | 0.001 | 0.0015 | 0.01 | 0.01 |
| Protease | 0.05 | 0.02 | 0.01 | 0.02 |
| Lipase | — | — | 0.003 | 0.003 |
| Amylase | 0.004 | 0.01 | 0.01 | 0.01 |
| Cellulase | — | — | 0.004 | 0.003 |
| SRP 2 | — | — | 0.2 | 0.1 |
| Boric acid | 1.0 | 1.5 | 2.5 | 2.5 |
| Bentonite clay | 4.0 | 4.0 | — | — |
| Brightener 1 | 0.1 | 0.2 | 0.3 | — |
| Suds suppressor | 0.4 | — | — | — |
| Opacifier | 0.8 | 0.7 | — | — |
| NaOH up to pH | 8.0 | 7.5 | 8.0 | 8.2 |
| Miscellaneous and water | | | | |

EXAMPLE 28

The following liquid detergent compositions were prepared according to the present invention (Levels are given in parts per weight, enzyme are expressed in pure enzyme):

|  | I | II |
|---|---|---|
| LAS | 27.6 | 18.9 |
| C45AS | 13.8 | 5.9 |
| C13E8 | 3.0 | 3.1 |
| Oleic acid | 3.4 | 2.5 |
| Citric | 5.4 | 5.4 |
| Na hydroxide | 0.4 | 3.6 |
| Ca Formate | 0.2 | 0.1 |
| Na Formate | — | 0.5 |
| Ethanol | 7.0 | — |
| Monoethanolamine | 16.5 | 8.0 |
| 1,2 propanediol | 5.9 | 5.5 |
| Xylene sulfonic acid | — | 2.4 |
| TEPAE | 1.5 | 0.8 |
| Protease | 0.05 | 0.02 |
| Mannanase | 0.001 | 0.01 |
| PEG | — | 0.7 |
| Brightener 2 | 0.4 | 0.1 |
| Perfume | 0.5 | 0.3 |
| Water and Minors |  |  |

EXAMPLE 29

The following granular fabric detergent compositions which provide "softening through the wash" capability were prepared according to the present invention:

|  | I | II |
|---|---|---|
| C45AS | — | 10.0 |
| LAS | 7.6 | — |
| C68AS | 1.3 | — |
| C45E7 | 4.0 | — |
| C25E3 | — | 5.0 |
| Coco-alkyl-dimethyl hydroxy-ethyl ammonium chloride | 1.4 | 1.0 |
| Citrate | 5.0 | 3.0 |
| Na-SKS-6 | — | 11.0 |
| Zeolite A | 15.0 | 15.0 |
| MA/AA | 4.0 | 4.0 |
| DETPMP | 0.4 | 0.4 |
| PB1 | 15.0 | — |
| Percarbonate | — | 15.0 |
| TAED | 5.0 | 5.0 |
| Smectite clay | 10.0 | 10.0 |
| HMWPEO | — | 0.1 |
| Mannanase | 0.001 | 0.01 |
| Protease | 0.02 | 0.01 |
| Lipase | 0.02 | 0.01 |
| Amylase | 0.03 | 0.005 |
| Cellulase | 0.001 | — |
| Silicate | 3.0 | 5.0 |
| Carbonate | 10.0 | 10.0 |

-continued

|  | I | II |
|---|---|---|
| Suds suppressor | 1.0 | 4.0 |
| CMC | 0.2 | 0.1 |
| Miscellaneous and minors |  | Up to 100% |

EXAMPLE 30

The following rinse added fabric softener composition was prepared according to the present invention:

|  |  |
|---|---|
| DEQA (2) | 20.0 |
| Mannanase | 0.0008 |
| Cellulase | 0.001 |
| HCL | 0.03 |
| Antifoam agent | 0.01 |
| Blue dye | 25 ppm |
| $CaCl_2$ | 0.20 |
| Perfume | 0.90 |
| Miscellaneous and water | Up to 100% |

EXAMPLE 31

The following fabric softener and dryer added fabric conditioner compositions were prepared according to the present invention:

|  | I | II | III | IV | V |
|---|---|---|---|---|---|
| DEQA | 2.6 | 19.0 | — | — | — |
| DEQA(2) | — | — | — | — | 51.8 |
| DTMAMS | — | — | — | 26.0 | — |
| SDASA | — | — | 70.0 | 42.0 | 40.2 |
| Stearic acid of IV = 0 | 0.3 | — | — | — | — |
| Neodol 45-13 | — | — | 13.0 | — | — |
| Hydrochloride acid | 0.02 | 0.02 | — | — | — |
| Ethanol | — | — | 1.0 | — | — |
| Mannanase | 0.0008 | 0.0002 | 0.0005 | 0.005 | 0.0002 |
| Perfume | 1.0 | 1.0 | 0.75 | 1.0 | 1.5 |
| Glycoperse S-20 | — | — | — | — | 15.4 |
| Glycerol monostearate | — | — | — | 26.0 | — |
| Digeranyl Succinate | — | — | 0.38 | — | — |
| Silicone antifoam | 0.01 | 0.01 | — | — | — |
| Electrolyte | — | 0.1 | — | — | — |
| Clay | — | — | — | 3.0 | — |
| Dye | 10 ppm | 25 ppm | 0.01 | — | — |
| Water and minors | 100% | 100% | — | — | — |

EXAMPLE 32

The following laundry bar detergent compositions were prepared according to the present invention (Levels are given in parts per weight, enzyme are expressed in pure enzyme):

|  | I | II | III | VI | V | III | VI | V |
|---|---|---|---|---|---|---|---|---|
| LAS | — | — | 19.0 | 15.0 | 21.0 | 6.75 | 8.8 | — |
| C28AS | 30.0 | 13.5 | — | — | — | 15.75 | 11.2 | 22.5 |
| Na Laurate | 2.5 | 9.0 | — | — | — | — | — | — |
| Zeolite A | 2.0 | 1.25 | — | — | — | 1.25 | 1.25 | 1.25 |
| Carbonate | 20.0 | 3.0 | 13.0 | 8.0 | 10.0 | 15.0 | 15.0 | 10.0 |
| Ca Carbonate | 27.5 | 39.0 | 35.0 | — | — | 40.0 | — | 40.0 |
| Sulfate | 5.0 | 5.0 | 3.0 | 5.0 | 3.0 | — | — | 5.0 |
| TSPP | 5.0 | — | — | — | — | 5.0 | 2.5 | — |
| STPP | 5.0 | 15.0 | 10.0 | — | — | 7.0 | 8.0 | 10.0 |

-continued

|  | I | II | III | VI | V | III | VI | V |
|---|---|---|---|---|---|---|---|---|
| Bentonite clay | — | 10.0 | — | — | 5.0 | — | — | — |
| DETPMP | — | 0.7 | 0.6 | — | 0.6 | 0.7 | 0.7 | 0.7 |
| CMC | — | 1.0 | 1.0 | 1.0 | 1.0 | — | — | 1.0 |
| Talc | — | — | 10.0 | 15.0 | 10.0 | — | — | — |
| Silicate | — | — | 4.0 | 5.0 | 3.0 | — | — | — |
| PVNO | 0.02 | 0.03 | — | 0.01 | — | 0.02 | — | — |
| MA/AA | 0.4 | 1.0 | — | — | 0.2 | 0.4 | 0.5 | 0.4 |
| SRP 1 | 0.3 | 0.3 | 0.3 | 0.3 | 0.3 | 0.3 | 0.3 | 0.3 |
| Mannanase | 0.001 | 0.001 | 0.01 | 0.01 | 0.015 | 0.001 | 0.05 | 0.01 |
| Amylase | — | — | 0.01 | — | — | — | 0.002 | — |
| Protease | 0.001 | 0.004 | 0.001 | 0.003 | 0.003 | 0.001 | 0.001 | 0.003 |
| Lipase | — | 0.002 | — | 0.002 | — | — | — | — |
| Cellulase | — | .0003 | — | — | .0003 | .0002 | — | — |
| PEO | — | 0.2 | — | 0.2 | 0.3 | — | — | 0.3 |
| Perfume | 1.0 | 0.5 | 0.3 | 0.2 | 0.4 | — | — | 0.4 |
| Mg sulfate | — | — | 3.0 | 3.0 | 3.0 | — | — | — |
| Brightener | 0.15 | 0.1 | 0.15 | — | — | — | — | 0.1 |
| Photoactivated bleach (ppm) | — | 15.0 | 15.0 | 15.0 | 15.0 | — | — | 15.0 |

EXAMPLE 33

The following detergent additive compositions were prepared according to the present invention:

|  | I | II | III |
|---|---|---|---|
| LAS | — | 5.0 | 5.0 |
| STPP | 30.0 | — | 20.0 |
| Zeolite A | — | 35.0 | 20.0 |
| PB1 | 20.0 | 15.0 | — |
| TAED | 10.0 | 8.0 | — |
| Mannanase | 0.001 | 0.01 | 0.01 |
| Protease | 0.3 | 0.3 | 0.3 |
| Amylase | — | 0.06 | 0.06 |
| Minors, water and miscellaneous | | | Up to 100% |

EXAMPLE 34

The following compact high density (0.96 Kg/l) dishwashing detergent compositions were prepared according to the present invention:

|  | I | II | III | IV | V | VI | VII | VIII |
|---|---|---|---|---|---|---|---|---|
| STPP | — | — | 54.3 | 51.4 | 51.4 | — | — | 50.9 |
| Citrate | 35.0 | 17.0 | — | — | — | 46.1 | 40.2 | — |
| Carbonate | — | 17.5 | 14.0 | 14.0 | 14.0 | — | 8.0 | 32.1 |
| Bicarbonate | — | — | — | — | — | 25.4 | — | — |
| Silicate | 32.0 | 14.8 | 14.8 | 10.0 | 10.0 | 1.0 | 25.0 | 3.1 |
| Metasilicate | — | 2.5 | — | 9.0 | 9.0 | — | — | — |
| PB1 | 1.9 | 9.7 | 7.8 | 7.8 | 7.8 | — | — | — |
| PB4 | 8.6 | — | — | — | — | — | — | — |
| Percarbonate | — | — | — | — | — | 6.7 | 11.8 | 4.8 |
| Nonionic | 1.5 | 2.0 | 1.5 | 1.7 | 1.5 | 2.6 | 1.9 | 5.3 |
| TAED | 5.2 | 2.4 | — | — | — | 2.2 | — | 1.4 |
| HEDP | — | 1.0 | — | — | — | — | — | — |
| DETPMP | — | 0.6 | — | — | — | — | — | — |
| MnTACN | — | — | — | — | — | — | 0.008 | — |
| PAAC | — | — | 0.008 | 0.01 | 0.007 | — | — | — |
| BzP | — | — | — | — | 1.4 | — | — | — |
| Paraffin | 0.5 | 0.5 | 0.5 | 0.5 | 0.5 | 0.6 | — | — |
| Mannanase | 0.001 | 0.001 | 0.002 | 0.002 | 0.001 | 0.003 | 0.002 | 0.002 |
| Protease | 0.072 | 0.072 | 0.029 | 0.053 | 0.046 | 0.026 | 0.059 | 0.06 |
| Amylase | 0.012 | 0.012 | 0.006 | 0.012 | 0.013 | 0.009 | 0.017 | 0.03 |
| Lipase | — | 0.001 | — | 0.005 | — | — | — | — |
| BTA | 0.3 | 0.3 | 0.3 | 0.3 | 0.3 | — | 0.3 | 0.3 |
| MA/AA | — | — | — | — | — | — | 4.2 | — |
| 480 N | 3.3 | 6.0 | — | — | — | — | — | 0.9 |
| Perfume | 0.2 | 0.2 | 0.2 | 0.2 | 0.2 | 0.2 | 0.1 | 0.1 |
| Sulphate | 7.0 | 20.0 | 5.0 | 2.2 | 0.8 | 12.0 | 4.6 | — |
| pH | 10.8 | 11.0 | 10.8 | 11.3 | 11.3 | 9.6 | 10.8 | 10.9 |
| Miscellaneous and water | | | | Up to 100% | | | | |

EXAMPLE 35

The following granular dishwashing detergent compositions of bulk density 1.02 Kg/L were prepared according to the present invention:

|  | I | II | III | IV | V | VI | VII | VII |
|---|---|---|---|---|---|---|---|---|
| STPP | 30.0 | 30.0 | 33.0 | 34.2 | 29.6 | 31.1 | 26.6 | 17.6 |
| Carbonate | 30.5 | 30.5 | 31.0 | 30.0 | 23.0 | 39.4 | 4.2 | 45.0 |
| Silicate | 7.4 | 7.4 | 7.5 | 7.2 | 13.3 | 3.4 | 43.7 | 12.4 |
| Metasilicate | — | — | 4.5 | 5.1 | — | — | — | — |
| Percarbonate | — | — | — | — | — | 4.0 | — | — |
| PB1 | 4.4 | 4.2 | 4.5 | 4.5 | — | — | — | — |
| NADCC | — | — | — | — | 2.0 | — | 1.6 | 1.0 |
| Nonionic | 1.2 | 1.0 | 0.7 | 0.8 | 1.9 | 0.7 | 0.6 | 0.3 |
| TAED | 1.0 | — | — | — | — | 0.8 | — | — |
| PAAC | — | 0.004 | 0.004 | 0.004 | — | — | — | — |
| BzP | — | — | — | 1.4 | — | — | — | — |
| Paraffin | 0.25 | 0.25 | 0.25 | 0.25 | — | — | — | — |
| Mannanase | 0.001 | 0.001 | 0.001 | 0.001 | 0.001 | 0.001 | 0.001 | 0.001 |
| Protease | 0.036 | 0.015 | 0.03 | 0.028 | — | 0.03 | — | — |
| Amylase | 0.003 | 0.003 | 0.01 | 0.006 | — | 0.01 | — | — |
| Lipase | 0.005 | — | 0.001 | — | — | — | — | — |
| BTA | 0.15 | 0.15 | 0.15 | 0.15 | — | — | — | — |
| Perfume | 0.2 | 0.2 | 0.2 | 0.2 | 0.1 | 0.2 | 0.2 | — |
| Sulphate | 23.4 | 25.0 | 22.0 | 18.5 | 30.1 | 19.3 | 23.1 | 23.6 |
| pH | 10.8 | 10.8 | 11.3 | 11.3 | 10.7 | 11.5 | 12.7 | 10.9 |
| Miscellaneous and water | | | | | | Up to 100% | | |

EXAMPLE 36

The following tablet detergent compositions were prepared according to the present invention by compression of a granular dishwashing detergent composition at a pressure of 13 KN/cm² using a standard 12 head rotary press:

|  | I | II | III | IV | V | VI |
|---|---|---|---|---|---|---|
| STPP | — | 48.8 | 49.2 | 38.0 | — | 46.8 |
| Citrate | 26.4 | — | — | — | 31.1 | — |
| Carbonate | — | 5.0 | 14.0 | 15.4 | 14.4 | 23.0 |
| Silicate | 26.4 | 14.8 | 15.0 | 12.6 | 17.7 | 2.4 |
| Mannanase | 0.001 | 0.001 | 0.001 | 0.001 | 0.001 | 0.02 |
| Protease | 0.058 | 0.072 | 0.041 | 0.033 | 0.052 | 0.013 |
| Amylase | 0.01 | 0.03 | 0.012 | 0.007 | 0.016 | 0.002 |
| Lipase | 0.005 | — | — | — | — | — |
| PB1 | 1.6 | 7.7 | 12.2 | 10.6 | 15.7 | — |
| PB4 | 6.9 | — | — | — | — | 14.4 |
| Nonionic | 1.5 | 2.0 | 1.5 | 1.65 | 0.8 | 6.3 |
| PAAC | — | — | 0.02 | 0.009 | — | — |
| MnTACN | — | — | — | — | 0.007 | — |
| TAED | 4.3 | 2.5 | — | — | 1.3 | 1.8 |
| HEDP | 0.7 | — | — | 0.7 | — | 0.4 |
| DETPMP | 0.65 | — | — | — | — | — |
| Paraffin | 0.4 | 0.5 | 0.5 | 0.55 | — | — |
| BTA | 0.2 | 0.3 | 0.3 | 0.3 | — | — |
| PA30 | 3.2 | — | — | — | — | — |
| MA/AA | — | — | — | — | 4.5 | 0.55 |
| Perfume | — | — | 0.05 | 0.05 | 0.2 | 0.2 |
| Sulphate | 24.0 | 13.0 | 2.3 | — | 10.7 | 3.4 |
| Weight of tablet | 25 g | 25 g | 20 g | 30 g | 18 g | 20 g |
| pH | 10.6 | 10.6 | 10.7 | 10.7 | 10.9 | 11.2 |
| Miscellaneous and water | | | | | Up to 100% | |

EXAMPLE 37

The following liquid dishwashing detergent compositions of density 1.40 Kg/L were prepared according to the present invention:

|  | I | II | III | IV |
|---|---|---|---|---|
| STPP | 17.5 | 17.5 | 17.2 | 16.0 |
| Carbonate | 2.0 | — | 2.4 | — |
| Silicate | 5.3 | 6.1 | 14.6 | 15.7 |
| NaOCl | 1.15 | 1.15 | 1.15 | 1.25 |
| Polygen/carbopol | 1.1 | 1.0 | 1.1 | 1.25 |
| Nonionic | — | — | 0.1 | — |
| NaBz | 0.75 | 0.75 | — | — |
| Mannanase | 0.001 | 0.005 | 0.01 | 0.001 |
| NaOH | — | 1.9 | — | 3.5 |
| KOH | 2.8 | 3.5 | 3.0 | — |
| pH | 11.0 | 11.7 | 10.9 | 11.0 |
| Sulphate, miscellaneous and water | | | up to 100% | |

EXAMPLE 38

The following liquid dishwashing compositions were prepared according to the present invention:

|  | I | II | III | IV | V |
|---|---|---|---|---|---|
| C17ES | 28.5 | 27.4 | 19.2 | 34.1 | 34.1 |
| Amine oxide | 2.6 | 5.0 | 2.0 | 3.0 | 3.0 |
| C12 glucose amide | — | — | 6.0 | — | — |
| Betaine | 0.9 | — | — | 2.0 | 2.0 |
| Xylene sulfonate | 2.0 | 4.0 | — | 2.0 | — |

-continued

|  | I | II | III | IV | V |
|---|---|---|---|---|---|
| Neodol C11E9 | — | — | 5.0 | — | — |
| Polyhydroxy fatty acid amide | — | — | — | 6.5 | 6.5 |
| Sodium diethylene penta acetate (40%) | — | — | 0.03 | — | — |
| TAED | — | — | — | 0.06 | 0.06 |
| Sucrose | — | — | — | 1.5 | 1.5 |
| Ethanol | 4.0 | 5.5 | 5.5 | 9.1 | 9.1 |
| Alkyl diphenyl oxide disulfonate | — | — | — | — | 2.3 |
| Ca formate | — | — | — | 0.5 | 1.1 |
| Ammonium citrate | 0.06 | 0.1 | — | — | — |
| Na chloride | — | 1.0 | — | — | — |
| Mg chloride | 3.3 | — | 0.7 | — | — |
| Ca chloride | — | — | 0.4 | — | — |
| Na sulfate | — | — | 0.06 | — | — |
| Mg sulfate | 0.08 | — | — | — | — |
| Mg hydroxide | — | — | — | 2.2 | 2.2 |
| Na hydroxide | — | — | — | 1.1 | 1.1 |
| Hydrogen peroxide | 200 ppm | 0.16 | 0.006 | — | — |
| Mannanase | 0.001 | 0.05 | 0.001 | 0.001 | 0.015 |
| Protease | 0.017 | 0.005 | 0.035 | 0.003 | 0.002 |
| Perfume | 0.18 | 0.09 | 0.09 | 0.2 | 0.2 |
| Water and minors |  |  |  | Up to 100% |  |

|  | I | II | III | IV | V |
|---|---|---|---|---|---|
| Perfume | 1.0 | 1.0 | 1.0 | 0.5 | 0.2 |
| Propanediol | — | — | — | 1.5 | — |
| Ethoxylated tetraethylene pentaimine | — | — | — | 1.0 | — |
| 2, Butyl octanol | — | — | — | — | 0.5 |
| Hexyl carbitol** | 1.0 | 1.0 | 1.0 | — | — |
| SCS | 1.3 | 1.3 | 1.3 | — | — |
| pH adjusted to | 7–12 | 7–12 | 7–12 | 4 | — |
| Miscellaneous and water |  |  |  | Up to 100% |  |

*Na4 ethylenediamine diacetic acid
**Diethylene glycol monohexyl ether

EXAMPLE 40

The following spray composition for cleaning of hard surfaces and removing household mildew was prepared according to the present invention:

| Mannanase | 0.01 |
|---|---|
| Amylase | 0.01 |
| Protease | 0.01 |
| Na octyl sulfate | 2.0 |
| Na dodecyl sulfate | 4.0 |
| Na hydroxide | 0.8 |
| Silicate | 0.04 |
| Butyl carbitol* | 4.0 |
| Perfume | 0.35 |
| Water/minors | up to 100% |

*Diethylene glycol monobutyl ether

EXAMPLE 39

The following liquid hard surface cleaning compositions were prepared according to the present invention:

|  | I | II | III | IV | V |
|---|---|---|---|---|---|
| Mannanase | 0.001 | 0.0015 | 0.0015 | 0.05 | 0.01 |
| Amylase | 0.01 | 0.002 | 0.005 | — | — |
| Protease | 0.05 | 0.01 | 0.02 | — | — |
| Hydrogen peroxide | — | — | — | 6.0 | 6.8 |
| Acetyl triethyl citrate | — | — | — | 2.5 | — |
| DTPA | — | — | — | 0.2 | — |
| Butyl hydroxy toluene | — | — | — | 0.05 | — |
| EDTA* | 0.05 | 0.05 | 0.05 | — | — |
| Citric/Citrate | 2.9 | 2.9 | 2.9 | 1.0 | — |
| LAS | 0.5 | 0.5 | 0.5 | — | — |
| C12 AS | 0.5 | 0.5 | 0.5 | — | — |
| C10 AS | — | — | — | — | 1.7 |
| C12 (E) S | 0.5 | 0.5 | 0.5 | — | — |
| C12, 13 E6.5 nonionic | 7.0 | 7.0 | 7.0 | — | — |
| Neodol 23-6.5 | — | — | — | 12.0 | — |
| Dobanol 23-3 | — | — | — | — | 1.5 |
| Dobanol 91-10 | — | — | — | — | 1.6 |
| C25AE1.8S | — | — | — | 6.0 | — |
| Na paraffin sulphonate | — | — | — | 6.0 | — |

LITERATURE

Aviv, H. & Leder, P. 1972. Proc. Natl. Acad. Sci. U.S.A. 69: 1408–1412.

Becker, D. M. & Guarante, L. 1991. Methods Enzymol. 194: 182–187.

Chirgwin, J. M., Przybyla, A. E., MacDonald, R. J. & Rutter, W. J. 1979. Biochemistry 18: 5294–5299.

Gubler, U. & Hoffman, B. J. 1983. Gene 25: 263–269.

Sambrook, J., Fritsch, E. F. & Maniatis, T. 1989. Molecular Cloning: A Laboratory Manual. Cold Spring Harbor Lab., Cold Spring Harbor, N.Y.

Sanger, F., Nicklen, S. & Coulson, A. R. 1977. Proc. Natl. Acad. Sci. U.S.A. 74: 5463–5467.

Lever, M. (1972) A new reaction for colormetric determination of carbohydrates. Anal. Biochem. 47, 273–279.

N. C. Carpita and D. M. Gibeaut (1993) The Plant Journal 3: 1–30.

Diderichsen, B., Wedsted, U., Hedegaard, L., Jensen, B. R., Sjøholm, C. (1990) Cloning of aldB, which encodes alpha-acetolactate decarboxylase, an exoenzyme from *Bacillus brevis*. J. Bacteriol. 172: 4315–4321.

What is claimed is:

1. An isolated mannanase, which is
   (a) a polypeptide encoded by the mannanase encoding part of the DNA sequence cloned into the plasmid present in *Escherichia coli* DSM 12197, or
   (b) a polypeptide comprising a sequence of amino acids 32–330 or amino acids 32–490 of SEQ ID NO:2 or a fragment thereof that has mannanase activity, or
   (c) a polypeptide encoded by a DNA sequence that hybridizes with nucleotides 94–990 or 94–1470 of SEQ ID NO:1 under high stringency conditions, or
   (d) a polypeptide which has a relative mannanase activity of at least 60% after incubation for 20 minutes at 40° C. and any pH in the range of 7.5–10 and an amino acid sequence that is at least 80% homologous with the polypeptide of (a) or (b).

2. The mannanase of claim 1, which is encoded by the mannanase encoding part of the DNA sequence cloned into the plasmid present in *Escherichia coli* DSM 12197.

3. The mannanase of claim 1, which has a sequence comprising amino acids 32–330 of SEQ ID NO:2.

4. The mannanase of claim 1, which has a sequence comprising amino acids 32–490 of SEQ ID NO:2.

5. The mannanase of claim 1, which is a fragment of the sequence of amino acids 32–330 of SEQ ID NO:2, wherein the fragment has mannanase activity.

6. The mannanase of claim 1, which is a fragment of the sequence of amino acids 32–490, wherein the fragment has mannanase activity.

7. The mannanase of claim 1, which has a relative mannanase activity of at least 60% after incubation for 20 minutes at 40° C. and any pH in the range of 7.5–10 and an amino acid sequence that is at least 80% homologous with the polypeptide having an amino acid sequence of residues 32–330 of SEQ ID NO:2.

8. The mannanase of claim 7, which has an amino acid sequence that is at least 85% homologous with the polypeptide having an amino acid sequence of residues 32–330 of SEQ ID NO:2.

9. The mannanase of claim 8, which has an amino acid sequence that is at least 90% homologous with the polypeptide having an amino acid sequence of residues 32–330 of SEQ ID NO:2.

10. The mannanase of claim 9, which has an amino acid sequence that is at least 95% homologous with the polypeptide having an amino acid sequence of residues 32–330 of SEQ ID NO:2.

11. The mannanase of claim 10, which has an amino acid sequence that is at least 98% homologous with the polypeptide having an amino acid sequence of residues 32–330 of SEQ ID NO:2.

12. The mannanase of claim 1, which has a relative mannanase activity of at least 60% after incubation for 20 minutes at 40° C. and any pH in the range of 7.5–10 and an amino acid sequence that is at least 80% homologous with the polypeptide having an amino acid sequence of residues 32–490 of SEQ ID NO:2.

13. The mannanase of claim 12, which has an amino acid sequence that is at least 85% homologous with the polypeptide having an amino acid sequence of residues 32–490 of SEQ ID NO:2.

14. The mannanase of claim 13, which has an amino acid sequence that is at least 90% homologous with the polypeptide having an amino acid sequence of residues 32–490 of SEQ ID NO:2.

15. The mannanase of claim 14, which has an amino acid sequence that is at least 95% homologous with the polypeptide having an amino acid sequence of residues 32–490 of SEQ ID NO:2.

16. The mannanase of claim 15, which has an amino acid sequence that is at least 95% homologous with the polypeptide having an amino acid sequence of residues 32–490 of SEQ ID NO:2.

17. The mannanase of claim 1, which has a molecular weight of 34±10 kDa, as determined by SDS-PAGE.

18. The mannanase of claim 1, which has an N-terminal amino acid sequence of ANSGFYVSGTTLYDANG (amino acids 32–48 of SEQ ID NO:2).

19. The mannanase of claim 1 which is a Bacillus mannanase.

20. The mannanase of claim 19, which is a Bacillus sp. I633 mannanase.

21. An enzyme preparation comprising a mannanase of claim 1 and one or more enzymes selected from the group consisting of proteases, cellulases (endoglucanases), beta-glucanases, hemicellulases, lipases, peroxidases, laccases, alpha-amylases, glucoamylases, cutinases, pectinases, reductases, oxidases, phenoloxidases, ligninases, pullulanases, pectate lyases, xyloglucanases, xylanases, pectin acetyl esterases, polygalacturonases, rhamnogalacturonases, pectin lyases, other mannanases, pectin methylesterases, cellobiohydrolases, transglutaminases; and mixtures thereof.

22. A cleaning composition, comprising a mannanase of claim 1 and a surfactant.

23. A fabric softening composition, comprising a mannanase of claim 1, an enzyme selected from the group consisting of amylases, cellulases, lipases, pectin degrading enzymes, proteases and xyloglucanases, and a cationic surfactant comprising two long chain lengths.

24. The mannanase of claim 1, comprising an amino acid sequence which comprises a catalytic domain and a linker of amino acids 331–342 of SEQ ID NO:2.

25. The mannanase of claim 24, which is a Bacillus mannanase.

26. An enzyme preparation comprising a mannanase of claim 24 and one or more enzymes selected from the group consisting of proteases, cellulases (endoglucanases), beta-glucanases, hemicellulases, lipases, peroxidases, laccases, alpha-amylases, glucoamylases, cutinases, pectinases, reductases, oxidases, phenoloxidases, ligninases, pullulanases, pectate lyases, xyloglucanases, xylanases, pectin acetyl esterases, polygalacturonases, rhamnogalacturonases, pectin lyases, other mannanases, pectin methylesterases, cellobiohydrolases, transglutaminases; and mixtures thereof.

27. A cleaning composition, comprising a mannanase of claim 24 and a surfactant.

28. A fabric softening composition, comprising a mannanase of claim 24, an enzyme selected from the group consisting of amylases, cellulases, lipases, pectin degrading enzymes, proteases and xyloglucanases, and a cationic surfactant comprising two long chain lengths.

29. The mannanase of claim 1, comprising a catalytic domain and a C-terminal region of amino acids 343–490 of SEQ ID NO:2.

30. The mannanase of claim 29, which is a Bacillus mannanase.

31. An enzyme preparation comprising a mannanase of claim 29 and one or more enzymes selected from the group consisting of proteases, cellulases (endoglucanases), beta-glucanases, hemicellulases, lipases, peroxidases, laccases, alpha-amylases, glucoamylases, cutinases, pectinases, reductases, oxidases, phenoloxidases, ligninases, pullulanases, pectate lyases, xyloglucanases, xylanases, pectin acetyl esterases, polygalacturonases, rhamnogalacturonases, pectin lyases, other mannanases, pectin methylesterases, cellobiohydrolases, transglutaminases; and mixtures thereof.

32. A cleaning composition, comprising the mannanase of claim 29 and a surfactant.

33. A fabric softening composition, comprising the mannanase of claim 29, an enzyme selected from the group consisting of amylases, cellulases, lipases, pectin degrading enzymes, proteases and xyloglucanases, and a cationic surfactant comprising two long chain lengths.

* * * * *

UNITED STATES PATENT AND TRADEMARK OFFICE
CERTIFICATE OF CORRECTION

| | | |
|---|---|---|
| PATENT NO. | : 6,566,114 B1 | Page 1 of 1 |
| APPLICATION NO. | : 09/339159 | |
| DATED | : May 20, 2003 | |
| INVENTOR(S) | : Kauppinen et al. | |

It is certified that error appears in the above-identified patent and that said Letters Patent is hereby corrected as shown below:

On the title page, item (63), which lists the Related U.S. Application Data ,amend the paragraph as follows:

~~Continuation of application No. 09/111,256, filed on Jun. 10, 1998, now abandoned~~
Continuation of application No. PCT/DK99/00314 filed on June 10, 1999, now abandoned, which is a continuation-in-part of application No. 09/111,256 filed on June 10, 1998, now abandoned.

In column 1, lines 3-10, should read as follows:

~~This application is a provisional of 60/106,054 filed Oct. 28, 1998 which is a provisional of 60/105,970 filed Oct. 28, 1998 which is a provisional of 60/123,543 filed Mar. 9, 1999 which is a provisional of 60/123,623 filed Mar. 10, 1999 which is a provisional of 60/123,641 filed Mar. 10, 1999 which is a provisional of 60/123,642 filed Mar. 10, 1999 and a con of Ser. No. 09/111,256, filed Jun. 10, 1998 now abandoned and a con of PCT/USDK99/00314 Jun 10, 1998.~~
This application is a continuation of international application no. PCT/DK99/00314 filed on June 10, 1999, now abandoned, which is a continuation-in-part of U.S. application no. 09/111,256 filed on June 10, 1998, and claims the benefit under 35 USC 119 of U.S. provisional application nos. 60/106,054, 60/105,970, 60/123,543, 60/123,623, 60/123,641 and 60/123,642 filed on October 28, 1998, October 28, 1998, March 9, 1999, March 10, 1999, March 10, 1999 and March 10, 1999, respectively.

Signed and Sealed this
Twentieth Day of December, 2011

David J. Kappos
*Director of the United States Patent and Trademark Office*